(12) United States Patent
Ladner et al.

(10) Patent No.: US 8,901,045 B2
(45) Date of Patent: Dec. 2, 2014

(54) METHODS OF CONSTRUCTING LIBRARIES COMPRISING DISPLAYED AND/OR EXPRESSED MEMBERS OF A DIVERSE FAMILY OF PEPTIDES, POLYPEPTIDES OR PROTEINS AND THE NOVEL LIBRARIES

(75) Inventors: Robert C. Ladner, Ijamsville, MD (US); Edward H. Cohen, Belmont, MA (US); Horacio G. Nastri, Newton, MA (US); Kristin L. Rookey, Revere, MA (US); Rene Hoet, Maastricht (NL); Hendricus Renerus Jacobus Mattheus Hoogenboom, Maastricht (NL)

(73) Assignee: Dyax Corp., Burlington, MA (US)

( * ) Notice: Subject to any disclaimer, the term of this patent is extended or adjusted under 35 U.S.C. 154(b) by 0 days.

(21) Appl. No.: 13/464,047

(22) Filed: May 4, 2012

(65) Prior Publication Data

US 2013/0040861 A1    Feb. 14, 2013

Related U.S. Application Data

(63) Continuation of application No. 10/045,674, filed on Oct. 25, 2001, now Pat. No. 8,288,322, which is a continuation-in-part of application No. 10/000,516, filed on Oct. 24, 2001, now abandoned, which is a continuation-in-part of application No. 09/837,306, filed on Apr. 17, 2001, now abandoned.

(60) Provisional application No. 60/198,069, filed on Apr. 17, 2000.

(51) Int. Cl.
*C40B 40/08* (2006.01)
*C12N 15/10* (2006.01)
*C12N 15/66* (2006.01)
*C40B 40/02* (2006.01)

(52) U.S. Cl.
CPC ............ *C40B 40/02* (2013.01); *C12N 15/1037* (2013.01); *C12N 15/10* (2013.01); *C12N 15/66* (2013.01); *C12N 15/1093* (2013.01)
USPC ............................................................ 506/17

(58) Field of Classification Search
None
See application file for complete search history.

(56) References Cited

U.S. PATENT DOCUMENTS

| | | |
|---|---|---|
| 5,118,605 A | 6/1992 | Urdea |
| 5,223,409 A | 6/1993 | Ladner et al. |
| 5,380,833 A | 1/1995 | Urdea |

(Continued)

FOREIGN PATENT DOCUMENTS

| | | |
|---|---|---|
| DE | 19624562 A1 | 1/1998 |
| JP | 2000-500647 A | 1/2000 |

(Continued)

OTHER PUBLICATIONS

Wang et al. (1996) Methods in Enzymology vol. 267 pp. 52 to 68.*

(Continued)

*Primary Examiner* — Christian Boesen
(74) *Attorney, Agent, or Firm* — Wolf, Greenfield & Sacks, P.C.

(57) ABSTRACT

Methods useful in constructing libraries that collectively display and/or express members of diverse families of peptides, polypeptides or proteins and the libraries produced using those methods are disclose. Methods of screening those libraries and the peptides, polypeptides or proteins identified by such screens are also disclosed.

14 Claims, 22 Drawing Sheets

(56) References Cited

U.S. PATENT DOCUMENTS

| | | |
|---|---|---|
| 5,565,332 A | 10/1996 | Hoogenboom et al. |
| 5,618,920 A | 4/1997 | Robinson et al. |
| 5,658,727 A | 8/1997 | Barbas et al. |
| 5,688,666 A | 11/1997 | Bass et al. |
| 5,714,320 A | 2/1998 | Kool |
| 5,723,323 A | 3/1998 | Kauffman et al. |
| 5,733,743 A | 3/1998 | Johnson et al. |
| 5,739,281 A | 4/1998 | Thøgersen et al. |
| 5,750,373 A | 5/1998 | Garrard et al. |
| 5,780,279 A | 7/1998 | Matthews et al. |
| 5,798,208 A | 8/1998 | Crea |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,830,663 A | 11/1998 | Embleton et al. |
| 5,837,242 A | 11/1998 | Holliger et al. |
| 5,840,479 A | 11/1998 | Little et al. |
| 5,846,765 A | 12/1998 | Matthews et al. |
| 5,854,033 A | 12/1998 | Lizardi |
| 5,858,657 A | 1/1999 | Winter et al. |
| 5,858,671 A | 1/1999 | Jones |
| 5,871,907 A | 2/1999 | Winter et al. |
| 5,871,911 A | 2/1999 | Dahlberg et al. |
| 5,872,215 A | 2/1999 | Osbourne et al. |
| 5,885,793 A | 3/1999 | Griffiths et al. |
| 5,917,018 A | 6/1999 | Thøgersen et al. |
| 5,935,831 A | 8/1999 | Quax et al. |
| 5,962,255 A | 10/1999 | Griffiths et al. |
| 5,962,271 A | 10/1999 | Chenchik et al. |
| 5,962,272 A | 10/1999 | Chenchik et al. |
| 5,969,108 A | 10/1999 | McCafferty et al. |
| 5,976,862 A | 11/1999 | Kauffman et al. |
| 5,994,519 A | 11/1999 | Osbourn et al. |
| 6,010,884 A | 1/2000 | Griffiths et al. |
| 6,017,732 A | 1/2000 | Jespers et al. |
| 6,040,136 A | 3/2000 | Garrard et al. |
| 6,057,098 A | 5/2000 | Buechler et al. |
| 6,140,471 A | 10/2000 | Johnson et al. |
| 6,172,197 B1 | 1/2001 | McCafferty et al. |
| 6,180,336 B1 | 1/2001 | Osbourn et al. |
| 6,225,447 B1 | 5/2001 | Winter et al. |
| 6,238,904 B1 | 5/2001 | Morgan |
| 6,248,516 B1 | 6/2001 | Winter et al. |
| 6,291,158 B1 | 9/2001 | Winter et al. |
| 6,291,159 B1 | 9/2001 | Winter et al. |
| 6,291,160 B1 | 9/2001 | Lerner et al. |
| 6,291,161 B1 | 9/2001 | Lerner et al. |
| 6,291,650 B1 | 9/2001 | Winter et al. |
| 6,300,064 B1 | 10/2001 | Knappik et al. |
| 6,319,690 B1 | 11/2001 | Little et al. |
| 6,342,588 B1 | 1/2002 | Osbourn et al. |
| 6,420,113 B1 | 7/2002 | Buechler et al. |
| 6,489,123 B2 | 12/2002 | Osbourn et al. |
| 6,492,107 B1 | 12/2002 | Kauffman et al. |
| 6,492,123 B1 | 12/2002 | Holliger et al. |
| 6,492,160 B1 | 12/2002 | Griffiths et al. |
| 6,521,404 B1 | 2/2003 | Griffiths et al. |
| 6,531,580 B1 | 3/2003 | Huse et al. |
| 6,544,731 B1 | 4/2003 | Griffiths et al. |
| 6,545,142 B1 | 4/2003 | Winter et al. |
| 6,555,313 B1 | 4/2003 | Griffiths et al. |
| 6,569,641 B1 | 5/2003 | Kauffman et al. |
| 6,582,915 B1 | 6/2003 | Griffiths et al. |
| 6,589,527 B1 | 7/2003 | Winter et al. |
| 6,593,081 B1 | 7/2003 | Griffiths et al. |
| 6,680,192 B1 | 1/2004 | Lerner et al. |
| 6,696,245 B2 | 2/2004 | Winter et al. |
| 6,696,248 B1 | 2/2004 | Knappik et al. |
| 6,706,484 B1 | 3/2004 | Knappik et al. |
| 6,753,136 B2 | 6/2004 | Lohning |
| 6,806,079 B1 | 10/2004 | McCafferty et al. |
| 6,828,422 B1 | 12/2004 | Achim et al. |
| 6,846,634 B1 | 1/2005 | Tomlinson et al. |
| 6,916,605 B1 | 7/2005 | McCafferty et al. |
| 6,969,586 B1 | 11/2005 | Lerner et al. |
| 7,063,943 B1 | 6/2006 | McCafferty et al. |
| 7,189,841 B2 | 3/2007 | Lerner et al. |
| 8,288,322 B2 | 10/2012 | Ladner et al. |
| 2002/0004215 A1 | 1/2002 | Osbourn et al. |
| 2003/0114659 A1 | 6/2003 | Winter et al. |
| 2003/0130496 A1 | 7/2003 | Winter et al. |
| 2003/0148372 A1 | 8/2003 | Tomlinson et al. |
| 2003/0190674 A1 | 10/2003 | Griffiths et al. |
| 2003/0232333 A1 | 12/2003 | Ladner et al. |
| 2004/0029113 A1 | 2/2004 | Ladner et al. |
| 2004/0038921 A1 | 2/2004 | Kreutzer et al. |
| 2004/0110941 A2 | 6/2004 | Winter et al. |
| 2004/0157214 A1 | 8/2004 | McCafferty et al. |
| 2004/0157215 A1 | 8/2004 | McCafferty et al. |
| 2005/0202512 A1 | 9/2005 | Tomlinson et al. |
| 2006/0003334 A1 | 1/2006 | Achim et al. |
| 2006/0019260 A1 | 1/2006 | Lerner et al. |
| 2006/0166252 A1 | 7/2006 | Ladner et al. |
| 2006/0257937 A1 | 11/2006 | Ladner |
| 2007/0031879 A1 | 2/2007 | Ley et al. |

FOREIGN PATENT DOCUMENTS

| | | |
|---|---|---|
| WO | 94/07922 A1 | 4/1994 |
| WO | 96/35781 A1 | 11/1996 |
| WO | 97/08320 A1 | 3/1997 |
| WO | 97/15690 A1 | 5/1997 |
| WO | 97/20923 A1 | 6/1997 |
| WO | 97/49809 A1 | 12/1997 |
| WO | 99/06834 A2 | 2/1999 |
| WO | 9955367 A1 | 11/1999 |
| WO | 00/18905 A1 | 4/2000 |
| WO | 01/79481 A2 | 10/2001 |

OTHER PUBLICATIONS

Griffin et al. (1995) Blood vol. 86 pp. 4430 to 4436.*

Alves, Jurgen et al., Accuracy of the EcoRV Restriction Endonuclease: Binding and Cleavage Studies with Oligodeoxynucleotide Substrates Containing Degenerate Recognition Sequences, Biochemistry, 1995, pp. 11191-11197, vol. 34.

Arden, "Conserved motifs in T-cell receptor CDR1 and CDR2: implication for ligand and CD8 co-receptor binding," Current Opinion in Immunology, Current Biology Ltd., 1998, vol. 10, No. 1, pp. 74-81, XP004313624.

Aujame et al., "High affinity human antibodies by phage display," Human Antibodies, 1997, vol. 8, No. 4, pp. 155-168.

Balint et al., "Antibody engineering by parsimonious mutagenesis," Gene, 1993, vol. 137, pp. 109-118.

Barbas et al., "Human autoantibody recognition of DNA," PNAS USA, 1995, vol. 92, pp. 2529-2533, XP002927212.

Barbas et al., "Semisynthetic combinatorial antibody libraries: a chemical solution to the diversity problem," PNAS USA, 1992, vol. 89, pp. 4457-4461.

Barbas, "Assembly of combinatorial antibody libraries on phage surfaces: The gene III site," PNAS USA, Sep. 1991, vol. 88, pp. 7978-7982.

Blakesley et al., "Duplex regions in 'single-stranded' ΦX174 DNA are cleaved by a restriction endonuclease from *Haemophilus aegyptius*," The Journal of Biological Chemistry, 1977, vol. 252, pp. 7300-7306.

Brezinschek et al., "Analysis of the human VH gene repertoire," Journal of Clinical Investigation, May 1997, vol. 99, pp. 2488-2501.

Clackson et al., "In vitro selection from protein and peptide libraries," Elsevier Science Ltd., May 1, 1994, vol. 12, pp. 173-184.

Corbett et al., "Sequence of the human immunoglobulin diversity (D) segment locus: a systematic analysis provides no evidence for the use of DIR segments, inverted D segments, "minor" D segments or D-D recombination," J. Mol. Biol., 1997, vol. 270, No. 4, pp. 587-597.

Courtney et al., "A phage display vector with improved stability, applicability and ease of manipulation," Gene, Nov. 7, 1995, vol. 165, No. 1, pp. 139-140.

Davies et al., "Affinity improvement of single antibody VH domains: residues in all three hypervariable regions affect antigen binding," Immunotechnology, 1996, vol. 2, No. 3, pp. 169-179, XP004070292.

(56) References Cited

OTHER PUBLICATIONS

De Haard et al., "A large non-immunized human Fab fragment phage library that permits rapid isolation and kinetic analysis of high affinity antibodies," Journal of Biological Chemistry, 1999, vol. 274, No. 26, pp. 18218-18230, XP002128301.
Extended European Search Report dated Mar. 10, 2011 from European Application No. 10179786.8.
Extended European Search Report dated May 26, 2010 from European Application No. 10156326.0.
Extended European Search Report from European Application No. 10179777.7 dated Feb. 2, 2011.
Fan, "Three-dimensional structure of an Fv from a human IgM immunoglobulin," J. Mol. Biol., Nov. 5, 1992, vol. 228, No. 1, pp. 188-207.
Grimes et al., "Achilles' heel cleavage: creation of rare restriction sites in I phage genomes and evaluation of additional operators, repressors and restriction/modification systems," 1990, Gene, vol. 90, No. 1, pp. 1-7.
Gushiken et al., "Polymorphism of b2-glycoprotein I at codons 306 and 316 in patients with systemic lupus erythematosus and antiphospholipid syndrome," Arthritis and Rheumatism, Jun. 1999, vol. 42, No. 6, pp. 1189-1193.
Hasan et al., "Control of cloned gene expression by promoter inversion in vivo: construction of improved vectors with a multiple cloning site and the Ptac promoter," Gene, 1987, vol. 56, No. 1, pp. 145-151.
Heddle et al., "Dog immunoglobulins. I. Immunochemical characterization of dog serun, parotid saliva, colostrum milk and small bowel fluid," Immunology, 1975, vol. 29, No. 1, pp. 185-195.
Hoet et al., "Generation of high-affinity human antibodies by combining donor-derived and synthetic complementarity-determining-region diversity," Nature Biotechnology, Mar. 2005, vol. 23, No. 3, pp. 344-348.
Hoet et al., "The importance of the light chain for the epitope specificity of human anti-U1 small nuclear RNA autoantibodies present in systemic lupus erythematosus patients," Journal of Immunology, 1999, vol. 163, No. 6, pp. 3304-3312.
Hoogenboom et al., "Antibody phage display technology and its applications," Immunotechnology, 1998, vol. 4, No. 1, pp. 1-20.
Hoogenboom et al., "By-passing immunisation human antibodies from synthetic repertoires of germline VH gene segments rearranged in vitro," Journal of Molecular Biology, 1992, vol. 227, pp. 381-388, XP002974448.
Hoogenboom, "Multi-subunit proteins on the surface of filamentous phage: methodologies for displaying antibody (Fab) heavy and light chains," Nuclei Acid Research, Jan. 1, 1991, vol. 19, No. 15, pp. 4133-4137.
Hrncir et al., "Anticardiolipin antibodies in diffuse connective tissue diseases in the IgG, IgM and IgA isotypes," Cnitrni Lekarstvi, Nov. 1999, vol. 36, No. 11, pp. 1041-1049, translation pp. 1-13.
Jirholt et al., "Exploiting sequence space: shuffling in vivo formed complementarity determining regions into a master framework," Gene 1998, vol. 215, No. 2, pp. 471-476.
Kaczorowski et al., "Genomic DNA sequencing by SPEL-6 primer walking using hexamer ligation," Gene, 1998, vol. 223, No. 1-2, pp. 83-91.
Kim et al., "Cleaving DNA at any predetermined site with adapter-primers and class IIS restriction enzymes," Science, 1988, vol. 240, No. 4851, pp. 504-506.
Kim et al., "Structural requirements for FokI-DNA interaction and oligodeoxyribonucleotide-instructed cleavage," J. Mol. Biol., 1996, vol. 258, No. 4, pp. 638-649.
Knappik et al., "Fully synthetic human combinatorial antibody libraries (HuCAL) based on modular consensus frameworks and CDRs randomized with trinucleotides," J. Mol. Biol., 2000, vol. 296, pp. 57-86.
Koob et al., "Cleaving yeast and *Escherichia coli* genomes at a single site," Science, 1990, vol. 250, No. 4978, pp. 271-273.
Koob et al., "Conferring new specificity upon restriction endonucleases by combining repressor-operator interaction and methylation," Gene, 1988, vol. 74, No. 1, pp. 165-167.
Koob et al., "Conferring operator specificity on restriction endonucleases," Science, 1988, vol. 241, No. 4869, pp. 1084-1086.
Koob et al., "RecA-AC: single-stie cleavage of plasmids and chromosomes at any predetermined restriction site," Nucleic Acids Res., 1992, vol. 20, No. 21, pp. 5831-5836.
Kriuf et al., "Selection and application of human single chain Fv antibody fragments from a semi-synthetic phage antibody display library with designed CDR3 regions," J. Mol. Biol., 1995, vol. 248, No. 1, pp. 97-105.
Kur et al., "A novel method for converting common restriction enzymes into rare cutters: intergration host factor-mediated Achilles' cleavage (IHF-AC)," Gene, 1992, vol. 110, No. 1, pp. 1-7.
Lowman et al., "Affinity maturation of human growth hormone by monovalent phage display," J. Mol. Biol., 1993, vol. 234, pp. 564-578.
Marks et al., "Bypassing immunization: Building high affinity human antibodies by chain shuffling" Bio/technology vol. 10, pp. 779-783 (1992).
Nishigaki et al., "Type II restriction endonucleases cleave single-stranded DNAs in general," Nucleic Acids Research, 1985, vol. 13, pp. 5747-5760.
Pini et al., "Design and use of a phage display library," Journal of Biological Chemistry, Aug. 21, 1998, vol. 273, pp. 21769-21776.
Podhajska et al., "Conferring new specificities on restriction enzymes: cleavage at any predetermined site by combining adapter oligodeoxynucleotide and class IIS enzyme," Methods Enzymol., 1992, vol. 216 (G), pp. 303309.
Podhajska et al., "Conversion of the Fok-I endonuclease to a universal restriction enzyme: cleavage of phage M13mp7 DNA at predetermined sites," Gene, 1985, vol. 40, No. 1, pp. 175-182.
Posfai et al., "A simple method for locating methylated bases in DNA using class-IIS restriction enzymes," Gene, 1988, vol. 74, No. 1, pp. 179-181.
Powell et al., "Construction, assembly and selection of combinatorial antibody libraries," The Current Innovations in Molecular Biology, Genetic Engineering with PCR, 1998, vol. 5, pp. 155-172, Horton and Tait, Eds.
Qi et al., "Restriction of single-stranded M13 DNA using synthetic oligonucleotides: the structural requirement of restriction enzymes," Cell Biolo., 1986, vol. 65, pp. 50-55.
Roitt et al., Immunology Sixth Edition, 2001, pp. 67-70 and 80, New York: Mosby.
Ryu et al., "Recent progress in biomolecular engineering," Biotechnology Progress, 2000, vol. 15, No. 1, pp. 2-16.
Saviranta et al., "Engineering the steroid-specificity of an anti-17B-estradiol Fab by random mutagenesis of phage-displayed Fab 26-10," Protein Engineering, 1998, vol. 11, No. 2, pp. 143-152.
Schoonbroodt, "Oligonucleotide-assisted cleavage and ligation: a novel directional DNA cloning technology to capture cDNAs. Application in the construction of a human immune antibody phage-display library," Nucleic Acids Research, 2005, vol. 33, No. 9, pp. E81.
Seed, "Developments in expression cloning," Current Opinion in Biotechnology, 1995, vol. 6, pp. 567-573.
Sheets et al., "Efficient construction of a large nonimmune phage antibody library: the production of high-affinity human single-chain anitbodies to protein antigens," PNAS USA, 1998, vol. 95, pp. 6157-6162.
Short et al., "Contribution of antibody heavy chain CDR1 to digoxin binding analyzed by random mutagenesis of phage-displayed Fab 26-10," Journal of Biol. Chem., 1995, vol. 270, No. 1, pp. 28541-28550.
Smith, "Phage display," Chem. Rev., Mar. 1, 1997, vol. 97, No. 2, pp. 391-410.
Soderlind et al., "Domain libraries: synthetic diversity for de novo design of antibody V-regions," Gene, 1995, vol. 160, No. 2, pp. 269-272.
Soderlind et al., "The immune diversity in a test tube—non-immunised antibody libraries and functional variability in defined protein scaffolds," Combinatorial Chemistry and High Throughput Screening, 2001, vol. 4, pp. 409-416.
Stewart et al., "High-frequency representation of a sing VH gene in the expressed human B cell repertoire," Journal of Experimental Medicine, Feb. 1, 1993, vol. 177, pp. 409-418.

(56) References Cited

OTHER PUBLICATIONS

Suzuki et al., "Light chain determines the binding property of human anti-dsDNA IgG autoantibodies," Biochem. Biophys. Res. Commun., Apr. 29, 2000, vol. 271, pp. 240-243.
Szybalski et al., "Class-IIS restriction enzymes—a review," Gene, 1991, vol. 100, pp. 13-26.
Szybalski et al., "Nobel prizes and restriction enzymes," Gene, 1978, vol. 4, No. 3, pp. 181-182.
Szybalski, "Reasons and risks to study restriction/modification enzymes from extreme thremophiles: chillly coldrooms, 13th sample, 13th-codon overlap," Gene, 1992, vol. 112, No. 1, pp. 1-2.
Szybalski, "Universal restriction endonucleases: designing novel cleavage specificities by combining adapter oligodeoxynucleotide and enzyme moieties," Gene, 1985, vol. 40, No. 2-3, pp. 169-173.
Söderlind et al., "Recombining germline-derived CDR sequences for creating diverse single-framework antibody libraries" Nature Biotechnology, vol. 18, pp. 862-868 (2000).
Thielking et al., "Accuracy of the EcoRI restriction endonuclease: binding and cleavage studies with oligodeoxynucleotide substrates containing degenerate recognition sequences," Biochemistry, 1990, vol. 29, No. 19, pp. 4682-4691.
Tomlinson et al., "The repertoire of human germline VH sequences reveals about fifty groups of VH segments with different hypervariable loops," Journal of Molecular Biology, 1992, vol. 227, pp. 776-798, XP000990787.
Wu, et al., "Length Distribution of CDRH3 in Antibodies" Protiens: Structure, Function, and Genetics, vol. 16, pp. 1-7 (1993).
Yang et al., "CDR walking mutagenesis for the affinity maturation of a potent human anti-HIV-1 antibody into the picomolar range," Journal of Molecular Biology, 1995, vol. 254, pp. 392-403.
Zhu, Delin, Oligodeoxynucleotide-Directed Cleavage and Repair of a Single-Stranded Vector: A Method of Site-Specific Mutagenesis, Analytical Biochemistry, 1989, pp. 120-124, vol. 177.
Zucconi et al., "Domain repertoires as a tool to derive protein recognition rules," FEBS Letters, 2000, vol. 480, No. 1, pp. 49-54.
Barbas et al., Selection and evolution of high-affinity human antiviral antibodies. Trends Biotechnol. Jul. 1996;14(7):230-4.
Beers et al., Immunotoxins with increased activity against epidermal growth factor receptor vIII-expressing cells produced by antibody phage display. Clin Cancer Res. Jul. 2000;6(7):2835-43.
Deng et al., Basis for selection of improved carbohydrate-binding single-chain antibodies from synthetic gene libraries. Proc Natl Acad Sci U S A. May 23, 1995;92(11):4992-6.
Hemminki et al., Fine tuning of an anti-testosterone antibody binding site by stepwise optimisation of the CDRs. Immunotechnology. Jun. 1998;4(1):59-69.
Jackson et al., In vitro antibody maturation. Improvement of a high affinity, neutralizing antibody against IL-1 beta. J Immunol. Apr. 1, 1995;154(7):3310-9.
Matthyssens et al., Structure and multiplicity of genes for the human immunoglobulin heavy chain variable region. Proc Natl Acad Sci U S A. Nov. 1980;77(11):6561-5.
NEB Heat Inactivation Chart (retrieved on Sep. 18, 2013 from the internet: <https://www.neb.com/tools-and-resources/usage-guidelines/heat-inactivation>.
Persic et al., An integrated vector system for the eukaryotic expression of antibodies or their fragments after selection from phage display libraries. Gene. Mar. 10, 1997;187(1):9-18.
Roben et al., Repertoire cloning of lupus anti-DNA autoantibodies. J Clin Invest. Dec. 15, 1996;98(12):2827-37.
Smith et al., Building synthetic antibodies as adhesive ligands for integrins. J Biol Chem. Dec. 30, 1994;269(52):32788-95.
Van Den Beucken et al., Building novel binding ligands to B7.1 and B7.2 based on human antibody single variable light chain domains. J Mol Biol. Jul. 13, 2001;310(3):591-601.
Zemlin et al., Expressed murine and human CDR-H3 intervals of equal length exhibit distinct repertoires that differ in their amino acid composition and predicted range of structures. J Mol Biol. Dec. 5, 2003;334(4):733-49.

\* cited by examiner

Gel analysis of PCR product from extender-kappa amplification
Approx. 75ng/5μl ➔ 15ng/μl 1 - 100bp
2 - LDM
3 - 50ng template
4 - 10ng template
5 - ssDNA unligated
6 - negative control
7 - LDM
8 - 100bp

Gel purified PCR product from extender-kappa amplification
Concentration : ± 35ng/µl 1 - LDM
2 - 1µl purif.

Gel-analysis of digested κ-ssDNA

1μl digested ssDNA ≈ 8ng ssDNA
Total volume of 50μl = 400ng ssDNA
➔ 400ng ssDNA available for ligation of the bridge-extenders 1 - 100bp
2 - LDM
3 - 1μl ssDNA pure
4 - 4μl beads after dig.
5 - 8μl beads after dig.
6 - LDM
7 - 100bp Gel analysis of extender – cleaved kappa ligation
20ng/5µl eluted material → 4ng/µl 1 - 100bp
2 - LDM
3 - Ligationmix, 4µl
4 - Unligated ssDNA
5 - LDM

Cleavage and ligation Kappa light chains

A) BsmA1 cleavage 1 2 3 4 5

800 nt
400 nt 1. 100 bp marker
2. LDM marker
3. Sup. ssDNA after dig.
4. beads after dig. (uncleaved material)
5. DNA before cleavage

80% cleavage

B) Bridge Ligation 1 2 3 4

800 nt
400 nt 1. 100 bp marker
2. LDM marker
3. Ligationmix
4. Unligated ssDNA

90% ligation

C) PCR 1 2 3

800 nt
400 nt 1. 100 bp marker
2. LDM marker
3. 50 ng template (13 cycles)

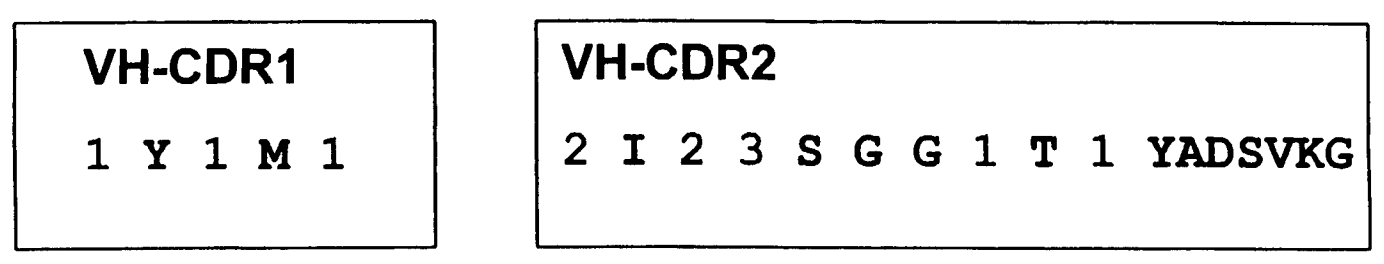

| VH-CDR1 |
|---|
| 1 Y 1 M 1 |

| VH-CDR2 |
|---|
| 2 I 2 3 S G G 1 T 1 YADSVKG |

FIG. 10

Figure 3: Cleavage and ligation lambda light chains

A) HinfI cleavage

B) Bridge ligation

C) PCR

M1 = LDM MW marker
1 = sup. after HinfI-cleavage (10ng ssDNA)
2 = beads after HinfI-cleavage (10ng ssDNA) (not cleaved)
M2 = 100bp marker, bottom to top: 300nt, 400nt, 500nt, 600nt, 800nt 1 = Ligated DNA
2 = Unligated DNA 1 = 1ul purified PCR product / 50 ul (15 cycles)

70% cleavage

95% ligation

3. PCR

```
PCRpr.:
     5'-GAC TGG GTG TAG TGA TCT AG-3
                     +70
(FR3)            V    *    *    S    R    D    N    S       Y    Y    Y    C    A    K
Bridge: 5'-G GTG TAG TGA TCT AGA TCT AGT GAC AAC TCT ... TAC TAT TGT GCG AAA-3'
Ext   : 3'-C CAC ATC ACT AGA TCT CTG TTG AGA ... ATG ATA-5'
                        -XbaI-                                                      +92    1. Annealing
                                                                                    ↙↙↙↙↙↙↙↙
                                                              2. Ligation    3'-XXX XXX XXX-VH
```

FIG. 20

SEQUENCE LISTING

```
<160> NUMBER OF SEQ ID NOS: 639

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catgtgtatt actgtgc                                                    17

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```
cacatccgtg cttcttgcac ggatgtggca cagtaataca catg                44

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtgtattaga ctgctgcc                                                 18

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcagcagtc taatacacca catccgtgtt cttcacggat gtg                     43

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cacatccgtg tttgttacac ggatgtggtg tcttacagtc cattctg                 47

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagaatggac tgtaagacac                                               20

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atcgagtctc actgagccac atccgtggtt ttccacggat gtg                     43

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
gctcagtgag actcgat                                                    17

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(24)
<223> OTHER INFORMATION: a, t, c, g, unknown or other

<400> SEQUENCE: 9
cacgaggagn nnnnnnnnnn nnnn                                            24

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgaccgaat tgctacaag                                                  19

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gactcctcag cttcttgctg aggagtcctt gtagcaattc ggtcat                    46

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: 6 His tag

<400> SEQUENCE: 12

His His His His His His
1               5

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, t, c, g, unknown or other

<400> SEQUENCE: 13 gtctcnnnnn                                                            10

<210> SEQ ID NO 14
<211> LENGTH: 11
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 14
nnnnnngaga c                                                            11

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (11)..(24)
<223> OTHER INFORMATION: a, t, c, g, unknown or other

<400> SEQUENCE: 15
cacggatgtg nnnnnnnnnn nnnn                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(14)
<223> OTHER INFORMATION: a, t, c, g, unknown or other

<400> SEQUENCE: 16
nnnnnnnnnn nnnncacatc cgtg                                              24

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
gtgtattact gtgc                                                         14

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
cacatccgtg cacggatgtg gcacagtaat acac                                   34

<210> SEQ ID NO 19
<211> LENGTH: 14
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 19
gtgtattaga ctgc                                                           14

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcagtctaat acaccacatc cgtgcacgga tgtg                                     34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cacatccgtg cacggatgtg gtgtcttaca gtcc                                     34

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggactgtaag acac                                                           14

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagtctcact gagccacatc cgtgcacgga tgtg                                     34

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gctcagtgag actc                                                           14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 25
gtgtattact gtgc                                                           14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtatattact gtgc                                                           14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtgtattact gtaa                                                           14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgtattact gtac                                                           14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttgtattact gtgc                                                           14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttgtatcact gtgc                                                           14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acatattact gtgc                                                         14

<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
acgtattact gtgc                                                         14

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgtattact gtgc                                                         14

<210> SEQ ID NO 34
<211> LENGTH: 101
<212> TYPE: DNA
<213> ORGANISM: Homo sapiens

<400> SEQUENCE: 34
agggtcacca tgaccaggga cacgtccatc agcacagcct acatgabcga gctgagcagg        60
ctgagatctg acgacacggc cgtgtattac tgtgcgagag a                          101

<210> SEQ ID NO 35
<211> LENGTH: 98
<212> TYPE: DNA
<213> ORGANISM: Homo sapiens

<400> SEQUENCE: 35
agagtcacca ttaccaggga cacatccgcg agcacagcct acatggagct gagcagcctg        60
agatctgaag acacggctgt gtattactgt gcgagaga                               98

<210> SEQ ID NO 36
<211> LENGTH: 98
<212> TYPE: DNA
<213> ORGANISM: Homo sapiens

<400> SEQUENCE: 36
agagtcacca tgaccaggaa cacctccata agcacagcct acatggagct gagcagcctg        60
agatctgagg acacggccgt gtattactgt gcgagagg                               98

<210> SEQ ID NO 37
<211> LENGTH: 98
<212> TYPE: DNA
<213> ORGANISM: Homo sapiens

<400> SEQUENCE: 37
agagtcacca tgaccacaga cacatccacg agcacagcct acatggagct gaggagcctg        60
agatctgacg acacggccgt gtattactgt gcgagaga                               98

```
<210> SEQ ID NO 38
<211> LENGTH: 98
<212> TYPE: DNA
<213> ORGANISM: Homo sapiens

<400> SEQUENCE: 38
agagtcacca tgaccgagga cacatctaca gacacagcct acatggagct gagcagcctg      60
agatctgagg acacggccgt gtattactgt gcaacaga                             98

<210> SEQ ID NO 39
<211> LENGTH: 98
<212> TYPE: DNA
<213> ORGANISM: Homo sapiens

<400> SEQUENCE: 39
agagtcacca ttaccaggga caggtctatg agcacagcct acatggagct gagcagcctg      60
agatctgagg acacagccat gtattactgt gcaagata                             98

<210> SEQ ID NO 40
<211> LENGTH: 98
<212> TYPE: DNA
<213> ORGANISM: Homo sapiens

<400> SEQUENCE: 40
agagtcacca tgaccaggga cacgtccacg agcacagtct acatggagct gagcagcctg      60
agatctgagg acacggccgt gtattactgt gcgagaga                             98

<210> SEQ ID NO 41
<211> LENGTH: 98
<212> TYPE: DNA
<213> ORGANISM: Homo sapiens

<400> SEQUENCE: 41
agagtcacca ttaccaggga catgtccaca agcacagcct acatggagct gagcagcctg      60
agatccgagg acacggccgt gtattactgt gcggcaga                             98

<210> SEQ ID NO 42
<211> LENGTH: 98
<212> TYPE: DNA
<213> ORGANISM: Homo sapiens

<400> SEQUENCE: 42
agagtcacga ttaccgcgga cgaatccacg agcacagcct acatggagct gagcagcctg      60
agatctgagg acacggccgt gtattactgt gcgagaga                             98

<210> SEQ ID NO 43
<211> LENGTH: 98
<212> TYPE: DNA
<213> ORGANISM: Homo sapiens

<400> SEQUENCE: 43
agagtcacga ttaccgcgga caaatccacg agcacagcct acatggagct gagcagcctg      60
agatctgagg acacggccgt gtattactgt gcgagaga                             98

<210> SEQ ID NO 44
<211> LENGTH: 98
<212> TYPE: DNA
<213> ORGANISM: Homo sapiens

<400> SEQUENCE: 44
```
agagtcacca taaccgcgga cacgtctaca gacacagcct acatggagct gagcagcctg     60
agatctgagg acacggccgt gtattactgt gcaacaga                             98

<210> SEQ ID NO 45
<211> LENGTH: 100
<212> TYPE: DNA
<213> ORGANISM: Homo sapiens

<400> SEQUENCE: 45
aggctcacca tcaccaagga cacctccaaa aaccaggtgg tccttacaat gaccaacatg     60
gaccctgtgg acacagccac atattactgt gcacacagac                          100

<210> SEQ ID NO 46
<211> LENGTH: 100
<212> TYPE: DNA
<213> ORGANISM: Homo sapiens

<400> SEQUENCE: 46
aggctcacca tctccaagga cacctccaaa agccaggtgg tccttaccat gaccaacatg     60
gaccctgtgg acacagccac atattactgt gcacggatac                          100

<210> SEQ ID NO 47
<211> LENGTH: 100
<212> TYPE: DNA
<213> ORGANISM: Homo sapiens

<400> SEQUENCE: 47
aggctcacca tctccaagga cacctccaaa aaccaggtgg tccttacaat gaccaacatg     60
gaccctgtgg acacagccac gtattactgt gcacggatac                          100

<210> SEQ ID NO 48
<211> LENGTH: 98
<212> TYPE: DNA
<213> ORGANISM: Homo sapiens

<400> SEQUENCE: 48
cgattcacca tctccagaga caacgccaag aactcactgt atctgcaaat gaacagcctg     60
agagccgagg acacggctgt gtattactgt gcgagaga                             98

<210> SEQ ID NO 49
<211> LENGTH: 100
<212> TYPE: DNA
<213> ORGANISM: Homo sapiens

<400> SEQUENCE: 49
cgattcacca tctccagaga caacgccaag aactccctgt atctgcaaat gaacagtctg     60
agagctgagg acacggcctt gtattactgt gcaaaagata                          100

<210> SEQ ID NO 50
<211> LENGTH: 98
<212> TYPE: DNA
<213> ORGANISM: Homo sapiens

<400> SEQUENCE: 50
cgattcacca tctccaggga caacgccaag aactcactgt atctgcaaat gaacagcctg     60
agagccgagg acacggccgt gtattactgt gcgagaga                             98

<210> SEQ ID NO 51

```
<211> LENGTH: 98
<212> TYPE: DNA
<213> ORGANISM: Homo sapiens

<400> SEQUENCE: 51
cgattcacca tctccagaga aaatgccaag aactccttgt atcttcaaat gaacagcctg      60
agagccgggg acacggctgt gtattactgt gcaagaga                             98

<210> SEQ ID NO 52
<211> LENGTH: 98
<212> TYPE: DNA
<213> ORGANISM: Homo sapiens

<400> SEQUENCE: 52
agattcacca tctcaagaga tgattcaaaa aacacgctgt atctgcaaat gaacagcctg      60
aaaaccgagg acacagccgt gtattactgt accacaga                             98

<210> SEQ ID NO 53
<211> LENGTH: 98
<212> TYPE: DNA
<213> ORGANISM: Homo sapiens

<400> SEQUENCE: 53
cgattcacca tctccagaga caacgccaag aactccctgt atctgcaaat gaacagtctg      60
agagccgagg acacggcctt gtatcactgt gcgagaga                             98

<210> SEQ ID NO 54
<211> LENGTH: 98
<212> TYPE: DNA
<213> ORGANISM: Homo sapiens

<400> SEQUENCE: 54
cgattcacca tctccagaga caacgccaag aactcactgt atctgcaaat gaacagcctg      60
agagccgagg acacggctgt gtattactgt gcgagaga                             98

<210> SEQ ID NO 55
<211> LENGTH: 98
<212> TYPE: DNA
<213> ORGANISM: Homo sapiens

<400> SEQUENCE: 55
cggttcacca tctccagaga caattccaag aacacgctgt atctgcaaat gaacagcctg      60
agagccgagg acacggccgt atattactgt gcgaaaga                             98

<210> SEQ ID NO 56
<211> LENGTH: 98
<212> TYPE: DNA
<213> ORGANISM: Homo sapiens

<400> SEQUENCE: 56
cgattcacca tctccagaga caattccaag aacacgctgt atctgcaaat gaacagcctg      60
agagctgagg acacggctgt gtattactgt gcgaaaga                             98

<210> SEQ ID NO 57
<211> LENGTH: 98
<212> TYPE: DNA
<213> ORGANISM: Homo sapiens

<400> SEQUENCE: 57
cgattcacca tctccagaga caattccaag aacacgctgt atctgcaaat gaacagcctg      60
```

```
agagctgagg acacggctgt gtattactgt gcgagaga                            98
```

<210> SEQ ID NO 58
<211> LENGTH: 98
<212> TYPE: DNA
<213> ORGANISM: Homo sapiens

<400> SEQUENCE: 58

```
cgattcacca tctccagaga caattccaag aacacgctgt atctgcaaat gaacagcctg    60
agagctgagg acacggctgt gtattactgt gcgaaaga                            98
```

<210> SEQ ID NO 59
<211> LENGTH: 98
<212> TYPE: DNA
<213> ORGANISM: Homo sapiens

<400> SEQUENCE: 59

```
cgattcacca tctccagaga caattccaag aacacgctgt atctgcaaat gaacagcctg    60
agagccgagg acacggctgt gtattactgt gcgagaga                            98
```

<210> SEQ ID NO 60
<211> LENGTH: 100
<212> TYPE: DNA
<213> ORGANISM: Homo sapiens

<400> SEQUENCE: 60

```
cgattcacca tctccagaga caacagcaaa aactccctgt atctgcaaat gaacagtctg    60
agaactgagg acaccgcctt gtattactgt gcaaaagata                         100
```

<210> SEQ ID NO 61
<211> LENGTH: 98
<212> TYPE: DNA
<213> ORGANISM: Homo sapiens

<400> SEQUENCE: 61

```
cgattcacca tctccagaga caatgccaag aactcactgt atctgcaaat gaacagcctg    60
agagacgagg acacggctgt gtattactgt gcgagaga                            98
```

<210> SEQ ID NO 62
<211> LENGTH: 98
<212> TYPE: DNA
<213> ORGANISM: Homo sapiens

<400> SEQUENCE: 62

```
agattcacca tctcaagaga tggttccaaa agcatcgcct atctgcaaat gaacagcctg    60
aaaaccgagg acacagccgt gtattactgt actagaga                            98
```

<210> SEQ ID NO 63
<211> LENGTH: 98
<212> TYPE: DNA
<213> ORGANISM: Homo sapiens

<400> SEQUENCE: 63

```
cgattcacca tctccagaga caattccaag aacacgctgt atcttcaaat gaacagcctg    60
agagccgagg acacggccgt gtattactgt gcgagaga                            98
```

<210> SEQ ID NO 64
<211> LENGTH: 98
<212> TYPE: DNA

<213> ORGANISM: Homo sapiens

<400> SEQUENCE: 64
agattcacca tctccagaga caattccaag aacacgctgt atcttcaaat gggcagcctg    60
agagctgagg acatggctgt gtattactgt gcgagaga                            98

<210> SEQ ID NO 65
<211> LENGTH: 98
<212> TYPE: DNA
<213> ORGANISM: Homo sapiens

<400> SEQUENCE: 65
agattcacca tctccagaga caattccaag aacacgctgt atcttcaaat gaacagcctg    60
agagctgagg acacggctgt gtattactgt gcgagaga                            98

<210> SEQ ID NO 66
<211> LENGTH: 98
<212> TYPE: DNA
<213> ORGANISM: Homo sapiens

<400> SEQUENCE: 66
agattcacca tctcaagaga tgattcaaag aactcactgt atctgcaaat gaacagcctg    60
aaaaccgagg acacggccgt gtattactgt gctagaga                            98

<210> SEQ ID NO 67
<211> LENGTH: 98
<212> TYPE: DNA
<213> ORGANISM: Homo sapiens

<400> SEQUENCE: 67
aggttcacca tctccagaga tgattcaaag aacacggcgt atctgcaaat gaacagcctg    60
aaaaccgagg acacggccgt gtattactgt actagaca                            98

<210> SEQ ID NO 68
<211> LENGTH: 98
<212> TYPE: DNA
<213> ORGANISM: Homo sapiens

<400> SEQUENCE: 68
cgattcacca tctccagaga caacgccaag aacacgctgt atctgcaaat gaacagtctg    60
agagccgagg acacggctgt gtattactgt gcaagaga                            98

<210> SEQ ID NO 69
<211> LENGTH: 98
<212> TYPE: DNA
<213> ORGANISM: Homo sapiens

<400> SEQUENCE: 69
agattcacca tctccagaga caattccaag aacacgctgc atcttcaaat gaacagcctg    60
agagctgagg acacggctgt gtattactgt aagaaaga                            98

<210> SEQ ID NO 70
<211> LENGTH: 98
<212> TYPE: DNA
<213> ORGANISM: Homo sapiens

<400> SEQUENCE: 70
cgagtcacca tatcagtaga caagtccaag aaccagttct ccctgaagct gagctctgtg    60
accgccgcgg acacggccgt gtattactgt gcgagaga                            98

-continued

```
<210> SEQ ID NO 71
<211> LENGTH: 98
<212> TYPE: DNA
<213> ORGANISM: Homo sapiens

<400> SEQUENCE: 71
cgagtcacca tgtcagtaga cacgtccaag aaccagttct ccctgaagct gagctctgtg      60
accgccgtgg acacggccgt gtattactgt gcgagaaa                             98

<210> SEQ ID NO 72
<211> LENGTH: 98
<212> TYPE: DNA
<213> ORGANISM: Homo sapiens

<400> SEQUENCE: 72
cgagttacca tatcagtaga cacgtctaag aaccagttct ccctgaagct gagctctgtg      60
actgccgcgg acacggccgt gtattactgt gcgagaga                             98

<210> SEQ ID NO 73
<211> LENGTH: 98
<212> TYPE: DNA
<213> ORGANISM: Homo sapiens

<400> SEQUENCE: 73
cgagtcacca tatcagtaga caggtccaag aaccagttct ccctgaagct gagctctgtg      60
accgccgcgg acacggccgt gtattactgt gccagaga                             98

<210> SEQ ID NO 74
<211> LENGTH: 98
<212> TYPE: DNA
<213> ORGANISM: Homo sapiens

<400> SEQUENCE: 74
cgagttacca tatcagtaga cacgtccaag aaccagttct ccctgaagct gagctctgtg      60
actgccgcag acacggccgt gtattactgt gccagaga                             98

<210> SEQ ID NO 75
<211> LENGTH: 98
<212> TYPE: DNA
<213> ORGANISM: Homo sapiens

<400> SEQUENCE: 75
cgagttacca tatcagtaga cacgtctaag aaccagttct ccctgaagct gagctctgtg      60
actgccgcgg acacggccgt gtattactgt gcgagaga                             98

<210> SEQ ID NO 76
<211> LENGTH: 98
<212> TYPE: DNA
<213> ORGANISM: Homo sapiens

<400> SEQUENCE: 76
cgagtcacca tatcagtaga cacgtccaag aaccagttct ccctgaagct gagctctgtg      60
accgccgcgg acacggctgt gtattactgt gcgagaga                             98

<210> SEQ ID NO 77
<211> LENGTH: 98
<212> TYPE: DNA
<213> ORGANISM: Homo sapiens
```

<400> SEQUENCE: 77
cgagtcacca tatccgtaga cacgtccaag aaccagttct ccctgaagct gagctctgtg    60
accgccgcag acacggctgt gtattactgt gcgagaca                             98

<210> SEQ ID NO 78
<211> LENGTH: 98
<212> TYPE: DNA
<213> ORGANISM: Homo sapiens

<400> SEQUENCE: 78
cgagtcacca tatcagtaga cacgtccaag aaccagttct ccctgaagct gagctctgtg    60
accgctgcgg acacggccgt gtattactgt gcgagaga                             98

<210> SEQ ID NO 79
<211> LENGTH: 98
<212> TYPE: DNA
<213> ORGANISM: Homo sapiens

<400> SEQUENCE: 79
cgagtcacca tatcagtaga cacgtccaag aaccagttct ccctgaagct gagctctgtg    60
accgctgcgg acacggccgt gtattactgt gcgagaga                             98

<210> SEQ ID NO 80
<211> LENGTH: 98
<212> TYPE: DNA
<213> ORGANISM: Homo sapiens

<400> SEQUENCE: 80
cgagtcacca tatcagtaga cacgtccaag aaccagttct ccctgaagct gagctctgtg    60
accgccgcag acacggccgt gtattactgt gcgagaga                             98

<210> SEQ ID NO 81
<211> LENGTH: 98
<212> TYPE: DNA
<213> ORGANISM: Homo sapiens

<400> SEQUENCE: 81
caggtcacca tctcagccga caagtccatc agcaccgcct acctgcagtg gagcagcctg    60
aaggcctcgg acaccgccat gtattactgt gcgagaca                             98

<210> SEQ ID NO 82
<211> LENGTH: 96
<212> TYPE: DNA
<213> ORGANISM: Homo sapiens

<400> SEQUENCE: 82
cacgtcacca tctcagctga caagtccatc agcactgcct acctgcagtg gagcagcctg    60
aaggcctcgg acaccgccat gtattactgt gcgaga                               96

<210> SEQ ID NO 83
<211> LENGTH: 98
<212> TYPE: DNA
<213> ORGANISM: Homo sapiens

<400> SEQUENCE: 83
cgaataacca tcaacccaga cacatccaag aaccagttct ccctgcagct gaactctgtg    60
actcccgagg acacggctgt gtattactgt gcaagaga                             98

```
<210> SEQ ID NO 84
<211> LENGTH: 98
<212> TYPE: DNA
<213> ORGANISM: Homo sapiens

<400> SEQUENCE: 84
cggtttgtct tctccttgga cacctctgtc agcacggcat atctgcagat ctgcagccta      60
aaggctgagg acactgccgt gtattactgt gcgagaga                             98

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, t, c, g, unknown or other

<400> SEQUENCE: 85
gcnnnnnnng c                                                          11

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 86 caynnnnrtg                                                            10

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 87
gagtcnnnnn n                                                          11

<210> SEQ ID NO 88
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 88
nnnnnngaga c                                                          11
```

-continued

```
<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 89 gaannnnttc                                                                 10

<210> SEQ ID NO 90
<211> LENGTH: 90
<212> TYPE: DNA
<213> ORGANISM: Artificial Sequence
<220> FEATURE:
<223> OTHER INFORMATION: Description of Artificial Sequence: Synthetic
      3-23 FR3 nucleotide sequence
<220> FEATURE:
<221> NAME/KEY: CDS
<222> LOCATION: (1)..(90)
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (9)
<223> OTHER INFORMATION: a, t, c or g
<220> FEATURE:
<221> NAME/KEY: modified_base
<222> LOCATION: (12)
<223> OTHER INFORMATION: a, t, c or g
<220> FEATURE:
<221> NAME/KEY: modified_base
<222> LOCATION: (21)
<223> OTHER INFORMATION: a, t, c or g
<220> FEATURE:
<221> NAME/KEY: modified_base
<222> LOCATION: (30)
<223> OTHER INFORMATION: a, t, c or g
<220> FEATURE:
<221> NAME/KEY: modified_base
<222> LOCATION: (33)
<223> OTHER INFORMATION: a, t, c or g
<220> FEATURE:
<221> NAME/KEY: modified_base
<222> LOCATION: (39)
<223> OTHER INFORMATION: a, t, c or g
<220> FEATURE:
<221> NAME/KEY: modified_base
<222> LOCATION: (51)
<223> OTHER INFORMATION: a, t, c or g
<220> FEATURE:
<221> NAME/KEY: modified_base
<222> LOCATION: (57)
<223> OTHER INFORMATION: a, t, c or g
<220> FEATURE:
<221> NAME/KEY: modified_base
<222> LOCATION: (60)
<223> OTHER INFORMATION: a, t, c or g
<220> FEATURE:
<221> NAME/KEY: modified_base
<222> LOCATION: (69)
<223> OTHER INFORMATION: a, t, c or g
<220> FEATURE:
<221> NAME/KEY: modified_base
<222> LOCATION: (72)
<223> OTHER INFORMATION: a, t, c or g
<220> FEATURE:
<221> NAME/KEY: modified_base
<222> LOCATION: (75)
```

<223> OTHER INFORMATION: a, t, c or g
<220> FEATURE:
<221> NAME/KEY: modified_base
<222> LOCATION: (87)
<223> OTHER INFORMATION: a, t, c or g

<400> SEQUENCE: 90

```
acn ath wsn mgn gay aay wsn aar aay acn ytn tay ttn car atg aay      48
Thr Ile Ser Arg Asp Asn Ser Lys Asn Thr Leu Tyr Leu Gln Met Asn
 1               5                  10                  15 wsn ttr mgn gcn gar gay acn gcn gtn tay tay tgy gcn aar              90
Ser Leu Arg Ala Glu Asp Thr Ala Val Tyr Tyr Cys Ala Lys
            20                  25                  30
```

<210> SEQ ID NO 91
<211> LENGTH: 30
<212> TYPE: PRT
<213> ORGANISM: Artificial Sequence
<220> FEATURE:
<223> OTHER INFORMATION: Description of Artificial Sequence: Synthetic
      3-23 FR3 protein sequence

<400> SEQUENCE: 91

```
Thr Ile Ser Arg Asp Asn Ser Lys Asn Thr Leu Tyr Leu Gln Met Asn
 1               5                  10                  15

Ser Leu Arg Ala Glu Asp Thr Ala Val Tyr Tyr Cys Ala Lys
            20                  25                  30
```

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
agttctccct gcagctgaac tc                                             22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
cactgtatct gcaaatgaac ag                                             22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
ccctgtatct gcaaatgaac ag                                             22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 95
ccgcctacct gcagtggagc ag                                           22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
cgctgtatct gcaaatgaac ag                                           22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
cggcatatct gcagatctgc ag                                           22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
cggcgtatct gcaaatgaac ag                                           22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ctgcctacct gcagtggagc ag                                           22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
tcgcctatct gcaaatgaac ag                                           22

<210> SEQ ID NO 101
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cgcttcacta agtctagaga caactctaag aatactctct acttgcagat gaacagctta    60
agg    63

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
caagtagaga gtattcttag agttgtctct agacttagtg aagcg    45

<210> SEQ ID NO 103
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cgcttcacta agtctagaga caactctaag aatactctct acttgcagct gaac    54

<210> SEQ ID NO 104
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cgcttcacta agtctagaga caactctaag aatactctct acttgcaaat gaac    54

<210> SEQ ID NO 105
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cgcttcacta agtctagaga caactctaag aatactctct acttgcagtg gagc    54

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cgcttcacta agtctagaga c    21

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic

```
                    probe

<400> SEQUENCE: 107
acatggagct gagcagcctg ag                                              22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
acatggagct gagcaggctg ag                                              22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
acatggagct gaggagcctg ag                                              22

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
acctgcagtg gagcagcctg aa                                              22

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
atctgcaaat gaacagcctg aa                                              22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
atctgcaaat gaacagcctg ag                                              22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 113
atctgcaaat gaacagtctg ag                                          22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
atctgcagat ctgcagccta aa                                          22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
atcttcaaat gaacagcctg ag                                          22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
atcttcaaat gggcagcctg ag                                          22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ccctgaagct gagctctgtg ac                                          22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
ccctgcagct gaactctgtg ac                                          22

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
tccttacaat gaccaacatg ga                                              22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
tccttaccat gaccaacatg ga                                              22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
acatggagct gagcagcctg ag                                              22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccctgaagct gagctctgtg ac                                              22

<210> SEQ ID NO 123
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cgcttcacta agtctagaga caactctaag aatactctct acttgcagat gaac           54

<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cgcttcactc agtctagaga taacagtaaa aatactttgt acttgcagct gagcagcctg     60

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cgcttcactc agtctagaga taacagtaaa aatactttgt acttgcagct gagctctgtg    60

<210> SEQ ID NO 126
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tcagctgcaa gtacaaagta tttttactgt tatctctaga ctgagtgaag cg    52

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cgcttcactc agtctagaga taac    24

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccgtgtatta ctgtgcgaga ga    22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ctgtgtatta ctgtgcgaga ga    22

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccgtgtatta ctgtgcgaga gg    22

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

```
<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccatgtatta ctgtgcaaga ta                                          22

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ccgtgtatta ctgtgcggca ga                                          22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccacatatta ctgtgcacac ag                                          22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ccacatatta ctgtgcacgg at                                          22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccacgtatta ctgtgcacgg at                                          22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ccttgtatta ctgtgcaaaa ga                                          22
```

(continued from previous page)

```
ccgtgtatta ctgtgcaaca ga                                          22
```

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ctgtgtatta ctgtgcaaga ga                                              22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ccgtgtatta ctgtaccaca ga                                              22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ccttgtatca ctgtgcgaga ga                                              22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccgtatatta ctgtgcgaaa ga                                              22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ctgtgtatta ctgtgcgaaa ga                                              22

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ccgtgtatta ctgtactaga ga                                              22

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ccgtgtatta ctgtgctaga ga                                              22

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ccgtgtatta ctgtactaga ca                                              22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ctgtgtatta ctgtaagaaa ga                                              22

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ccgtgtatta ctgtgcgaga aa                                              22

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ccgtgtatta ctgtgccaga ga                                              22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ctgtgtatta ctgtgcgaga ca                                              22

```
<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ccatgtatta ctgtgcgaga ca                                              22

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ccatgtatta ctgtgcgaga                                                 20

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ccgtgtatta ctgtgcgaga g                                               21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctgtgtatta ctgtgcgaga g                                               21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ccgtgtatta ctgtgcgaga g                                               21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ccgtatatta ctgtgcgaaa g                                               21

<210> SEQ ID NO 156
```

<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ctgtgtatta ctgtgcgaaa g                                        21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctgtgtatta ctgtgcgaga c                                        21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ccatgtatta ctgtgcgaga c                                        21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ccatgtatta ctgtgcgaga                                          20

<210> SEQ ID NO 160
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggtgtagtga tctagtgaca actctaagaa tactctctac ttgcagatga acagctttag      60
ggctgaggac actgcagtct actattgtgc gaga                                 94

<210> SEQ ID NO 161
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggtgtagtga tctagtgaca actctaagaa tactctctac ttgcagatga acagctttag      60
ggctgaggac actgcagtct actattgtgc gaaa                                 94

<210> SEQ ID NO 162
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
atagtagact gcagtgtcct cagcccttaa gctgttcatc tgcaagtaga gagtattctt        60
agagttgtct ctagatcact acacc                                              85

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggtgtagtga tctagagaca ac                                                 22

<210> SEQ ID NO 164
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggtgtagtga aacagcttta gggctgagga cactgcagtc tactattgtg cgaga             55

<210> SEQ ID NO 165
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggtgtagtga aacagcttta gggctgagga cactgcagtc tactattgtg cgaaa             55

<210> SEQ ID NO 166
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
atagtagact gcagtgtcct cagcccttaa gctgtttcac tacacc                       46

<210> SEQ ID NO 167
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167

```
ggtgtagtga aacagcttaa gggctgagga cactgcagtc tactat            46
```

<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

```
ggtgtagtga aacagcttaa gggctg                                  26
```

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169

```
agttctccct gcagctgaac tc                                      22
```

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170

```
cactgtatct gcaaatgaac ag                                      22
```

<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171

```
ccctgtatct gcaaatgaac ag                                      22
```

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172

```
ccgcctacct gcagtggagc ag                                      22
```

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173

```
cgctgtatct gcaaatgaac ag                                      22
```

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
cggcatatct gcagatctgc ag                                              22

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
cggcgtatct gcaaatgaac ag                                              22

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
ctgcctacct gcagtggagc ag                                              22

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
tcgcctatct gcaaatgaac ag                                              22

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
acatggagct gagcagcctg ag                                              22

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
acatggagct gagcaggctg ag                                              22

```
<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
acatggagct gaggagcctg ag                                              22

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
acctgcagtg gagcagcctg aa                                              22

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atctgcaaat gaacagcctg aa                                              22

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
atctgcaaat gaacagcctg ag                                              22

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
atctgcaaat gaacagtctg ag                                              22

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
atctgcagat ctgcagccta aa                                              22
```

```
<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
atcttcaaat gaacagcctg ag                                              22

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
atcttcaaat gggcagcctg ag                                              22

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ccctgaagct gagctctgtg ac                                              22

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ccctgcagct gaactctgtg ac                                              22

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tccttacaat gaccaacatg ga                                              22

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tccttaccat gaccaacatg ga                                              22

<210> SEQ ID NO 192
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ccgtgtatta ctgtgcgaga ga                                              22

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctgtgtatta ctgtgcgaga ga                                              22

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccgtgtatta ctgtgcgaga gg                                              22

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ccgtgtatta ctgtgcaaca ga                                              22

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ccatgtatta ctgtgcaaga ta                                              22

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ccgtgtatta ctgtgcggca ga                                              22

<210> SEQ ID NO 198
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ccacatatta ctgtgcacac ag                                              22

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ccacatatta ctgtgcacgg at                                              22

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ccacgtatta ctgtgcacgg at                                              22

<210> SEQ ID NO 201
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ccttgtatta ctgtgcaaaa ga                                              22

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ctgtgtatta ctgtgcaaga ga                                              22

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ccgtgtatta ctgtaccaca ga                                              22

<210> SEQ ID NO 204
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 204
ccttgtatca ctgtgcgaga ga                                              22

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ccgtatatta ctgtgcgaaa ga                                              22

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ctgtgtatta ctgtgcgaaa ga                                              22

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ccgtgtatta ctgtactaga ga                                              22

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ccgtgtatta ctgtgctaga ga                                              22

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ccgtgtatta ctgtactaga ca                                              22

<210> SEQ ID NO 210
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 210
ctgtgtatta ctgtaagaaa ga                                                   22

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ccgtgtatta ctgtgcgaga aa                                                   22

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ccgtgtatta ctgtgccaga ga                                                   22

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ctgtgtatta ctgtgcgaga ca                                                   22

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ccatgtatta ctgtgcgaga ca                                                   22

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ccatgtatta ctgtgcgaga aa                                                   22

<210> SEQ ID NO 216
<211> LENGTH: 90
<212> TYPE: DNA
<213> ORGANISM: Homo sapiens
```

```
<400> SEQUENCE: 216
caggtgcagc tggtgcagtc tggggctgag gtgaagaagc ctggggcctc agtgaaggtc      60
tcctgcaagg cttctggata caccttcacc                                       90

<210> SEQ ID NO 217
<211> LENGTH: 90
<212> TYPE: DNA
<213> ORGANISM: Homo sapiens

<400> SEQUENCE: 217
caggtccagc ttgtgcagtc tggggctgag gtgaagaagc ctggggcctc agtgaaggtt      60
tcctgcaagg cttctggata caccttcact                                       90

<210> SEQ ID NO 218
<211> LENGTH: 90
<212> TYPE: DNA
<213> ORGANISM: Homo sapiens

<400> SEQUENCE: 218
caggtgcagc tggtgcagtc tggggctgag gtgaagaagc ctggggcctc agtgaaggtc      60
tcctgcaagg cttctggata caccttcacc                                       90

<210> SEQ ID NO 219
<211> LENGTH: 90
<212> TYPE: DNA
<213> ORGANISM: Homo sapiens

<400> SEQUENCE: 219
caggttcagc tggtgcagtc tggagctgag gtgaagaagc ctggggcctc agtgaaggtc      60
tcctgcaagg cttctggtta cacctttacc                                       90

<210> SEQ ID NO 220
<211> LENGTH: 90
<212> TYPE: DNA
<213> ORGANISM: Homo sapiens

<400> SEQUENCE: 220
caggtccagc tggtacagtc tggggctgag gtgaagaagc ctggggcctc agtgaaggtc      60
tcctgcaagg tttccggata caccctcact                                       90

<210> SEQ ID NO 221
<211> LENGTH: 90
<212> TYPE: DNA
<213> ORGANISM: Homo sapiens

<400> SEQUENCE: 221
cagatgcagc tggtgcagtc tggggctgag gtgaagaaga ctgggtcctc agtgaaggtt      60
tcctgcaagg cttccggata caccttcacc                                       90

<210> SEQ ID NO 222
<211> LENGTH: 90
<212> TYPE: DNA
<213> ORGANISM: Homo sapiens

<400> SEQUENCE: 222
caggtgcagc tggtgcagtc tggggctgag gtgaagaagc ctggggcctc agtgaaggtt      60
tcctgcaagg catctggata caccttcacc                                       90
```

```
<210> SEQ ID NO 223
<211> LENGTH: 90
<212> TYPE: DNA
<213> ORGANISM: Homo sapiens

<400> SEQUENCE: 223
caaatgcagc tggtgcagtc tgggcctgag gtgaagaagc ctgggacctc agtgaaggtc      60
tcctgcaagg cttctggatt caccttact                                       90

<210> SEQ ID NO 224
<211> LENGTH: 90
<212> TYPE: DNA
<213> ORGANISM: Homo sapiens

<400> SEQUENCE: 224
caggtgcagc tggtgcagtc tggggctgag gtgaagaagc ctgggtcctc ggtgaaggtc      60
tcctgcaagg cttctggagg caccttcagc                                      90

<210> SEQ ID NO 225
<211> LENGTH: 90
<212> TYPE: DNA
<213> ORGANISM: Homo sapiens

<400> SEQUENCE: 225
caggtgcagc tggtgcagtc tggggctgag gtgaagaagc ctgggtcctc ggtgaaggtc      60
tcctgcaagg cttctggagg caccttcagc                                      90

<210> SEQ ID NO 226
<211> LENGTH: 90
<212> TYPE: DNA
<213> ORGANISM: Homo sapiens

<400> SEQUENCE: 226
gaggtccagc tggtacagtc tggggctgag gtgaagaagc ctggggctac agtgaaaatc      60
tcctgcaagg tttctggata caccttcacc                                      90

<210> SEQ ID NO 227
<211> LENGTH: 90
<212> TYPE: DNA
<213> ORGANISM: Homo sapiens

<400> SEQUENCE: 227
cagatcacct tgaaggagtc tggtcctacg ctggtgaaac ccacacagac cctcacgctg      60
acctgcacct tctctgggtt ctcactcagc                                      90

<210> SEQ ID NO 228
<211> LENGTH: 90
<212> TYPE: DNA
<213> ORGANISM: Homo sapiens

<400> SEQUENCE: 228
caggtcacct tgaaggagtc tggtcctgtg ctggtgaaac ccacagagac cctcacgctg      60
acctgcaccg tctctgggtt ctcactcagc                                      90

<210> SEQ ID NO 229
<211> LENGTH: 90
<212> TYPE: DNA
<213> ORGANISM: Homo sapiens

<400> SEQUENCE: 229
```

```
caggtcacct tgaaggagtc tggtcctgcg ctggtgaaac ccacacagac cctcacactg    60
acctgcacct tctctgggtt ctcactcagc                                    90

<210> SEQ ID NO 230
<211> LENGTH: 90
<212> TYPE: DNA
<213> ORGANISM: Homo sapiens

<400> SEQUENCE: 230
gaggtgcagc tggtggagtc tgggggaggc ttggtccagc ctggggggtc cctgagactc    60
tcctgtgcag cctctggatt cacctttagt                                    90

<210> SEQ ID NO 231
<211> LENGTH: 90
<212> TYPE: DNA
<213> ORGANISM: Homo sapiens

<400> SEQUENCE: 231
gaagtgcagc tggtggagtc tgggggaggc ttggtacagc ctggcaggtc cctgagactc    60
tcctgtgcag cctctggatt cacctttgat                                    90

<210> SEQ ID NO 232
<211> LENGTH: 90
<212> TYPE: DNA
<213> ORGANISM: Homo sapiens

<400> SEQUENCE: 232
caggtgcagc tggtggagtc tgggggaggc ttggtcaagc ctggagggtc cctgagactc    60
tcctgtgcag cctctggatt caccttcagt                                    90

<210> SEQ ID NO 233
<211> LENGTH: 90
<212> TYPE: DNA
<213> ORGANISM: Homo sapiens

<400> SEQUENCE: 233
gaggtgcagc tggtggagtc tgggggaggc ttggtacagc ctggggggtc cctgagactc    60
tcctgtgcag cctctggatt caccttcagt                                    90

<210> SEQ ID NO 234
<211> LENGTH: 90
<212> TYPE: DNA
<213> ORGANISM: Homo sapiens

<400> SEQUENCE: 234
gaggtgcagc tggtggagtc tgggggaggc ttggtaaagc ctggggggtc ccttagactc    60
tcctgtgcag cctctggatt cactttcagt                                    90

<210> SEQ ID NO 235
<211> LENGTH: 90
<212> TYPE: DNA
<213> ORGANISM: Homo sapiens

<400> SEQUENCE: 235
gaggtgcagc tggtggagtc tgggggaggt gtggtacggc ctggggggtc cctgagactc    60
tcctgtgcag cctctggatt cacctttgat                                    90

<210> SEQ ID NO 236
<211> LENGTH: 90
```

<212> TYPE: DNA
<213> ORGANISM: Homo sapiens

<400> SEQUENCE: 236
gaggtgcagc tggtggagtc tgggggaggc ctggtcaagc ctgggggtc cctgagactc    60 tcctgtgcag cctctggatt caccttcagt                                     90

<210> SEQ ID NO 237
<211> LENGTH: 90
<212> TYPE: DNA
<213> ORGANISM: Homo sapiens

<400> SEQUENCE: 237
gaggtgcagc tgttggagtc tgggggaggc ttggtacagc ctgggggtc cctgagactc    60 tcctgtgcag cctctggatt cacctttagc                                     90

<210> SEQ ID NO 238
<211> LENGTH: 90
<212> TYPE: DNA
<213> ORGANISM: Homo sapiens

<400> SEQUENCE: 238
caggtgcagc tggtggagtc tgggggaggc gtggtccagc ctgggaggtc cctgagactc    60
tcctgtgcag cctctggatt caccttcagt                                     90

<210> SEQ ID NO 239
<211> LENGTH: 90
<212> TYPE: DNA
<213> ORGANISM: Homo sapiens

<400> SEQUENCE: 239
caggtgcagc tggtggagtc tgggggaggc gtggtccagc ctgggaggtc cctgagactc    60
tcctgtgcag cctctggatt caccttcagt                                     90

<210> SEQ ID NO 240
<211> LENGTH: 90
<212> TYPE: DNA
<213> ORGANISM: Homo sapiens

<400> SEQUENCE: 240
caggtgcagc tggtggagtc tgggggaggc gtggtccagc ctgggaggtc cctgagactc    60
tcctgtgcag cctctggatt caccttcagt                                     90

<210> SEQ ID NO 241
<211> LENGTH: 90
<212> TYPE: DNA
<213> ORGANISM: Homo sapiens

<400> SEQUENCE: 241
caggtgcagc tggtggagtc tgggggaggc gtggtccagc ctgggaggtc cctgagactc    60
tcctgtgcag cgtctggatt caccttcagt                                     90

<210> SEQ ID NO 242
<211> LENGTH: 90
<212> TYPE: DNA
<213> ORGANISM: Homo sapiens

<400> SEQUENCE: 242
gaagtgcagc tggtggagtc tgggggagtc gtggtacagc ctgggggtc cctgagactc    60

```
tcctgtgcag cctctggatt caccttttgat                                         90
```

<210> SEQ ID NO 243
<211> LENGTH: 90
<212> TYPE: DNA
<213> ORGANISM: Homo sapiens

<400> SEQUENCE: 243

```
gaggtgcagc tggtggagtc tgggggaggc ttggtacagc ctgggggtc cctgagactc          60 tcctgtgcag cctctggatt caccttcagt                                         90
```

<210> SEQ ID NO 244
<211> LENGTH: 90
<212> TYPE: DNA
<213> ORGANISM: Homo sapiens

<400> SEQUENCE: 244

```
gaggtgcagc tggtggagtc tgggggaggc ttggtacagc caggcggtc cctgagactc          60 tcctgtacag cttctggatt cacctttggt                                         90
```

<210> SEQ ID NO 245
<211> LENGTH: 90
<212> TYPE: DNA
<213> ORGANISM: Homo sapiens

<400> SEQUENCE: 245

```
gaggtgcagc tggtggagac tggaggaggc ttgatccagc ctgggggtc cctgagactc          60 tcctgtgcag cctctgggtt caccgtcagt                                         90
```

<210> SEQ ID NO 246
<211> LENGTH: 90
<212> TYPE: DNA
<213> ORGANISM: Homo sapiens

<400> SEQUENCE: 246

```
gaggtgcagc tggtggagtc tgggggaggc ttggtccagc ctgggggtc cctgagactc          60 tcctgtgcag cctctggatt caccttcagt                                         90
```

<210> SEQ ID NO 247
<211> LENGTH: 90
<212> TYPE: DNA
<213> ORGANISM: Homo sapiens

<400> SEQUENCE: 247

```
gaggtgcagc tggtggagtc tgggggaggc ttggtccagc ctgggggtc cctgagactc          60 tcctgtgcag cctctggatt caccgtcagt                                         90
```

<210> SEQ ID NO 248
<211> LENGTH: 90
<212> TYPE: DNA
<213> ORGANISM: Homo sapiens

<400> SEQUENCE: 248

```
gaggtgcagc tggtggagtc tgggggaggc ttggtccagc ctggagggtc cctgagactc          60
tcctgtgcag cctctggatt caccttcagt                                         90
```

<210> SEQ ID NO 249
<211> LENGTH: 90
<212> TYPE: DNA
<213> ORGANISM: Homo sapiens

<400> SEQUENCE: 249
gaggtgcagc tggtggagtc tgggggaggc ttggtccagc ctggggggtc cctgaaactc    60
tcctgtgcag cctctgggtt caccttcagt                                    90

<210> SEQ ID NO 250
<211> LENGTH: 90
<212> TYPE: DNA
<213> ORGANISM: Homo sapiens

<400> SEQUENCE: 250
gaggtgcagc tggtggagtc cggggggaggc ttagttcagc ctggggggtc cctgagactc   60
tcctgtgcag cctctggatt caccttcagt                                    90

<210> SEQ ID NO 251
<211> LENGTH: 90
<212> TYPE: DNA
<213> ORGANISM: Homo sapiens

<400> SEQUENCE: 251
gaggtgcagc tggtggagtc tcggggagtc ttggtacagc ctggggggtc cctgagactc    60
tcctgtgcag cctctggatt caccgtcagt                                    90

<210> SEQ ID NO 252
<211> LENGTH: 90
<212> TYPE: DNA
<213> ORGANISM: Homo sapiens

<400> SEQUENCE: 252
caggtgcagc tgcaggagtc gggcccagga ctggtgaagc cttcggggac cctgtccctc    60
acctgcgctg tctctggtgg ctccatcagc                                    90

<210> SEQ ID NO 253
<211> LENGTH: 90
<212> TYPE: DNA
<213> ORGANISM: Homo sapiens

<400> SEQUENCE: 253
caggtgcagc tgcaggagtc gggcccagga ctggtgaagc cttcggacac cctgtccctc    60
acctgcgctg tctctggtta ctccatcagc                                    90

<210> SEQ ID NO 254
<211> LENGTH: 90
<212> TYPE: DNA
<213> ORGANISM: Homo sapiens

<400> SEQUENCE: 254
caggtgcagc tgcaggagtc gggcccagga ctggtgaagc cttcacagac cctgtccctc    60
acctgcactg tctctggtgg ctccatcagc                                    90

<210> SEQ ID NO 255
<211> LENGTH: 90
<212> TYPE: DNA
<213> ORGANISM: Homo sapiens

<400> SEQUENCE: 255
cagctgcagc tgcaggagtc cggctcagga ctggtgaagc cttcacagac cctgtccctc    60
acctgcgctg tctctggtgg ctccatcagc                                    90

<210> SEQ ID NO 256
<211> LENGTH: 90
<212> TYPE: DNA
<213> ORGANISM: Homo sapiens

<400> SEQUENCE: 256
caggtgcagc tgcaggagtc gggcccagga ctggtgaagc cttcacagac cctgtccctc      60
acctgcactg tctctggtgg ctccatcagc                                      90

<210> SEQ ID NO 257
<211> LENGTH: 90
<212> TYPE: DNA
<213> ORGANISM: Homo sapiens

<400> SEQUENCE: 257
caggtgcagc tgcaggagtc gggcccagga ctggtgaagc cttcacagac cctgtccctc      60
acctgcactg tctctggtgg ctccatcagc                                      90

<210> SEQ ID NO 258
<211> LENGTH: 90
<212> TYPE: DNA
<213> ORGANISM: Homo sapiens

<400> SEQUENCE: 258
caggtgcagc tacagcagtg gggcgcagga ctgttgaagc cttcggagac cctgtccctc      60
acctgcgctg tctatggtgg gtccttcagt                                      90

<210> SEQ ID NO 259
<211> LENGTH: 90
<212> TYPE: DNA
<213> ORGANISM: Homo sapiens

<400> SEQUENCE: 259
cagctgcagc tgcaggagtc gggcccagga ctggtgaagc cttcggagac cctgtccctc      60
acctgcactg tctctggtgg ctccatcagc                                      90

<210> SEQ ID NO 260
<211> LENGTH: 90
<212> TYPE: DNA
<213> ORGANISM: Homo sapiens

<400> SEQUENCE: 260
caggtgcagc tgcaggagtc gggcccagga ctggtgaagc cttcggagac cctgtccctc      60
acctgcactg tctctggtgg ctccatcagt                                      90

<210> SEQ ID NO 261
<211> LENGTH: 90
<212> TYPE: DNA
<213> ORGANISM: Homo sapiens

<400> SEQUENCE: 261
caggtgcagc tgcaggagtc gggcccagga ctggtgaagc cttcggagac cctgtccctc      60
acctgcactg tctctggtgg ctccgtcagc                                      90

<210> SEQ ID NO 262
<211> LENGTH: 90
<212> TYPE: DNA
<213> ORGANISM: Homo sapiens

<400> SEQUENCE: 262
caggtgcagc tgcaggagtc gggcccagga ctggtgaagc cttcggagac cctgtccctc    60
acctgcgctg tctctggtta ctccatcagc    90

<210> SEQ ID NO 263
<211> LENGTH: 90
<212> TYPE: DNA
<213> ORGANISM: Homo sapiens

<400> SEQUENCE: 263
gaggtgcagc tggtgcagtc tggagcagag gtgaaaaagc ccggggagtc tctgaagatc    60
tcctgtaagg gttctggata cagctttacc    90

<210> SEQ ID NO 264
<211> LENGTH: 90
<212> TYPE: DNA
<213> ORGANISM: Homo sapiens

<400> SEQUENCE: 264
gaagtgcagc tggtgcagtc tggagcagag gtgaaaaagc ccggggagtc tctgaggatc    60
tcctgtaagg gttctggata cagctttacc    90

<210> SEQ ID NO 265
<211> LENGTH: 90
<212> TYPE: DNA
<213> ORGANISM: Homo sapiens

<400> SEQUENCE: 265
caggtacagc tgcagcagtc aggtccagga ctggtgaagc cctcgcagac cctctcactc    60
acctgtgcca tctccgggga cagtgtctct    90

<210> SEQ ID NO 266
<211> LENGTH: 90
<212> TYPE: DNA
<213> ORGANISM: Homo sapiens

<400> SEQUENCE: 266
caggtgcagc tggtgcaatc tgggtctgag ttgaagaagc ctggggcctc agtgaaggtt    60
tcctgcaagg cttctggata caccttcact    90

<210> SEQ ID NO 267
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ccgtgtatta ctgtgcgaga ga    22

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctgtgtatta ctgtgcgaga ga    22

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ccgtgtatta ctgtgcgaga gg                                              22

<210> SEQ ID NO 270
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ccgtatatta ctgtgcgaaa ga                                              22

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ctgtgtatta ctgtgcgaaa ga                                              22

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctgtgtatta ctgtgcgaga ca                                              22

<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ccatgtatta ctgtgcgaga ca                                              22

<210> SEQ ID NO 274
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ccatgtatta ctgtgcgaga aa                                              22

```
<210> SEQ ID NO 275
<211> LENGTH: 69
<212> TYPE: DNA
<213> ORGANISM: Homo sapiens

<400> SEQUENCE: 275
gacatccaga tgacccagtc tccatcctcc ctgtctgcat ctgtaggaga cagagtcacc    60
atcacttgc                                                           69

<210> SEQ ID NO 276
<211> LENGTH: 69
<212> TYPE: DNA
<213> ORGANISM: Homo sapiens

<400> SEQUENCE: 276
gacatccaga tgacccagtc tccatcctcc ctgtctgcat ctgtaggaga cagagtcacc    60
atcacttgc                                                           69

<210> SEQ ID NO 277
<211> LENGTH: 69
<212> TYPE: DNA
<213> ORGANISM: Homo sapiens

<400> SEQUENCE: 277
gacatccaga tgacccagtc tccatcctcc ctgtctgcat ctgtaggaga cagagtcacc    60
atcacttgc                                                           69

<210> SEQ ID NO 278
<211> LENGTH: 69
<212> TYPE: DNA
<213> ORGANISM: Homo sapiens

<400> SEQUENCE: 278
gacatccaga tgacccagtc tccatcctcc ctgtctgcat ctgtaggaga cagagtcacc    60
atcacttgc                                                           69

<210> SEQ ID NO 279
<211> LENGTH: 69
<212> TYPE: DNA
<213> ORGANISM: Homo sapiens

<400> SEQUENCE: 279
gacatccaga tgacccagtc tccatcctcc ctgtctgcat ctgtaggaga cagagtcacc    60
atcacttgc                                                           69

<210> SEQ ID NO 280
<211> LENGTH: 69
<212> TYPE: DNA
<213> ORGANISM: Homo sapiens

<400> SEQUENCE: 280
gacatccaga tgacccagtc tccatcctcc ctgtctgcat ctgtaggaga cagagtcacc    60
atcacttgc                                                           69

<210> SEQ ID NO 281
<211> LENGTH: 69
<212> TYPE: DNA
<213> ORGANISM: Homo sapiens

<400> SEQUENCE: 281
```

```
aacatccaga tgacccagtc tccatctgcc atgtctgcat ctgtaggaga cagagtcacc    60
atcacttgt                                                           69

<210> SEQ ID NO 282
<211> LENGTH: 69
<212> TYPE: DNA
<213> ORGANISM: Homo sapiens

<400> SEQUENCE: 282
gacatccaga tgacccagtc tccatcctca ctgtctgcat ctgtaggaga cagagtcacc    60
atcacttgt                                                           69

<210> SEQ ID NO 283
<211> LENGTH: 69
<212> TYPE: DNA
<213> ORGANISM: Homo sapiens

<400> SEQUENCE: 283
gacatccaga tgacccagtc tccatcctca ctgtctgcat ctgtaggaga cagagtcacc    60
atcacttgt                                                           69

<210> SEQ ID NO 284
<211> LENGTH: 69
<212> TYPE: DNA
<213> ORGANISM: Homo sapiens

<400> SEQUENCE: 284
gccatccagt tgacccagtc tccatcctcc ctgtctgcat ctgtaggaga cagagtcacc    60
atcacttgc                                                           69

<210> SEQ ID NO 285
<211> LENGTH: 69
<212> TYPE: DNA
<213> ORGANISM: Homo sapiens

<400> SEQUENCE: 285
gccatccagt tgacccagtc tccatcctcc ctgtctgcat ctgtaggaga cagagtcacc    60
atcacttgc                                                           69

<210> SEQ ID NO 286
<211> LENGTH: 69
<212> TYPE: DNA
<213> ORGANISM: Homo sapiens

<400> SEQUENCE: 286
gacatccaga tgacccagtc tccatcttcc gtgtctgcat ctgtaggaga cagagtcacc    60
atcacttgt                                                           69

<210> SEQ ID NO 287
<211> LENGTH: 69
<212> TYPE: DNA
<213> ORGANISM: Homo sapiens

<400> SEQUENCE: 287
gacatccaga tgacccagtc tccatcttct gtgtctgcat ctgtaggaga cagagtcacc    60
atcacttgt                                                           69

<210> SEQ ID NO 288
<211> LENGTH: 69
```

```
<212> TYPE: DNA
<213> ORGANISM: Homo sapiens

<400> SEQUENCE: 288
gacatccagt tgacccagtc tccatccttc ctgtctgcat ctgtaggaga cagagtcacc      60
atcacttgc                                                              69

<210> SEQ ID NO 289
<211> LENGTH: 69
<212> TYPE: DNA
<213> ORGANISM: Homo sapiens

<400> SEQUENCE: 289
gccatccgga tgacccagtc tccattctcc ctgtctgcat ctgtaggaga cagagtcacc      60
atcacttgc                                                              69

<210> SEQ ID NO 290
<211> LENGTH: 69
<212> TYPE: DNA
<213> ORGANISM: Homo sapiens

<400> SEQUENCE: 290
gccatccgga tgacccagtc tccatcctca ttctctgcat ctacaggaga cagagtcacc      60
atcacttgt                                                              69

<210> SEQ ID NO 291
<211> LENGTH: 69
<212> TYPE: DNA
<213> ORGANISM: Homo sapiens

<400> SEQUENCE: 291
gtcatctgga tgacccagtc tccatcctta ctctctgcat ctacaggaga cagagtcacc      60
atcagttgt                                                              69

<210> SEQ ID NO 292
<211> LENGTH: 69
<212> TYPE: DNA
<213> ORGANISM: Homo sapiens

<400> SEQUENCE: 292
gccatccaga tgacccagtc tccatcctcc ctgtctgcat ctgtaggaga cagagtcacc      60
atcacttgc                                                              69

<210> SEQ ID NO 293
<211> LENGTH: 69
<212> TYPE: DNA
<213> ORGANISM: Homo sapiens

<400> SEQUENCE: 293
gacatccaga tgacccagtc tccttccacc ctgtctgcat ctgtaggaga cagagtcacc      60
atcacttgc                                                              69

<210> SEQ ID NO 294
<211> LENGTH: 69
<212> TYPE: DNA
<213> ORGANISM: Homo sapiens

<400> SEQUENCE: 294
gatattgtga tgacccagac tccactctcc ctgcccgtca cccctggaga gccggcctcc      60
``` atctcctgc 69

<210> SEQ ID NO 295
<211> LENGTH: 69
<212> TYPE: DNA
<213> ORGANISM: Homo sapiens

<400> SEQUENCE: 295
gatattgtga tgacccagac tccactctcc ctgcccgtca ccccctggaga gccggcctcc    60 atctcctgc                                                            69

<210> SEQ ID NO 296
<211> LENGTH: 69
<212> TYPE: DNA
<213> ORGANISM: Homo sapiens

<400> SEQUENCE: 296
gatgttgtga tgactcagtc tccactctcc ctgcccgtca cccttggaca gccggcctcc    60
atctcctgc                                                            69

<210> SEQ ID NO 297
<211> LENGTH: 69
<212> TYPE: DNA
<213> ORGANISM: Homo sapiens

<400> SEQUENCE: 297
gatgttgtga tgactcagtc tccactctcc ctgcccgtca cccttggaca gccggcctcc    60
atctcctgc                                                            69

<210> SEQ ID NO 298
<211> LENGTH: 69
<212> TYPE: DNA
<213> ORGANISM: Homo sapiens

<400> SEQUENCE: 298
gatattgtga tgacccagac tccactctct ctgtccgtca ccccctggaca gccggcctcc    60 atctcctgc                                                            69

<210> SEQ ID NO 299
<211> LENGTH: 69
<212> TYPE: DNA
<213> ORGANISM: Homo sapiens

<400> SEQUENCE: 299
gatattgtga tgacccagac tccactctct ctgtccgtca ccccctggaca gccggcctcc    60 atctcctgc                                                            69

<210> SEQ ID NO 300
<211> LENGTH: 69
<212> TYPE: DNA
<213> ORGANISM: Homo sapiens

<400> SEQUENCE: 300
gatattgtga tgactcagtc tccactctcc ctgcccgtca ccccctggaga gccggcctcc    60 atctcctgc                                                            69

<210> SEQ ID NO 301
<211> LENGTH: 69
<212> TYPE: DNA
<213> ORGANISM: Homo sapiens

```
<400> SEQUENCE: 301
gatattgtga tgactcagtc tccactctcc ctgcccgtca cccctggaga gccggcctcc    60
atctcctgc                                                              69

<210> SEQ ID NO 302
<211> LENGTH: 69
<212> TYPE: DNA
<213> ORGANISM: Homo sapiens

<400> SEQUENCE: 302
gatattgtga tgacccagac tccactctcc tcacctgtca cccttggaca gccggcctcc    60
atctcctgc                                                              69

<210> SEQ ID NO 303
<211> LENGTH: 69
<212> TYPE: DNA
<213> ORGANISM: Homo sapiens

<400> SEQUENCE: 303
gaaattgtgt tgacgcagtc tccaggcacc ctgtctttgt ctccagggga aagagccacc    60
ctctcctgc                                                              69

<210> SEQ ID NO 304
<211> LENGTH: 69
<212> TYPE: DNA
<213> ORGANISM: Homo sapiens

<400> SEQUENCE: 304
gaaattgtgt tgacgcagtc tccagccacc ctgtctttgt ctccagggga aagagccacc    60
ctctcctgc                                                              69

<210> SEQ ID NO 305
<211> LENGTH: 69
<212> TYPE: DNA
<213> ORGANISM: Homo sapiens

<400> SEQUENCE: 305
gaaatagtga tgacgcagtc tccagccacc ctgtctgtgt ctccagggga aagagccacc    60
ctctcctgc                                                              69

<210> SEQ ID NO 306
<211> LENGTH: 69
<212> TYPE: DNA
<213> ORGANISM: Homo sapiens

<400> SEQUENCE: 306
gaaatagtga tgacgcagtc tccagccacc ctgtctgtgt ctccagggga aagagccacc    60
ctctcctgc                                                              69

<210> SEQ ID NO 307
<211> LENGTH: 69
<212> TYPE: DNA
<213> ORGANISM: Homo sapiens

<400> SEQUENCE: 307
gaaattgtgt tgacacagtc tccagccacc ctgtctttgt ctccagggga aagagccacc    60
ctctcctgc                                                              69
```

```
<210> SEQ ID NO 308
<211> LENGTH: 69
<212> TYPE: DNA
<213> ORGANISM: Homo sapiens

<400> SEQUENCE: 308
gaaattgtgt tgacacagtc tccagccacc ctgtctttgt ctccagggga aagagccacc      60
ctctcctgc                                                             69

<210> SEQ ID NO 309
<211> LENGTH: 69
<212> TYPE: DNA
<213> ORGANISM: Homo sapiens

<400> SEQUENCE: 309
gaaattgtaa tgacacagtc tccagccacc ctgtctttgt ctccagggga aagagccacc      60
ctctcctgc                                                             69

<210> SEQ ID NO 310
<211> LENGTH: 69
<212> TYPE: DNA
<213> ORGANISM: Homo sapiens

<400> SEQUENCE: 310
gacatcgtga tgacccagtc tccagactcc ctggctgtgt ctctgggcga gagggccacc      60
atcaactgc                                                             69

<210> SEQ ID NO 311
<211> LENGTH: 69
<212> TYPE: DNA
<213> ORGANISM: Homo sapiens

<400> SEQUENCE: 311
gaaacgacac tcacgcagtc tccagcattc atgtcagcga ctccaggaga caaagtcaac      60
atctcctgc                                                             69

<210> SEQ ID NO 312
<211> LENGTH: 69
<212> TYPE: DNA
<213> ORGANISM: Homo sapiens

<400> SEQUENCE: 312
gaaattgtgc tgactcagtc tccagacttt cagtctgtga ctccaaagga gaaagtcacc      60
atcacctgc                                                             69

<210> SEQ ID NO 313
<211> LENGTH: 69
<212> TYPE: DNA
<213> ORGANISM: Homo sapiens

<400> SEQUENCE: 313
gaaattgtgc tgactcagtc tccagacttt cagtctgtga ctccaaagga gaaagtcacc      60
atcacctgc                                                             69

<210> SEQ ID NO 314
<211> LENGTH: 69
<212> TYPE: DNA
<213> ORGANISM: Homo sapiens

<400> SEQUENCE: 314
```

```
gatgttgtga tgacacagtc tccagctttc ctctctgtga ctccagggga gaaagtcacc      60
atcacctgc                                                              69

<210> SEQ ID NO 315
<211> LENGTH: 66
<212> TYPE: DNA
<213> ORGANISM: Homo sapiens

<400> SEQUENCE: 315
cagtctgtgc tgactcagcc accctcggtg tctgaagccc ccaggcagag ggtcaccatc      60
tcctgt                                                                 66

<210> SEQ ID NO 316
<211> LENGTH: 66
<212> TYPE: DNA
<213> ORGANISM: Homo sapiens

<400> SEQUENCE: 316
cagtctgtgc tgacgcagcc gccctcagtg tctggggccc cagggcagag ggtcaccatc      60
tcctgc                                                                 66

<210> SEQ ID NO 317
<211> LENGTH: 66
<212> TYPE: DNA
<213> ORGANISM: Homo sapiens

<400> SEQUENCE: 317
cagtctgtgc tgactcagcc accctcagcg tctgggaccc ccgggcagag ggtcaccatc      60
tcttgt                                                                 66

<210> SEQ ID NO 318
<211> LENGTH: 66
<212> TYPE: DNA
<213> ORGANISM: Homo sapiens

<400> SEQUENCE: 318
cagtctgtgc tgactcagcc accctcagcg tctgggaccc ccgggcagag ggtcaccatc      60
tcttgt                                                                 66

<210> SEQ ID NO 319
<211> LENGTH: 66
<212> TYPE: DNA
<213> ORGANISM: Homo sapiens

<400> SEQUENCE: 319
cagtctgtgt tgacgcagcc gccctcagtg tctgcggccc caggacagaa ggtcaccatc      60
tcctgc                                                                 66

<210> SEQ ID NO 320
<211> LENGTH: 66
<212> TYPE: DNA
<213> ORGANISM: Homo sapiens

<400> SEQUENCE: 320
cagtctgccc tgactcagcc tccctccgcg tccgggtctc ctggacagtc agtcaccatc      60
tcctgc                                                                 66

<210> SEQ ID NO 321
```

```
<211> LENGTH: 66
<212> TYPE: DNA
<213> ORGANISM: Homo sapiens

<400> SEQUENCE: 321
cagtctgccc tgactcagcc tcgctcagtg tccgggtctc ctggacagtc agtcaccatc    60
tcctgc                                                               66

<210> SEQ ID NO 322
<211> LENGTH: 66
<212> TYPE: DNA
<213> ORGANISM: Homo sapiens

<400> SEQUENCE: 322
cagtctgccc tgactcagcc tgcctccgtg tctgggtctc ctggacagtc gatcaccatc    60
tcctgc                                                               66

<210> SEQ ID NO 323
<211> LENGTH: 66
<212> TYPE: DNA
<213> ORGANISM: Homo sapiens

<400> SEQUENCE: 323
cagtctgccc tgactcagcc tccctccgtg tccgggtctc ctggacagtc agtcaccatc    60
tcctgc                                                               66

<210> SEQ ID NO 324
<211> LENGTH: 66
<212> TYPE: DNA
<213> ORGANISM: Homo sapiens

<400> SEQUENCE: 324
cagtctgccc tgactcagcc tgcctccgtg tctgggtctc ctggacagtc gatcaccatc    60
tcctgc                                                               66

<210> SEQ ID NO 325
<211> LENGTH: 66
<212> TYPE: DNA
<213> ORGANISM: Homo sapiens

<400> SEQUENCE: 325
tcctatgagc tgactcagcc accctcagtg tccgtgtccc caggacagac agccagcatc    60
acctgc                                                               66

<210> SEQ ID NO 326
<211> LENGTH: 66
<212> TYPE: DNA
<213> ORGANISM: Homo sapiens

<400> SEQUENCE: 326
tcctatgagc tgactcagcc actctcagtg tcagtggccc tgggacagac ggccaggatt    60
acctgt                                                               66

<210> SEQ ID NO 327
<211> LENGTH: 66
<212> TYPE: DNA
<213> ORGANISM: Homo sapiens

<400> SEQUENCE: 327
tcctatgagc tgacacagcc accctcggtg tcagtgtccc caggacaaac ggccaggatc    60
```

```
acctgc                                                              66

<210> SEQ ID NO 328
<211> LENGTH: 66
<212> TYPE: DNA
<213> ORGANISM: Homo sapiens

<400> SEQUENCE: 328
tcctatgagc tgacacagcc accctcggtg tcagtgtccc taggacagat ggccaggatc      60
acctgc                                                              66

<210> SEQ ID NO 329
<211> LENGTH: 66
<212> TYPE: DNA
<213> ORGANISM: Homo sapiens

<400> SEQUENCE: 329
tcttctgagc tgactcagga ccctgctgtg tctgtggcct tgggacagac agtcaggatc      60
acatgc                                                              66

<210> SEQ ID NO 330
<211> LENGTH: 66
<212> TYPE: DNA
<213> ORGANISM: Homo sapiens

<400> SEQUENCE: 330
tcctatgtgc tgactcagcc accctcagtg tcagtggccc caggaaagac ggccaggatt      60
acctgt                                                              66

<210> SEQ ID NO 331
<211> LENGTH: 66
<212> TYPE: DNA
<213> ORGANISM: Homo sapiens

<400> SEQUENCE: 331
tcctatgagc tgacacagct accctcggtg tcagtgtccc caggacagac agccaggatc      60
acctgc                                                              66

<210> SEQ ID NO 332
<211> LENGTH: 66
<212> TYPE: DNA
<213> ORGANISM: Homo sapiens

<400> SEQUENCE: 332
tcctatgagc tgatgcagcc accctcggtg tcagtgtccc caggacagac ggccaggatc      60
acctgc                                                              66

<210> SEQ ID NO 333
<211> LENGTH: 66
<212> TYPE: DNA
<213> ORGANISM: Homo sapiens

<400> SEQUENCE: 333
tcctatgagc tgacacagcc atcctcagtg tcagtgtctc cgggacagac agccaggatc      60
acctgc                                                              66

<210> SEQ ID NO 334
<211> LENGTH: 66
<212> TYPE: DNA
```

```
<213> ORGANISM: Homo sapiens

<400> SEQUENCE: 334
ctgcctgtgc tgactcagcc cccgtctgca tctgccttgc tgggagcctc gatcaagctc    60
acctgc                                                              66

<210> SEQ ID NO 335
<211> LENGTH: 66
<212> TYPE: DNA
<213> ORGANISM: Homo sapiens

<400> SEQUENCE: 335
cagcctgtgc tgactcaatc atcctctgcc tctgcttccc tgggatcctc ggtcaagctc    60
acctgc                                                              66

<210> SEQ ID NO 336
<211> LENGTH: 66
<212> TYPE: DNA
<213> ORGANISM: Homo sapiens

<400> SEQUENCE: 336
cagcttgtgc tgactcaatc gccctctgcc tctgcctccc tgggagcctc ggtcaagctc    60
acctgc                                                              66

<210> SEQ ID NO 337
<211> LENGTH: 66
<212> TYPE: DNA
<213> ORGANISM: Homo sapiens

<400> SEQUENCE: 337
cagcctgtgc tgactcagcc accttcctcc tccgcatctc ctggagaatc cgccagactc    60
acctgc                                                              66

<210> SEQ ID NO 338
<211> LENGTH: 66
<212> TYPE: DNA
<213> ORGANISM: Homo sapiens

<400> SEQUENCE: 338
caggctgtgc tgactcagcc ggcttccctc tctgcatctc ctggagcatc agccagtctc    60
acctgc                                                              66

<210> SEQ ID NO 339
<211> LENGTH: 66
<212> TYPE: DNA
<213> ORGANISM: Homo sapiens

<400> SEQUENCE: 339
cagcctgtgc tgactcagcc atcttcccat tctgcatctt ctggagcatc agtcagactc    60
acctgc                                                              66

<210> SEQ ID NO 340
<211> LENGTH: 66
<212> TYPE: DNA
<213> ORGANISM: Homo sapiens

<400> SEQUENCE: 340
aattttatgc tgactcagcc ccactctgtg tcggagtctc cggggaagac ggtaaccatc    60
tcctgc                                                              66
```

<210> SEQ ID NO 341
<211> LENGTH: 66
<212> TYPE: DNA
<213> ORGANISM: Homo sapiens

<400> SEQUENCE: 341
cagactgtgg tgactcagga gccctcactg actgtgtccc caggagggac agtcactctc      60
acctgt                                                                66

<210> SEQ ID NO 342
<211> LENGTH: 66
<212> TYPE: DNA
<213> ORGANISM: Homo sapiens

<400> SEQUENCE: 342
caggctgtgg tgactcagga gccctcactg actgtgtccc caggagggac agtcactctc      60
acctgt                                                                66

<210> SEQ ID NO 343
<211> LENGTH: 66
<212> TYPE: DNA
<213> ORGANISM: Homo sapiens

<400> SEQUENCE: 343
cagactgtgg tgacccagga gccatcgttc tcagtgtccc ctggagggac agtcacactc      60
acttgt                                                                66

<210> SEQ ID NO 344
<211> LENGTH: 66
<212> TYPE: DNA
<213> ORGANISM: Homo sapiens

<400> SEQUENCE: 344
cagcctgtgc tgactcagcc accttctgca tcagcctccc tgggagcctc ggtcacactc      60
acctgc                                                                66

<210> SEQ ID NO 345
<211> LENGTH: 66
<212> TYPE: DNA
<213> ORGANISM: Homo sapiens

<400> SEQUENCE: 345
caggcagggc tgactcagcc accctcggtg tccaagggct tgagacagac cgccacactc      60
acctgc                                                                66

<210> SEQ ID NO 346
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 346
nnnnnngact c                                                          11

-continued

<210> SEQ ID NO 347
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 347
gagtcnnnnn n                                                              11

<210> SEQ ID NO 348
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, t, c, g, unknown or other

<400> SEQUENCE: 348
gcnnnnnnng c                                                              11

<210> SEQ ID NO 349
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 349
acctgcnnnn n                                                              11

<210> SEQ ID NO 350
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
cacatccgtg ttgttcacgg atgtg                                               25

<210> SEQ ID NO 351
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
aatagtagac tgcagtgtcc tcagcccttaa agctgttcat ctgcaagtag agagtattct        60
tagagttgtc tctagactta gtgaagcg                                            88

```
<210> SEQ ID NO 352
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
cgcttcacta agtctagaga caactctaag aatactctct acttgcagat gaacagctta    60
agggctgagg acactgcagt ctactatt                                       88

<210> SEQ ID NO 353
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
cgcttcacta agtctagaga caactctaag aatactctct acttgcagat gaacagctta    60
agggctgagg acactgcagt ctactattgt gcgag                               95

<210> SEQ ID NO 354
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
cgcttcacta agtctagaga caactctaag aatactctct acttgcagat gaacagctta    60
agggctgagg acactgcagt ctactattgt acgag                               95

<210> SEQ ID NO 355
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cgcttcacta agtctagaga caac                                           24

<210> SEQ ID NO 356
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(15)
<223> OTHER INFORMATION: a, t, c, g, unknown or other

<400> SEQUENCE: 356
cacctgcnnn nnnnn                                                     15

<210> SEQ ID NO 357
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 357
cagctcnnnn nnnnnnn                                                  17

<210> SEQ ID NO 358
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 358
gaagacnnnn nnnnnnn                                                  17

<210> SEQ ID NO 359
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(17)
<223> OTHER INFORMATION: a, t, c, g, unknown or other

<400> SEQUENCE: 359
gcagcnnnnn nnnnnnn                                                  17

<210> SEQ ID NO 360
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 360
gaagacnnnn nn                                                       12

<210> SEQ ID NO 361
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, t, c, g, unknown or other

<400> SEQUENCE: 361
cttgagnnnn nnnnnnnnnn nn                                            22
```

```
<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, t, c, g, unknown or other

<400> SEQUENCE: 362 acggcnnnn nnnnnnnnn                                                 19

<210> SEQ ID NO 363
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, t, c, g, unknown or other

<400> SEQUENCE: 363 acggcnnnn nnnnnnnn                                                  18

<210> SEQ ID NO 364
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 364
gtatccnnnn nn                                                       12

<210> SEQ ID NO 365
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 365
actgggnnnn n                                                        11

<210> SEQ ID NO 366
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (6)..(10)
<223> OTHER INFORMATION: a, t, c, g, unknown or other

<400> SEQUENCE: 366 ggatcnnnnn                                                                10

<210> SEQ ID NO 367
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 367
gcatcnnnnn n                                                              11

<210> SEQ ID NO 368
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, t, c, g, unknown or other

<400> SEQUENCE: 368
gaggagnnnn nnnnnn                                                         16

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, t, c, g, unknown or other

<400> SEQUENCE: 369
gggacnnnnn nnnnnnnnn                                                      19

<210> SEQ ID NO 370
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(14)
<223> OTHER INFORMATION: a, t, c, g, unknown or other

<400> SEQUENCE: 370
acctgcnnnn nnnn                                                           14

<210> SEQ ID NO 371
<211> LENGTH: 17
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 371
ggcggannnn nnnnnnn                                                        17

<210> SEQ ID NO 372
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, t, c, g, unknown or other

<400> SEQUENCE: 372
ctgaagnnnn nnnnnnnnnn nn                                                  22

<210> SEQ ID NO 373
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 373
cccgcnnnnn n                                                              11

<210> SEQ ID NO 374
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, t, c, g, unknown or other

<400> SEQUENCE: 374
ggatgnnnnn nnnnnnnn                                                       18

<210> SEQ ID NO 375
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, t, c, g, unknown or other

<400> SEQUENCE: 375
```
ctggagnnnn nnnnnnnnnn nn                                          22

<210> SEQ ID NO 376
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, t, c, g, unknown or other

<400> SEQUENCE: 376
gacgcnnnnn nnnnn                                                  15

<210> SEQ ID NO 377
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, t, c, g, unknown or other

<400> SEQUENCE: 377
ggtgannnnn nnn                                                    13

<210> SEQ ID NO 378
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, t, c, g, unknown or other

<400> SEQUENCE: 378
gaagannnnn nnn                                                    13

<210> SEQ ID NO 379
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, t, c, g, unknown or other

<400> SEQUENCE: 379 gagtcnnnnn                                                        10

<210> SEQ ID NO 380
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (7)..(26)
<223> OTHER INFORMATION: a, t, c, g, unknown or other

<400> SEQUENCE: 380
tccracnnnn nnnnnnnnnn nnnnnn                                26

<210> SEQ ID NO 381
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(11)
<223> OTHER INFORMATION: a, t, c, g, unknown or other

<400> SEQUENCE: 381
cctcnnnnnn n                                                11

<210> SEQ ID NO 382
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, t, c, g, unknown or other

<400> SEQUENCE: 382 gagtcnnnnn                                                  10

<210> SEQ ID NO 383
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(18)
<223> OTHER INFORMATION: a, t, c, g, unknown or other

<400> SEQUENCE: 383
cccacannnn nnnnnnnn                                         18

<210> SEQ ID NO 384
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, t, c, g, unknown or other

<400> SEQUENCE: 384
gcatcnnnnn nnnn                                             14

<210> SEQ ID NO 385
<211> LENGTH: 13

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, t, c, g, unknown or other

<400> SEQUENCE: 385
ggtgannnnn nnn                                                              13

<210> SEQ ID NO 386
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, t, c, g, unknown or other

<400> SEQUENCE: 386
cccgnnnnnn nn                                                               12

<210> SEQ ID NO 387
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, t, c, g, unknown or other

<400> SEQUENCE: 387
ggatgnnnnn nnnnnnnn                                                         19

<210> SEQ ID NO 388
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 388
gaccgannnn nnnnnnn                                                          17

<210> SEQ ID NO 389
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 389
```

```
cacccannnn nnnnnnn                                               17

<210> SEQ ID NO 390
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 390
caarcannnn nnnnnnn                                               17

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 391
gctgtgtatt actgtgcgag                                            20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 392
gccgtgtatt actgtgcgag                                            20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 393
gccgtatatt actgtgcgag                                            20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394
gccgtgtatt actgtacgag                                            20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                                    probe

<400> SEQUENCE: 395
gccatgtatt actgtgcgag                                                    20

<210> SEQ ID NO 396
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
cacatccgtg ttgttcacgg atgtg                                              25

<210> SEQ ID NO 397
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
aatagtagac tgcagtgtcc tcagcccta agctgttcat ctgcaagtag agagtattct         60
tagagttgtc tctagactta gtgaagcg                                           88

<210> SEQ ID NO 398
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
cgcttcacta agtctagaga caactctaag aatactctct acttgcagat gaacagctta       60
agggctgagg acactgcagt ctactattgt gcgag                                   95

<210> SEQ ID NO 399
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cgcttcacta agtctagaga caac                                               24

<210> SEQ ID NO 400
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
cacatccgtg ttgttcacgg atgtgggagg atggagactg ggtc                         44

<210> SEQ ID NO 401
<211> LENGTH: 44
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 401
cacatccgtg ttgttcacgg atgtgggaga gtggagactg agtc        44

<210> SEQ ID NO 402
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
cacatccgtg ttgttcacgg atgtgggtgc ctggagactg cgtc        44

<210> SEQ ID NO 403
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
cacatccgtg ttgttcacgg atgtgggtgg ctggagactg cgtc        44

<210> SEQ ID NO 404
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
cctctactct tgtcacagtg cacaagacat ccag        34

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
cctctactct tgtcacagtg        20

<210> SEQ ID NO 406
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
ggaggatgga ctggatgtct tgtgcactgt gacaagagta gagg        44

<210> SEQ ID NO 407
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ggagagtgga ctggatgtct tgtgcactgt gacaagagta gagg            44

<210> SEQ ID NO 408
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ggtgcctgga ctggatgtct tgtgcactgt gacaagagta gagg            44

<210> SEQ ID NO 409
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ggtggctgga ctggatgtct tgtgcactgt gacaagagta gagg            44

<210> SEQ ID NO 410
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
cacatccgtg ttgttcacgg atgtggatcg actgtccagg agac            44

<210> SEQ ID NO 411
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
cacatccgtg ttgttcacgg atgtggactg tctgtcccaa ggcc            44

<210> SEQ ID NO 412
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
cacatccgtg ttgttcacgg atgtggactg actgtccagg agac            44

<210> SEQ ID NO 413
<211> LENGTH: 44
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 413
cacatccgtg ttgttcacgg atgtggaccc tctgccctgg ggcc                    44

<210> SEQ ID NO 414
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
cctctgactg agtgcacaga gtgctttaac ccaaccggct agtgttagcg gttccccgg     59

<210> SEQ ID NO 415
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
cctctgactg agtgcacaga gtgctttaac ccaaccggct agtgttagcg gttccccggg    60
acagtcgat                                                           69

<210> SEQ ID NO 416
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
cctctgactg agtgcacaga gtgctttaac ccaaccggct agtgttagcg gttccccggg    60
acagacagt                                                           69

<210> SEQ ID NO 417
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
cctctgactg agtgcacaga gtgctttaac ccaaccggct agtgttagcg gttccccggg    60
acagtcagt                                                           69

<210> SEQ ID NO 418
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
cctctgactg agtgcacaga gtgctttaac ccaaccggct agtgttagcg gtstccccgg    60
ggcagagggt                                                          70

<210> SEQ ID NO 419
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
cctctgactg agtgcacaga gtgc                                          24

<210> SEQ ID NO 420
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 420
ggccnnnnng gcc                                                      13

<210> SEQ ID NO 421
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 421
ccannnnnnn nntgg                                                    15

<210> SEQ ID NO 422
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 422
cgannnnnnt gc                                                       12

<210> SEQ ID NO 423
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 423
gccnnnnngg c                                                        11

<210> SEQ ID NO 424
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 424 gatnnnnatc                                                          10

<210> SEQ ID NO 425
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 425
gacnnnnngt c                                                        11

<210> SEQ ID NO 426
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 426
gcannnnntg c                                                        11

<210> SEQ ID NO 427
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 427
gtatccnnnn nn                                                       12

<210> SEQ ID NO 428
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (4)..(9)
<223> OTHER INFORMATION: a, t, c, g, unknown or other

<400> SEQUENCE: 428
gacnnnnnng tc                                                              12

<210> SEQ ID NO 429
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 429 ccannnntg g                                                                11

<210> SEQ ID NO 430
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 430
nnnnnngaga cg                                                              12

<210> SEQ ID NO 431
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 431
ccannnnnnt gg                                                              12

<210> SEQ ID NO 432
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 432 gaannnttc                                                                  10

<210> SEQ ID NO 433
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 433
ggtctcnnnn n                                                         11

<210> SEQ ID NO 434
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 434
nnnnnnnnnn ctcctc                                                    16

<210> SEQ ID NO 435
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 435
nnnnnnnnnt ccgcc                                                     15

<210> SEQ ID NO 436
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 436
ggccnnnnng gcc                                                       13

<210> SEQ ID NO 437
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other
```

```
<400> SEQUENCE: 437
ccannnnnnt gg                                                          12

<210> SEQ ID NO 438
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 438
gacnnnnnng tc                                                          12

<210> SEQ ID NO 439
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 439
cgannnnnnt gc                                                          12

<210> SEQ ID NO 440
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 440
gcannnnntg c                                                           11

<210> SEQ ID NO 441
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 441
ccannnnntg g                                                           11

<210> SEQ ID NO 442
<211> LENGTH: 10
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 442 gaannnnttc                                                                                10

<210> SEQ ID NO 443
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 443
nnnnnngaga cg                                                                             12

<210> SEQ ID NO 444
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 444
gtatccnnnn nn                                                                             12

<210> SEQ ID NO 445
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 445
gacnnnnngt c                                                                              11

<210> SEQ ID NO 446
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 446
ggtctcnnnn n                                                                              11

-continued

```
<210> SEQ ID NO 447
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 447
gccnnnnngg c                                                              11

<210> SEQ ID NO 448
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 448
ccannnnnnn nntgg                                                          15

<210> SEQ ID NO 449
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 449
nnnnnnnnnn ctcctc                                                         16

<210> SEQ ID NO 450
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 450 nnnnnnnnt ccgcc                                                           15

<210> SEQ ID NO 451
<211> LENGTH: 9532
<212> TYPE: DNA
<213> ORGANISM: Unknown
<220> FEATURE:
<223> OTHER INFORMATION: Description of Unknown: MALIA3 nucleotide
      sequence
<220> FEATURE:
<221> NAME/KEY: CDS
<222> LOCATION: (1579)..(1638)
<220> FEATURE:
```

```
<221> NAME/KEY: CDS
<222> LOCATION: (2343)..(3443)
<220> FEATURE:
<221> NAME/KEY: CDS
<222> LOCATION: (3945)..(4400)
<220> FEATURE:
<221> NAME/KEY: CDS
<222> LOCATION: (4406)..(4450)
<220> FEATURE:
<221> NAME/KEY: CDS
<222> LOCATION: (4746)..(5789)

<400> SEQUENCE: 451
```

| | |
|---|---|
| aatgctacta ctattagtag aattgatgcc acctttcag ctcgcgcccc aaatgaaaat | 60 |
| atagctaaac aggttattga ccatttgcga aatgtatcta atggtcaaac taaatctact | 120 |
| cgttcgcaga attgggaatc aactgttaca tggaatgaaa cttccagaca ccgtacttta | 180 |
| gttgcatatt taaaacatgt tgagctacag caccagattc agcaattaag ctctaagcca | 240 |
| tccgcaaaaa tgacctctta tcaaaaggag caattaaagg tactctctaa tcctgacctg | 300 |
| ttggagtttg cttccggtct ggttcgcttt gaagctcgaa ttaaaacgcg atatttgaag | 360 |
| tctttcgggc ttcctcttaa tcttttgat gcaatccgct ttgcttctga ctataatagt | 420 |
| cagggtaaag acctgatttt tgattatgg tcattctcgt tttctgaact gtttaaagca | 480 |
| tttgagggg attcaatgaa tatttatgac gattccgcag tattggacgc tatccagtct | 540 |
| aaacatttta ctattacccc ctctggcaaa acttcttttg caaagcctc tcgctatttt | 600 |
| ggttttatc gtcgtctggt aaacgagggt tatgatagtg ttgctcttac tatgcctcgt | 660 |
| aattcctttt ggcgttatgt atctgcatta gttgaatgtg gtattcctaa atctcaactg | 720 |
| atgaatcttt ctacctgtaa taatgttgtt ccgttagttc gttttattaa cgtagatttt | 780 |
| tcttcccaac gtcctgactg gtataatgag ccagttctta aaatcgcata aggtaattca | 840 |
| caatgattaa agttgaaatt aaaccatctc aagcccaatt tactactcgt tctggtgttt | 900 |
| ctcgtcaggg caagccttat tcactgaatg agcagctttg ttacgttgat ttgggtaatg | 960 |
| aatatccggt tcttgtcaag attactcttg atgaaggtca gccagcctat gcgcctggtc | 1020 |
| tgtacaccgt tcatctgtcc tctttcaaag ttggtcagtt cggttccctt atgattgacc | 1080 |
| gtctgcgcct cgttccggct aagtaacatg gagcaggtcg cggatttcga cacaatttat | 1140 |
| caggcgatga tacaaatctc cgttgtactt tgtttcgcgc ttggtataat cgctgggggt | 1200 |
| caaagatgag tgttttagtg tattctttcg cctctttcgt tttaggttgg tgccttcgta | 1260 |
| gtggcattac gtattttacc cgtttaatgg aaacttcctc atgaaaaagt ctttagtcct | 1320 |
| caaagcctct gtagccgttg ctaccctcgt tccgatgctg tctttcgctg ctgagggtga | 1380 |
| cgatcccgca aaagcggcct ttaactccct gcaagcctca gcgaccgaat atatcggtta | 1440 |
| tgcgtgggcg atggttgttg tcattgtcgg cgcaactatc ggtatcaagc tgtttaagaa | 1500 |
| attcacctcg aaagcaagct gataaaccga tacaattaaa ggctccttt ggagccttt | 1560 |

| | | | | | | | | | | |
|---|---|---|---|---|---|---|---|---|---|---|
| tttttggaga | tttcaac | gtg | aaa | aaa | tta | tta | ttc | gca | att cct tta gtt | 1611 |
| | | Met | Lys | Lys | Leu | Leu | Phe | Ala | Ile Pro Leu Val | |
| | | 1 | | | 5 | | | | 10 | |

| | |
|---|---|
| gtt cct ttc tat tct cac agt gca cag tctgtcgtga cgcagccgcc | 1658 |
| Val Pro Phe Tyr Ser His Ser Ala Gln | |
| 15 20 | |

| | |
|---|---|
| ctcagtgtct ggggccccag gcagagggt caccatctcc tgcactggga gcagctccaa | 1718 |
| catcggggca ggttatgatg tacactggta ccagcagctt ccaggaacag cccccaaact | 1778 |
| cctcatctat ggtaacagca atcggccctc agggtccct gaccgattct ctggctccaa | 1838 |

```
gtctggcacc tcagcctccc tggccatcac tgggctccag gctgaggatg aggctgatta      1898
ttactgccag tcctatgaca gcagcctgag tggcctttat gtcttcggaa ctgggaccaa      1958
ggtcaccgtc ctaggtcagc ccaaggccaa ccccactgtc actctgttcc cgccctcctc      2018
tgaggagctc caagccaaca aggccacact agtgtgtctg atcagtgact tctacccggg      2078
agctgtgaca gtggcctgga aggcagatag cagccccgtc aaggcgggag tggagaccac      2138
cacaccctcc aaacaaagca caacaagta cgcggccagc agctatctga gcctgacgcc       2198
tgagcagtgg aagtcccaca gaagctacag ctgccaggtc acgcatgaag ggagcaccgt      2258
ggagaagaca gtggccccta cagaatgttc ataataaacc gcctccaccg ggcgcgccaa      2318
ttctatttca aggagacagt cata atg aaa tac cta ttg cct acg gca gcc         2369
                          Met Lys Tyr Leu Leu Pro Thr Ala Ala
                                                25 gct gga ttg tta tta ctc gcg gcc cag ccg gcc atg gcc gaa gtt caa        2417
Ala Gly Leu Leu Leu Leu Ala Ala Gln Pro Ala Met Ala Glu Val Gln
30                  35                  40                  45 ttg tta gag tct ggt ggc ggt ctt gtt cag cct ggt ggt tct tta cgt        2465
Leu Leu Glu Ser Gly Gly Gly Leu Val Gln Pro Gly Gly Ser Leu Arg
            50                  55                  60 ctt tct tgc gct gct tcc gga ttc act ttc tct tcg tac gct atg tct        2513
Leu Ser Cys Ala Ala Ser Gly Phe Thr Phe Ser Ser Tyr Ala Met Ser
        65                  70                  75 tgg gtt cgc caa gct cct ggt aaa ggt ttg gag tgg gtt tct gct atc        2561
Trp Val Arg Gln Ala Pro Gly Lys Gly Leu Glu Trp Val Ser Ala Ile
    80                  85                  90 tct ggt tct ggt ggc agt act tac tat gct gac tcc gtt aaa ggt cgc        2609
Ser Gly Ser Gly Gly Ser Thr Tyr Tyr Ala Asp Ser Val Lys Gly Arg
95                  100                 105 ttc act atc tct aga gac aac tct aag aat act ctc tac ttg cag atg        2657
Phe Thr Ile Ser Arg Asp Asn Ser Lys Asn Thr Leu Tyr Leu Gln Met
110                 115                 120                 125 aac agc tta agg gct gag gac act gca gtc tac tat tgc gct aaa gac        2705
Asn Ser Leu Arg Ala Glu Asp Thr Ala Val Tyr Tyr Cys Ala Lys Asp
            130                 135                 140 tat gaa ggt act ggt tat gct ttc gac ata tgg ggt caa ggt act atg        2753
Tyr Glu Gly Thr Gly Tyr Ala Phe Asp Ile Trp Gly Gln Gly Thr Met
        145                 150                 155 gtc acc gtc tct agt gcc tcc acc aag ggc cca tcg gtc ttc ccc ctg        2801
Val Thr Val Ser Ser Ala Ser Thr Lys Gly Pro Ser Val Phe Pro Leu
    160                 165                 170 gca ccc tcc tcc aag agc acc tct ggg ggc aca gcg gcc ctg ggc tgc        2849
Ala Pro Ser Ser Lys Ser Thr Ser Gly Gly Thr Ala Ala Leu Gly Cys
175                 180                 185 ctg gtc aag gac tac ttc ccc gaa ccg gtg acg gtg tcg tgg aac tca        2897
Leu Val Lys Asp Tyr Phe Pro Glu Pro Val Thr Val Ser Trp Asn Ser
190                 195                 200                 205 ggc gcc ctg acc agc ggc gtc cac acc ttc ccg gct gtc cta cag tct        2945
Gly Ala Leu Thr Ser Gly Val His Thr Phe Pro Ala Val Leu Gln Ser
            210                 215                 220 agc gga ctc tac tcc ctc agc agc gta gtg acc gtg ccc tct tct agc        2993
Ser Gly Leu Tyr Ser Leu Ser Ser Val Val Thr Val Pro Ser Ser Ser
        225                 230                 235 ttg ggc acc cag acc tac atc tgc aac gtg aat cac aag ccc agc aac        3041
Leu Gly Thr Gln Thr Tyr Ile Cys Asn Val Asn His Lys Pro Ser Asn
    240                 245                 250 acc aag gtg gac aag aaa gtt gag ccc aaa tct tgt gcg gcc gct cat        3089
Thr Lys Val Asp Lys Lys Val Glu Pro Lys Ser Cys Ala Ala Ala His
```

```
         255                 260                 265
cac cac cat cat cac tct gct gaa caa aaa ctc atc tca gaa gag gat    3137
His His His His His Ser Ala Glu Gln Lys Leu Ile Ser Glu Glu Asp
270                 275                 280                 285 ctg aat ggt gcc gca gat atc aac gat gat cgt atg gct ggc gcc gct    3185
Leu Asn Gly Ala Ala Asp Ile Asn Asp Asp Arg Met Ala Gly Ala Ala
            290                 295                 300 gaa act gtt gaa agt tgt tta gca aaa ccc cat aca gaa aat tca ttt    3233
Glu Thr Val Glu Ser Cys Leu Ala Lys Pro His Thr Glu Asn Ser Phe
        305                 310                 315 act aac gtc tgg aaa gac gac aaa act tta gat cgt tac gct aac tat    3281
Thr Asn Val Trp Lys Asp Asp Lys Thr Leu Asp Arg Tyr Ala Asn Tyr
    320                 325                 330 gag ggt tgt ctg tgg aat gct aca ggc gtt gta gtt tgt act ggt gac    3329
Glu Gly Cys Leu Trp Asn Ala Thr Gly Val Val Val Cys Thr Gly Asp
335                 340                 345 gaa act cag tgt tac ggt aca tgg gtt cct att ggg ctt gct atc cct    3377
Glu Thr Gln Cys Tyr Gly Thr Trp Val Pro Ile Gly Leu Ala Ile Pro
350                 355                 360                 365 gaa aat gag ggt ggt ggc tct gag ggt ggc ggt tct gag ggt ggc ggt    3425
Glu Asn Glu Gly Gly Gly Ser Glu Gly Gly Gly Ser Glu Gly Gly Gly
            370                 375                 380 tct gag ggt ggc ggt act aaacctcctg agtacggtga tacacctatt           3473
Ser Glu Gly Gly Gly Thr
            385 ccgggctata cttatatcaa ccctctcgac ggcacttatc cgcctggtac tgagcaaaac  3533 cccgctaatc ctaatccttc tcttgaggag tctcagcctc ttaatacttt catgtttcag  3593 aataataggt tccgaaatag gcagggggca ttaactgttt atacgggcac tgttactcaa  3653 ggcactgacc ccgttaaaac ttattaccag tacactcctg tatcatcaaa agccatgtat  3713 gacgcttact ggaacggtaa attcagagac tgcgctttcc attctggctt taatgaagat  3773 ccattcgttt gtgaatatca aggccaatcg tctgacctgc tcaacctcc tgtcaatgct   3833 ggcggcggct ctggtggtgg ttctggtggc ggctctgagg gtggtggctc tgagggtggc  3893 ggttctgagg gtggcggctc tgagggaggc ggttccggtg gtggctctgg t tcc ggt   3950
                                                       Ser Gly gat ttt gat tat gaa aag atg gca aac gct aat aag ggg gct atg acc    3998
Asp Phe Asp Tyr Glu Lys Met Ala Asn Ala Asn Lys Gly Ala Met Thr
390                 395                 400                 405 gaa aat gcc gat gaa aac gcg cta cag tct gac gct aaa ggc aaa ctt    4046
Glu Asn Ala Asp Glu Asn Ala Leu Gln Ser Asp Ala Lys Gly Lys Leu
            410                 415                 420 gat tct gtc gct act gat tac ggt gct gct atc gat ggt ttc att ggt    4094
Asp Ser Val Ala Thr Asp Tyr Gly Ala Ala Ile Asp Gly Phe Ile Gly
        425                 430                 435 gac gtt tcc ggc ctt gct aat ggt aat ggt gct act ggt gat ttt gct    4142
Asp Val Ser Gly Leu Ala Asn Gly Asn Gly Ala Thr Gly Asp Phe Ala
    440                 445                 450 ggc tct aat tcc caa atg gct caa gtc ggt gac ggt gat aat tca cct    4190
Gly Ser Asn Ser Gln Met Ala Gln Val Gly Asp Gly Asp Asn Ser Pro
455                 460                 465 tta atg aat aat ttc cgt caa tat tta cct tcc ctc cct caa tcg gtt    4238
Leu Met Asn Asn Phe Arg Gln Tyr Leu Pro Ser Leu Pro Gln Ser Val
470                 475                 480                 485 gaa tgt cgc cct ttt gtc ttt agc gct ggt aaa cca tat gaa ttt tct    4286
Glu Cys Arg Pro Phe Val Phe Ser Ala Gly Lys Pro Tyr Glu Phe Ser
            490                 495                 500
```

| | | |
|---|---|---|
| att gat tgt gac aaa ata aac tta ttc cgt ggt gtc ttt gcg ttt ctt<br>Ile Asp Cys Asp Lys Ile Asn Leu Phe Arg Gly Val Phe Ala Phe Leu<br>505 510 515 | | 4334 |
| tta tat gtt gcc acc ttt atg tat gta ttt tct acg ttt gct aac ata<br>Leu Tyr Val Ala Thr Phe Met Tyr Val Phe Ser Thr Phe Ala Asn Ile<br>520 525 530 | | 4382 |
| ctg cgt aat aag gag tct taatc atg cca gtt ctt ttg ggt att ccg tta<br>Leu Arg Asn Lys Glu Ser      Met Pro Val Leu Leu Gly Ile Pro Leu<br>535 540 545 | | 4432 |
| tta ttg cgt ttc ctc ggt ttccttctgg taactttgtt cggctatctg<br>Leu Leu Arg Phe Leu Gly<br>550 | | 4480 |
| cttactttc ttaaaaggg cttcggtaag atagctattg ctatttcatt gtttcttgct | | 4540 |
| cttattattg ggcttaactc aattcttgtg ggttatctct ctgatattag cgctcaatta | | 4600 |
| ccctctgact ttgttcaggg tgttcagtta attctcccgt ctaatgcgct tccctgtttt | | 4660 |
| tatgttattc tctctgtaaa ggctgctatt ttcattttg acgttaaaca aaaaatcgtt | | 4720 |
| tcttatttgg attgggataa ataat atg gct gtt tat ttt gta act ggc aaa<br>                                                     Met Ala Val Tyr Phe Val Thr Gly Lys<br>                                                      555 560 | | 4772 |
| tta ggc tct gga aag acg ctc gtt agc gtt ggt aag att cag gat aaa<br>Leu Gly Ser Gly Lys Thr Leu Val Ser Val Gly Lys Ile Gln Asp Lys<br>565 570 575 | | 4820 |
| att gta gct ggg tgc aaa ata gca act aat ctt gat tta agg ctt caa<br>Ile Val Ala Gly Cys Lys Ile Ala Thr Asn Leu Asp Leu Arg Leu Gln<br>580 585 590 595 | | 4868 |
| aac ctc ccg caa gtc ggg agg ttc gct aaa acg cct cgc gtt ctt aga<br>Asn Leu Pro Gln Val Gly Arg Phe Ala Lys Thr Pro Arg Val Leu Arg<br>600 605 610 | | 4916 |
| ata ccg gat aag cct tct ata tct gat ttg ctt gct att ggg cgc ggt<br>Ile Pro Asp Lys Pro Ser Ile Ser Asp Leu Leu Ala Ile Gly Arg Gly<br>615 620 625 | | 4964 |
| aat gat tcc tac gat gaa aat aaa aac ggc ttg ctt gtt ctc gat gag<br>Asn Asp Ser Tyr Asp Glu Asn Lys Asn Gly Leu Leu Val Leu Asp Glu<br>630 635 640 | | 5012 |
| tgc ggt act tgg ttt aat acc cgt tct tgg aat gat aag gaa aga cag<br>Cys Gly Thr Trp Phe Asn Thr Arg Ser Trp Asn Asp Lys Glu Arg Gln<br>645 650 655 | | 5060 |
| ccg att att gat tgg ttt cta cat gct cgt aaa tta gga tgg gat att<br>Pro Ile Ile Asp Trp Phe Leu His Ala Arg Lys Leu Gly Trp Asp Ile<br>660 665 670 675 | | 5108 |
| att ttt ctt gtt cag gac tta tct att gtt gat aaa cag gcg cgt tct<br>Ile Phe Leu Val Gln Asp Leu Ser Ile Val Asp Lys Gln Ala Arg Ser<br>680 685 690 | | 5156 |
| gca tta gct gaa cat gtt gtt tat tgt cgt cgt ctg gac aga att act<br>Ala Leu Ala Glu His Val Val Tyr Cys Arg Arg Leu Asp Arg Ile Thr<br>695 700 705 | | 5204 |
| tta cct ttt gtc ggt act tta tat tct ctt att act ggc tcg aaa atg<br>Leu Pro Phe Val Gly Thr Leu Tyr Ser Leu Ile Thr Gly Ser Lys Met<br>710 715 720 | | 5252 |
| cct ctg cct aaa tta cat gtt ggc gtt gtt aaa tat ggc gat tct caa<br>Pro Leu Pro Lys Leu His Val Gly Val Val Lys Tyr Gly Asp Ser Gln<br>725 730 735 | | 5300 |
| tta agc cct act gtt gag cgt tgg ctt tat act ggt aag aat ttg tat<br>Leu Ser Pro Thr Val Glu Arg Trp Leu Tyr Thr Gly Lys Asn Leu Tyr<br>740 745 750 755 | | 5348 |
| aac gca tat gat act aaa cag gct ttt tct agt aat tat gat tcc ggt<br>Asn Ala Tyr Asp Thr Lys Gln Ala Phe Ser Ser Asn Tyr Asp Ser Gly<br>760 765 770 | | 5396 |

```
gtt tat tct tat tta acg cct tat tta tca cac ggt cgg tat ttc aaa    5444
Val Tyr Ser Tyr Leu Thr Pro Tyr Leu Ser His Gly Arg Tyr Phe Lys
            775                 780                 785 cca tta aat tta ggt cag aag atg aaa tta act aaa ata tat ttg aaa    5492
Pro Leu Asn Leu Gly Gln Lys Met Lys Leu Thr Lys Ile Tyr Leu Lys
        790                 795                 800 aag ttt tct cgc gtt ctt tgt ctt gcg att gga ttt gca tca gca ttt    5540
Lys Phe Ser Arg Val Leu Cys Leu Ala Ile Gly Phe Ala Ser Ala Phe
    805                 810                 815 aca tat agt tat ata acc caa cct aag ccg gag gtt aaa aag gta gtc    5588
Thr Tyr Ser Tyr Ile Thr Gln Pro Lys Pro Glu Val Lys Lys Val Val
820                 825                 830                 835 tct cag acc tat gat ttt gat aaa ttc act att gac tct tct cag cgt    5636
Ser Gln Thr Tyr Asp Phe Asp Lys Phe Thr Ile Asp Ser Ser Gln Arg
                840                 845                 850 ctt aat cta agc tat cgc tat gtt ttc aag gat tct aag gga aaa tta    5684
Leu Asn Leu Ser Tyr Arg Tyr Val Phe Lys Asp Ser Lys Gly Lys Leu
            855                 860                 865 att aat agc gac gat tta cag aag caa ggt tat tca ctc aca tat att    5732
Ile Asn Ser Asp Asp Leu Gln Lys Gln Gly Tyr Ser Leu Thr Tyr Ile
        870                 875                 880 gat tta tgt act gtt tcc att aaa aaa ggt aat tca aat gaa att gtt    5780
Asp Leu Cys Thr Val Ser Ile Lys Lys Gly Asn Ser Asn Glu Ile Val
    885                 890                 895 aaa tgt aat  taattttgtt tcttgatgt tgtttcatc atcttctttt             5829
Lys Cys Asn
900 gctcaggtaa ttgaaatgaa taattcgcct ctgcgcgatt ttgtaacttg gtattcaaag   5889 caatcaggcg aatccgttat tgtttctccc gatgtaaaag gtactgttac tgtatattca   5949 tctgacgtta aacctgaaaa tctacgcaat ttctttattt ctgttttacg tgctaataat   6009 tttgatatgg ttggttcaat tccttccata attcagaagt ataatccaaa caatcaggat   6069 tatattgatg aattgccatc atctgataat caggaatatg atgataattc cgctccttct   6129 ggtggtttct ttgttccgca aaatgataat gttactcaaa cttttaaaat taataacgtt   6189 cgggcaaagg atttaatacg agttgtcgaa ttgtttgtaa agtctaatac ttctaaatcc   6249 tcaaatgtat tatctattga cggctctaat ctattagttg tttctgcacc taaagatatt   6309 ttagataacc ttcctcaatt cctttctact gttgatttgc caactgacca gatattgatt   6369 gagggtttga tatttgaggt tcagcaaggt gatgctttag attttcatt tgctgctggc    6429 tctcagcgtg gcactgttgc aggcggtgtt aatactgacc gcctcacctc tgttttatct   6489 tctgctggtg gttcgttcgg tattttaat ggcgatgttt tagggctatc agttcgcgca    6549 ttaaagacta atagccattc aaaaatattg tctgtgccac gtattcttac gctttcaggt   6609 cagaagggtt ctatctctgt tggccagaat gtcccttta ttactggtcg tgtgactggt    6669 gaatctgcca atgtaaataa tccatttcag acgattgagc gtcaaaatgt aggtatttcc   6729 atgagcgttt ttcctgttgc aatggctggc ggtaatattg ttctggatat taccagcaag   6789 gccgatagtt tgagttcttc tactcaggca agtgatgtta ttactaatca agaagtatt    6849 gctacaacgg ttaattgcg tgatggacag actcttttac tcggtggcct cactgattat    6909 aaaaacactt ctcaagattc tggcgtaccg ttcctgtcta aaatccttt aatcggcctc    6969 ctgtttagct cccgctctga ttccaacgag gaaagcacgt tatacgtgct cgtcaaagca   7029 accatagtac gcgccctgta gcggcgcatt aagcgcggcg ggtgtggtgg ttacgcgcag   7089
```

```
cgtgaccgct acacttgcca gcgccctagc gcccgctcct ttcgctttct tcccttcctt      7149
tctcgccacg ttcgccggct ttccccgtca agctctaaat cgggggctcc ctttagggtt      7209
ccgatttagt gctttacggc acctcgaccc caaaaaactt gatttgggtg atggttcacg      7269
tagtgggcca tcgccctgat agacggtttt tcgcccttg acgttggagt ccacgttctt       7329
taatagtgga ctcttgttcc aaactggaac aacactcaac cctatctcgg gctattcttt      7389
tgatttataa gggattttgc cgatttcgga accaccatca aacaggattt tcgcctgctg      7449
gggcaaacca gcgtggaccg cttgctgcaa ctctctcagg gccaggcggt gaagggcaat      7509
cagctgttgc ccgtctcact ggtgaaaaga aaaaccaccc tggatccaag cttgcaggtg      7569
gcacttttcg gggaaatgtg cgcggaaccc ctatttgttt attttctaa atacattcaa       7629
atatgtatcc gctcatgaga caataaccct gataaatgct tcataatat tgaaaaagga       7689
agagtatgag tattcaacat ttccgtgtcg cccttattcc ctttttgcg gcattttgcc       7749
ttcctgtttt tgctcaccca gaaacgctgg tgaaagtaaa agatgctgaa gatcagttgg      7809
gcgcacgagt gggttacatc gaactggatc tcaacagcgg taagatcctt gagagttttc      7869
gccccgaaga acgttttcca atgatgagca cttttaaagt tctgctatgt catacactat      7929
tatcccgtat tgacgccggg caagagcaac tcggtcgccg ggcgcggtat tctcagaatg      7989
acttggttga gtactcacca gtcacagaaa agcatcttac ggatggcatg acagtaagag      8049
aattatgcag tgctgccata accatgagtg ataacactgc ggccaactta cttctgacaa      8109
cgatcggagg accgaaggag ctaaccgctt ttttgcacaa catgggggat catgtaactc      8169
gccttgatcg ttgggaaccg gagctgaatg aagccatacc aaacgacgag cgtgacacca      8229
cgatgcctgt agcaatgcca acaacgttgc gcaaactatt aactggcgaa ctacttactc      8289
tagcttcccg gcaacaatta atagactgga tggaggcgga taaagttgca ggaccacttc      8349
tgcgctcggc ccttccggct ggctggttta ttgctgataa atctggagcc ggtgagcgtg      8409
ggtctcgcgg tatcattgca gcactggggc cagatggtaa gccctcccgt atcgtagtta      8469
tctacacgac ggggagtcag gcaactatgg atgaacgaaa tagacagatc gctgagatag      8529
gtgcctcact gattaagcat tggtaactgt cagaccaagt ttactcatat atactttaga      8589
ttgatttaaa acttcatttt taatttaaaa ggatctaggt gaagatcctt tttgataatc      8649
tcatgaccaa aatcccttaa cgtgagtttt cgttccactg tacgtaagac ccccaagctt      8709
gtcgactgaa tggcgaatgg cgctttgcct ggtttccggc accagaagcg gtgccggaaa      8769
gctggctgga gtgcgatctt cctgaggccg atactgtcgt cgtcccctca aactggcaga      8829
tgcacggtta cgatgcgccc atctacacca acgtaaccta tcccattacg gtcaatccgc      8889
cgtttgttcc cacggagaat ccgacgggtt gttactcgct cacatttaat gttgatgaaa      8949
gctggctaca ggaaggccag acgcgaatta ttttgatgg cgttcctatt ggttaaaaaa       9009
tgagctgatt taacaaaaat ttaacgcgaa ttttaacaaa atattaacgt ttacaattta      9069
aatatttgct tatacaatct tcctgttttt ggggcttttc tgattatcaa ccggggtaca      9129
tatgattgac atgctagttt tacgattacc gttcatcgat tctcttgttt gctccagact      9189
ctcaggcaat gacctgatag cctttgtaga tctctcaaaa atagctaccc tctccggcat      9249
gaatttatca gctagaacgg ttgaatatca tattgatggt gatttgactg tctccggcct      9309
ttctcaccct tttgaatctt tacctacaca ttactcaggc attgcattta aaatatatga      9369
gggttctaaa aatttttatc cttgcgttga aataaaggct tctcccgcaa aagtattaca      9429
gggtcataat gtttttggta caaccgattt agctttatgc tctgaggctt tattgcttaa      9489
```

```
ttttgctaat tctttgcctt gcctgtatga tttattggat gtt            9532
```

<210> SEQ ID NO 452
<211> LENGTH: 20
<212> TYPE: PRT
<213> ORGANISM: Unknown
<220> FEATURE:
<223> OTHER INFORMATION: Description of Unknown: MALIA3 peptide
      sequence

<400> SEQUENCE: 452

Met Lys Lys Leu Leu Phe Ala Ile Pro Leu Val Val Pro Phe Tyr Ser
 1               5                  10                  15

His Ser Ala Gln
            20

<210> SEQ ID NO 453
<211> LENGTH: 367
<212> TYPE: PRT
<213> ORGANISM: Unknown
<220> FEATURE:
<223> OTHER INFORMATION: Description of Unknown: MALIA3 protein
      sequence

<400> SEQUENCE: 453

Met Lys Tyr Leu Leu Pro Thr Ala Ala Ala Gly Leu Leu Leu Leu Ala
 1               5                  10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Asp Tyr Glu Gly Thr Gly Tyr Ala
        115                 120                 125

Phe Asp Ile Trp Gly Gln Gly Thr Met Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Ala Ala Ala His His His His His His Ser Ala
                245                 250                 255

```
Glu Gln Lys Leu Ile Ser Glu Glu Asp Leu Asn Gly Ala Ala Asp Ile
            260                 265                 270

Asn Asp Asp Arg Met Ala Gly Ala Glu Thr Val Glu Ser Cys Leu
            275                 280                 285

Ala Lys Pro His Thr Glu Asn Ser Phe Thr Asn Val Trp Lys Asp Asp
            290                 295                 300

Lys Thr Leu Asp Arg Tyr Ala Asn Tyr Glu Gly Cys Leu Trp Asn Ala
305                 310                 315                 320

Thr Gly Val Val Val Cys Thr Gly Asp Glu Thr Gln Cys Tyr Gly Thr
                325                 330                 335

Trp Val Pro Ile Gly Leu Ala Ile Pro Glu Asn Glu Gly Gly Gly Ser
            340                 345                 350

Glu Gly Gly Gly Ser Glu Gly Gly Ser Glu Gly Gly Gly Thr
            355                 360                 365

<210> SEQ ID NO 454
<211> LENGTH: 152
<212> TYPE: PRT
<213> ORGANISM: Unknown
<220> FEATURE:
<223> OTHER INFORMATION: Description of Unknown: MALIA3 protein
      sequence

<400> SEQUENCE: 454

Ser Gly Asp Phe Asp Tyr Glu Lys Met Ala Asn Ala Asn Lys Gly Ala
  1               5                  10                  15

Met Thr Glu Asn Ala Asp Glu Asn Ala Leu Gln Ser Asp Ala Lys Gly
             20                  25                  30

Lys Leu Asp Ser Val Ala Thr Asp Tyr Gly Ala Ala Ile Asp Gly Phe
         35                  40                  45

Ile Gly Asp Val Ser Gly Leu Ala Asn Gly Asn Gly Ala Thr Gly Asp
     50                  55                  60

Phe Ala Gly Ser Asn Ser Gln Met Ala Gln Val Gly Asp Gly Asp Asn
 65                  70                  75                  80

Ser Pro Leu Met Asn Asn Phe Arg Gln Tyr Leu Pro Ser Leu Pro Gln
                 85                  90                  95

Ser Val Glu Cys Arg Pro Phe Val Phe Ser Ala Gly Lys Pro Tyr Glu
            100                 105                 110

Phe Ser Ile Asp Cys Asp Lys Ile Asn Leu Phe Arg Gly Val Phe Ala
        115                 120                 125

Phe Leu Leu Tyr Val Ala Thr Phe Met Tyr Val Phe Ser Thr Phe Ala
    130                 135                 140

Asn Ile Leu Arg Asn Lys Glu Ser
145                 150

<210> SEQ ID NO 455
<211> LENGTH: 15
<212> TYPE: PRT
<213> ORGANISM: Unknown
<220> FEATURE:
<223> OTHER INFORMATION: Description of Unknown: MALIA3 peptide
      sequence

<400> SEQUENCE: 455

Met Pro Val Leu Leu Gly Ile Pro Leu Leu Leu Arg Phe Leu Gly
  1               5                  10                  15

<210> SEQ ID NO 456
<211> LENGTH: 348
```

```
<212> TYPE: PRT
<213> ORGANISM: Unknown
<220> FEATURE:
<223> OTHER INFORMATION: Description of Unknown: MALIA3 protein
      sequence

<400> SEQUENCE: 456

Met Ala Val Tyr Phe Val Thr Gly Lys Leu Gly Ser Gly Lys Thr Leu
 1               5                  10                  15

Val Ser Val Gly Lys Ile Gln Asp Lys Ile Val Ala Gly Cys Lys Ile
            20                  25                  30

Ala Thr Asn Leu Asp Leu Arg Leu Gln Asn Leu Pro Gln Val Gly Arg
        35                  40                  45

Phe Ala Lys Thr Pro Arg Val Leu Arg Ile Pro Asp Lys Pro Ser Ile
50                  55                  60

Ser Asp Leu Leu Ala Ile Gly Arg Gly Asn Asp Ser Tyr Asp Glu Asn
65                  70                  75                  80

Lys Asn Gly Leu Leu Val Leu Asp Glu Cys Gly Thr Trp Phe Asn Thr
                85                  90                  95

Arg Ser Trp Asn Asp Lys Glu Arg Gln Pro Ile Ile Asp Trp Phe Leu
            100                 105                 110

His Ala Arg Lys Leu Gly Trp Asp Ile Ile Phe Leu Val Gln Asp Leu
        115                 120                 125

Ser Ile Val Asp Lys Gln Ala Arg Ser Ala Leu Ala Glu His Val Val
130                 135                 140

Tyr Cys Arg Arg Leu Asp Arg Ile Thr Leu Pro Phe Val Gly Thr Leu
145                 150                 155                 160

Tyr Ser Leu Ile Thr Gly Ser Lys Met Pro Leu Pro Lys Leu His Val
                165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
        195                 200                 205

Ala Phe Ser Ser Asn Tyr Asp Ser Gly Val Tyr Ser Tyr Leu Thr Pro
210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
            260                 265                 270

Pro Lys Pro Glu Val Lys Lys Val Ser Gln Thr Tyr Asp Phe Asp
        275                 280                 285

Lys Phe Thr Ile Asp Ser Ser Gln Arg Leu Asn Leu Ser Tyr Arg Tyr
290                 295                 300

Val Phe Lys Asp Ser Lys Gly Lys Leu Ile Asn Ser Asp Leu Gln
305                 310                 315                 320

Lys Gln Gly Tyr Ser Leu Thr Tyr Ile Asp Leu Cys Thr Val Ser Ile
                325                 330                 335

Lys Lys Gly Asn Ser Asn Glu Ile Val Lys Cys Asn
            340                 345

<210> SEQ ID NO 457
<211> LENGTH: 24
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 457
tggaagaggc acgttctttt cttt                                              24

<210> SEQ ID NO 458
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
cttttctttg ttgccgttgg ggtg                                              24

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
acactctccc ctgttgaagc tctt                                              24

<210> SEQ ID NO 460
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
accgcctcca ccgggcgcgc cttattaaca ctctccctg ttgaagctct t                 51

<210> SEQ ID NO 461
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
tgaacattct gtagggggcca ctg                                              23

<210> SEQ ID NO 462
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
agagcattct gcagggggcca ctg                                              23

<210> SEQ ID NO 463
<211> LENGTH: 50
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 463
accgcctcca ccgggcgcgc cttattatga acattctgta ggggccactg            50

<210> SEQ ID NO 464
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
accgcctcca ccgggcgcgc cttattaaga gcattctgca ggggccactg            50

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
cgactggagc acgaggacac tga                                         23

<210> SEQ ID NO 466
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
ggacactgac atggactgaa ggagta                                      26

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
gggaggatgg agactgggtc                                             20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
gggaagatgg agactgggtc                                             20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 469
gggagagtgg agactgagtc                                          20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gggtgcctgg agactgcgtc                                          20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
gggtggctgg agactgcgtc                                          20

<210> SEQ ID NO 472
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gggaggatgg agactgggtc atctggatgt cttgtgcact gtgacagagg          50

<210> SEQ ID NO 473
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gggaagatgg agactgggtc atctggatgt cttgtgcact gtgacagagg          50

<210> SEQ ID NO 474
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
gggagagtgg agactgggtc atctggatgt cttgtgcact gtgacagagg          50

<210> SEQ ID NO 475
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gggtgcctgg agactgggtc atctggatgt cttgtgcact gtgacagagg       50

<210> SEQ ID NO 476
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gggtggctgg agactgggtc atctggatgt cttgtgcact gtgacagagg       50

<210> SEQ ID NO 477
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gggagtctgg agactgggtc atctggatgt cttgtgcact gtgacagagg       50

<210> SEQ ID NO 478
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
cctctgtcac agtgcacaag acatccagat gacccagtct cc               42

<210> SEQ ID NO 479
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
cctctgtcac agtgcacaag ac                                     22

<210> SEQ ID NO 480
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480
acactctccc ctgttgaagc tctt                                   24

<210> SEQ ID NO 481
<211> LENGTH: 669
<212> TYPE: DNA
<213> ORGANISM: Homo sapiens
<220> FEATURE:
<221> NAME/KEY: CDS
<222> LOCATION: (1)..(669)
<220> FEATURE:

<221> NAME/KEY: modified_base
<222> LOCATION: (669)..(669)
<223> OTHER INFORMATION: a, c, t or g

<400> SEQUENCE: 481

```
agt gca caa gac atc cag atg acc cag tct cca gcc acc ctg tct gtg     48
Ser Ala Gln Asp Ile Gln Met Thr Gln Ser Pro Ala Thr Leu Ser Val
 1               5                  10                  15 tct cca ggg gaa agg gcc acc ctc tcc tgc agg gcc agt cag agt gtt     96
Ser Pro Gly Glu Arg Ala Thr Leu Ser Cys Arg Ala Ser Gln Ser Val
             20                  25                  30 agt aac aac tta gcc tgg tac cag cag aaa cct ggc cag gtt ccc agg    144
Ser Asn Asn Leu Ala Trp Tyr Gln Gln Lys Pro Gly Gln Val Pro Arg
         35                  40                  45 ctc ctc atc tat ggt gca tcc acc agg gcc act gat atc cca gcc agg    192
Leu Leu Ile Tyr Gly Ala Ser Thr Arg Ala Thr Asp Ile Pro Ala Arg
     50                  55                  60 ttc agt ggc agt ggg tct ggg aca gac ttc act ctc acc atc agc aga    240
Phe Ser Gly Ser Gly Ser Gly Thr Asp Phe Thr Leu Thr Ile Ser Arg
 65                  70                  75                  80 ctg gag cct gaa gat ttt gca gtg tat tac tgt cag cgg tat ggt agc    288
Leu Glu Pro Glu Asp Phe Ala Val Tyr Tyr Cys Gln Arg Tyr Gly Ser
                 85                  90                  95 tca ccg ggg tgg acg ttc ggc caa ggg acc aag gtg gaa atc aaa cga    336
Ser Pro Gly Trp Thr Phe Gly Gln Gly Thr Lys Val Glu Ile Lys Arg
            100                 105                 110 act gtg gct gca cca tct gtc ttc atc ttc ccg cca tct gat gag cag    384
Thr Val Ala Ala Pro Ser Val Phe Ile Phe Pro Pro Ser Asp Glu Gln
        115                 120                 125 ttg aaa tct gga act gcc tct gtt gtg tgc ctg ctg aat aac ttc tat    432
Leu Lys Ser Gly Thr Ala Ser Val Val Cys Leu Leu Asn Asn Phe Tyr
    130                 135                 140 ccc aga gag gcc aaa gta cag tgg aag gtg gat aac gcc ctc caa tcg    480
Pro Arg Glu Ala Lys Val Gln Trp Lys Val Asp Asn Ala Leu Gln Ser
145                 150                 155                 160 ggt aac tcc cag gag agt gtc aca gag cag gac agc aag gac agc acc    528
Gly Asn Ser Gln Glu Ser Val Thr Glu Gln Asp Ser Lys Asp Ser Thr
                165                 170                 175 tac agc ctc agc agc acc ctg acg ctg agc aaa gca gac tac gag aaa    576
Tyr Ser Leu Ser Ser Thr Leu Thr Leu Ser Lys Ala Asp Tyr Glu Lys
            180                 185                 190 cac aaa gtc tac gcc tgc gaa gtc acc cat cag ggc ctg agc tcg cct    624
His Lys Val Tyr Ala Cys Glu Val Thr His Gln Gly Leu Ser Ser Pro
        195                 200                 205 gtc aca aag agc ttc aac aaa gga gag tgt aag ggc gaa ttc gcn        669
Val Thr Lys Ser Phe Asn Lys Gly Glu Cys Lys Gly Glu Phe Ala
    210                 215                 220
```

<210> SEQ ID NO 482
<211> LENGTH: 223
<212> TYPE: PRT
<213> ORGANISM: Homo sapiens

<400> SEQUENCE: 482

```
Ser Ala Gln Asp Ile Gln Met Thr Gln Ser Pro Ala Thr Leu Ser Val
 1               5                  10                  15

Ser Pro Gly Glu Arg Ala Thr Leu Ser Cys Arg Ala Ser Gln Ser Val
             20                  25                  30

Ser Asn Asn Leu Ala Trp Tyr Gln Gln Lys Pro Gly Gln Val Pro Arg
         35                  40                  45
```

```
Leu Leu Ile Tyr Gly Ala Ser Thr Arg Ala Thr Asp Ile Pro Ala Arg
 50                  55                  60

Phe Ser Gly Ser Gly Ser Gly Thr Asp Phe Thr Leu Thr Ile Ser Arg
 65                  70                  75                  80

Leu Glu Pro Glu Asp Phe Ala Val Tyr Tyr Cys Gln Arg Tyr Gly Ser
             85                  90                  95

Ser Pro Gly Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Lys Gly Glu Cys Lys Gly Glu Phe Ala
210                 215                 220

<210> SEQ ID NO 483
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
agccaccctg tct                                                       13

<210> SEQ ID NO 484
<211> LENGTH: 700
<212> TYPE: DNA
<213> ORGANISM: Homo sapiens
<220> FEATURE:
<221> NAME/KEY: CDS
<222> LOCATION: (1)..(699)

<400> SEQUENCE: 484 agt gca caa gac atc cag atg acc cag tct cct gcc acc ctg tct gtg    48
Ser Ala Gln Asp Ile Gln Met Thr Gln Ser Pro Ala Thr Leu Ser Val
 1               5                  10                  15 tct cca ggt gaa aga gcc acc ctc tcc tgc agg gcc agt cag gtg tct    96
Ser Pro Gly Glu Arg Ala Thr Leu Ser Cys Arg Ala Ser Gln Val Ser
             20                  25                  30 cca ggg gaa aga gcc acc ctc tcc tgc aat ctt ctc agc aac tta gcc   144
Pro Gly Glu Arg Ala Thr Leu Ser Cys Asn Leu Leu Ser Asn Leu Ala
         35                  40                  45 tgg tac cag cag aaa cct ggc cag gct ccc agg ctc ctc atc tat ggt   192
Trp Tyr Gln Gln Lys Pro Gly Gln Ala Pro Arg Leu Leu Ile Tyr Gly
     50                  55                  60 gct tcc acc ggg gcc att ggt atc cca gcc agg ttc agt ggc agt ggg   240
Ala Ser Thr Gly Ala Ile Gly Ile Pro Ala Arg Phe Ser Gly Ser Gly
 65                  70                  75                  80 tct ggg aca gag ttc act ctc acc atc agc agc ctg cag tct gaa gat   288
Ser Gly Thr Glu Phe Thr Leu Thr Ile Ser Ser Leu Gln Ser Glu Asp
             85                  90                  95
```

```
                        85                  90                   95
ttt gca gtg tat ttc tgt cag cag tat ggt acc tca ccg ccc act ttc       336
Phe Ala Val Tyr Phe Cys Gln Gln Tyr Gly Thr Ser Pro Pro Thr Phe
            100                 105                 110 ggc gga ggg acc aag gtg gag atc aaa cga act gtg gct gca cca tct       384
Gly Gly Gly Thr Lys Val Glu Ile Lys Arg Thr Val Ala Ala Pro Ser
            115                 120                 125 gtc ttc atc ttc ccg cca tct gat gag cag ttg aaa tct gga act gcc       432
Val Phe Ile Phe Pro Pro Ser Asp Glu Gln Leu Lys Ser Gly Thr Ala
130                 135                 140 tct gtt gtg tgc ctg aat aac ttc tat ccc aga gag gcc aaa gta           480
Ser Val Val Cys Pro Leu Asn Asn Phe Tyr Pro Arg Glu Ala Lys Val
145                 150                 155                 160 cag tgg aag gtg gat aac gcc ctc caa tcg ggt aac tcc cag gag agt       528
Gln Trp Lys Val Asp Asn Ala Leu Gln Ser Gly Asn Ser Gln Glu Ser
                165                 170                 175 gtc aca gag cag gac aac aag gac agc acc tac agc ctc agc agc acc       576
Val Thr Glu Gln Asp Asn Lys Asp Ser Thr Tyr Ser Leu Ser Ser Thr
            180                 185                 190 ctg acg ctg agc aaa gta gac tac gag aaa cac gaa gtc tac gcc tgc       624
Leu Thr Leu Ser Lys Val Asp Tyr Glu Lys His Glu Val Tyr Ala Cys
            195                 200                 205 gaa gtc acc cat cag ggc ctt agc tcg ccc gtc acg aag agc ttc aac       672
Glu Val Thr His Gln Gly Leu Ser Ser Pro Val Thr Lys Ser Phe Asn
210                 215                 220 agg gga gag tgt aag aaa gaa ttc gtt t                                 700
Arg Gly Glu Cys Lys Lys Glu Phe Val
225                 230
```

<210> SEQ ID NO 485
<211> LENGTH: 233
<212> TYPE: PRT
<213> ORGANISM: Homo sapiens

<400> SEQUENCE: 485

```
Ser Ala Gln Asp Ile Gln Met Thr Gln Ser Pro Ala Thr Leu Ser Val
 1               5                  10                  15

Ser Pro Gly Glu Arg Ala Thr Leu Ser Cys Arg Ala Ser Gln Val Ser
            20                  25                  30

Pro Gly Glu Arg Ala Thr Leu Ser Cys Asn Leu Leu Ser Asn Leu Ala
        35                  40                  45

Trp Tyr Gln Gln Lys Pro Gly Gln Ala Pro Arg Leu Leu Ile Tyr Gly
    50                  55                  60

Ala Ser Thr Gly Ala Ile Gly Ile Pro Ala Arg Phe Ser Gly Ser Gly
65                  70                  75                  80

Ser Gly Thr Glu Phe Thr Leu Thr Ile Ser Ser Leu Gln Ser Glu Asp
                85                  90                  95

Phe Ala Val Tyr Phe Cys Gln Gln Tyr Gly Thr Ser Pro Pro Thr Phe
            100                 105                 110

Gly Gly Gly Thr Lys Val Glu Ile Lys Arg Thr Val Ala Ala Pro Ser
        115                 120                 125

Val Phe Ile Phe Pro Pro Ser Asp Glu Gln Leu Lys Ser Gly Thr Ala
130                 135                 140

Ser Val Val Cys Pro Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175
```

```
Val Thr Glu Gln Asp Asn Lys Asp Ser Thr Tyr Ser Leu Ser Ser Thr
            180                 185                 190

Leu Thr Leu Ser Lys Val Asp Tyr Glu Lys His Glu Val Tyr Ala Cys
        195                 200                 205

Glu Val Thr His Gln Gly Leu Ser Ser Pro Val Thr Lys Ser Phe Asn
    210                 215                 220

Arg Gly Glu Cys Lys Lys Glu Phe Val
225                 230
```

```
<210> SEQ ID NO 486
<211> LENGTH: 419
<212> TYPE: DNA
<213> ORGANISM: Artificial Sequence
<220> FEATURE:
<223> OTHER INFORMATION: Description of Artificial Sequence: Synthetic
      3-23 VH nucleotide sequence
<220> FEATURE:
<221> NAME/KEY: CDS
<222> LOCATION: (12)..(419)

<400> SEQUENCE: 486
ctgtctgaac g gcc cag ccg gcc atg gcc gaa gtt caa ttg tta gag tct      50
             Ala Gln Pro Ala Met Ala Glu Val Gln Leu Leu Glu Ser
               1               5                  10 ggt ggc ggt ctt gtt cag cct ggt ggt tct tta cgt ctt tct tgc gct      98
Gly Gly Gly Leu Val Gln Pro Gly Gly Ser Leu Arg Leu Ser Cys Ala
 15                  20                  25 gct tcc gga ttc act ttc tct tcg tac gct atg tct tgg gtt cgc caa     146
Ala Ser Gly Phe Thr Phe Ser Ser Tyr Ala Met Ser Trp Val Arg Gln
 30                  35                  40                  45 gct cct ggt aaa ggt ttg gag tgg gtt tct gct atc tct ggt tct ggt     194
Ala Pro Gly Lys Gly Leu Glu Trp Val Ser Ala Ile Ser Gly Ser Gly
                 50                  55                  60 ggc agt act tac tat gct gac tcc gtt aaa ggt cgc ttc act atc tct     242
Gly Ser Thr Tyr Tyr Ala Asp Ser Val Lys Gly Arg Phe Thr Ile Ser
             65                  70                  75 aga gac aac tct aag aat act ctc tac ttg cag atg aac agc tta agg     290
Arg Asp Asn Ser Lys Asn Thr Leu Tyr Leu Gln Met Asn Ser Leu Arg
         80                  85                  90 gct gag gac act gca gtc tac tat tgc gct aaa gac tat gaa ggt act     338
Ala Glu Asp Thr Ala Val Tyr Tyr Cys Ala Lys Asp Tyr Glu Gly Thr
     95                 100                 105 ggt tat gct ttc gac ata tgg ggt caa ggt act atg gtc acc gtc tct     386
Gly Tyr Ala Phe Asp Ile Trp Gly Gln Gly Thr Met Val Thr Val Ser
110                 115                 120                 125 agt gcc tcc acc aag ggc cca tcg gtc ttc ccc                         419
Ser Ala Ser Thr Lys Gly Pro Ser Val Phe Pro
                130                 135
```

```
<210> SEQ ID NO 487
<211> LENGTH: 136
<212> TYPE: PRT
<213> ORGANISM: Artificial Sequence
<220> FEATURE:
<223> OTHER INFORMATION: Description of Artificial Sequence: Synthetic
      3-23 VH protein sequence

<400> SEQUENCE: 487

Ala Gln Pro Ala Met Ala Glu Val Gln Leu Leu Glu Ser Gly Gly Gly
  1               5                  10                  15

Leu Val Gln Pro Gly Gly Ser Leu Arg Leu Ser Cys Ala Ala Ser Gly
             20                  25                  30
```

```
Phe Thr Phe Ser Ser Tyr Ala Met Ser Trp Val Arg Gln Ala Pro Gly
             35                  40                  45

Lys Gly Leu Glu Trp Val Ser Ala Ile Ser Gly Ser Gly Gly Ser Thr
 50                  55                  60

Tyr Tyr Ala Asp Ser Val Lys Gly Arg Phe Thr Ile Ser Arg Asp Asn
 65                  70                  75                  80

Ser Lys Asn Thr Leu Tyr Leu Gln Met Asn Ser Leu Arg Ala Glu Asp
                 85                  90                  95

Thr Ala Val Tyr Tyr Cys Ala Lys Asp Tyr Glu Gly Thr Gly Tyr Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro
    130                 135
```

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
ctgtctgaac ggcccagccg                                                      20

<210> SEQ ID NO 489
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
ctgtctgaac ggcccagccg gccatggccg aagttcaatt gttagagtct ggtggcggtc         60
ttgttcagcc tggtggttct tta                                                 83

<210> SEQ ID NO 490
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gaaagtgaat ccggaagcag cgcaagaaag acgtaaagaa ccaccaggct gaac              54

<210> SEQ ID NO 491
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
agaaacccac tccaaacctt taccaggagc ttggcgaacc ca                            42

<210> SEQ ID NO 492
<211> LENGTH: 94
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 492
agtgtcctca gcccttaagc tgttcatctg caagtagaga gtattcttag agttgtctct    60
agagatagtg aagcgacctt taacggagtc agca                                94

<210> SEQ ID NO 493
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gcttaagggc tgaggacact gcagtctact attgcgctaa agactatgaa ggtactggtt    60
atgctttcga catatggggt c                                              81

<210> SEQ ID NO 494
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
ggggaagacc gatgggccct tggtggaggc actagagacg gtgaccatag taccttgacc    60
tatgtcgaaa gc                                                        72

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
ggggaagacc gatgggccct tgg                                            23

<210> SEQ ID NO 496
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(24)
<223> OTHER INFORMATION: a, t, c, g, unknown or other
<220> FEATURE:
<221> NAME/KEY: modified_base
<222> LOCATION: (28)..(30)
<223> OTHER INFORMATION: a, t, c, g, unknown or other
<220> FEATURE:
<221> NAME/KEY: modified_base
<222> LOCATION: (34)..(36)
<223> OTHER INFORMATION: a, t, c, g, unknown or other
<220> FEATURE:
<223> OTHER INFORMATION: nnn codes for any amino acid but Cys

<400> SEQUENCE: 496
```
gcttccggat tcactttctc tnnntacnnn atgnnntggg ttcgccaagc tcctgg    56

<210> SEQ ID NO 497
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, t, c or g
<220> FEATURE:
<221> NAME/KEY: modified_base
<222> LOCATION: (25)..(30)
<223> OTHER INFORMATION: a, t, c or g
<220> FEATURE:
<221> NAME/KEY: modified_base
<222> LOCATION: (40)..(42)
<223> OTHER INFORMATION: a, t, c or g
<220> FEATURE:
<221> NAME/KEY: modified_base
<222> LOCATION: (46)..(48)
<223> OTHER INFORMATION: a, t, c or g

<400> SEQUENCE: 497
ggtttggagt gggtttctnn natcnnnnnn tctggtggcn nnactnnnta tgctgactcc    60
gttaaagg    68

<210> SEQ ID NO 498
<211> LENGTH: 912
<212> TYPE: DNA
<213> ORGANISM: Escherichia coli

<400> SEQUENCE: 498
tccggagctt cagatctgtt tgcctttttg tggggtggtg cagatcgcgt tacggagatc    60
gaccgactgc ttgagcaaaa gccacgctta actgctgatc aggcatggga tgttattcgc    120
caaaccagtc gtcaggatct taacctgagg ctttttttac ctactctgca agcagcgaca    180
tctggtttga cacagagcga tccgcgtcgt cagttggtag aaacattaac acgttgggat    240
ggcatcaatt tgcttaatga tgatggtaaa acctggcagc agccaggctc tgccatcctg    300
aacgtttggc tgaccagtat gttgaagcgt accgtagtgg ctgccgtacc tatgccattt    360
gataagtggt acagcgccag tggctacgaa acaacccagg acggcccaac tggttcgctg    420
aatataagtg ttggagcaaa aattttgtat gaggcggtgc agggagacaa atcaccaatc    480
ccacaggcgg ttgatctgtt tgctgggaaa ccacagcagg aggttgtgtt ggctgcgctg    540
gaagatacct gggagactct ttccaaacgc tatggcaata atgtgagtaa ctggaaaaca    600
cctgcaatgg ccttaacgtt ccgggcaaat aatttctttg gtgtaccgca ggccgcagcg    660
gaagaaacgc gtcatcaggc ggagtatcaa aaccgtggaa cagaaaacga tatgattgtt    720
ttctcaccaa cgacaagcga tcgtcctgtg cttgcctggg atgtggtcgc acccggtcag    780
agtgggttta ttgctcccga tggaacagtt gataagcact atgaagatca gctgaaaatg    840
tacgaaaatt ttggccgtaa gtcgctctgg ttaacgaagc aggatgtgga ggcgcataag    900
gagtcgtcta ga    912

<210> SEQ ID NO 499
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 499 gatnnnnatc                                                          10

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, t, c, g, unknown or other

<400> SEQUENCE: 500
nnnnnnnnnn nnnnngtccc                                               20

<210> SEQ ID NO 501
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 501
gcannnnntg c                                                        11

<210> SEQ ID NO 502
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 502 gacnnnngtc                                                          10

<210> SEQ ID NO 503
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, t, c, g, unknown or other

<400> SEQUENCE: 503
nnnnnnngcg gg                                                       12
```

<210> SEQ ID NO 504
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 504
gtatccnnnn nn                                                         12

<210> SEQ ID NO 505
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 505
gcannnnnnt cg                                                         12

<210> SEQ ID NO 506
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 506
gccnnnnngg c                                                          11

<210> SEQ ID NO 507
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 507
ggtctcnnnn n                                                          11

<210> SEQ ID NO 508
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(8)

-continued

```
<223> OTHER INFORMATION: a, t, c, g, unknown or other

<400> SEQUENCE: 508
gacnnnnngt c                                                           11

<210> SEQ ID NO 509
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 509 gacnnnngt c                                                            11

<210> SEQ ID NO 510
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 510
gacnnnnnng tc                                                          12

<210> SEQ ID NO 511
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 511 ccannnntg g                                                            11

<210> SEQ ID NO 512
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 512
nnnnnnnnng caggt                                                       15

<210> SEQ ID NO 513
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 513
acctgcnnnn n                                                           11

<210> SEQ ID NO 514
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 514
ggccnnnnng gcc                                                         13

<210> SEQ ID NO 515
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 515
ccannnnnnn nntgg                                                       15

<210> SEQ ID NO 516
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 516
cgtctcnnnn n                                                           11

<210> SEQ ID NO 517
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 517
nnnnnngaga cg                                                          12
```

<210> SEQ ID NO 518
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 518
nnnnnnnnnn ctcctc                                              16

<210> SEQ ID NO 519
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, t, c, g, unknown or other

<400> SEQUENCE: 519
gaggagnnnn nnnnnn                                              16

<210> SEQ ID NO 520
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 520
cctnnnnnag g                                                   11

<210> SEQ ID NO 521
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 521
ccannnnnnt gg                                                  12

<210> SEQ ID NO 522
<211> LENGTH: 6680
<212> TYPE: DNA
<213> ORGANISM: Artificial Sequence
<220> FEATURE:
<223> OTHER INFORMATION: Description of Artificial Sequence: Vector
      pCES5 nucleotide sequence
<220> FEATURE:
<221> NAME/KEY: CDS

```
<222> LOCATION: (201)..(1058)
<220> FEATURE:
<221> NAME/KEY: CDS
<222> LOCATION: (2269)..(2682)
<220> FEATURE:
<221> NAME/KEY: CDS
<222> LOCATION: (2723)..(2866)
<220> FEATURE:
<221> NAME/KEY: CDS
<222> LOCATION: (3767)..(3850)
<220> FEATURE:
<221> NAME/KEY: CDS
<222> LOCATION: (4198)..(5799)

<400> SEQUENCE: 522
```

| | | |
|---|---|---|
| gacgaaaggg cctcgtgata cgcctatttt tataggttaa tgtcatgata ataatggttt | 60 | |
| cttagacgtc aggtggcact tttcggggaa atgtgcgcgg aaccccctatt tgtttatttt | 120 | |
| tctaaataca ttcaaatatg tatccgctca tgagacaata accctgataa atgcttcaat | 180 | |
| aatattgaaa aggaagagt atg agt att caa cat ttc cgt gtc gcc ctt att | 233 | |
|                                    Met Ser Ile Gln His Phe Arg Val Ala Leu Ile | | |
|                                     1            5              10 | | |

```
ccc ttt ttt gcg gca ttt tgc ctt cct gtt ttt gct cac cca gaa acg        281
Pro Phe Phe Ala Ala Phe Cys Leu Pro Val Phe Ala His Pro Glu Thr
             15                  20                  25 ctg gtg aaa gta aaa gat gct gaa gat cag ttg ggt gcc cga gtg ggt        329
Leu Val Lys Val Lys Asp Ala Glu Asp Gln Leu Gly Ala Arg Val Gly
     30                  35                  40 tac atc gaa ctg gat ctc aac agc ggt aag atc ctt gag agt ttt cgc        377
Tyr Ile Glu Leu Asp Leu Asn Ser Gly Lys Ile Leu Glu Ser Phe Arg
 45                  50                  55 ccc gaa gaa cgt ttt cca atg atg agc act ttt aaa gtt ctg cta tgt        425
Pro Glu Glu Arg Phe Pro Met Met Ser Thr Phe Lys Val Leu Leu Cys
 60                  65                  70                  75 ggc gcg gta tta tcc cgt att gac gcc ggg caa gag caa ctc ggt cgc        473
Gly Ala Val Leu Ser Arg Ile Asp Ala Gly Gln Glu Gln Leu Gly Arg
             80                  85                  90 cgc ata cac tat tct cag aat gac ttg gtt gag tac tca cca gtc aca        521
Arg Ile His Tyr Ser Gln Asn Asp Leu Val Glu Tyr Ser Pro Val Thr
         95                 100                 105 gaa aag cat ctt acg gat ggc atg aca gta aga gaa tta tgc agt gct        569
Glu Lys His Leu Thr Asp Gly Met Thr Val Arg Glu Leu Cys Ser Ala
     110                 115                 120 gcc ata acc atg agt gat aac act gcg gcc aac tta ctt ctg aca acg        617
Ala Ile Thr Met Ser Asp Asn Thr Ala Ala Asn Leu Leu Leu Thr Thr
 125                 130                 135 atc gga gga ccg aag gag cta acc gct ttt ttg cac aac atg ggg gat        665
Ile Gly Gly Pro Lys Glu Leu Thr Ala Phe Leu His Asn Met Gly Asp
140                 145                 150                 155 cat gta act cgc ctt gat cgt tgg gaa ccg gag ctg aat gaa gcc ata        713
His Val Thr Arg Leu Asp Arg Trp Glu Pro Glu Leu Asn Glu Ala Ile
             160                 165                 170 cca aac gac gag cgt gac acc acg atg cct gta gca atg gca aca acg        761
Pro Asn Asp Glu Arg Asp Thr Thr Met Pro Val Ala Met Ala Thr Thr
         175                 180                 185 ttg cgc aaa cta tta act ggc gaa cta ctt act cta gct tcc cgg caa        809
Leu Arg Lys Leu Leu Thr Gly Glu Leu Leu Thr Leu Ala Ser Arg Gln
     190                 195                 200 caa tta ata gac tgg atg gag gcg gat aaa gtt gca gga cca ctt ctg        857
Gln Leu Ile Asp Trp Met Glu Ala Asp Lys Val Ala Gly Pro Leu Leu
 205                 210                 215 cgc tcg gcc ctt ccg gct ggc tgg ttt att gct gat aaa tct gga gcc        905
```

```
Arg Ser Ala Leu Pro Ala Gly Trp Phe Ile Ala Asp Lys Ser Gly Ala
220                 225                 230                 235
ggt gag cgt ggg tct cgc ggt atc att gca gca ctg ggg cca gat ggt        953
Gly Glu Arg Gly Ser Arg Gly Ile Ile Ala Ala Leu Gly Pro Asp Gly
                240                 245                 250
aag ccc tcc cgt atc gta gtt atc tac acg acg ggg agt cag gca act       1001
Lys Pro Ser Arg Ile Val Val Ile Tyr Thr Thr Gly Ser Gln Ala Thr
        255                 260                 265
atg gat gaa cga aat aga cag atc gct gag ata ggt gcc tca ctg att       1049
Met Asp Glu Arg Asn Arg Gln Ile Ala Glu Ile Gly Ala Ser Leu Ile
        270                 275                 280
aag cat tgg taactgtcag accaagttta ctcatatata ctttagattg               1098
Lys His Trp
        285 atttaaaact tcattttaa tttaaaagga tctaggtgaa gatccttttt gataatctca       1158
tgaccaaaat cccttaacgt gagttttcgt tccactgagc gtcagacccc gtagaaaaga     1218
tcaaaggatc ttcttgagat cctttttttc tgcgcgtaat ctgctgcttg caaacaaaaa     1278
aaccaccgct accagcggtg gtttgtttgc cggatcaaga gctaccaact ctttttccga     1338
aggtaactgg cttcagcaga gcgcagatac caaatactgt ccttctagtg tagccgtagt     1398
taggccacca cttcaagaac tctgtagcac cgcctacata cctcgctctg ctaatcctgt     1458
taccagtggc tgctgccagt ggcgataagt cgtgtcttac cgggttggac tcaagacgat     1518
agttaccgga taaggcgcag cggtcgggct gaacggggg ttcgtgcata cagcccagct      1578
tggagcgaac gacctacacc gaactgagat acctacagcg tgagcattga aaagcgcca     1638
cgcttcccga agggagaaag gcggacaggt atccggtaag cggcagggtc ggaacaggag     1698
agcgcacgag ggagcttcca gggggaaacg cctggtatct ttatagtcct gtcgggtttc    1758
gccacctctg acttgagcgt cgatttttgt gatgctcgtc aggggggcgg agcctatgga    1818
aaaacgccag caacgcggcc tttttacggt tcctggcctt ttgctggcct ttgctcaca     1878
tgttctttcc tgcgttatcc cctgattctg tggataaccg tattaccgcc tttgagtgag    1938
ctgataccgc tcgccgcagc cgaacgaccg agcgcagcga gtcagtgagc gaggaagcgg    1998
aagagcgccc aatacgcaaa ccgcctctcc ccgcgcgttg gccgattcat taatgcagct    2058
ggcacgacag gtttcccgac tggaaagcgg gcagtgagcg caacgcaatt aatgtgagtt    2118
agctcactca ttaggcaccc caggctttac actttatgct tccggctcgt atgttgtgtg    2178
gaattgtgag cggataacaa tttcacacag gaaacagcta tgaccatgat tacgccaagc    2238
tttggagcct tttttttgga gattttcaac gtg aaa aaa tta tta ttc gca att     2292
                                  Met Lys Lys Leu Leu Phe Ala Ile
                                                              290
cct tta gtt gtt cct ttc tat tct cac agt gca cag gtc caa ctg cag       2340
Pro Leu Val Val Pro Phe Tyr Ser His Ser Ala Gln Val Gln Leu Gln
295                 300                 305                 310
gtc gac ctc gag atc aaa cgt gga act gtg gct gca cca tct gtc ttc       2388
Val Asp Leu Glu Ile Lys Arg Gly Thr Val Ala Ala Pro Ser Val Phe
                315                 320                 325
atc ttc ccg cca tct gat gag cag ttg aaa tct gga act gcc tct gtt       2436
Ile Phe Pro Pro Ser Asp Glu Gln Leu Lys Ser Gly Thr Ala Ser Val
        330                 335                 340
gtg tgc ctg ctg aat aac ttc tat ccc aga gag gcc aaa gta cag tgg       2484
Val Cys Leu Leu Asn Asn Phe Tyr Pro Arg Glu Ala Lys Val Gln Trp
        345                 350                 355
aag gtg gat aac gcc ctc caa tcg ggt aac tcc cag gag agt gtc aca       2532
Lys Val Asp Asn Ala Leu Gln Ser Gly Asn Ser Gln Glu Ser Val Thr
```

-continued

```
            360                 365                 370
gag cag gac agc aag gac agc acc tac agc ctc agc agc acc ctg acg      2580
Glu Gln Asp Ser Lys Asp Ser Thr Tyr Ser Leu Ser Ser Thr Leu Thr
375                 380                 385                 390 ctg agc aaa gca gac tac gag aaa cac aaa gtc tac gcc tgc gaa gtc      2628
Leu Ser Lys Ala Asp Tyr Glu Lys His Lys Val Tyr Ala Cys Glu Val
                395                 400                 405 acc cat cag ggc ctg agt tca ccg gtg aca aag agc ttc aac agg gga      2676
Thr His Gln Gly Leu Ser Ser Pro Val Thr Lys Ser Phe Asn Arg Gly
            410                 415                 420 gag tgt taataaggcg cgccaattct atttcaagga gacagtcata atg aaa tac      2731
Glu Cys                                              Met Lys Tyr
                                                         425 cta ttg cct acg gca gcc gct gga ttg tta tta ctc gcg gcc cag ccg      2779
Leu Leu Pro Thr Ala Ala Ala Gly Leu Leu Leu Leu Ala Ala Gln Pro
            430                 435                 440 gcc atg gcc gaa gtt caa ttg tta gag tct ggt ggc ggt ctt gtt cag      2827
Ala Met Ala Glu Val Gln Leu Leu Glu Ser Gly Gly Gly Leu Val Gln
            445                 450                 455 cct ggt ggt tct tta cgt ctt tct tgc gct gct tcc gga gcttcagatc      2876
Pro Gly Gly Ser Leu Arg Leu Ser Cys Ala Ala Ser Gly
460                 465                 470 tgtttgcctt tttgtggggt ggtgcagatc gcgttacgga gatcgaccga ctgcttgagc    2936
aaaagccacg cttaactgct gatcaggcat gggatgttat cgccaaacc agtcgtcagg    2996
atcttaacct gaggcttttt ttacctactc tgcaagcagc gacatctggt ttgacacaga    3056
gcgatccgcg tcgtcagttg gtagaaacat taacacgttg ggatggcatc aatttgctta    3116
atgatgatgg taaaacctgg cagcagccag gctctgccat cctgaacgtt ggctgacca    3176
gtatgttgaa gcgtaccgta gtggctgccg tacctatgcc atttgataag tggtacagcg    3236
ccagtggcta cgaaacaacc caggacggcc caactggttc gctgaatata agtgttggag    3296
caaaattttt gtatgaggcg gtgcaggag acaaatcacc aatcccacag gcggttgatc     3356
tgtttgctgg gaaaccacag caggaggttg tgttggctgc gctggaagat acctgggaga    3416
ctctttccaa acgctatggc aataatgtga gtaactggaa acacctgca atggccttaa    3476
cgttccgggc aaataatttc tttggtgtac cgcaggccgc agcggaagaa acgcgtcatc    3536
aggcggagta tcaaaccgt ggaacagaaa acgatatgat tgttttctca ccaacgacaa    3596
gcgatcgtcc tgtgcttgcc tgggatgtgg tcgcacccgg tcagagtggg tttattgctc    3656
ccgatggaac agttgataag cactatgaag atcagctgaa aatgtacgaa attttggcc    3716
gtaagtcgct ctggttaacg aagcaggatg tggaggcgca taaggagtcg tct aga      3772
                                                         Ser Arg gac aac tct aag aat act ctc tac ttg cag atg aac agc tta agt ctg      3820
Asp Asn Ser Lys Asn Thr Leu Tyr Leu Gln Met Asn Ser Leu Ser Leu
475                 480                 485                 490 agc att cgg tcc ggg caa cat tct cca aac tgaccagacg acacaaacgg       3870
Ser Ile Arg Ser Gly Gln His Ser Pro Asn
                495                 500 cttacgctaa atcccgcgca tgggatggta aagaggtggc gtctttgctg gcctggactc    3930
atcagatgaa ggccaaaaat tggcaggagt ggacacagca ggcagcgaaa caagcactga    3990
ccatcaactg gtactatgct gatgtaaacg gcaatattgg ttatgttcat actggtgctt    4050
atccagatcg tcaatcaggc catgatccgc gattacccgt tcctggtacg ggaaaatggg    4110
actggaaagg gctattgcct tttgaaatga accctaaggt gtataacccc cagaagctag    4170
```

-continued

| | |
|---|---|
| cctgcggctt cggtcaccgt ctcaagc gcc tcc acc aag ggc cca tcg gtc ttc<br>                                                Ala Ser Thr Lys Gly Pro Ser Val Phe<br>                                                         505 | 4224 |
| ccc ctg gca ccc tcc tcc aag agc acc tct ggg ggc aca gcg gcc ctg<br>Pro Leu Ala Pro Ser Ser Lys Ser Thr Ser Gly Gly Thr Ala Ala Leu<br>510                       515                    520                      525 | 4272 |
| ggc tgc ctg gtc aag gac tac ttc ccc gaa ccg gtg acg gtg tcg tgg<br>Gly Cys Leu Val Lys Asp Tyr Phe Pro Glu Pro Val Thr Val Ser Trp<br>                          530                            535                      540 | 4320 |
| aac tca ggc gcc ctg acc agc ggc gtc cac acc ttc ccg gct gtc cta<br>Asn Ser Gly Ala Leu Thr Ser Gly Val His Thr Phe Pro Ala Val Leu<br>                     545                          550 | 4368 |
| cag tcc tca gga ctc tac tcc ctc agc agc gta gtg acc gtg ccc tcc<br>Gln Ser Ser Gly Leu Tyr Ser Leu Ser Ser Val Val Thr Val Pro Ser<br>            560                    565                    570 | 4416 |
| agc agc ttg ggc acc cag acc tac atc tgc aac gtg aat cac aag ccc<br>Ser Ser Leu Gly Thr Gln Thr Tyr Ile Cys Asn Val Asn His Lys Pro<br>575                       580                    585 | 4464 |
| agc aac acc aag gtg gac aag aaa gtt gag ccc aaa tct tgt gcg gcc<br>Ser Asn Thr Lys Val Asp Lys Lys Val Glu Pro Lys Ser Cys Ala Ala<br>590                       595                    600                    605 | 4512 |
| gca cat cat cat cac cat cac ggg gcc gca gaa caa aaa ctc atc tca<br>Ala His His His His His His Gly Ala Ala Glu Gln Lys Leu Ile Ser<br>                     610                        615                    620 | 4560 |
| gaa gag gat ctg aat ggg gcc gca tag act gtt gaa agt tgt tta gca<br>Glu Glu Asp Leu Asn Gly Ala Ala     Thr Val Glu Ser Cys Leu Ala<br>                   625                           630                    635 | 4608 |
| aaa cct cat aca gaa aat tca ttt act aac gtc tgg aaa gac gac aaa<br>Lys Pro His Thr Glu Asn Ser Phe Thr Asn Val Trp Lys Asp Asp Lys<br>            640                    645                    650 | 4656 |
| act tta gat cgt tac gct aac tat gag ggc tgt ctg tgg aat gct aca<br>Thr Leu Asp Arg Tyr Ala Asn Tyr Glu Gly Cys Leu Trp Asn Ala Thr<br>                     655                        660                    665 | 4704 |
| ggc gtt gtg gtt tgt act ggt gac gaa act cag tgt tac ggt aca tgg<br>Gly Val Val Val Cys Thr Gly Asp Glu Thr Gln Cys Tyr Gly Thr Trp<br>            670                    675                    680 | 4752 |
| gtt cct att ggg ctt gct atc cct gaa aat gag ggt ggt ggc tct gag<br>Val Pro Ile Gly Leu Ala Ile Pro Glu Asn Glu Gly Gly Gly Ser Glu<br>685                       690                    695                    700 | 4800 |
| ggt ggc ggt tct gag ggt ggc ggt tct gag ggt ggc ggt act aaa cct<br>Gly Gly Gly Ser Glu Gly Gly Gly Ser Glu Gly Gly Gly Thr Lys Pro<br>                     705                        710                    715 | 4848 |
| cct gag tac ggt gat aca cct att ccg ggc tat act tat atc aac cct<br>Pro Glu Tyr Gly Asp Thr Pro Ile Pro Gly Tyr Thr Tyr Ile Asn Pro<br>            720                    725                    730 | 4896 |
| ctc gac ggc act tat ccg cct ggt act gag caa aac ccc gct aat cct<br>Leu Asp Gly Thr Tyr Pro Pro Gly Thr Glu Gln Asn Pro Ala Asn Pro<br>                   735                        740                    745 | 4944 |
| aat cct tct ctt gag gag tct cag cct ctt aat act ttc atg ttt cag<br>Asn Pro Ser Leu Glu Glu Ser Gln Pro Leu Asn Thr Phe Met Phe Gln<br>750                       755                    760 | 4992 |
| aat aat agg ttc cga aat agg cag ggt gca tta act gtt tat acg ggc<br>Asn Asn Arg Phe Arg Asn Arg Gln Gly Ala Leu Thr Val Tyr Thr Gly<br>765                       770                    775                    780 | 5040 |
| act gtt act caa ggc act gac ccc gtt aaa act tat tac cag tac act<br>Thr Val Thr Gln Gly Thr Asp Pro Val Lys Thr Tyr Tyr Gln Tyr Thr<br>                   785                        790                    795 | 5088 |
| cct gta tca tca aaa gcc atg tat gac gct tac tgg aac ggt aaa ttc<br>Pro Val Ser Ser Lys Ala Met Tyr Asp Ala Tyr Trp Asn Gly Lys Phe<br>            800                    805                    810 | 5136 |

```
aga gac tgc gct ttc cat tct ggc ttt aat gag gat cca ttc gtt tgt    5184
Arg Asp Cys Ala Phe His Ser Gly Phe Asn Glu Asp Pro Phe Val Cys
        815                 820                 825 gaa tat caa ggc caa tcg tct gac ctg cct caa cct cct gtc aat gct    5232
Glu Tyr Gln Gly Gln Ser Ser Asp Leu Pro Gln Pro Pro Val Asn Ala
830                 835                 840 ggc ggc ggc tct ggt ggt ggt tct ggt ggc ggc tct gag ggt ggc ggc    5280
Gly Gly Gly Ser Gly Gly Gly Ser Gly Gly Gly Ser Glu Gly Gly Gly
845                 850                 855                 860 tct gag ggt ggc ggt tct gag ggt ggc ggc tct gag ggt ggc ggt tcc    5328
Ser Glu Gly Gly Gly Ser Glu Gly Gly Gly Ser Glu Gly Gly Gly Ser
        865                 870                 875 ggt ggc ggc tcc ggt tcc ggt gat ttt gat tat gaa aaa atg gca aac    5376
Gly Gly Gly Ser Gly Ser Gly Asp Phe Asp Tyr Glu Lys Met Ala Asn
                880                 885                 890 gct aat aag ggg gct atg acc gaa aat gcc gat gaa aac gcg cta cag    5424
Ala Asn Lys Gly Ala Met Thr Glu Asn Ala Asp Glu Asn Ala Leu Gln
            895                 900                 905 tct gac gct aaa ggc aaa ctt gat tct gtc gct act gat tac ggt gct    5472
Ser Asp Ala Lys Gly Lys Leu Asp Ser Val Ala Thr Asp Tyr Gly Ala
910                 915                 920 gct atc gat ggt ttc att ggt gac gtt tcc ggc ctt gct aat ggt aat    5520
Ala Ile Asp Gly Phe Ile Gly Asp Val Ser Gly Leu Ala Asn Gly Asn
925                 930                 935                 940 ggt gct act ggt gat ttt gct ggc tct aat tcc caa atg gct caa gtc    5568
Gly Ala Thr Gly Asp Phe Ala Gly Ser Asn Ser Gln Met Ala Gln Val
        945                 950                 955 ggt gac ggt gat aat tca cct tta atg aat aat ttc cgt caa tat tta    5616
Gly Asp Gly Asp Asn Ser Pro Leu Met Asn Asn Phe Arg Gln Tyr Leu
                960                 965                 970 cct tct ttg cct cag tcg gtt gaa tgt cgc cct tat gtc ttt ggc gct    5664
Pro Ser Leu Pro Gln Ser Val Glu Cys Arg Pro Tyr Val Phe Gly Ala
            975                 980                 985 ggt aaa cca tat gaa ttt tct att gat tgt gac aaa ata aac tta ttc    5712
Gly Lys Pro Tyr Glu Phe Ser Ile Asp Cys Asp Lys Ile Asn Leu Phe
990                 995                 1000 cgt ggt gtc ttt gcg ttt ctt tta tat gtt gcc acc ttt atg tat gta    5760
Arg Gly Val Phe Ala Phe Leu Leu Tyr Val Ala Thr Phe Met Tyr Val
1005                1010                1015                1020 ttt tcg acg ttt gct aac ata ctg cgt aat aag gag tct taataagaat    5809
Phe Ser Thr Phe Ala Asn Ile Leu Arg Asn Lys Glu Ser
                1025                1030 tcactggccg tcgttttaca acgtcgtgac tgggaaaacc ctggcgttac ccaacttaat    5869
cgccttgcag cacatccccc tttcgccagc tggcgtaata gcgaagaggc ccgcaccgat    5929
cgcccttccc aacagttgcg cagcctgaat ggcgaatggc gcctgatgcg gtattttctc    5989
cttacgcatc tgtgcggtat ttcacaccgc atataaattg taaacgttaa tattttgtta    6049
aaattcgcgt taaattttg ttaaatcagc tcattttta accataggc cgaaatcggc    6109 aaaatccctt ataaatcaaa agaatagccc gagatagggt tgagtgttgt tccagtttgg    6169
aacaagagtc cactattaaa gaacgtggac tccaacgtca aagggcgaaa aaccgtctat    6229
cagggcgatg gcccactacg tgaaccatca cccaaatcaa gttttttggg gtcgaggtgc    6289
cgtaaagcac taaatcggaa ccctaaaggg agcccccgat ttagagcttg acggggaaag    6349
ccggcgaacg tggcgagaaa ggaagggaag aaagcgaaag gagcgggcgc tagggcgctg    6409
gcaagtgtag cggtcacgct gcgcgtaacc accacacccg ccgcgcttaa tgcgccgcta    6469
```

```
caggqcqcgt actatggttg cttttgacggg tgcagtctca gtacaatctg ctctgatgcc    6529
gcatagttaa gccagccccg acacccgcca acacccgctg acgcgccctg acgggcttgt    6589
ctgctcccgg catccgctta cagacaagct gtgaccgtct ccgggagctg catgtgtcag    6649
aggttttcac cgtcatcacc gaaacgcgcg a                                    6680
```

<210> SEQ ID NO 523
<211> LENGTH: 286
<212> TYPE: PRT
<213> ORGANISM: Artificial Sequence
<220> FEATURE:
<223> OTHER INFORMATION: Description of Artificial Sequence: Vector
pCES5 protein sequence

<400> SEQUENCE: 523

```
Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
           100                 105                 110

Asp Gly Met Thr Val Arg Glu Leu Cys Ser Ala Ala Ile Thr Met Ser
       115                 120                 125

Asp Asn Thr Ala Ala Asn Leu Leu Leu Thr Thr Ile Gly Gly Pro Lys
   130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
           180                 185                 190

Thr Gly Glu Leu Leu Thr Leu Ala Ser Arg Gln Gln Leu Ile Asp Trp
       195                 200                 205

Met Glu Ala Asp Lys Val Ala Gly Pro Leu Leu Arg Ser Ala Leu Pro
   210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
           260                 265                 270

Arg Gln Ile Ala Glu Ile Gly Ala Ser Leu Ile Lys His Trp
       275                 280                 285
```

<210> SEQ ID NO 524
<211> LENGTH: 138
<212> TYPE: PRT
<213> ORGANISM: Artificial Sequence
<220> FEATURE:

<223> OTHER INFORMATION: Description of Artificial Sequence: Vector
      pCES5 protein sequence

<400> SEQUENCE: 524

Met Lys Lys Leu Leu Phe Ala Ile Pro Leu Val Val Pro Phe Tyr Ser
1               5                   10                  15

His Ser Ala Gln Val Gln Leu Gln Val Asp Leu Glu Ile Lys Arg Gly
            20                  25                  30

Thr Val Ala Ala Pro Ser Val Phe Ile Phe Pro Pro Ser Asp Glu Gln
        35                  40                  45

Leu Lys Ser Gly Thr Ala Ser Val Val Cys Leu Leu Asn Asn Phe Tyr
    50                  55                  60

Pro Arg Glu Ala Lys Val Gln Trp Lys Val Asp Asn Ala Leu Gln Ser
65                  70                  75                  80

Gly Asn Ser Gln Glu Ser Val Thr Glu Gln Asp Ser Lys Asp Ser Thr
                85                  90                  95

Tyr Ser Leu Ser Ser Thr Leu Thr Leu Ser Lys Ala Asp Tyr Glu Lys
            100                 105                 110

His Lys Val Tyr Ala Cys Glu Val Thr His Gln Gly Leu Ser Ser Pro
        115                 120                 125

Val Thr Lys Ser Phe Asn Arg Gly Glu Cys
    130                 135

<210> SEQ ID NO 525
<211> LENGTH: 48
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 525

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

<210> SEQ ID NO 526
<211> LENGTH: 28
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 526

Ser Arg Asp Asn Ser Lys Asn Thr Leu Tyr Leu Gln Met Asn Ser Leu
1               5                   10                  15

Ser Leu Ser Ile Arg Ser Gly Gln His Ser Pro Asn
            20                  25

<210> SEQ ID NO 527
<211> LENGTH: 533
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 527

-continued

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Ala Ala Ala His His His His His His
            100                 105                 110

Gly Ala Ala Glu Gln Lys Leu Ile Ser Glu Glu Asp Leu Asn Gly Ala
            115                 120                 125

Ala Thr Val Glu Ser Cys Leu Ala Lys Pro His Thr Glu Asn Ser Phe
            130                 135                 140

Thr Asn Val Trp Lys Asp Asp Lys Thr Leu Asp Arg Tyr Ala Asn Tyr
145                 150                 155                 160

Glu Gly Cys Leu Trp Asn Ala Thr Gly Val Val Cys Thr Gly Asp
                165                 170                 175

Glu Thr Gln Cys Tyr Gly Thr Trp Val Pro Ile Gly Leu Ala Ile Pro
                180                 185                 190

Glu Asn Glu Gly Gly Gly Ser Glu Gly Gly Ser Glu Gly Gly
            195                 200                 205

Ser Glu Gly Gly Gly Thr Lys Pro Pro Glu Tyr Gly Asp Thr Pro Ile
            210                 215                 220

Pro Gly Tyr Thr Tyr Ile Asn Pro Leu Asp Gly Thr Tyr Pro Pro Gly
225                 230                 235                 240

Thr Glu Gln Asn Pro Ala Asn Pro Asn Pro Ser Leu Glu Glu Ser Gln
                245                 250                 255

Pro Leu Asn Thr Phe Met Phe Gln Asn Asn Arg Phe Arg Asn Arg Gln
            260                 265                 270

Gly Ala Leu Thr Val Tyr Thr Gly Thr Val Thr Gln Gly Thr Asp Pro
            275                 280                 285

Val Lys Thr Tyr Tyr Gln Tyr Thr Pro Val Ser Ser Lys Ala Met Tyr
            290                 295                 300

Asp Ala Tyr Trp Asn Gly Lys Phe Arg Asp Cys Ala Phe His Ser Gly
305                 310                 315                 320

Phe Asn Glu Asp Pro Phe Val Cys Glu Tyr Gln Gly Gln Ser Ser Asp
                325                 330                 335

Leu Pro Gln Pro Pro Val Asn Ala Gly Gly Gly Ser Gly Gly Gly Ser
            340                 345                 350

Gly Gly Gly Ser Glu Gly Gly Ser Glu Gly Gly Ser Glu Gly
            355                 360                 365

Gly Gly Ser Glu Gly Gly Ser Gly Gly Ser Gly Ser Gly Asp
        370                 375                 380

Phe Asp Tyr Glu Lys Met Ala Asn Ala Asn Lys Gly Ala Met Thr Glu
385                 390                 395                 400

Asn Ala Asp Glu Asn Ala Leu Gln Ser Asp Ala Lys Gly Lys Leu Asp
                405                 410                 415
```

```
Ser Val Ala Thr Asp Tyr Gly Ala Ala Ile Asp Gly Phe Ile Gly Asp
            420                 425                 430

Val Ser Gly Leu Ala Asn Gly Asn Gly Ala Thr Gly Asp Phe Ala Gly
        435                 440                 445

Ser Asn Ser Gln Met Ala Gln Val Gly Asp Gly Asp Asn Ser Pro Leu
    450                 455                 460

Met Asn Asn Phe Arg Gln Tyr Leu Pro Ser Leu Pro Gln Ser Val Glu
465                 470                 475                 480

Cys Arg Pro Tyr Val Phe Gly Ala Gly Lys Pro Tyr Glu Phe Ser Ile
                485                 490                 495

Asp Cys Asp Lys Ile Asn Leu Phe Arg Gly Val Phe Ala Phe Leu Leu
            500                 505                 510

Tyr Val Ala Thr Phe Met Tyr Val Phe Ser Thr Phe Ala Asn Ile Leu
        515                 520                 525

Arg Asn Lys Glu Ser
    530
```

<210> SEQ ID NO 528
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
acctcactgg cttccggatt cactttctct                30

<210> SEQ ID NO 529
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
agaaacccac tccaaacctt taccaggagc ttggcgaacc ca          42

<210> SEQ ID NO 530
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ggaaggcagt gatctagaga tagtgaagcg acctttaacg gagtcagcat a     51

<210> SEQ ID NO 531
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ggaaggcagt gatctagaga tag                  23

<210> SEQ ID NO 532
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gtgctgactc agccaccctc                                                   20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gccctgactc agcctgcctc                                                   20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gagctgactc aggaccctgc                                                   20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
gagctgactc agccaccctc                                                   20

<210> SEQ ID NO 536
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
cctcgacagc gaagtgcaca gagcgtcttg actcagcc                               38

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
cctcgacagc gaagtgcaca gagcgtcttg                                        30

<210> SEQ ID NO 538
<211> LENGTH: 38
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 538
cctcgacagc gaagtgcaca gagcgctttg actcagcc                              38

<210> SEQ ID NO 539
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
cctcgacagc gaagtgcaca gagcgctttg                                       30

<210> SEQ ID NO 540
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
cctcgacagc taagtgcaca gagcgctttg actcagcc                              38

<210> SEQ ID NO 541
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
cctcgacagc gaagtgcaca gagcgctttg                                       30

<210> SEQ ID NO 542
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
cctcgacagc gaagtgcaca gagcgaattg actcagcc                              38

<210> SEQ ID NO 543
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
cctcgacagc gaagtgcaca gagcgaattg                                       30

<210> SEQ ID NO 544
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 544
cctcgacagc gaagtgcaca gtacgaattg actcagcc                                38

<210> SEQ ID NO 545
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
cctcgacagc gaagtgcaca gtacgaattg                                         30

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
cctcgacagc gaagtgcaca g                                                  21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
ccgtgtatta ctgtgcgaga g                                                  21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
ctgtgtatta ctgtgcgaga g                                                  21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
ccgtatatta ctgtgcgaaa g                                                  21

<210> SEQ ID NO 550
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 550
ctgtgtatta ctgtgcgaaa g                                               21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
ctgtgtatta ctgtgcgaga c                                               21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
ccatgtatta ctgtgcgaga c                                               21

<210> SEQ ID NO 553
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
ggtgtagtga tctagtgaca actctaagaa tactctctac ttgcagatga acagctttag     60
ggctgaggac actgcagtct actattgtgc gaga                                 94

<210> SEQ ID NO 554
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
ggtgtagtga tctagtgaca actctaagaa tactctctac ttgcagatga acagctttag     60
ggctgaggac actgcagtct actattgtgc gaaa                                 94

<210> SEQ ID NO 555
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
atagtagact gcagtgtcct cagcccttaa gctgttcatc tgcaagtaga gagtattctt     60
agagttgtct ctagatcact acacc                                           85
```

```
<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556
gactgggtgt agtgatctag                                                   20

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
cttttctttg ttgccgttgg ggtg                                              24

<210> SEQ ID NO 558
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 558
nnnnnnnnng caggt                                                        15

<210> SEQ ID NO 559
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 559
acctgcnnnn n                                                            11

<210> SEQ ID NO 560
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 560 gatnnnnatc                                                              10

<210> SEQ ID NO 561
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, t, c, g, unknown or other

<400> SEQUENCE: 561
gaggagnnnn nnnnnn                                                      16

<210> SEQ ID NO 562
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 562
nnnnnnnnnn ctcctc                                                      16

<210> SEQ ID NO 563
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, t, c, g, unknown or other

<400> SEQUENCE: 563 ctcttcnnnn                                                             10

<210> SEQ ID NO 564
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, t, c, g, unknown or other

<400> SEQUENCE: 564
nnnnngaaga g                                                           11

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, t, c, g, unknown or other

<400> SEQUENCE: 565
```

```
nnnnnnnnnn nnnnngtccc                                                    20

<210> SEQ ID NO 566
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 566
gacnnnnnng tc                                                            12

<210> SEQ ID NO 567
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 567
cgtctcnnnn n                                                             11

<210> SEQ ID NO 568
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 568
gtatccnnnn nn                                                            12

<210> SEQ ID NO 569
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 569
gcannnnnnt cg                                                            12

<210> SEQ ID NO 570
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (4)..(8)
<223> OTHER INFORMATION: a, t, c, g, unknown or other

<400> SEQUENCE: 570
gccnnnnngg c                                                              11

<210> SEQ ID NO 571
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 571
ggtctcnnnn n                                                              11

<210> SEQ ID NO 572
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 572
gacnnnnngt c                                                              11

<210> SEQ ID NO 573
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 573
gacnnnnngt c                                                              11

<210> SEQ ID NO 574
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 574
ccannnnntg g                                                              11

<210> SEQ ID NO 575
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 575
ccannnnnnn nntgg                                                          15

<210> SEQ ID NO 576
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 576
ggccnnnnng gcc                                                            13

<210> SEQ ID NO 577
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 577
ccannnnnnt gg                                                             12

<210> SEQ ID NO 578
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 578
cctnnnnnag g                                                              11

<210> SEQ ID NO 579
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other
```

-continued

<400> SEQUENCE: 579 gacnnnngtc                                                            10

<210> SEQ ID NO 580
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 580
ccannnnnnn nntgg                                                      15

<210> SEQ ID NO 581
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 581
gcannnnntg c                                                          11

<210> SEQ ID NO 582
<211> LENGTH: 10251
<212> TYPE: DNA
<213> ORGANISM: Artificial Sequence
<220> FEATURE:
<223> OTHER INFORMATION: Description of Artificial Sequence: CJRA05
      nucleotide sequence
<220> FEATURE:
<221> NAME/KEY: CDS
<222> LOCATION: (1578)..(1916)
<220> FEATURE:
<221> NAME/KEY: CDS
<222> LOCATION: (2388)..(2843)
<220> FEATURE:
<221> NAME/KEY: CDS
<222> LOCATION: (2849)..(2893)
<220> FEATURE:
<221> NAME/KEY: CDS
<222> LOCATION: (3189)..(4232)
<220> FEATURE:
<221> NAME/KEY: CDS
<222> LOCATION: (7418)..(8119)
<220> FEATURE:
<221> NAME/KEY: CDS
<222> LOCATION: (8160)..(9452)

<400> SEQUENCE: 582
aatgctacta ctattagtag aattgatgcc acctttcag ctcgcgcccc aaatgaaaat      60
atagctaaac aggttattga ccatttgcga aatgtatcta atggtcaaac taaatctact    120
cgttcgcaga attgggaatc aactgttata tggaatgaaa cttccagaca ccgtacttta   180
gttgcatatt taaacatgt tgagctacag cattatattc agcaattaag ctctaagcca    240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag   360

```
tctttcgggc ttcctcttaa tcttttgat gcaatccgct ttgcttctga ctataatagt      420
cagggtaaag acctgatttt tgatttatgg tcattctcgt tttctgaact gtttaaagca      480
tttgagggg attcaatgaa tatttatgac gattccgcag tattggacgc tatccagtct      540
aaacatttta ctattacccc ctctggcaaa acttcttttg caaaagcctc tcgctatttt      600
ggtttttatc gtcgtctggt aaacgagggt tatgatagtg ttgctcttac tatgcctcgt      660
aattcctttt ggcgttatgt atctgcatta gttgaatgtg gtattcctaa atctcaactg      720
atgaatcttt ctacctgtaa taatgttgtt ccgttagttc gttttattaa cgtagatttt      780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg agcaggtcg cggatttcga cacaatttat     1140
caggcgatga tacaaatctc cgttgtactt tgtttcgcgc ttggtataat cgctggggt      1200
caaagatgag tgttttagtg tattcttttg cctctttcgt tttaggttgg tgccttcgta     1260
gtggcattac gtattttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactccct gcaagcctca gcgaccgaat atatcggtta     1440
tgcgtgggcg atggttgttg tcattgtcgg cgcaactatc ggtatcaagc tgtttaagaa     1500
attcacctcg aaagcaagct gataaaccga tacaattaaa ggctcctttt ggagcctttt     1560
ttttggagat tttcaac gtg aaa aaa tta tta ttc gca att cct tta gtt        1610
                     Met Lys Lys Leu Leu Phe Ala Ile Pro Leu Val
                       1               5                  10
gtt cct ttc tat tct ggc gcg gcc gaa tca cat cta gac ggc gcc gct        1658
Val Pro Phe Tyr Ser Gly Ala Ala Glu Ser His Leu Asp Gly Ala Ala
            15                  20                  25
gaa act gtt gaa agt tgt tta gca aaa tcc cat aca gaa aat tca ttt        1706
Glu Thr Val Glu Ser Cys Leu Ala Lys Ser His Thr Glu Asn Ser Phe
        30                  35                  40
act aac gtc tgg aaa gac gac aaa act tta gat cgt tac gct aac tat        1754
Thr Asn Val Trp Lys Asp Asp Lys Thr Leu Asp Arg Tyr Ala Asn Tyr
    45                  50                  55
gag ggc tgt ctg tgg aat gct aca ggc gtt gta gtt tgt act ggt gac        1802
Glu Gly Cys Leu Trp Asn Ala Thr Gly Val Val Val Cys Thr Gly Asp
60                  65                  70                  75
gaa act cag tgt tac ggt aca tgg gtt cct att ggg ctt gct atc cct        1850
Glu Thr Gln Cys Tyr Gly Thr Trp Val Pro Ile Gly Leu Ala Ile Pro
                80                  85                  90
gaa aat gag ggt ggt ggc tct gag ggt ggc ggt tct gag ggt ggc ggt        1898
Glu Asn Glu Gly Gly Gly Ser Glu Gly Gly Gly Ser Glu Gly Gly Gly
                95                 100                 105
tct gag ggt ggc ggt act aaacctcctg agtacggtga tacacctatt                1946
Ser Glu Gly Gly Gly Thr
            110
ccgggctata cttatatcaa ccctctcgac ggcacttatc cgcctggtac tgagcaaaac     2006
cccgctaatc ctaatccttc tcttgaggag tctcagcctc ttaatacttt catgtttcag     2066
aataataggt tccgaaatag gcaggggca ttaactgttt atacgggcac tgttactcaa     2126
ggcactgacc ccgttaaaac ttattaccag tacactcctg tatcatcaaa agccatgtat     2186
```

```
gacgcttact ggaacggtaa attcagagac tgcgctttcc attctggctt taatgaggat    2246
ttatttgttt gtgaatatca aggccaatcg tctgacctgc ctcaacctcc tgtcaatgct    2306
ggcggcggct ctggtggtgg ttctggtggc ggctctgagg gtggtggctc tgagggaggc    2366
ggttccggtg gtggctctgg t tcc ggt gat ttt gat tat gaa aag atg gca    2417
                        Ser Gly Asp Phe Asp Tyr Glu Lys Met Ala
                        115                 120 aac gct aat aag ggg gct atg acc gaa aat gcc gat gaa aac gcg cta    2465
Asn Ala Asn Lys Gly Ala Met Thr Glu Asn Ala Asp Glu Asn Ala Leu
        125                 130                 135 cag tct gac gct aaa ggc aaa ctt gat tct gtc gct act gat tac ggt    2513
Gln Ser Asp Ala Lys Gly Lys Leu Asp Ser Val Ala Thr Asp Tyr Gly
140                 145                 150                 155 gct gct atc gat ggt ttc att ggt gac gtt tcc ggc ctt gct aat ggt    2561
Ala Ala Ile Asp Gly Phe Ile Gly Asp Val Ser Gly Leu Ala Asn Gly
                160                 165                 170 aat ggt gct act ggt gat ttt gct ggc tct aat tcc caa atg gct caa    2609
Asn Gly Ala Thr Gly Asp Phe Ala Gly Ser Asn Ser Gln Met Ala Gln
        175                 180                 185 gtc ggt gac ggt gat aat tca cct tta atg aat aat ttc cgt caa tat    2657
Val Gly Asp Gly Asp Asn Ser Pro Leu Met Asn Asn Phe Arg Gln Tyr
190                 195                 200 tta cct tcc ctc cct caa tcg gtt gaa tgt cgc cct ttt gtc ttt ggc    2705
Leu Pro Ser Leu Pro Gln Ser Val Glu Cys Arg Pro Phe Val Phe Gly
205                 210                 215 gct ggt aaa cca tat gaa ttt tct att gat tgt gac aaa ata aac tta    2753
Ala Gly Lys Pro Tyr Glu Phe Ser Ile Asp Cys Asp Lys Ile Asn Leu
220                 225                 230                 235 ttc cgt ggt gtc ttt gcg ttt ctt tta tat gtt gcc acc ttt atg tat    2801
Phe Arg Gly Val Phe Ala Phe Leu Leu Tyr Val Ala Thr Phe Met Tyr
                240                 245                 250 gta ttt tct acg ttt gct aac ata ctg cgt aat aag gag tct taatc atg    2851
Val Phe Ser Thr Phe Ala Asn Ile Leu Arg Asn Lys Glu Ser           Met
                255                 260                 265 cca gtt ctt ttg ggt att ccg tta tta ttg cgt ttc ctc ggt           2893
Pro Val Leu Leu Gly Ile Pro Leu Leu Leu Arg Phe Leu Gly
        270                 275                 280 ttccttctgg taactttgtt cggctatctg cttactttc ttaaaaaggg cttcggtaag    2953
atagctattg ctatttcatt gtttcttgct cttattattg gcttaactc aattcttgtg    3013 ggttatctct ctgatattag cgctcaatta ccctctgact tgttcaggg tgttcagtta    3073 attctcccgt ctaatgcgct tccctgtttt tatgttattc tctctgtaaa ggctgctatt    3133 ttcattttg acgttaaaca aaaaatcgtt tcttatttgg attgggataa ataat atg    3191
                                                                Met gct gtt tat ttt gta act ggc aaa tta ggc tct gga aag acg ctc gtt    3239
Ala Val Tyr Phe Val Thr Gly Lys Leu Gly Ser Gly Lys Thr Leu Val
            285                 290                 295 agc gtt ggt aag att cag gat aaa att gta gct ggg tgc aaa ata gca    3287
Ser Val Gly Lys Ile Gln Asp Lys Ile Val Ala Gly Cys Lys Ile Ala
        300                 305                 310 act aat ctt gat tta agg ctt caa aac ctc ccg caa gtc ggg agg ttc    3335
Thr Asn Leu Asp Leu Arg Leu Gln Asn Leu Pro Gln Val Gly Arg Phe
315                 320                 325 gct aaa acg cct cgc gtt ctt aga ata ccg gat aag cct tct ata tct    3383
Ala Lys Thr Pro Arg Val Leu Arg Ile Pro Asp Lys Pro Ser Ile Ser
330                 335                 340                 345 gat ttg ctt gct att ggg cgc ggt aat gat tcc tac gat gaa aat aaa    3431
```

```
                Asp Leu Leu Ala Ile Gly Arg Gly Asn Asp Ser Tyr Asp Glu Asn Lys
                                350                 355                 360 aac ggc ttg ctt gtt ctc gat gag tgc ggt act tgg ttt aat acc cgt        3479
Asn Gly Leu Leu Val Leu Asp Glu Cys Gly Thr Trp Phe Asn Thr Arg
            365                 370                 375 tct tgg aat gat aag gaa aga cag ccg att att gat tgg ttt cta cat        3527
Ser Trp Asn Asp Lys Glu Arg Gln Pro Ile Ile Asp Trp Phe Leu His
        380                 385                 390 gct cgt aaa tta gga tgg gat att att ttt ctt gtt cag gac tta tct        3575
Ala Arg Lys Leu Gly Trp Asp Ile Ile Phe Leu Val Gln Asp Leu Ser
    395                 400                 405 att gtt gat aaa cag gcg cgt tct gca tta gct gaa cat gtt gtt tat        3623
Ile Val Asp Lys Gln Ala Arg Ser Ala Leu Ala Glu His Val Val Tyr
410                 415                 420                 425 tgt cgt cgt ctg gac aga att act tta cct ttt gtc ggt act tta tat        3671
Cys Arg Arg Leu Asp Arg Ile Thr Leu Pro Phe Val Gly Thr Leu Tyr
                430                 435                 440 tct ctt att act ggc tcg aaa atg cct ctg cct aaa tta cat gtt ggc        3719
Ser Leu Ile Thr Gly Ser Lys Met Pro Leu Pro Lys Leu His Val Gly
            445                 450                 455 gtt gtt aaa tat ggc gat tct caa tta agc cct act gtt gag cgt tgg        3767
Val Val Lys Tyr Gly Asp Ser Gln Leu Ser Pro Thr Val Glu Arg Trp
        460                 465                 470 ctt tat act ggt aag aat ttg tat aac gca tat gat act aaa cag gct        3815
Leu Tyr Thr Gly Lys Asn Leu Tyr Asn Ala Tyr Asp Thr Lys Gln Ala
    475                 480                 485 ttt tct agt aat tat gat tcc ggt gtt tat tct tat tta acg cct tat        3863
Phe Ser Ser Asn Tyr Asp Ser Gly Val Tyr Ser Tyr Leu Thr Pro Tyr
490                 495                 500                 505 tta tca cac ggt cgg tat ttc aaa cca tta aat tta ggt cag aag atg        3911
Leu Ser His Gly Arg Tyr Phe Lys Pro Leu Asn Leu Gly Gln Lys Met
                510                 515                 520 aaa tta act aaa ata tat ttg aaa aag ttt tct cgc gtt ctt tgt ctt        3959
Lys Leu Thr Lys Ile Tyr Leu Lys Lys Phe Ser Arg Val Leu Cys Leu
            525                 530                 535 gcg att gga ttt gca tca gca ttt aca tat agt tat ata acc caa cct        4007
Ala Ile Gly Phe Ala Ser Ala Phe Thr Tyr Ser Tyr Ile Thr Gln Pro
        540                 545                 550 aag ccg gag gtt aaa aag gta gtc tct cag acc tat gat ttt gat aaa        4055
Lys Pro Glu Val Lys Lys Val Val Ser Gln Thr Tyr Asp Phe Asp Lys
    555                 560                 565 ttc act att gac tct tct cag cgt ctt aat cta agc tat cgc tat gtt        4103
Phe Thr Ile Asp Ser Ser Gln Arg Leu Asn Leu Ser Tyr Arg Tyr Val
570                 575                 580                 585 ttc aag gat tct aag gga aaa tta att aat agc gac gat tta cag aag        4151
Phe Lys Asp Ser Lys Gly Lys Leu Ile Asn Ser Asp Asp Leu Gln Lys
                590                 595                 600 caa ggt tat tca ctc aca tat att gat tta tgt act gtt tcc att aaa        4199
Gln Gly Tyr Ser Leu Thr Tyr Ile Asp Leu Cys Thr Val Ser Ile Lys
            605                 610                 615 aaa ggt aat tca aat gaa att gtt aaa tgt aat taattttgtt ttcttgatgt      4252
Lys Gly Asn Ser Asn Glu Ile Val Lys Cys Asn
        620                 625 ttgtttcatc atcttctttt gctcaggtaa ttgaaatgaa taattcgcct ctgcgcgatt      4312
ttgtaacttg gtattcaaag caatcaggcg aatccgttat tgtttctccc gatgtaaaag      4372
gtactgttac tgtatattca tctgacgtta aacctgaaaa tctacgcaat ttctttattt      4432
ctgttttacg tgcaaataat tttgatatgg taggttctaa cccttccatt attcagaagt      4492
```

```
ataatccaaa caatcaggat tatattgatg aattgccatc atctgataat caggaatatg    4552
atgataattc cgctccttct ggtggtttct ttgttccgca aaatgataat gttactcaaa    4612
cttttaaaat taataacgtt cgggcaaagg atttaatacg agttgtcgaa ttgtttgtaa    4672
agtctaatac ttctaaatcc tcaaatgtat tatctattga cggctctaat ctattagttg    4732
ttagtgctcc taaagatatt ttagataacc ttcctcaatt cctttcaact gttgatttgc    4792
caactgacca gatattgatt gagggtttga tatttgaggt tcagcaaggt gatgctttag    4852
attttcatt tgctgctggc tctcagcgtg gcactgttgc aggcggtgtt aatactgacc    4912
gcctcacctc tgttttatct tctgctggtg gttcgttcgg tattttaat ggcgatgttt    4972
tagggctatc agttcgcgca ttaaagacta atagccattc aaaaatattg tctgtgccac    5032
gtattcttac gctttcaggt cagaagggtt ctatctctgt tggccagaat gtcccttta    5092
ttactggtcg tgtgactggt gaatctgcca atgtaaataa tccatttcag acgattgagc    5152
gtcaaaatgt aggtatttcc atgagcgttt ttcctgttgc aatggctggc ggtaatattg    5212
ttctggatat taccagcaag gccgatagtt tgagttcttc tactcaggca agtgatgtta    5272
ttactaatca agaagtatt gctacaacgg ttaatttgcg tgatggacag actcttttac    5332
tcggtggcct cactgattat aaaaacactt ctcaggattc tggcgtaccg ttcctgtcta    5392
aaatcccttt aatcggcctc ctgtttagct cccgctctga ttctaacgag gaaagcacgt    5452
tatacgtgct cgtcaaagca accatagtac gcgccctgta gcggcgcatt aagcgcggcg    5512
ggtgtggtgg ttacgcgcag cgtgaccgct acacttgcca gcgccctagc gcccgctcct    5572
ttcgctttct tcccttcctt tctcgccacg ttcgccggct ttccccgtca gctctaaat    5632
cgggggctcc ctttagggtt ccgatttagt gctttacggc acctcgaccc caaaaaactt    5692
gatttgggtg atggttcacg tagtgggcca tcgccctgat agacggtttt tcgccctttg    5752
acgttggagt ccacgttctt taatagtgga ctcttgttcc aaactggaac aacactcaac    5812
cctatctcgg gctattcttt tgatttataa gggattttgc cgatttcgga accaccatca    5872
aacaggattt tcgcctgctg gggcaaacca gcgtggaccg cttgctgcaa ctctctcagg    5932
gccaggcggt gaagggcaat cagctgttgc ccgtctcact ggtgaaaaga aaaaccaccc    5992
tggatccaag cttgcaggtg cacttttcg gggaaatgtg cgcggaaccc ctatttgttt    6052
attttctaa atacattcaa atatgtatcc gctcatgaga caataaccct gataaatgct    6112
tcaataatat tgaaaaagga agagtatgag tattcaacat ttccgtgtcg cccttattcc    6172
cttttttgcg gcattttgcc ttcctgtttt tgctcaccca gaaacgctgg tgaaagtaaa    6232
agatgctgaa gatcagttgg gcgcactagt gggttacatc gaactggatc tcaacagcgg    6292
taagatcctt gagagttttc gccccgaaga acgttttcca atgatgagca cttttaaagt    6352
tctgctatgt ggcgcggtat tatcccgtat tgacgccggg caagagcaac tcggtcgccg    6412
catacactat tctcagaatg acttggttga gtactcacca gtcacagaaa agcatcttac    6472
ggatggcatg acagtaagag aattatgcag tgctgccata accatgagtg ataacactgc    6532
ggccaactta cttctgacaa cgatcggagg accgaaggag ctaaccgctt ttttgcacaa    6592
catggggat catgtaactc gccttgatcg ttgggaaccg gagctgaatg aagccatacc    6652
aaacgacgag cgtgacacca cgatgcctgt agcaatggca acaacgttgc gcaaactatt    6712
aactggcgaa ctacttactc tagcttcccg gcaacaatta atagactgga tggaggcgga    6772
taaagttgca ggaccacttc tgcgctcggc ccttccggct ggctggttta ttgctgataa    6832
atctggagcc ggtgagcgtg ggtctcgcgg tatcattgca gcactgggc cagatggtaa    6892
```

```
gccctcccgt atcgtagtta tctacacgac ggggagtcag gcaactatgg atgaacgaaa    6952
tagacagatc gctgagatag gtgcctcact gattaagcat tggtaactgt cagaccaagt    7012
ttactcatat atactttaga ttgatttaaa acttcatttt taatttaaaa ggatctaggt    7072
gaagatcctt tttgataatc tcatgaccaa atcccttaa  cgtgagtttt cgttccactg    7132
tacgtaagac ccccaagctt gtcgactgaa tggcgaatgg cgctttgcct ggtttccggc    7192
accagaagcg gtgccggaaa gctggctgga gtgcgatctt cctgacgctc gagcgcaacg    7252
caattaatgt gagttagctc actcattagg caccccaggc tttacacttt atgcttccgg    7312
ctcgtatgtt gtgtggaatt gtgagcggat aacaatttca cacaggaaac agctatgacc    7372
atgattacgc caagctttgg agcctttttt ttggagattt caac gtg aaa aaa tta    7429
                                              Met Lys Lys Leu
                                                      630 tta ttc gca att cct tta gtt gtt cct ttc tat tct cac agt gca caa    7477
Leu Phe Ala Ile Pro Leu Val Val Pro Phe Tyr Ser His Ser Ala Gln
            635                 640                 645 gac atc cag atg acc cag tct cca gcc acc ctg tct ttg tct cca ggg    7525
Asp Ile Gln Met Thr Gln Ser Pro Ala Thr Leu Ser Leu Ser Pro Gly
650                 655                 660 gaa aga gcc acc ctc tcc tgc agg gcc agt cag ggt gtt agc agc tac    7573
Glu Arg Ala Thr Leu Ser Cys Arg Ala Ser Gln Gly Val Ser Ser Tyr
665                 670                 675                 680 tta gcc tgg tac cag cag aaa cct ggc cag gct ccc agg ctc ctc atc    7621
Leu Ala Trp Tyr Gln Gln Lys Pro Gly Gln Ala Pro Arg Leu Leu Ile
                685                 690                 695 tat gat gca tcc aac agg gcc act ggc atc cca gcc agg ttc agt ggc    7669
Tyr Asp Ala Ser Asn Arg Ala Thr Gly Ile Pro Ala Arg Phe Ser Gly
            700                 705                 710 agt ggg cct ggg aca gac ttc act ctc acc atc agc agc cta gag cct    7717
Ser Gly Pro Gly Thr Asp Phe Thr Leu Thr Ile Ser Ser Leu Glu Pro
            715                 720                 725 gaa gat ttt gca gtt tat tac tgt cag cag cgt aac tgg cat ccg tgg    7765
Glu Asp Phe Ala Val Tyr Tyr Cys Gln Gln Arg Asn Trp His Pro Trp
730                 735                 740 acg ttc ggc caa ggg acc aag gtg gaa atc aaa cga act gtg gct gca    7813
Thr Phe Gly Gln Gly Thr Lys Val Glu Ile Lys Arg Thr Val Ala Ala
745                 750                 755                 760 cca tct gtc ttc atc ttc ccg cca tct gat gag cag ttg aaa tct gga    7861
Pro Ser Val Phe Ile Phe Pro Pro Ser Asp Glu Gln Leu Lys Ser Gly
                765                 770                 775 act gcc tct gtt gtg tgc ctg ctg aat aac ttc tat ccc aga gag gcc    7909
Thr Ala Ser Val Val Cys Leu Leu Asn Asn Phe Tyr Pro Arg Glu Ala
            780                 785                 790 aaa gta cag tgg aag gtg gat aac gcc ctc caa tcg ggt aac tcc cag    7957
Lys Val Gln Trp Lys Val Asp Asn Ala Leu Gln Ser Gly Asn Ser Gln
            795                 800                 805 gag agt gtc aca gag cgg gac agc aag gac agc acc tac agc ctc agc    8005
Glu Ser Val Thr Glu Arg Asp Ser Lys Asp Ser Thr Tyr Ser Leu Ser
            810                 815                 820 agc acc ctg acg ctg agc aaa gca gac tac gag aaa cac aaa gtc tac    8053
Ser Thr Leu Thr Leu Ser Lys Ala Asp Tyr Glu Lys His Lys Val Tyr
825                 830                 835                 840 gcc tgc gaa gtc acc cat cag ggc ctg agc tcg ccc gtc aca aag agc    8101
Ala Cys Glu Val Thr His Gln Gly Leu Ser Ser Pro Val Thr Lys Ser
                845                 850                 855 ttc aac agg gga gag tgt taataaggcg cgccaattct atttcaagga             8149
Phe Asn Arg Gly Glu Cys
```

```
                                                           -continued
            860
gacagtcata atg aaa tac cta ttg cct acg gca gcc gct gga ttg tta         8198
            Met Lys Tyr Leu Leu Pro Thr Ala Ala Ala Gly Leu Leu
                865                 870                 875 tta ctc gcg gcc cag ccg gcc atg gcc gaa gtt caa ttg tta gag tct         8246
Leu Leu Ala Ala Gln Pro Ala Met Ala Glu Val Gln Leu Leu Glu Ser
                    880                 885                 890 ggt ggc ggt ctt gtt cag cct ggt ggt tct tta cgt ctt tct tgc gct         8294
Gly Gly Gly Leu Val Gln Pro Gly Gly Ser Leu Arg Leu Ser Cys Ala
895                 900                 905 gct tcc gga ttc act ttc tct act tac gag atg cgt tgg gtt cgc caa         8342
Ala Ser Gly Phe Thr Phe Ser Thr Tyr Glu Met Arg Trp Val Arg Gln
        910                 915                 920 gct cct ggt aaa ggt ttg gag tgg gtt tct tat atc gct cct tct ggt         8390
Ala Pro Gly Lys Gly Leu Glu Trp Val Ser Tyr Ile Ala Pro Ser Gly
            925                 930                 935 ggc gat act gct tat gct gac tcc gtt aaa ggt cgc ttc act atc tct         8438
Gly Asp Thr Ala Tyr Ala Asp Ser Val Lys Gly Arg Phe Thr Ile Ser
940                 945                 950                 955 aga gac aac tct aag aat act ctc tac ttg cag atg aac agc tta agg         8486
Arg Asp Asn Ser Lys Asn Thr Leu Tyr Leu Gln Met Asn Ser Leu Arg
                960                 965                 970 gct gag gac act gca gtc tac tat tgt gcg agg agg ctc gat ggc tat         8534
Ala Glu Asp Thr Ala Val Tyr Tyr Cys Ala Arg Arg Leu Asp Gly Tyr
                    975                 980                 985 att tcc tac tac tac ggt atg gac gtc tgg ggc caa ggg acc acg gtc         8582
Ile Ser Tyr Tyr Tyr Gly Met Asp Val Trp Gly Gln Gly Thr Thr Val
990                 995                 1000 acc gtc tca agc gcc tcc acc aag ggc cca tcg gtc ttc ccc ctg gca         8630
Thr Val Ser Ser Ala Ser Thr Lys Gly Pro Ser Val Phe Pro Leu Ala
    1005                1010                1015 ccc tcc tcc aag agc acc tct ggg ggc aca gcg gcc ctg ggc tgc ctg         8678
Pro Ser Ser Lys Ser Thr Ser Gly Gly Thr Ala Ala Leu Gly Cys Leu
1020                1025                1030                1035 gtc aag gac tac ttc ccc gaa ccg gtg acg gtg tcg tgg aac tca ggc         8726
Val Lys Asp Tyr Phe Pro Glu Pro Val Thr Val Ser Trp Asn Ser Gly
                1040                1045                1050 gcc ctg acc agc ggc gtc cac acc ttc ccg gct gtc cta cag tcc tca         8774
Ala Leu Thr Ser Gly Val His Thr Phe Pro Ala Val Leu Gln Ser Ser
                    1055                1060                1065 gga ctc tac tcc ctc agc agc gta gtg acc gtg ccc tcc agc agc ttg         8822
Gly Leu Tyr Ser Leu Ser Ser Val Val Thr Val Pro Ser Ser Ser Leu
1070                1075                1080 ggc acc cag acc tac atc tgc aac gtg aat cac aag ccc agc aac acc         8870
Gly Thr Gln Thr Tyr Ile Cys Asn Val Asn His Lys Pro Ser Asn Thr
    1085                1090                1095 aag gtg gac aag aaa gtt gag ccc aaa tct tgt gcg gcc gca cat cat         8918
Lys Val Asp Lys Lys Val Glu Pro Lys Ser Cys Ala Ala Ala His His
1100                1105                1110                1115 cat cac cat cac ggg gcc gca gaa caa aaa ctc atc tca gaa gag gat         8966
His His His His Gly Ala Ala Glu Gln Lys Leu Ile Ser Glu Glu Asp
                1120                1125                1130 ctg aat ggg gcc gca tag gct agc tct gct wsy ggy tty gay tay             9014
Leu Asn Gly Ala Ala Gln Ala Ser Ser Ala Ser Gly Asp Phe Asp Tyr
                    1135                1140                1145 gar aar atg gct aaw gcy aay aar ggs gcy atg acy gar aay gcy gay         9062
Glu Lys Met Ala Asn Ala Asn Lys Gly Ala Met Thr Glu Asn Ala Asp
1150                1155                1160 gar aay gck ytr car wsy gay gcy aar ggy aar ytw gay wsy gtc gck         9110
```

```
                Glu Asn Ala Leu Gln Ser Asp Ala Lys Gly Lys Leu Asp Ser Val Ala
                1165                1170                1175 acy gay tay ggy gcy gcc atc gay ggy tty aty ggy gay gtc wsy ggy          9158
Thr Asp Tyr Gly Ala Ala Ile Asp Gly Phe Ile Gly Asp Val Ser Gly
1180                1185                1190                1195 ytk gcy aay ggy aay ggy gcy acy ggw gay tty gcw ggy tck aat tcy          9206
Leu Ala Asn Gly Asn Gly Ala Thr Gly Asp Phe Ala Gly Ser Asn Ser
                1200                1205                1210 car atg gcy car gty ggw gay ggk gay aay wsw cck ytw atg aay aay          9254
Gln Met Ala Gln Val Gly Asp Gly Asp Asn Ser Pro Leu Met Asn Asn
            1215                1220                1225 tty mgw car tay ytw cck tcy cty cck car wsk gty gar tgy cgy ccw          9302
Phe Arg Gln Tyr Leu Pro Ser Leu Pro Gln Ser Val Glu Cys Arg Pro
        1230                1235                1240 tty gty tty wsy gcy ggy aar ccw tay gar tty wsy aty gay tgy gay          9350
Phe Val Phe Ser Ala Gly Lys Pro Tyr Glu Phe Ser Ile Asp Cys Asp
    1245                1250                1255 aar atm aay ytw tty cgy ggy gty tty gck tty ytk yta tay gty gcy          9398
Lys Ile Asn Leu Phe Arg Gly Val Phe Ala Phe Leu Leu Tyr Val Ala
1260                1265                1270                1275 acy tty atg tay gtw tty wsy ack tty gcy aay atw ytr cgy aay aar          9446
Thr Phe Met Tyr Val Phe Ser Thr Phe Ala Asn Ile Leu Arg Asn Lys
                1280                1285                1290 gar wsy tagtgatctc taggaagcc cgcctaatga gcgggctttt ttttctggt             9502
Glu Ser atgcatcctg aggccgatac tgtcgtcgtc ccctcaaact ggcagatgca cggttacgat        9562
gcgcccatct acaccaacgt gacctatccc attacggtca atccgccgtt tgttcccacg        9622
gagaatccga cgggttgtta ctcgctcaca tttaatgttg atgaaagctg gctacaggaa        9682
ggccagacgc gaattatttt tgatggcgtt cctattggtt aaaaaatgag ctgatttaac        9742
aaaaatttaa tgcgaatttt aacaaaatat taacgtttac aatttaaata tttgcttata        9802
caatcttcct gtttttgggg cttttctgat tatcaaccgg ggtacatatg attgacatgc        9862
tagttttacg attaccgttc atcgattctc ttgtttgctc cagactctca ggcaatgacc        9922
tgatagcctt tgtagatctc tcaaaaatag ctaccctctc cggcattaat ttatcagcta        9982
gaacggttga atatcatatt gatggtgatt tgactgtctc cggcctttct caccctttg        10042 aatctttacc tacacattac tcaggcattg catttaaaat atatgagggt tctaaaaatt       10102
tttatccttg cgttgaaata aaggcttctc ccgcaaaagt attacagggt cataatgttt       10162
ttggtacaac cgatttagct ttatgctctg aggcttattt gcttaatttt gctaattctt       10222
tgccttgcct gtatgattta ttggatgtt                                         10251

<210> SEQ ID NO 583
<211> LENGTH: 113
<212> TYPE: PRT
<213> ORGANISM: Artificial Sequence
<220> FEATURE:
<223> OTHER INFORMATION: Description of Artificial Sequence: CJRA05
      protein sequence

<400> SEQUENCE: 583

Met Lys Lys Leu Leu Phe Ala Ile Pro Leu Val Val Pro Phe Tyr Ser
1               5                   10                  15

Gly Ala Ala Glu Ser His Leu Asp Gly Ala Ala Glu Thr Val Glu Ser
            20                  25                  30

Cys Leu Ala Lys Ser His Thr Glu Asn Ser Phe Thr Asn Val Trp Lys
        35                  40                  45
```

```
Asp Asp Lys Thr Leu Asp Arg Tyr Ala Asn Tyr Glu Gly Cys Leu Trp
         50                  55                  60

Asn Ala Thr Gly Val Val Cys Thr Gly Asp Glu Thr Gln Cys Tyr
 65                  70                  75                  80

Gly Thr Trp Val Pro Ile Gly Leu Ala Ile Pro Glu Asn Glu Gly Gly
                     85                  90                  95

Gly Ser Glu Gly Gly Gly Ser Glu Gly Gly Gly Ser Glu Gly Gly Gly
                100                 105                 110

Thr
```

```
<210> SEQ ID NO 584
<211> LENGTH: 152
<212> TYPE: PRT
<213> ORGANISM: Artificial Sequence
<220> FEATURE:
<223> OTHER INFORMATION: Description of Artificial Sequence: CJRA05
      protein sequence

<400> SEQUENCE: 584

Ser Gly Asp Phe Asp Tyr Glu Lys Met Ala Asn Ala Asn Lys Gly Ala
 1               5                  10                  15

Met Thr Glu Asn Ala Asp Glu Asn Ala Leu Gln Ser Asp Ala Lys Gly
                20                  25                  30

Lys Leu Asp Ser Val Ala Thr Asp Tyr Gly Ala Ala Ile Asp Gly Phe
            35                  40                  45

Ile Gly Asp Val Ser Gly Leu Ala Asn Gly Asn Gly Ala Thr Gly Asp
         50                  55                  60

Phe Ala Gly Ser Asn Ser Gln Met Ala Gln Val Gly Asp Gly Asp Asn
 65                  70                  75                  80

Ser Pro Leu Met Asn Asn Phe Arg Gln Tyr Leu Pro Ser Leu Pro Gln
                 85                  90                  95

Ser Val Glu Cys Arg Pro Phe Val Phe Gly Ala Gly Lys Pro Tyr Glu
            100                 105                 110

Phe Ser Ile Asp Cys Asp Lys Ile Asn Leu Phe Arg Gly Val Phe Ala
        115                 120                 125

Phe Leu Leu Tyr Val Ala Thr Phe Met Tyr Val Phe Ser Thr Phe Ala
130                 135                 140

Asn Ile Leu Arg Asn Lys Glu Ser
145                 150
```

```
<210> SEQ ID NO 585
<211> LENGTH: 15
<212> TYPE: PRT
<213> ORGANISM: Artificial Sequence
<220> FEATURE:
<223> OTHER INFORMATION: Description of Artificial Sequence: CJRA05
      peptide sequence

<400> SEQUENCE: 585

Met Pro Val Leu Leu Gly Ile Pro Leu Leu Arg Phe Leu Gly
 1               5                  10                  15
```

```
<210> SEQ ID NO 586
<211> LENGTH: 348
<212> TYPE: PRT
<213> ORGANISM: Artificial Sequence
<220> FEATURE:
<223> OTHER INFORMATION: Description of Artificial Sequence: CJRA05
      protein sequence
```

<400> SEQUENCE: 586

| Met | Ala | Val | Tyr | Phe | Val | Thr | Gly | Lys | Leu | Gly | Ser | Gly | Lys | Thr | Leu |
|---|---|---|---|---|---|---|---|---|---|---|---|---|---|---|---|
| 1 | | | | 5 | | | | | 10 | | | | | 15 | |

| Val | Ser | Val | Gly | Lys | Ile | Gln | Asp | Lys | Ile | Val | Ala | Gly | Cys | Lys | Ile |
| | | | 20 | | | | | 25 | | | | | 30 | | |

| Ala | Thr | Asn | Leu | Asp | Leu | Arg | Leu | Gln | Asn | Leu | Pro | Gln | Val | Gly | Arg |
| | | 35 | | | | | 40 | | | | | 45 | | | |

| Phe | Ala | Lys | Thr | Pro | Arg | Val | Leu | Arg | Ile | Pro | Asp | Lys | Pro | Ser | Ile |
| | 50 | | | | | 55 | | | | | 60 | | | | |

| Ser | Asp | Leu | Leu | Ala | Ile | Gly | Arg | Gly | Asn | Asp | Ser | Tyr | Asp | Glu | Asn |
| 65 | | | | | 70 | | | | | 75 | | | | | 80 |

| Lys | Asn | Gly | Leu | Leu | Val | Leu | Asp | Glu | Cys | Gly | Thr | Trp | Phe | Asn | Thr |
| | | | | 85 | | | | | 90 | | | | | 95 | |

| Arg | Ser | Trp | Asn | Asp | Lys | Glu | Arg | Gln | Pro | Ile | Ile | Asp | Trp | Phe | Leu |
| | | | 100 | | | | | 105 | | | | | 110 | | |

| His | Ala | Arg | Lys | Leu | Gly | Trp | Asp | Ile | Ile | Phe | Leu | Val | Gln | Asp | Leu |
| | | 115 | | | | | 120 | | | | | 125 | | | |

| Ser | Ile | Val | Asp | Lys | Gln | Ala | Arg | Ser | Ala | Leu | Ala | Glu | His | Val | Val |
| | 130 | | | | | 135 | | | | | 140 | | | | |

| Tyr | Cys | Arg | Arg | Leu | Asp | Arg | Ile | Thr | Leu | Pro | Phe | Val | Gly | Thr | Leu |
| 145 | | | | | 150 | | | | | 155 | | | | | 160 |

| Tyr | Ser | Leu | Ile | Thr | Gly | Ser | Lys | Met | Pro | Leu | Pro | Lys | Leu | His | Val |
| | | | | 165 | | | | | 170 | | | | | 175 | |

| Gly | Val | Val | Lys | Tyr | Gly | Asp | Ser | Gln | Leu | Ser | Pro | Thr | Val | Glu | Arg |
| | | | 180 | | | | | 185 | | | | | 190 | | |

| Trp | Leu | Tyr | Thr | Gly | Lys | Asn | Leu | Tyr | Asn | Ala | Tyr | Asp | Thr | Lys | Gln |
| | | 195 | | | | | 200 | | | | | 205 | | | |

| Ala | Phe | Ser | Ser | Asn | Tyr | Asp | Ser | Gly | Val | Tyr | Ser | Tyr | Leu | Thr | Pro |
| | 210 | | | | | 215 | | | | | 220 | | | | |

| Tyr | Leu | Ser | His | Gly | Arg | Tyr | Phe | Lys | Pro | Leu | Asn | Leu | Gly | Gln | Lys |
| 225 | | | | | 230 | | | | | 235 | | | | | 240 |

| Met | Lys | Leu | Thr | Lys | Ile | Tyr | Leu | Lys | Lys | Phe | Ser | Arg | Val | Leu | Cys |
| | | | | 245 | | | | | 250 | | | | | 255 | |

| Leu | Ala | Ile | Gly | Phe | Ala | Ser | Ala | Phe | Thr | Tyr | Ser | Tyr | Ile | Thr | Gln |
| | | | 260 | | | | | 265 | | | | | 270 | | |

| Pro | Lys | Pro | Glu | Val | Lys | Lys | Val | Val | Ser | Gln | Thr | Tyr | Asp | Phe | Asp |
| | | 275 | | | | | 280 | | | | | 285 | | | |

| Lys | Phe | Thr | Ile | Asp | Ser | Ser | Gln | Arg | Leu | Asn | Leu | Ser | Tyr | Arg | Tyr |
| | 290 | | | | | 295 | | | | | 300 | | | | |

| Val | Phe | Lys | Asp | Ser | Lys | Gly | Lys | Leu | Ile | Asn | Ser | Asp | Asp | Leu | Gln |
| 305 | | | | | 310 | | | | | 315 | | | | | 320 |

| Lys | Gln | Gly | Tyr | Ser | Leu | Thr | Tyr | Ile | Asp | Leu | Cys | Thr | Val | Ser | Ile |
| | | | | 325 | | | | | 330 | | | | | 335 | |

| Lys | Lys | Gly | Asn | Ser | Asn | Glu | Ile | Val | Lys | Cys | Asn |
| | | | 340 | | | | | 345 | | | |

<210> SEQ ID NO 587
<211> LENGTH: 234
<212> TYPE: PRT
<213> ORGANISM: Artificial Sequence
<220> FEATURE:
<223> OTHER INFORMATION: Description of Artificial Sequence: CJRA05
    protein sequence

<400> SEQUENCE: 587

```
Met Lys Lys Leu Leu Phe Ala Ile Pro Leu Val Pro Phe Tyr Ser
 1               5                  10                  15

His Ser Ala Gln Asp Ile Gln Met Thr Gln Ser Pro Ala Thr Leu Ser
            20                  25                  30

Leu Ser Pro Gly Glu Arg Ala Thr Leu Ser Cys Arg Ala Ser Gln Gly
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Pro Gly Thr Asp Phe Thr Leu Thr Ile Ser
                85                  90                  95

Ser Leu Glu Pro Glu Asp Phe Ala Val Tyr Tyr Cys Gln Gln Arg Asn
            100                 105                 110

Trp His Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Arg Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 588
<211> LENGTH: 431
<212> TYPE: PRT
<213> ORGANISM: Artificial Sequence
<220> FEATURE:
<223> OTHER INFORMATION: Description of Artificial Sequence: CJRA05
      protein sequence

<400> SEQUENCE: 588

Met Lys Tyr Leu Leu Pro Thr Ala Ala Ala Gly Leu Leu Leu Leu Ala
 1               5                  10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Thr Tyr Glu Met Arg Trp Val Arg Gln Ala Pro Gly
    50                  55                  60

Lys Gly Leu Glu Trp Val Ser Tyr Ile Ala Pro Ser Gly Gly Asp Thr
65                  70                  75                  80

Ala Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Arg Leu Asp Gly Tyr Ile Ser Tyr
        115                 120                 125
```

Tyr Tyr Gly Met Asp Val Trp Gly Gln Gly Thr Thr Val Thr Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
        165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Lys Ser Cys Ala Ala Ala His His His His His
                245                 250                 255

His Gly Ala Ala Glu Gln Lys Leu Ile Ser Glu Glu Asp Leu Asn Gly
            260                 265                 270

Ala Ala Gln Ala Ser Ser Ala Ser Gly Asp Phe Asp Tyr Glu Lys Met
        275                 280                 285

Ala Asn Ala Asn Lys Gly Ala Met Thr Glu Asn Ala Asp Glu Asn Ala
290                 295                 300

Leu Gln Ser Asp Ala Lys Gly Lys Leu Asp Ser Val Ala Thr Asp Tyr
305                 310                 315                 320

Gly Ala Ala Ile Asp Gly Phe Ile Gly Asp Val Ser Gly Leu Ala Asn
                325                 330                 335

Gly Asn Gly Ala Thr Gly Asp Phe Ala Gly Ser Asn Ser Gln Met Ala
            340                 345                 350

Gln Val Gly Asp Gly Asp Asn Ser Pro Leu Met Asn Asn Phe Arg Gln
        355                 360                 365

Tyr Leu Pro Ser Leu Pro Gln Ser Val Glu Cys Arg Pro Phe Val Phe
370                 375                 380

Ser Ala Gly Lys Pro Tyr Glu Phe Ser Ile Asp Cys Asp Lys Ile Asn
385                 390                 395                 400

Leu Phe Arg Gly Val Phe Ala Phe Leu Leu Tyr Val Ala Thr Phe Met
                405                 410                 415

Tyr Val Phe Ser Thr Phe Ala Asn Ile Leu Arg Asn Lys Glu Ser
            420                 425                 430

<210> SEQ ID NO 589
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 589

Glu Gly Gly Gly Ser
 1               5

<210> SEQ ID NO 590
<211> LENGTH: 1275
<212> TYPE: DNA
<213> ORGANISM: Unknown
<220> FEATURE:
<221> NAME/KEY: CDS
<222> LOCATION: (1)..(1272)
<220> FEATURE:
<223> OTHER INFORMATION: Description of Unknown: M13 nucleotide sequence

<400> SEQUENCE: 590

```
gtg aaa aaa tta tta ttc gca att cct tta gtt gtt cct ttc tat tct         48
Met Lys Lys Leu Leu Phe Ala Ile Pro Leu Val Val Pro Phe Tyr Ser
 1               5                  10                  15 cac tcc gct gaa act gtt gaa agt tgt tta gca aaa ccc cat aca gaa         96
His Ser Ala Glu Thr Val Glu Ser Cys Leu Ala Lys Pro His Thr Glu
            20                  25                  30 aat tca ttt act aac gtc tgg aaa gac gac aaa act tta gat cgt tac        144
Asn Ser Phe Thr Asn Val Trp Lys Asp Asp Lys Thr Leu Asp Arg Tyr
        35                  40                  45 gct aac tat gag ggt tgt ctg tgg aat gct aca ggc gtt gta gtt tgt        192
Ala Asn Tyr Glu Gly Cys Leu Trp Asn Ala Thr Gly Val Val Val Cys
    50                  55                  60 act ggt gac gaa act cag tgt tac ggt aca tgg gtt cct att ggg ctt        240
Thr Gly Asp Glu Thr Gln Cys Tyr Gly Thr Trp Val Pro Ile Gly Leu
65                  70                  75                  80 gct atc cct gaa aat gag ggt ggt ggc tct gag ggt ggc ggt tct gag        288
Ala Ile Pro Glu Asn Glu Gly Gly Gly Ser Glu Gly Gly Gly Ser Glu
                85                  90                  95 ggt ggc ggt tct gag ggt ggc ggt act aaa cct cct gag tac ggt gat        336
Gly Gly Gly Ser Glu Gly Gly Gly Thr Lys Pro Pro Glu Tyr Gly Asp
            100                 105                 110 aca cct att ccg ggc tat act tat atc aac cct ctc gac ggc act tat        384
Thr Pro Ile Pro Gly Tyr Thr Tyr Ile Asn Pro Leu Asp Gly Thr Tyr
        115                 120                 125 ccg cct ggt act gag caa aac ccc gct aat cct aat cct tct ctt gag        432
Pro Pro Gly Thr Glu Gln Asn Pro Ala Asn Pro Asn Pro Ser Leu Glu
    130                 135                 140 gag tct cag cct ctt aat act ttc atg ttt cag aat aat agg ttc cga        480
Glu Ser Gln Pro Leu Asn Thr Phe Met Phe Gln Asn Asn Arg Phe Arg
145                 150                 155                 160 aat agg cag ggg gca tta act gtt tat acg ggc act gtt act caa ggc        528
Asn Arg Gln Gly Ala Leu Thr Val Tyr Thr Gly Thr Val Thr Gln Gly
                165                 170                 175 act gac ccc gtt aaa act tat tac cag tac act cct gta tca tca aaa        576
Thr Asp Pro Val Lys Thr Tyr Tyr Gln Tyr Thr Pro Val Ser Ser Lys
            180                 185                 190 gcc atg tat gac gct tac tgg aac ggt aaa ttc aga gac tgc gct ttc        624
Ala Met Tyr Asp Ala Tyr Trp Asn Gly Lys Phe Arg Asp Cys Ala Phe
        195                 200                 205 cat tct ggc ttt aat gag gat cca ttc gtt tgt gaa tat caa ggc caa        672
His Ser Gly Phe Asn Glu Asp Pro Phe Val Cys Glu Tyr Gln Gly Gln
    210                 215                 220 tcg tct gac ctg cct caa cct cct gtc aat gct ggc ggc ggc tct ggt        720
Ser Ser Asp Leu Pro Gln Pro Pro Val Asn Ala Gly Gly Gly Ser Gly
225                 230                 235                 240 ggt ggt tct ggt ggc ggc tct gag ggt ggt ggc tct gag ggt ggc ggt        768
Gly Gly Ser Gly Gly Gly Ser Glu Gly Gly Gly Ser Glu Gly Gly Gly
                245                 250                 255 tct gag ggt ggc ggc tct gag gga ggc ggt tcc ggt ggt ggc tct ggt        816
Ser Glu Gly Gly Gly Ser Glu Gly Gly Gly Ser Gly Gly Gly Ser Gly
            260                 265                 270 tcc ggt gat ttt gat tat gaa aag atg gca aac gct aat aag ggg gct        864
Ser Gly Asp Phe Asp Tyr Glu Lys Met Ala Asn Ala Asn Lys Gly Ala
        275                 280                 285
```

```
atg acc gaa aat gcc gat gaa aac gcg cta cag tct gac gct aaa ggc    912
Met Thr Glu Asn Ala Asp Glu Asn Ala Leu Gln Ser Asp Ala Lys Gly
290                 295                 300 aaa ctt gat tct gtc gct act gat tac ggt gct gct atc gat ggt ttc    960
Lys Leu Asp Ser Val Ala Thr Asp Tyr Gly Ala Ala Ile Asp Gly Phe
305                 310                 315                 320 att ggt gac gtt tcc ggc ctt gct aat ggt aat ggt gct act ggt gat   1008
Ile Gly Asp Val Ser Gly Leu Ala Asn Gly Asn Gly Ala Thr Gly Asp
                325                 330                 335 ttt gct ggc tct aat tcc caa atg gct caa gtc ggt gac ggt gat aat   1056
Phe Ala Gly Ser Asn Ser Gln Met Ala Gln Val Gly Asp Gly Asp Asn
            340                 345                 350 tca cct tta atg aat aat ttc cgt caa tat tta cct tcc ctc cct caa   1104
Ser Pro Leu Met Asn Asn Phe Arg Gln Tyr Leu Pro Ser Leu Pro Gln
        355                 360                 365 tcg gtt gaa tgt cgc cct ttt gtc ttt agc gct ggt aaa cca tat gaa   1152
Ser Val Glu Cys Arg Pro Phe Val Phe Ser Ala Gly Lys Pro Tyr Glu
370                 375                 380 ttt tct att gat tgt gac aaa ata aac tta ttc cgt ggt gtc ttt gcg   1200
Phe Ser Ile Asp Cys Asp Lys Ile Asn Leu Phe Arg Gly Val Phe Ala
385                 390                 395                 400 ttt ctt tta tat gtt gcc acc ttt atg tat gta ttt tct acg ttt gct   1248
Phe Leu Leu Tyr Val Ala Thr Phe Met Tyr Val Phe Ser Thr Phe Ala
                405                 410                 415 aac ata ctg cgt aat aag gag tct taa                               1275
Asn Ile Leu Arg Asn Lys Glu Ser
            420
```

<210> SEQ ID NO 591
<211> LENGTH: 424
<212> TYPE: PRT
<213> ORGANISM: Unknown
<220> FEATURE:
<223> OTHER INFORMATION: Description of Unknown: M13 protein
      sequence

<400> SEQUENCE: 591

```
Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Gly Ser Glu
                85                  90                  95

Gly Gly Gly Ser Glu Gly Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
        115                 120                 125

Pro Pro Gly Thr Glu Gln Asn Pro Ala Asn Pro Asn Pro Ser Leu Glu
    130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175
```

```
Thr Asp Pro Val Lys Thr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Ser Gly
225                 230                 235                 240

Gly Gly Ser Gly Gly Gly Ser Glu Gly Gly Ser Glu Gly Gly
                245                 250                 255

Ser Glu Gly Gly Ser Glu Gly Gly Ser Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
        355                 360                 365

Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 592
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
caacgatgat cgtatggcgc atgctgccga gacag                              35

<210> SEQ ID NO 593
<211> LENGTH: 1355
<212> TYPE: DNA
<213> ORGANISM: Artificial Sequence
<220> FEATURE:
<223> OTHER INFORMATION: Description of Artificial Sequence: M13-III
      nucleotide sequence
<220> FEATURE:
<221> NAME/KEY: CDS
<222> LOCATION: (1)..(1305)

<400> SEQUENCE: 593 gcg gcc gca cat cat cat cac cat cac ggg gcc gca gaa caa aaa ctc    48
Ala Ala Ala His His His His His His Gly Ala Ala Glu Gln Lys Leu
 1               5                  10                  15
```

| | | | | | | | | | | | | | | | |
|---|---|---|---|---|---|---|---|---|---|---|---|---|---|---|---|
| atc | tca | gaa | gag | gat | ctg | aat | ggg | gcc | gca | tag | gct | agc | gat | atc | aac | 96 |
| Ile | Ser | Glu | Glu | Asp | Leu | Asn | Gly | Ala | Ala | | Ala | Ser | Asp | Ile | Asn | |
| | | | 20 | | | | | 25 | | | | | 30 | | | |

```
atc tca gaa gag gat ctg aat ggg gcc gca tag gct agc gat atc aac    96
Ile Ser Glu Glu Asp Leu Asn Gly Ala Ala     Ala Ser Asp Ile Asn
             20                  25                      30 gat gat cgt atg gct tct act gcy gar acw gty gaa wsy tgy ytr gcm   144
Asp Asp Arg Met Ala Ser Thr Ala Glu Thr Val Glu Ser Cys Leu Ala
             35                  40                      45 aar ccy cay acw gar aat wsw tty acw aay gts tgg aar gay gay aar   192
Lys Pro His Thr Glu Asn Ser Phe Thr Asn Val Trp Lys Asp Asp Lys
             50                  55                      60 acy ytw gat cgw tay gcy aay tay gar ggy tgy ytr tgg aat gcy acm   240
Thr Leu Asp Arg Tyr Ala Asn Tyr Glu Gly Cys Leu Trp Asn Ala Thr
             65                  70                      75 ggc gty gtw gty tgy ack ggy gay gar acw car tgy tay ggy acr tgg   288
Gly Val Val Val Cys Thr Gly Asp Glu Thr Gln Cys Tyr Gly Thr Trp
             80                  85                      90         95 gtk cck atw ggs ytw gcy atm cck gar aay gar ggy ggy ggy wsy gar   336
Val Pro Ile Gly Leu Ala Ile Pro Glu Asn Glu Gly Gly Gly Ser Glu
             100                 105                     110 ggy ggy ggy wsy gar ggy ggy tcy gar ggw ggy ggw acy aar cck       384
Gly Gly Gly Ser Glu Gly Gly Ser Glu Gly Gly Gly Thr Lys Pro
             115                 120                     125 cck gar tay ggy gay acw cck atw cck ggy tay acy tay aty aay cck   432
Pro Glu Tyr Gly Asp Thr Pro Ile Pro Gly Tyr Thr Tyr Ile Asn Pro
             130                 135                     140 ytm gay ggm acy tay cck cck ggy acy gar car aay ccy gcy aay cck   480
Leu Asp Gly Thr Tyr Pro Pro Gly Thr Glu Gln Asn Pro Ala Asn Pro
             145                 150                     155 aay ccw wsy ytw gar gar wsy car cck ytw aay acy tty atg tty car   528
Asn Pro Ser Leu Glu Glu Ser Gln Pro Leu Asn Thr Phe Met Phe Gln
160                  165                 170                     175 aay aay mgk tty mgr aay mgk car ggk gcw ytw acy gtk tay ack ggm   576
Asn Asn Arg Phe Arg Asn Arg Gln Gly Ala Leu Thr Val Tyr Thr Gly
             180                 185                     190 acy gty acy car ggy acy gay ccy gty aar acy tay tay car tay acy   624
Thr Val Thr Gln Gly Thr Asp Pro Val Lys Thr Tyr Tyr Gln Tyr Thr
             195                 200                     205 cck gtm tcr wsw aar gcy atg tay gay gcy tay tgg aay ggy aar tty   672
Pro Val Ser Ser Lys Ala Met Tyr Asp Ala Tyr Trp Asn Gly Lys Phe
             210                 215                     220 mgw gay tgy gcy tty cay wsy ggy tty aay gar gay ccw tty gty tgy   720
Arg Asp Cys Ala Phe His Ser Gly Phe Asn Glu Asp Pro Phe Val Cys
             225                 230                     235 gar tay car ggy car wsk wsy gay ytr cck car ccw cck gty aay gck   768
Glu Tyr Gln Gly Gln Ser Ser Asp Leu Pro Gln Pro Pro Val Asn Ala
240                  245                 250                     255 ggy ggy ggy wsy ggy ggw ggy wsy ggy ggy ggy wsy gar ggy ggw ggy   816
Gly Gly Gly Ser Gly Gly Gly Ser Gly Gly Gly Ser Glu Gly Gly Gly
             260                 265                     270 wsy gar ggw ggy ggy wsy ggr ggy ggy wsy ggy wsy ggy gay tty gay   864
Ser Glu Gly Gly Gly Ser Gly Gly Gly Ser Gly Ser Gly Asp Phe Asp
             275                 280                     285 tay gar aar atg gcw aay gcy aay aar ggs gcy atg acy gar aay gcy   912
Tyr Glu Lys Met Ala Asn Ala Asn Lys Gly Ala Met Thr Glu Asn Ala
             290                 295                     300 gay gar aay gcr ctr car wst gay gcy aar ggy aar ytw gay wsy gtc   960
Asp Glu Asn Ala Leu Gln Ser Asp Ala Lys Gly Lys Leu Asp Ser Val
305                  310                 315 gcy acw gay tay ggt gct gcy atc gay ggy tty aty ggy gay gty wsy  1008
Ala Thr Asp Tyr Gly Ala Ala Ile Asp Gly Phe Ile Gly Asp -continued

```
                320                 325                 330                 335
ggy ctk gct aay ggy aay ggw gcy acy ggw gay tty gcw ggy tck aat         1056
Gly Leu Ala Asn Gly Asn Gly Ala Thr Gly Asp Phe Ala Gly Ser Asn
                    340                 345                 350 tcy car atg gcy car gty ggw gay ggk gay aay wsw cck ytw atg aay         1104
Ser Gln Met Ala Gln Val Gly Asp Gly Asp Asn Ser Pro Leu Met Asn
                    355                 360                 365 aay tty mgw car tay ytw cck tcy cty cck car wsk gty gar tgy cgy         1152
Asn Phe Arg Gln Tyr Leu Pro Ser Leu Pro Gln Ser Val Glu Cys Arg
                    370                 375                 380 ccw tty gty tty wsy gcy ggy aar ccw tay gar tty wsy aty gay tgy         1200
Pro Phe Val Phe Ser Ala Gly Lys Pro Tyr Glu Phe Ser Ile Asp Cys
                    385                 390                 395 gay aar atm aay ytw ttc cgy ggy gty tty gck tty ytk yta tay gty         1248
Asp Lys Ile Asn Leu Phe Arg Gly Val Phe Ala Phe Leu Leu Tyr Val
400                 405                 410                 415 gcy acy tty atg tay gtw tty wsy ack tty gcy aay atw ytr cgy aay         1296
Ala Thr Phe Met Tyr Val Phe Ser Thr Phe Ala Asn Ile Leu Arg Asn
                    420                 425                 430 aar gar wsy tagtgatctc ctaggaagcc cgcctaatga gcgggctttt                 1345
Lys Glu Ser ttttctggt                                                               1355

<210> SEQ ID NO 594
<211> LENGTH: 434
<212> TYPE: PRT
<213> ORGANISM: Artificial Sequence
<220> FEATURE:
<223> OTHER INFORMATION: Description of Artificial Sequence: M13-III
      protein sequence

<400> SEQUENCE: 594

Ala Ala Ala His His His His His Gly Ala Ala Glu Gln Lys Leu
1               5                   10                  15

Ile Ser Glu Glu Asp Leu Asn Gly Ala Ala Ala Ser Asp Ile Asn Asp
                20                  25                  30

Asp Arg Met Ala Ser Thr Ala Glu Thr Val Glu Ser Cys Leu Ala Lys
            35                  40                  45

Pro His Thr Glu Asn Ser Phe Thr Asn Val Trp Lys Asp Asp Lys Thr
        50                  55                  60

Leu Asp Arg Tyr Ala Asn Tyr Glu Gly Cys Leu Trp Asn Ala Thr Gly
65                  70                  75                  80

Val Val Val Cys Thr Gly Asp Glu Thr Gln Cys Tyr Gly Thr Trp Val
                85                  90                  95

Pro Ile Gly Leu Ala Ile Pro Glu Asn Glu Gly Gly Gly Ser Glu Gly
            100                 105                 110

Gly Gly Ser Glu Gly Gly Gly Ser Glu Gly Gly Gly Thr Lys Pro Pro
        115                 120                 125

Glu Tyr Gly Asp Thr Pro Ile Pro Gly Tyr Thr Tyr Ile Asn Pro Leu
    130                 135                 140

Asp Gly Thr Tyr Pro Pro Gly Thr Glu Gln Asn Pro Ala Asn Pro Asn
145                 150                 155                 160

Pro Ser Leu Glu Glu Ser Gln Pro Leu Asn Thr Phe Met Phe Gln Asn
                165                 170                 175

Asn Arg Phe Arg Asn Arg Gln Gly Ala Leu Thr Val Tyr Thr Gly Thr
            180                 185                 190

Val Thr Gln Gly Thr Asp Pro Val Lys Thr Tyr Tyr Gln Tyr Thr Pro
```

```
            195                 200                 205
Val Ser Ser Lys Ala Met Tyr Asp Ala Tyr Trp Asn Gly Lys Phe Arg
    210                 215                 220

Asp Cys Ala Phe His Ser Gly Phe Asn Glu Asp Pro Phe Val Cys Glu
225                 230                 235                 240

Tyr Gln Gly Gln Ser Ser Asp Leu Pro Gln Pro Val Asn Ala Gly
                245                 250                 255

Gly Gly Ser Gly Gly Gly Ser Gly Gly Ser Glu Gly Gly Gly Ser
            260                 265                 270

Glu Gly Gly Gly Ser Gly Gly Ser Gly Ser Gly Asp Phe Asp Tyr
        275                 280                 285

Glu Lys Met Ala Asn Ala Asn Lys Gly Ala Met Thr Glu Asn Ala Asp
    290                 295                 300

Glu Asn Ala Leu Gln Ser Asp Ala Lys Gly Lys Leu Asp Ser Val Ala
305                 310                 315                 320

Thr Asp Tyr Gly Ala Ala Ile Asp Gly Phe Ile Gly Asp Val Ser Gly
                325                 330                 335

Leu Ala Asn Gly Asn Gly Ala Thr Gly Asp Phe Ala Gly Ser Asn Ser
            340                 345                 350

Gln Met Ala Gln Val Gly Asp Gly Asp Asn Ser Pro Leu Met Asn Asn
        355                 360                 365

Phe Arg Gln Tyr Leu Pro Ser Leu Pro Gln Ser Val Glu Cys Arg Pro
370                 375                 380

Phe Val Phe Ser Ala Gly Lys Pro Tyr Glu Phe Ser Ile Asp Cys Asp
385                 390                 395                 400

Lys Ile Asn Leu Phe Arg Gly Val Phe Ala Phe Leu Leu Tyr Val Ala
                405                 410                 415

Thr Phe Met Tyr Val Phe Ser Thr Phe Ala Asn Ile Leu Arg Asn Lys
            420                 425                 430

Glu Ser

<210> SEQ ID NO 595
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
cgttgatatc gctagcctat gc                                          22

<210> SEQ ID NO 596
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
gataggctta gctagcccgg agaacgaagg                                  30

<210> SEQ ID NO 597
<211> LENGTH: 37
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 597
ctttcacagc ggtttcgcta gcgacccttt tgtctgc                                     37

<210> SEQ ID NO 598
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ctttcacagc ggtttcgcta gcgacccttt tgtcagcgag taccagggtc                       50

<210> SEQ ID NO 599
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
gactgtctcg gcagcatgcg ccatacgatc atcgttg                                     37

<210> SEQ ID NO 600
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 600 c aac gat gat cgt atg gcg cat gct gccgagacag tc                              37
  Asn Asp Asp Arg Met Ala His Ala
    1               5

<210> SEQ ID NO 601
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Asn Asp Asp Arg Met Ala His Ala
  1               5

<210> SEQ ID NO 602
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
ctttcacagc ggtttgcatg cagacccttt tgtctgc                                     37

<210> SEQ ID NO 603

```
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
ctttcacagc ggtttgcatg cagacccttt tgtcagcgag taccagggtc                50

<210> SEQ ID NO 604
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 604

Tyr Ala Asp Ser Val Lys Gly
  1               5

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
cctcgacagc gaagtgcaca g                                               21

<210> SEQ ID NO 606
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ggctgagtca agacgctctg tgcacttcgc tgtcgagg                             38

<210> SEQ ID NO 607
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 607

Gln Ser Ala Leu Thr Gln Pro
  1               5

<210> SEQ ID NO 608
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608
cctctgtcac agtgcacaag ac                                              22
```

```
<210> SEQ ID NO 609
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
cctctgtcac agtgcacaag acatccagat gacccagtct cc                         42

<210> SEQ ID NO 610
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
gggaggatgg agactgggtc gtctggatgt cttgtgcact gtgacagagg                 50

<210> SEQ ID NO 611
<211> LENGTH: 11
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 611

Gln Asp Ile Gln Met Thr Gln Ser Pro Ser Ser
 1               5                   10

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 612
gactgggtgt agtgatctag                                                  20

<210> SEQ ID NO 613
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
ggtgtagtga tcttctagtg acaactct                                         28

<210> SEQ ID NO 614
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Val Ser Ser Arg Asp Asn
 1               5
```

```
<210> SEQ ID NO 615
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 615 tac tat tgt gcg aaa                                                15
Tyr Tyr Cys Ala Lys
  1               5

<210> SEQ ID NO 616
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Tyr Tyr Cys Ala Lys
  1               5

<210> SEQ ID NO 617
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ggtgccgata ggcttgcatg caccggagaa cgaagg                            36

<210> SEQ ID NO 618
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
cgcttcacta agtctagaga caactctaag aatactctct acttgcagat gaacagctta   60
agggctgagg acactgcagt ctactattgt acgag                              95

<210> SEQ ID NO 619
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 619 gatnnnnatc                                                         10

<210> SEQ ID NO 620
```

<211> LENGTH: 10
<212> TYPE: PRT
<213> ORGANISM: Unknown
<220> FEATURE:
<223> OTHER INFORMATION: Description of Unknown: MALIA3-derived
      peptide

<400> SEQUENCE: 620

Met Lys Leu Leu Asn Val Ile Asn Phe Val
 1               5                  10

<210> SEQ ID NO 621
<211> LENGTH: 29
<212> TYPE: PRT
<213> ORGANISM: Artificial Sequence
<220> FEATURE:
<223> OTHER INFORMATION: Description of Artificial Sequence:
      CJRA05-derived peptide

<400> SEQUENCE: 621

Met Ser Val Leu Val Tyr Ser Phe Ala Ser Phe Val Leu Gly Trp Cys
 1               5                  10                  15

Leu Arg Ser Gly Ile Thr Tyr Phe Thr Arg Leu Met Glu
            20                  25

<210> SEQ ID NO 622
<211> LENGTH: 15
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 622 ttttttttt ttttt                                                          15

<210> SEQ ID NO 623
<211> LENGTH: 87
<212> TYPE: PRT
<213> ORGANISM: Unknown
<220> FEATURE:
<223> OTHER INFORMATION: Description of Unknown: MALIA3-derived
      peptide

<400> SEQUENCE: 623

Met Ile Lys Val Glu Ile Lys Pro Ser Gln Ala Gln Phe Thr Thr Arg
 1               5                  10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

Leu Asp Glu Gly Gln Pro Ala Tyr Ala Pro Gly Leu Tyr Thr Val His
    50                  55                  60

Leu Ser Ser Phe Lys Val Gly Gln Phe Gly Ser Leu Met Ile Asp Arg
65                  70                  75                  80

Leu Arg Leu Val Pro Ala Lys
                85

<210> SEQ ID NO 624
<211> LENGTH: 29
<212> TYPE: PRT
<213> ORGANISM: Unknown
<220> FEATURE:
<223> OTHER INFORMATION: Description of Unknown: MALIA3-derived
      peptide -continued

<400> SEQUENCE: 624

Met Ser Val Leu Val Tyr Ser Phe Ala Ser Phe Val Leu Gly Trp Cys
1               5                   10                  15

Leu Arg Ser Gly Ile Thr Tyr Phe Thr Arg Leu Met Glu
            20                  25

<210> SEQ ID NO 625
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, t, c, g, unknown or other

<400> SEQUENCE: 625 ctcttcnnnn                                                              10

<210> SEQ ID NO 626
<211> LENGTH: 87
<212> TYPE: PRT
<213> ORGANISM: Artificial Sequence
<220> FEATURE:
<223> OTHER INFORMATION: Description of Artificial Sequence:
      CJRA05-derived peptide

<400> SEQUENCE: 626

Met Ile Lys Val Glu Ile Lys Pro Ser Gln Ala Gln Phe Thr Thr Arg
1               5                   10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

Leu Asp Glu Gly Gln Pro Ala Tyr Ala Pro Gly Leu Tyr Thr Val His
    50                  55                  60

Leu Ser Ser Phe Lys Val Gly Gln Phe Gly Ser Leu Met Ile Asp Arg
65                  70                  75                  80

Leu Arg Leu Val Pro Ala Lys
                85

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence:
      CJRA05-derived peptide

<400> SEQUENCE: 627

Met Lys Leu Leu Asn Val Ile Asn Phe Val
1               5                   10

<210> SEQ ID NO 628
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gacccagtct ccatcctcc                                                19

<210> SEQ ID NO 629
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
gactcagtct ccactctcc                                                19

<210> SEQ ID NO 630
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
gacgcagtct ccaggcacc                                                19

<210> SEQ ID NO 631
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
gacgcagtct ccagccacc                                                19

<210> SEQ ID NO 632
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gtctcctgga cagtcgatc                                                19

<210> SEQ ID NO 633
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
ggccttggga cagacagtc                                                19

<210> SEQ ID NO 634
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634

```
gtctcctgga cagtcagtc                                                  19
```

<210> SEQ ID NO 635
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635

```
ggccccaggg cagagggtc                                                  19
```

<210> SEQ ID NO 636
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr
<220> FEATURE:
<221> NAME/KEY: MOD_RES
<222> LOCATION: (3)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr
<220> FEATURE:
<221> NAME/KEY: MOD_RES
<222> LOCATION: (5)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr

<400> SEQUENCE: 636

```
Xaa Tyr Xaa Met Xaa
 1               5
```

<210> SEQ ID NO 637
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)
<223> OTHER INFORMATION: Tyr, Arg, Trp, Val, Gly or Ser
<220> FEATURE:
<221> NAME/KEY: MOD_RES
<222> LOCATION: (3)
<223> OTHER INFORMATION: Tyr, Arg, Trp, Val, Gly or Ser
<220> FEATURE:
<221> NAME/KEY: MOD_RES
<222> LOCATION: (4)
<223> OTHER INFORMATION: Pro or Ser
<220> FEATURE:
<221> NAME/KEY: MOD_RES
<222> LOCATION: (8)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr
<220> FEATURE:
<221> NAME/KEY: MOD_RES
<222> LOCATION: (10)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr

<400> SEQUENCE: 637

```
Xaa Ile Xaa Xaa Ser Gly Gly Xaa Thr Xaa Tyr Ala Asp Ser Val Lys
 1               5                  10                  15
```

Gly

```
<210> SEQ ID NO 638
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 638
ggtgtagtga tctagagaca actctaagaa tactctctac ttgcagatga acagcttaag      60
ggctgaggac actgcagtct actat                                           85

<210> SEQ ID NO 639
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 639
ctgtgtatta ctatgcgaaa ga                                              22
```

METHODS OF CONSTRUCTING LIBRARIES COMPRISING DISPLAYED AND/OR EXPRESSED MEMBERS OF A DIVERSE FAMILY OF PEPTIDES, POLYPEPTIDES OR PROTEINS AND THE NOVEL LIBRARIES

This application is a continuation of U.S. patent application Ser. No. 10/045,674, filed Oct. 25, 2011, now U.S. Pat. No. 8,288,322 issued Oct. 16, 2012, which is a continuation-in-part of U.S. patent application Ser. No. 10/000,516, filed Oct. 24, 2001 (abandoned), which is a continuation-in-part of U.S. patent application Ser. No. 09/837,306, filed on Apr. 17, 2001 (abandoned), which claims the benefit of U.S. provisional application 60/198,069, filed on Apr. 17, 2000. All of the earlier applications are specifically incorporated by reference herein.

The present invention relates to libraries of genetic packages that display and/or express a member of a diverse family of peptides, polypeptides or proteins and collectively display and/or express at least a portion of the diversity of the family. In an alternative embodiment, the invention relates to libraries that include a member of a diverse family of peptides, polypeptides or proteins and collectively comprise at least a portion of the diversity of the family. In a preferred embodiment, the displayed and/or expressed polypeptides are human Fabs.

More specifically, the invention is directed to the methods of cleaving single-stranded nucleic acids at chosen locations, the cleaved nucleic acids encoding, at least in part, the peptides, polypeptides or proteins displayed on the genetic packages of, and/or expressed in, the libraries of the invention. In a preferred embodiment, the genetic packages are filamentous phage or phagemids or yeast.

The present invention further relates to vectors for displaying and/or expressing a diverse family of peptides, polypeptides or proteins.

The present invention further relates to methods of screening the libraries of the invention and to the peptides, polypeptides and proteins identified by such screening.

BACKGROUND OF THE INVENTION

It is now common practice in the art to prepare libraries of genetic packages that display, express or comprise a member of a diverse family of peptides, polypeptides or proteins and collectively display, express or comprise at least a portion of the diversity of the family. In many common libraries, the peptides, polypeptides or proteins are related to antibodies. Often, they are Fabs or single chain antibodies.

In general, the DNAs that encode members of the families to be displayed and/or expressed must be amplified before they are cloned and used to display and/or express the desired member. Such amplification typically makes use of forward and backward primers.

Such primers can be complementary to sequences native to the DNA to be amplified or complementary to oligonucleotides attached at the 5' or 3' ends of that DNA. Primers that are complementary to sequences native to the DNA to be amplified are disadvantaged in that they bias the members of the families to be displayed. Only those members that contain a sequence in the native DNA that is substantially complementary to the primer will be amplified. Those that do not will be absent from the family. For those members that are amplified, any diversity within the primer region will be suppressed.

For example, in European patent 368,684 B1, the primer that is used is at the 5' end of the $V_H$ region of an antibody gene. It anneals to a sequence region in the native DNA that is said to be "sufficiently well conserved" within a single species. Such primer will bias the members amplified to those having this "conserved" region. Any diversity within this region is extinguished.

It is generally accepted that human antibody genes arise through a process that involves a combinatorial selection of V and J or V, D, and J followed by somatic mutations. Although most diversity occurs in the Complementary Determining Regions (CDRs), diversity also occurs in the more conserved Framework Regions (FRs) and at least some of this diversity confers or enhances specific binding to antigens (Ag). As a consequence, libraries should contain as much of the CDR and FR diversity as possible.

To clone the amplified DNAs of the peptides, polypeptides or proteins that they encode for display on a genetic package and/or for expression, the DNAs must be cleaved to produce appropriate ends for ligation to a vector. Such cleavage is generally effected using restriction endonuclease recognition sites carried on the primers. When the primers are at the 5' end of DNA produced from reverse transcription of RNA, such restriction leaves deleterious 5' untranslated regions in the amplified DNA. These regions interfere with expression of the cloned genes and thus the display of the peptides, polypeptides and proteins coded for by them.

SUMMARY OF THE INVENTION

It is an object of this invention to provide novel methods for constructing libraries that display, express or comprise a member of a diverse family of peptides, polypeptides or proteins and collectively display, express or comprise at least a portion of the diversity of the family. These methods are not biased toward DNAs that contain-native sequences that are complementary to the primers used for amplification. They also enable any sequences that may be deleterious to expression to be removed from the amplified DNA before cloning and displaying and/or expressing.

It is another object of this invention to provide a method for cleaving single-stranded nucleic acid sequences at a desired location, the method comprising the steps of:
 (i) contacting the nucleic acid with a single-stranded oligonucleotide, the oligonucleotide being functionally complementary to the nucleic acid in the region in which cleavage is desired and including a sequence that with its complement in the nucleic acid forms a restriction endonuclease recognition site that on restriction results in cleavage of the nucleic acid at the desired location; and
 (ii) cleaving the nucleic acid solely at the recognition site formed by the complementation of the nucleic acid and the oligonucleotide;

the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

It is a further object of this invention to provide an alternative method for cleaving single-stranded nucleic acid sequences at a desired location, the method comprising the steps of:
 (i) contacting the nucleic acid with a partially double-stranded oligonucleotide, the single-stranded region of the oligonucleotide being functionally complementary to the nucleic acid in the region in which cleavage is desired, and the double-stranded region of the oligonucleotide having a restriction endonuclease recognition site; and (ii) cleaving the nucleic acid solely at the cleavage site formed by the complementation of the nucleic acid and the single-stranded region of the oligonucleotide;

the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

In an alternative embodiment of this object of the invention, the restriction endonuclease recognition site is not initially located in the double-stranded part of the oligonucleotide. Instead, it is part of an amplification primer, which primer is complementary to the double-stranded region of the oligonucleotide. On amplification of the DNA-partially double-stranded combination, the restriction endonuclease recognition site carried on the primer becomes part of the DNA. It can then be used to cleave the DNA.

Preferably, the restriction endonuclease recognition site is that of a Type II-S restriction endonuclease whose cleavage site is located at a known distance from its recognition site.

It is another object of the present invention to provide a method of capturing DNA molecules that comprise a member of a diverse family of DNAs and collectively comprise at least a portion of the diversity of the family. These DNA molecules in single-stranded form have been cleaved by one of the methods of this invention. This method involves ligating the individual single-stranded DNA members of the family to a partially duplex DNA complex. The method comprises the steps of:

(i) contacting a single-stranded nucleic acid sequence that has been cleaved with a restriction endonuclease with a partially double-stranded oligonucleotide, the single-stranded region of the oligonucleotide being functionally complementary to the nucleic acid in the region that remains after cleavage, the double-stranded region of the oligonucleotide including any sequences necessary to return the sequences that remain after cleavage into proper reading frame for expression and containing a restriction endonuclease recognition site 5' of those sequences; and (ii) cleaving the partially double-stranded oligonucleotide sequence solely at the restriction endonuclease cleavage site contained within the double-stranded region of the partially double-stranded oligonucleotide.

As before, in this object of the invention, the restriction endonuclease recognition site need not be located in the double-stranded portion of the oligonucleotide. Instead, it can be introduced on amplification with an amplification primer that is used to amplify the DNA-partially double-stranded oligonucleotide combination.

It is another object of this invention to prepare libraries, that display, express or comprise a diverse family of peptides, polypeptides or proteins and collectively display, express or comprise at least part of the diversity of the family, using the methods and DNAs described above.

It is an object of this invention to screen those libraries to identify useful peptides, polypeptides and proteins and to use those substances in human therapy.

Additional objects of the invention are reflected in the original claims. Each of these claims is specifically incorporated by reference in this specification.

BRIEF DESCRIPTION OF THE DRAWINGS

FIG. 10 is a schematic of the design for CDR1 and CDR2 synthetic diversity (SEQ ID NOS: 636 and 637, respectively). The YADSVKG peptide is shown as SEQ ID NO: 604.

FIG. 20 is a schematic of a process for incorporating fixed FR1 residues in an antibody heavy chain sequence. The PCRpr oligonucleotide is shown in SEQ ID NO: 612. The Bridge oligonucleotides are shown in SEQ ID NOS 613 & 615, respectively, in order of appearance, while the encoded peptides are shown in SEQ ID NOS 614 & 616, respectively, in order of appearance.

TERMS

Figure 1:
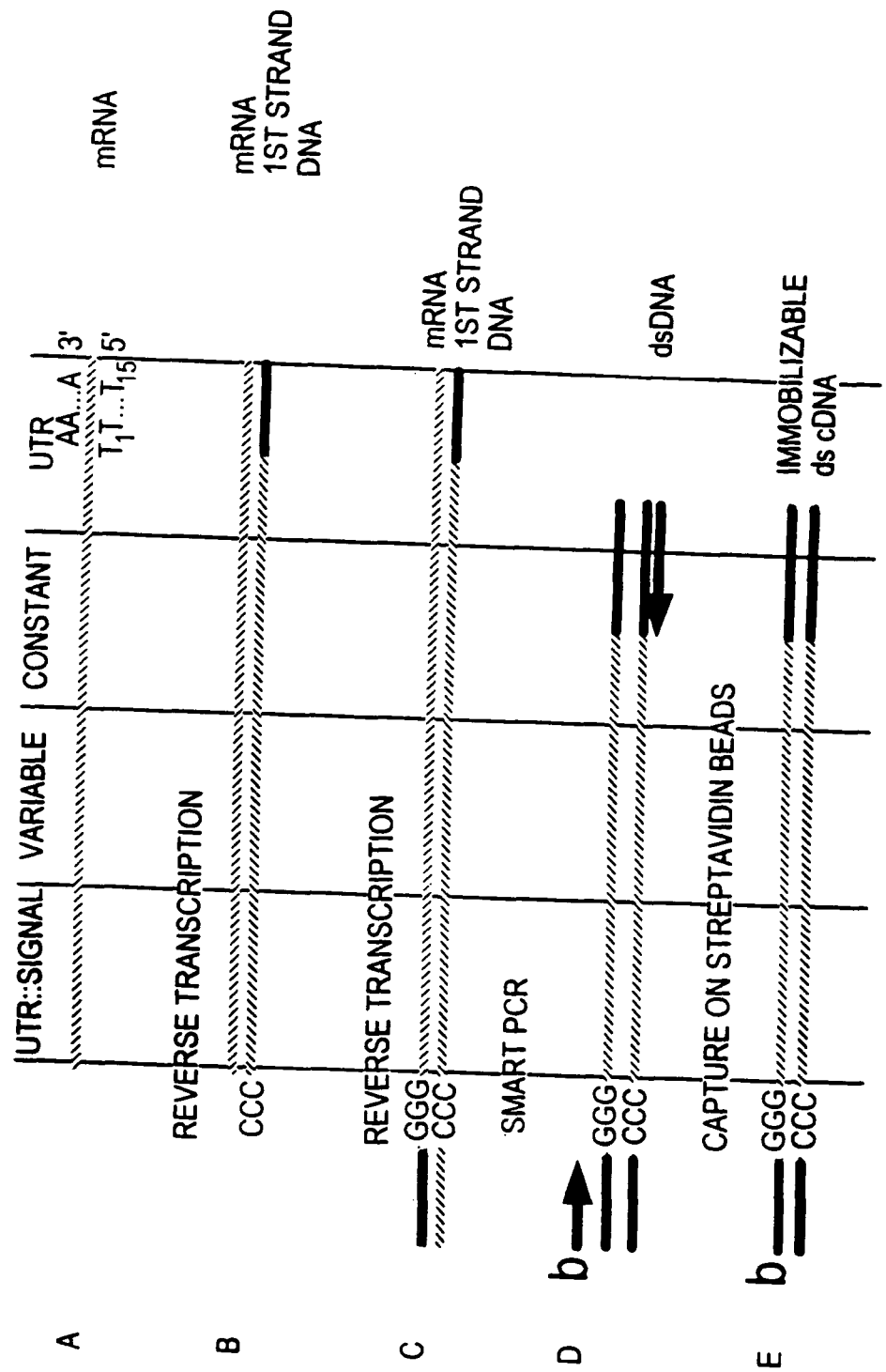
FIG. 1 is a schematic of various methods that may be employed to amplify VH genes without using primers specific for VH sequences. The $T_{15}$ oligonucleotide is shown in SEQ ID NO: 622.

In this application, the following terms and abbreviations are used:

| | |
|---|---|
| Sense strand | The upper strand of ds DNA as usually written. In the sense strand, 5-ATG-3' codes for Met. |

-continued

TERMS
In this application, the following terms and abbreviations are used:

| | |
|---|---|
| Antisense strand | The lower strand of ds DNA as usually written. In the antisense strand, 3'-TAC-5' would correspond to a Met codon in the sense strand. |
| Forward primer | A "forward" primer is complementary to a part of the sense strand and primes for synthesis of a new antisense-strand molecule. "Forward primer" and "lower-strand primer" are equivalent. |
| Backward primer | A "backward" primer is complementary to a part of the antisense strand and primes for synthesis of a new sense-strand molecule. "Backward primer" and "top-strand primer" are equivalent. |
| Bases | Bases are specified either by their position in a vector or gene as their position within a gene by codon and base. For example, "89.1" is the first base of codon 89, 89.2 is the second base of codon 89. |
| Sv | Streptavidin |
| Ap | Ampicillin |
| ap$^a$ | A gene conferring ampicillin resistance. |
| RERS | Restriction endonuclease recognition site |
| RE | Restriction endonuclease-cleaves preferentially at RERS |
| URE | Universal restriction endonuclease |
| Functionally complementary | Two sequences are sufficiently complementary so as to anneal under the chosen conditions. |
| AA | Amino acid |
| PCR | Polymerization chain reaction |
| GLGs | Germline genes |
| Ab | Antibody: an immunoglobin. The term also covers any protein having a binding domain which is homologous to an immunoglobin bindingdomain. A few examples of antibodies within this definition are, inter alia, immunoglobin isotypes and the Fab, F(ab$^1$)$_2$, scfv, Fv, dAb and Fd fragments. |
| Fab | Two chain molecule comprising an Ab light chain and part of a heavy-chain. |
| scFv | A single-chain Ab comprising either VH::linker::VL or VL::linker::VH |
| w.t. | Wild type |
| HC | Heavy chain |
| LC | Light chain |
| VK | A variable domain of a Kappa light chain. |
| VH | A variable domain of a heavy chain. |
| VL | A variable domain of a lambda light chain. |

In this application when it is said that nucleic acids are cleaved solely at the cleavage site of a restriction endonuclease, it should be understood that minor cleavage may occur at random, e.g., at non-specific sites other than the specific cleavage site that is characteristic of the restriction endonuclease. The skilled worker will recognize that such non-specific, random cleavage is the usual occurrence. Accordingly, "solely at the cleavage site" of a restriction endonuclease means that cleavage occurs preferentially at the site characteristic of that endonuclease.

As used in this application and claims, the term "cleavage site formed by the complementation of the nucleic acid and the single-stranded region of the oligonucleotide" includes cleavage sites formed by the single-stranded portion of the partially double-stranded oligonucleotide duplexing with the single-stranded DNA, cleavage sites in the double-stranded portion of the partially double-stranded oligonucleotide, and cleavage sites introduced by the amplification primer used to amplify the single-stranded DNA-partially double-stranded oligonucleotide combination.

In the two methods of this invention for preparing single-stranded nucleic acid sequences, the first of those cleavage sites is preferred. In the methods of this invention for capturing diversity and cloning a family of diverse nucleic acid sequences, the latter two cleavage sites are preferred.

In this application, all references referred to are specifically incorporated by reference.

DETAILED DESCRIPTION OF THE PREFERRED EMBODIMENTS

The nucleic acid sequences that are useful in the methods of this invention, i.e., those that encode at least in part the individual peptides, polypeptides and proteins displayed, or expressed in or comprising the libraries of this invention, may be native, synthetic or a combination thereof. They may be mRNA, DNA or cDNA. In the preferred embodiment, the nucleic acids encode antibodies. Most preferably, they encode Fabs.

The nucleic acids useful in this invention may be naturally diverse, synthetic diversity may be introduced into those naturally diverse members, or the diversity may be entirely synthetic. For example, synthetic diversity can be introduced into one or more CDRs of antibody genes. Preferably, it is introduced into CDR1 and CDR2 of immunoglobulins. Preferably, natural diversity is captured in the CDR3 regions of the immunoglogin genes of this invention from B cells. Most preferably, the nucleic acids of this invention comprise a population of immunoglobin genes that comprise synthetic diversity in at least one, and more preferably both of the CDR1 and CDR2 and diversity in CDR3 captured from B cells.

Synthetic diversity may be created, for example, through the use of TRIM technology (U.S. Pat. No. 5,869,644). TRIM technology allows control over exactly which amino-acid types are allowed at variegated positions and in what proportions. In TRIM technology, codons to be diversified are synthesized using mixtures of trinucleotides. This allows any set of amino acid types to be included in any proportion.

Another alternative that may be used to generate diversified DNA is mixed oligonucleotide synthesis. With TRIM technology, one could allow Ala and Trp. With mixed oligonucleotide synthesis, a mixture that included Ala and Trp would also necessarily include Ser and Gly. The amino-acid types allowed at the variegated positions are picked with reference to the structure of antibodies, or other peptides, polypeptides or proteins of the family, the observed diversity in germline genes, the observed somatic mutations frequently observed, and the desired areas and types of variegation.

In a preferred embodiment of this invention, the nucleic acid sequences for at least one CDR or other region of the peptides, polypeptides or proteins of the family are cDNAs produced by reverse transcription from mRNA. More preferably, the mRNAs are obtained from peripheral blood cells, bone marrow cells, spleen cells or lymph node cells (such as B-lymphocytes or plasma cells) that express members of naturally diverse sets of related genes. More preferable, the mRNAs encode a diverse family of antibodies. Most preferably, the mRNAs are obtained from patients suffering from at least one autoimmune disorder or cancer. Preferably, mRNAs containing a high diversity of autoimmune diseases, such as systemic lupus erythematosus, systemic sclerosis, rheumatoid arthritis, antiphospholipid syndrome and vasculitis are used.

In a preferred embodiment of this invention, the cDNAs are produced from the mRNAs using reverse transcription. In this preferred embodiment, the mRNAs are separated from the cell and degraded using standard methods, such that only the full length (i.e., capped) mRNAs remain. The cap is then removed and reverse transcription used to produce the cDNAs.

The reverse transcription of the first (antisense) strand can be done in any manner with any suitable primer. See, e.g., H J de Haard et al., *Journal of Biological Chemistry*, 274(26): 18218-30 (1999). In the preferred embodiment of this invention where the mRNAs encode antibodies, primers that are complementary to the constant regions of antibody genes may be used. Those primers are useful because they do not generate bias toward subclasses of antibodies. In another embodiment, poly-dT primers may be used (and may be preferred for the heavy-chain genes). Alternatively, sequences complementary to the primer may be attached to the termini of the antisense strand.

In one preferred embodiment of this invention, the reverse transcriptase primer may be biotinylated, thus allowing the cDNA product to be immobilized on streptavidin (Sv) beads. Immobilization can also be effected using a primer labeled at the 5' end with one of a) free amine group, b) thiol, c) carboxylic acid, or d) another group not found in DNA that can react to form a strong bond to a known partner on an insoluble medium. If, for example, a free amine (preferably primary amine) is provided at the 5' end of a DNA primer, this amine can be reacted with carboxylic acid groups on a polymer bead using standard amide-forming chemistry. If such preferred immobilization is used during reverse transcription, the top strand RNA is degraded using well-known enzymes, such as a combination of RNAseH and RNAseA, either before or after immobilization.

The nucleic acid sequences useful in the methods of this invention are generally amplified before being used to display and/or express the peptides, polypeptides or proteins that they encode. Prior to amplification, the single-stranded DNAs may be cleaved using either of the methods described before. Alternatively, the single-stranded DNAs may be amplified and then cleaved using one of those methods.

Any of the well known methods for amplifying nucleic acid sequences may be used for such amplification. Methods that maximize, and do not bias, diversity are preferred. In a preferred embodiment of this invention where the nucleic acid sequences are derived from antibody genes, the present invention preferably utilizes primers in the constant regions of the heavy and light chain genes and primers to a synthetic sequence that are attached at the 5' end of the sense strand. Priming at such synthetic sequence avoids the use of sequences within the variable regions of the antibody genes. Those variable region priming sites generate bias against V genes that are either of rare subclasses or that have been mutated at the priming sites. This bias is partly due to suppression of diversity within the primer region and partly due to lack of priming when many mutations are present in the region complementary to the primer. The methods disclosed in this invention have the advantage of not biasing the population of amplified antibody genes for particular V gene types.

The synthetic sequences may be attached to the 5' end of the DNA strand by various methods well known for ligating DNA sequences together. RT CapExtention is one preferred method.

In RT CapExtention (derived from Smart PCR™), a short overlap (5'- . . . GGG-3' in the upper-strand primer (USP-GGG) complements 3'-CCC . . . 5' in the lower strand) and reverse transcriptases are used so that the reverse complement of the upper-strand primer is attached to the lower strand.

Figure 2:
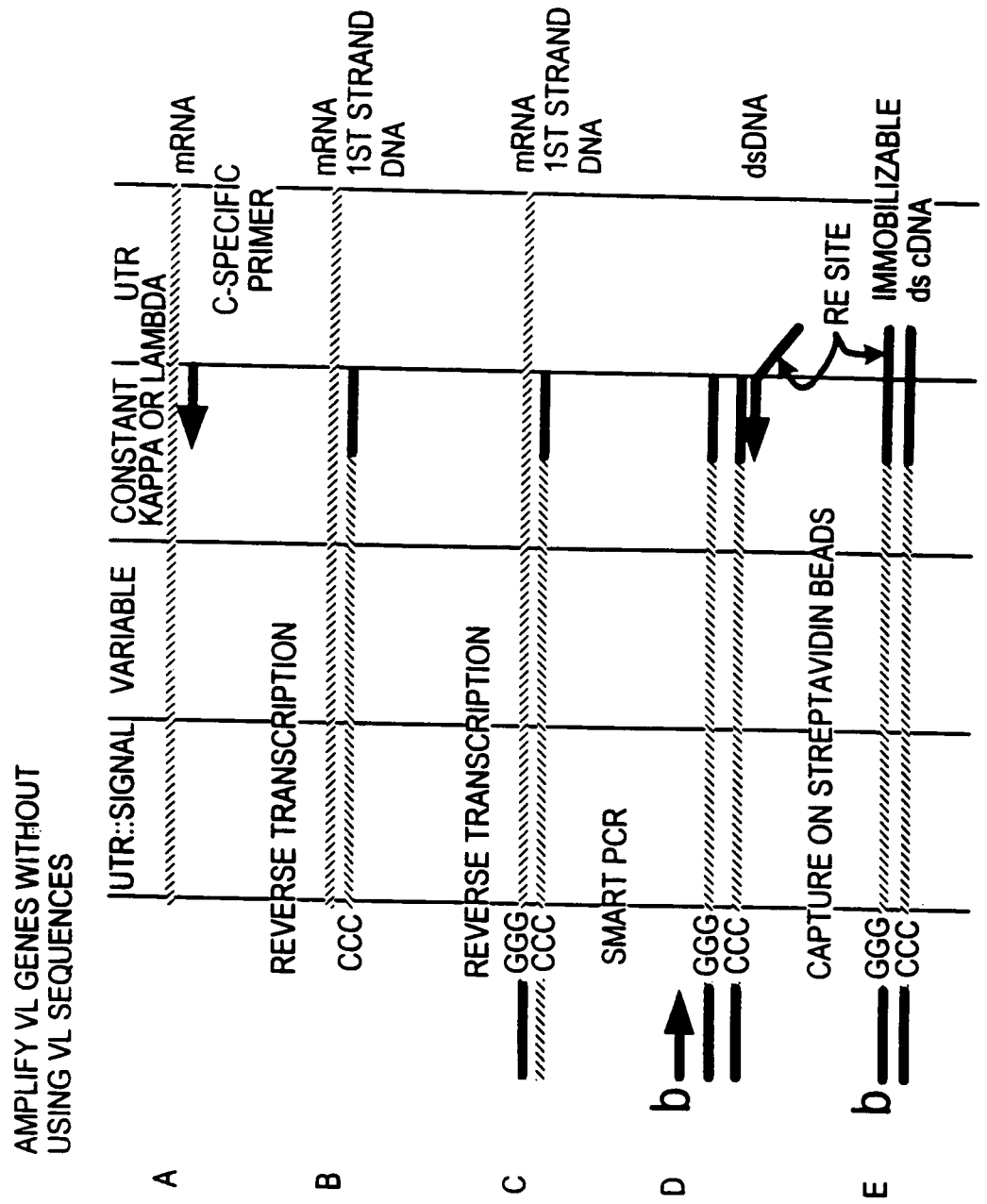
FIG. 2 is a schematic of various methods that may be employed to amplify VL genes without using primers specific for VL sequences.

FIGS. 1 and 2 show schematics to amplify VH and VL genes using RT CapExtention. FIG. 1 shows a schematic of the amplification of VH genes. FIG. 1, Panel A shows a primer specific to the poly-dT region of the 3' UTR priming synthesis of the first, lower strand. Primers that bind in the constant region are also suitable. Panel B shows the lower strand extended at its 3' end by three Cs that are not complementary to the mRNA. Panel C shows the result of annealing a synthetic top-strand primer ending in three GGGs that hybridize to the 3' terminal CCCs and extending the reverse transcription extending the lower strand by the reverse complement of the synthetic primer sequence. Panel D shows the result of PCR amplification using a 5' biotinylated synthetic top-strand primer that replicates the 5' end of the synthetic primer of panel C and a bottom-strand primer complementary to part of the constant domain. Panel E shows immobilized double-stranded (ds) cDNA obtained by using a 5'-biotinylated top-strand primer.

FIG. 2 shows a similar schematic for amplification of VL genes. FIG. 2, Panel A shows a primer specific to the constant region at or near the 3' end priming synthesis of the first, lower strand. Primers that bind in the poly-dT region are also suitable. Panel B shows the lower strand extended at its 3' end by three Cs that are not complementary to the mRNA. Panel C shows the result of annealing a synthetic top-strand primer ending in three GGGs that hybridize to the 3' terminal CCCs and extending the reverse transcription extending the lower strand by the reverse complement of the synthetic primer sequence. Panel D shows the result of PCR amplification using a 5' biotinylated synthetic top-strand primer that replicates the 5' end of the synthetic primer of panel C and a bottom-strand primer complementary to part of the constant domain. The bottom-strand primer also contains a useful restriction endonuclease site, such as AscI. Panel E shows immobilized ds cDNA obtained by using a 5'-biotinylated top-strand primer.

In FIGS. 1 and 2, each V gene consists of a 5' untranslated region (UTR) and a secretion signal, followed by the variable region, followed by a constant region, followed by a 3' untranslated region (which typically ends in poly-A). An initial primer for reverse transcription may be complementary to the constant region or to the polyA segment of the 3'-UTR. For human heavy-chain genes, a primer of 15 T is preferred. Reverse transcriptases attach several C residues to the 3' end of the newly synthesized DNA. RT CapExtention exploits this feature. The reverse transcription reaction is first run with only a lower-strand primer. After about 1 hour, a primer ending in GGG (USP-GGG) and more RTase are added. This causes the lower-strand cDNA to be extended by the reverse complement of the USP-GGG up to the final GGG. Using one primer identical to part of the attached synthetic sequence and a second primer complementary to a region of known sequence at the 3' end of the sense strand, all the V genes are amplified irrespective of their V gene subclass.

In another preferred embodiment, synthetic sequences may be added by Rapid Amplification of cDNA Ends (RACE) (see Frohman, M. A., Dush, M. K., & Martin, G. R. (1988) *Proc. Natl. Acad. Sci. USA* (85): 8998-9002).

FIG. 1 shows a schematic of RACE amplification of antibody heavy and light chains. First, mRNA is selected by treating total or poly(A+) RNA with calf intestinal phosphatase (CIP) to remove the 5'-phosphate from all molecules that have them such as ribosomal RNA, fragmented mRNA, tRNA and genomic DNA. Full length mRNA (containing a protective 7-methyl cap structure) is uneffected. The RNA is then treated with tobacco acid pyrophosphatase (TAP) to remove the cap structure from full length mRNAs leaving a 5'-monophosphate group. Next, a synthetic RNA adaptor is ligated to the RNA population, only molecules which have a 5-phosphate (uncapped, full length mRNAs) will accept the adaptor. Reverse trascriptase reactions using an oligodT primer, and nested PCR (using one adaptor primer (located in the 5' synthetic adaptor) and one primer for the gene) are then used to amplify the desired transcript.

In a preferred embodiment of this invention, the upper strand or lower strand primer may be also biotinylated or labeled at the 5' end with one of a) free amino group, b) thiol, c) carboxylic acid and d) another group not found in DNA that can react to form a strong bond to a known partner as an insoluble medium. These can then be used to immobilize the labeled strand after amplification. The immobilized DNA can be either single or double-stranded.

After amplification (using e.g., RT CapExtension or RACE), the DNAs of this invention are rendered single-stranded. For example, the strands can be separated by using a biotinylated primer, capturing the biotinylated product on streptavidin beads, denaturing the DNA, and washing away the complementary strand. Depending on which end of the captured DNA is wanted, one will choose to immobilize either the upper (sense) strand or the lower (antisense) strand.

To prepare the single-stranded amplified DNAs for cloning into genetic packages so as to effect display of, or for expression of, the peptides, polypeptides or proteins encoded, at least in part, by those DNAs, they must be manipulated to provide ends suitable for cloning and display and/or expression. In particular, any 5' untranslated regions and mammalian signal sequences must be removed and replaced, in frame, by a suitable signal sequence that functions in the display or expression host. Additionally, parts of the variable domains (in antibody genes) may be removed and replaced by synthetic segments containing synthetic diversity. The diversity of other gene families may likewise be expanded with synthetic diversity.

According to the methods of this invention, there are two ways to manipulate the single-stranded DNAs for display and/or expression. The first method comprises the steps of:
  (i) contacting the nucleic acid with a single-stranded oligonucleotide, the oligonucleotide being functionally complementary to the nucleic acid in the region in which cleavage is desired and including a sequence that with its complement in the nucleic acid forms a restriction endonuclease recognition site that on restriction results in cleavage of the nucleic acid at the desired location; and
  (ii) cleaving the nucleic acid solely at the recognition site formed by the complementation of the nucleic acid and the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

In this first method, short oligonucleotides are annealed to the single-stranded DNA so that restriction endonuclease recognition sites formed within the now locally double-stranded regions of the DNA can be cleaved. In particular, a recognition site that occurs at the same position in a substantial fraction of the single-stranded DNAs is identical.

For antibody genes, this can be done using a catalog of germline sequences. See, e.g., "http://www.mrc-cpe.cam.ac.uk/imt-doc/restricted/ok.html." Updates can be obtained from this site under the heading "Amino acid and nucleotide sequence alignments." For other families, similar comparisons exist and may be used to select appropriate regions for cleavage and to maintain diversity.

For example, Table 1 depicts the DNA sequences of the FR3 regions of the 51 known human VH germline genes. In this region, the genes contain restriction endonuclease recognition sites shown in Table 2. Restriction endonucleases that cleave a large fraction of germline genes at the same site are preferred over endonucleases that cut at a variety of sites. Furthermore, it is preferred that there be only one site for the restriction endonucleases within the region to which the short oligonucleotide binds on the single-stranded DNA, e.g., about 10 bases on either side of the restriction endonuclease recognition site.

An enzyme that cleaves downstream in FR3 is also more preferable because it captures fewer mutations in the framework. This may be advantageous is some cases. However, it is well known that framework mutations exist and confer and enhance antibody binding. The present invention, by choice of appropriate restriction site, allows all or part of FR3 diversity to be captured. Hence, the method also allows extensive diversity to be captured.

Finally, in the methods of this invention restriction endonucleases that are active between about 37° C. and about 75° C. are used. Preferably, restriction endonucleases that are active between about 45° C. and about 75° C. may be used. More preferably, enzymes that are active above 50° C., and most preferably active about 55° C., are used. Such temperatures maintain the nucleic acid sequence to be cleaved in substantially single-stranded form.

Enzymes shown in Table 2 that cut many of the heavy chain FR3 germline genes at a single position include: MaeIII (24@4), Tsp45I(21@4), HphI(44@5), BsaJI(23@65), AluI (23@47), BlpI(21@48), DdeI(29@58), BglII(10@61), MslI (44@72), BsiEI(23@74), EaeI(23@74), EagI(23@74), HaeIII(25@75), Bst4CI(51@86), HpyCH4III(51@B6), HinfI(38@2), MlyI(18@2), PleI(18@2), MnlI(31@67), HpyCH4V(21@44), BsmAI(16@11), BpmI(19@12), XmnI (12@30), and SacI(11@51). (The notation used means, for example, that BsmAI cuts 16 of the FR3 germline genes with a restriction endonuclease recognition site beginning at base 11 of FR3.)

For cleavage of human heavy chains in FR3, the preferred restriction endonucleases are: Bst4CI (or TaaI or HpyCH4III), BlpI, HpyCH4V, and MslI. Because ACNGT (the restriction endonuclease recognition site for Bst4CI, TaaI, and HpyCH4III) is found at a consistent site in all the human FR3 germline genes, one of those enzymes is the most preferred for capture of heavy chain CDR3 diversity. BlpI and HpyCH4V are complementary. BlpI cuts most members of the VH1 and VH4 families while HpyCH4V cuts most members of the VH3, VH5, VH6, and VH7 families. Neither enzyme cuts VH2s, but this is a very small family, containing only three members. Thus, these enzymes may also be used in preferred embodiments of the methods of this invention.

The restriction endonucleases HpyCH4III, Bst4CI, and TaaI all recognize 5'-ACnGT-3' and cut upper strand DNA after n and lower strand DNA before the base complementary to n. This is the most preferred restriction endonuclease recognition site for this method on human heavy chains because it is found in all germline genes. Furthermore, the restriction endonuclease recognition region (ACnGT) matches the second and third bases of a tyrosine codon (<u>tay</u>) and the following cysteine codon (<u>tgy</u>) as shown in Table 3. These codons are highly conserved, especially the cysteine in mature antibody genes.

Table 4 E shows the distinct oligonucleotides of length 22 (except the last one which is of length 20) bases. Table 5 C shows the analysis of 1617 actual heavy chain antibody genes. Of these, 1511 have the site and match one of the candidate oligonucleotides to within 4 mismatches. Eight oligonucleotides account for most of the matches and are given in Table 4 F.1. The 8 oligonucleotides are very similar so that it is likely that satisfactory cleavage will be achieved with only one oligonucleotide (such as H43.77.97.1-02#1) by adjusting temperature, pH, salinity, and the like. One or two oligonucleotides may likewise suffice whenever the germline gene sequences differ very little and especially if they differ very little close to the restriction endonuclease recognition region to be cleaved. Table 5 D shows a repeat analysis of 1617 actual heavy chain antibody genes using only the 8 chosen oligonucleotides. This shows that 1463 of the sequences match at least one of the oligonucleotides to within 4 mismatches and have the site as expected. Only 7 sequences have a second HpyCH4III restriction endonuclease recognition region in this region.

Another illustration of choosing an appropriate restriction endonuclease recognition site involves cleavage in FR1 of human heavy chains. Cleavage in FR1 allows capture of the entire CDR diversity of the heavy chain.

The germline genes for human heavy chain FR1 are shown in Table 6. Table 7 shows the restriction endonuclease recognition sites found in human germline genes FR1s. The preferred sites are BsgI(GTGCAG; 39@4), BsoFI(GCngc; 43@6, 11@9, 2@3, 1@12), TseI(Gcwgc; 43@6, 11@9, 2@3, 1@12), MspAII (CMGckg; 46@7, 2@1), PvuII (CAGctg; 46@7, 2@1), AluI(AGct; 48@82@2), DdeI(Ctnag; 22@52, 9@48), HphI(tcacc; 22@80), BssKI(Nccngg; 35@39, 2@40), BsaJI(Ccnngg; 32@40, 2@41), BstNI(C-Cwgg; 33@40), ScrFI(CCngg; 35@40, 2@41), EcoO109I (RGgnccy; 22@46, 11@43), Sau96I(Ggncc; 23@47, 11@44), AvaII(Ggwcc; 23@47, 4@44), PpuMI(RGgwccy; 22@46, 4@43), BsmFI(gtccc; 20@48), HinfI(Gantc; 34@16, 21@56, 21@77), TfiI(21@77), MlyI(GAGTC; 34@16), MlyI(gactc; 21@56), and AlwNI(CAGnnnctg; 22@68). The more preferred sites are MspAI and PvuII. MspAI and PvuII have 46 sites at 7-12 and 2 at 1-6. To avoid cleavage at both sites, oligonucleotides are used that do not fully cover the site at 1-6. Thus, the DNA will not be cleaved at that site. We have shown that DNA that extends 3, 4, or 5 bases beyond a PvuII-site can be cleaved efficiently.

Another illustration of choosing an appropriate restriction endonuclease recognition site involves cleavage in FR1 of human kappa light chains. Table 8 shows the human kappa FR1 germline genes and Table 9 shows restriction endonuclease recognition sites that are found in a substantial number of human kappa FR1 germline genes at consistent locations. Of the restriction endonuclease recognition sites listed, BsmAI and PflFI are the most preferred enzymes. BsmAI sites are found at base 18 in 35 of 40 germline genes. PflFI sites are found in 35 of 40 germline genes at base 12.

Another example of choosing an appropriate restriction endonuclease recognition site involves cleavage in FR1 of the human lambda light chain. Table shows the 31 known human lambda FR1 germline gene sequences. Table 11 shows restriction endonuclease recognition sites found in human lambda FR1 germline genes. HinfI and DdeI are the most preferred restriction endonucleases for cutting human lambda chains in FR1.

After the appropriate site or sites for cleavage are chosen, one or more short oligonucleotides are prepared so as to functionally complement, alone or in combination, the chosen recognition site. The oligonucleotides also include sequences that flank the recognition site in the majority of the amplified genes. This flanking region allows the sequence to anneal to the single-stranded DNA sufficiently to allow cleavage by the restriction endonuclease specific for the site chosen.

The actual length and sequence of the oligonucleotide depends on the recognition site and the conditions to be used for contacting and cleavage. The length must be sufficient so that the oligonucleotide is functionally complementary to the single-stranded DNA over a large enough region to allow the two strands to associate such that cleavage may occur at the chosen temperature and at the desired location.

Typically, the oligonucleotides of this preferred method of the invention are about 17 to about nucleotides in length. Below about 17 bases, annealing is too weak and above 30 bases there can be a loss of specificity. A preferred length is 18 to 24 bases.

Oligonucleotides of this length need not be identical complements of the germline genes. Rather, a few mismatches taken may be tolerated. Preferably, however, no more than 1-3 mismatches are allowed. Such mismatches do not adversely affect annealing of the oligonucleotide to the single-stranded DNA. Hence, the two DNAs are said to be functionally complementary.

The second method to manipulate the single-stranded DNAs of this invention for display and/or expression comprises the steps of:

(i) contacting the nucleic acid with a partially double-stranded oligonucleotide, the single-stranded region of the oligonucleotide being functionally complementary to the nucleic acid in the region in which cleavage is desired, and the double-stranded region of the oligonucleotide having a restriction endonuclease recognition site; and (ii) cleaving the nucleic acid solely at the cleavage site formed by the complementation of the nucleic acid and the single-stranded region of the oligonucleotide;

the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleaving being carried out using a restriction endonuclease that is active at the chosen temperature.

As explained above, the cleavage site may be formed by the single-stranded portion of the partially double-stranded oligonucleotide duplexing with the single-stranded DNA, the cleavage site may be carried in the double-stranded portion of the partially double-stranded oligonucleotide, or the cleavage site may be introduced by the amplification primer used to amplify the single-stranded DNA-partially double-stranded oligonucleotide combination. In this embodiment, the first is preferred. And, the restriction endonuclease recognition site may be located in either the double-stranded portion of the oligonucleotide or introduced by the amplification primer, which is complementary to that double-stranded region, as used to amplify the combination.

Preferably, the restriction endonuclease site is that of a Type II-S restriction endonuclease, whose cleavage site is located at a known distance from its recognition site.

This second method, preferably, employs Universal Restriction Endonucleases ("URE"). UREs are partially double-stranded oligonucleotides. The single-stranded portion or overlap of the URE consists of a DNA adapter that is functionally complementary to the sequence to be cleaved in the single-stranded DNA. The double-stranded portion consists of a restriction endonuclease recognition site, preferably type II-S.

The URE method of this invention is specific and precise and can tolerate some (e.g., 1-3) mismatches in the complementary regions, i.e., it is functionally complementary to that region. Further, conditions under which the URE is used can be adjusted so that most of the genes that are amplified can be cut, reducing bias in the library produced from those genes.

The sequence of the single-stranded DNA adapter or overlap portion of the URE typically consists of about 14-22 bases. However, longer or shorter adapters may be used. The size depends on the ability of the adapter to associate with its functional complement in the single-stranded DNA and the temperature used for contacting the URE and the single-stranded DNA at the temperature used for cleaving the DNA with the restriction enzyme. The adapter must be functionally complementary to the single-stranded DNA over a large enough region to allow the two strands to associate such that the cleavage may occur at the chosen temperature and at the desired location. We prefer singe-stranded or overlap portions of 14-17 bases in length, and more preferably 18-20 bases in length.

The site chosen for cleavage using the URE is preferably one that is substantially conserved in the family of amplified DNAs. As compared to the first cleavage method of this invention, these sites do not need to be endonuclease recognition sites. However, like the first method, the sites chosen can be synthetic rather than existing in the native DNA. Such sites may be chosen by reference to the sequences of known antibodies or other families of genes. For example, the sequences of many germline genes are reported at mrc-cpe.cam.ac.uk/imtdoc/restricted./ok.html. For example, one preferred site occurs near the end of FR3—codon 89 through the second base of codon 93. CDR3 begins at codon 95.

The sequences of 79 human heavy-chain genes are also available at ncbi.nlm.nih.gov/entre2/nucleotide.html. This site can be used to identify appropriate sequences for URE cleavage according to the methods of this invention, See, e.g., Table 12B.

Most preferably, one or more sequences are identified using these sites or other available sequence information. These sequences together are present in a substantial fraction of the amplified DNAs. For example, multiple sequences could be used to allow for known diversity in germline genes or for frequent somatic mutations. Synthetic degenerate sequences could also be used. Preferably, a sequence(s) that occurs in at least 65% of genes examined with no more than 2-3 mismatches is chosen URE single-stranded adapters or overlaps are then made to be complementary to the chosen regions. Conditions for using the UREs are determined empirically. These conditions should allow cleavage of DNA that contains the functionally complementary sequences with no more than 2 or 3 mismatches but that do not allow cleavage of DNA lacking such sequences.

As described above, the double-stranded portion of the URE includes an endonuclease recognition site, preferably a Type II-S recognition site. Any enzyme that is active at a temperature necessary to maintain the single-stranded DNA substantially in that form and to allow the single-stranded DNA adapter portion of the URE to anneal long enough to the single-stranded DNA to permit cleavage at the desired site may be used.

The preferred Type II-S enzymes for use in the URE methods of this invention provide asymmetrical cleavage of the single-stranded DNA. Among these are the enzymes listed in Table 13. The most preferred Type II-S enzyme is FokI.

When the preferred FokI containing URE is used, several conditions are preferably used to effect cleavage:

1). Excess of the URE over target. DNA should be present to activate the enzyme. URE present only in equimolar amounts to the target DNA would yield poor cleavage of ssDNA because the amount of active enzyme available would be limiting.

2) An activator may be used to activate part of the FokI enzyme to dimerize without causing cleavage. Examples of appropriate activators are shown in Table 14.

3) The cleavage reaction is performed at a temperature between 45°-75° C., preferably above 50° C. and most preferably above 55° C.

The UREs used in the prior art contained a 14-base single-stranded segment, a 10-base stem (containing a FokI site), followed by the palindrome of the 10-base stem. While such UREs may be used in the methods of this invention, the preferred UREs of this invention also include a segment of three to eight bases (a loop) between the FokI restriction endonuclease recognition site containing segments. In the preferred embodiment, the stem (containing the FokI site) and its palindrome are also longer than 10 bases. Preferably, they are 10-14 bases in length. Examples of these "lollipop" URE adapters are shown in Table 15.

One example of using a URE to cleave an single-stranded DNA involves the FR3 region of human heavy chain. Table 16 shows an analysis of 840 full-length mature human heavy chains with the URE recognition sequences shown. The vast majority (718/840=0.85) will be recognized with 2 or fewer mismatches using five UREs (VHS881-1.1, VHS881-1.2, VHS881-2.1, VHS881-4.1, and VHS881-9.1). Each has a 20-base adaptor sequence to complement the germline gene, a ten-base stem segment containing a FokI site, a five base loop, and the reverse complement of the first stem segment. Annealing those adapters, alone or in combination, to single-stranded antisense heavy chain DNA and treating with FokI in the presence of, e.g., the activator FOKIact, will lead to cleavage of the antisense strand at the position indicated.

Another example of using a URE(s) to cleave a single-stranded DNA involves the FR1 region of the human Kappa light chains. Table 17 shows an analysis of 182 full-length human kappa chains for matching by the four 19-base probe sequences shown. Ninety-six percent of the sequences match one of the probes with 2 or fewer mismatches. The URE adapters shown in Table 17 are for cleavage of the sense strand of kappa chains. Thus, the adaptor sequences are the reverse complement of the germline gene sequences. The URE consists of a ten-base stem, a five base loop, the reverse complement of the stem and the complementation sequence. The loop shown here is TTGTT, but other sequences could be used. Its function is to interrupt the palindrome of the stems so that formation of a lollypop monomer is favored over dimerization. Table 17 also shows where the sense strand is cleaved.

Another example of using a URE to cleave a single-stranded DNA involves the human lambda light chain. Table 18 shows analysis of 128 human lambda light chains for matching the four 19-base probes shown. With three or fewer mismatches, 88 of 128 (69%) of the chains match one of the probes. Table 18 also shows URE adapters corresponding to these probes. Annealing these adapters to upper-strand ssDNA of lambda chains and treatment with FokI in the presence of FOKIact at a temperature at or above 45° C. will lead to specific and precise cleavage of the chains.

The conditions under which the short oligonucleotide sequences of the first method and the UREs of the second method are contacted with the single-stranded DNAs may be empirically determined. The conditions must be such that the single-stranded DNA remains in substantially single-stranded form. More particularly, the conditions must be such that the single-stranded DNA does not form loops that may interfere with its association with the oligonucleotide sequence or the URE or that may themselves provide sites for cleavage by the chosen restriction endonuclease.

The effectiveness and specificity of short oligonucleotides (first method) and UREs (second method) can be adjusted by controlling the concentrations of the URE adapters/oligonucleotides and substrate DNA, the temperature, the pH, the concentration of metal ions, the ionic strength, the concentration of chaotropes (such as urea and formamide), the concentration of the restriction endonuclease (e.g., FokI), and the time of the digestion. These conditions can be optimized with synthetic oligonucleotides having: 1) target germline gene sequences, 2) mutated target gene sequences, or 3) somewhat related non-target sequences. The goal is to cleave most of the target sequences and minimal amounts of non-targets.

In accordance with this invention, the single-stranded DNA is maintained in substantially that form using a temperature between about 37° C. and about 75° C. Preferably, a temperature between about 45° C. and about 75° C. is used. More preferably, a temperature between 50° C. and 60° C., most preferably between 55° C. and 60° C., is used. These temperatures are employed both when contacting the DNA with the oligonucleotide or URE and when cleaving the DNA using the methods of this invention.

The two cleavage methods of this invention have several advantages. The first method allows the individual members of the family of single-stranded DNAs to be cleaved preferentially at one substantially conserved endonuclease recognition site. The method also does not require an endonuclease recognition site to be built into the reverse transcription or amplification primers. Any native or synthetic site in the family can be used.

The second method has both of these advantages. In addition, the preferred URE method allows the single-stranded DNAs to be cleaved at positions where no endonuclease recognition site naturally occurs or has been synthetically constructed.

Most importantly, both cleavage methods permit the use of 5' and 3' primers so as to maximize diversity and then cleavage to remove unwanted or deleterious sequences before cloning, display and/or expression.

After cleavage of the amplified DNAs using one of the methods of this invention, the DNA is prepared for cloning, display and/or expression. This is done by using a partially duplexed synthetic DNA adapter, whose terminal sequence is based on the specific cleavage site at which the amplified DNA has been cleaved.

The synthetic DNA is designed such that when it is ligated to the cleaved single-stranded DNA in proper reading frame so that the desired peptide, polypeptide or protein can be displayed on the surface of the genetic package and/or expressed. Preferably, the double-stranded portion of the adapter comprises the sequence of several codons that encode the amino acid sequence characteristic of the family of peptides, polypeptides or proteins up to the cleavage site. For human heavy chains, the amino acids of the 3-23 framework are preferably used to provide the sequences required for expression of the cleaved DNA.

Preferably, the double-stranded portion of the adapter is about 12 to 100 bases in length. More preferably, about 20 to 100 bases are used. The double-standard region of the adapter also preferably contains at least one endonuclease recognition site useful for cloning the DNA into a suitable display and/or expression vector (or a recipient vector used to archive the diversity). This endonuclease restriction site may be native to the germline gene sequences used to extend the DNA sequence. It may be also constructed using degenerate sequences to the native germline gene sequences. Or, it may be wholly synthetic.

The single-stranded portion of the adapter is complementary to the region of the cleavage in the single-stranded DNA. The overlap can be from about 2 bases up to about 15 bases. The longer the overlap, the more efficient the ligation is likely to be. A preferred length for the overlap is 7 to 10. This allows some mismatches in the region so that diversity in this region may be captured.

The single-stranded region or overlap of the partially duplexed adapter is advantageous because it allows DNA cleaved at the chosen site, but not other fragments to be captured. Such fragments would contaminate the library with genes encoding sequences that will not fold into proper antibodies and are likely to be non-specifically sticky.

One illustration of the use of a partially duplexed adaptor in the methods of this invention involves ligating such adaptor to a human FR3 region that has been cleaved, as described above, at 5'-ACnGT-3' using HpyCH4III, Bst4CI or TaaI.

Table 4 F.2 shows the bottom strand of the double-stranded portion of the adaptor for ligation to the cleaved bottom-strand DNA. Since the HpyCH4III-Site is so far to the right (as shown in Table 3), a sequence that includes the AflII-site as well as the XbaI site can be added. This bottom strand portion of the partially-duplexed adaptor, H43.XAExt, incorporates both XbaI and AflII-sites. The top strand of the double-stranded portion of the adaptor has neither site (due to planned mismatches in the segments opposite the XbaI and AflII-Sites of H43.XAExt), but will anneal very tightly to H43.XAExt. H43AExt contains only the AflII-site and is to be used with the top strands H43.ABr1 and H43.ABr2 (which have intentional alterations to destroy the AflII-site).

After ligation, the desired, captured DNA can be PCR amplified again, if desired, using in the preferred embodiment a primer to the downstream constant region of the antibody gene and a primer to part of the double-standard region of the adapter. The primers may also carry restriction endonuclease sites for use in cloning the amplified DNA.

After ligation, and perhaps amplification, of the partially double-stranded adapter to the single-stranded amplified DNA, the composite DNA is cleaved at chosen 5' and 3' endonuclease recognition sites.

The cleavage sites useful for cloning depend on the phage or phagemid or other vectors into which the cassette will be inserted and the available sites in the antibody genes. Table 19 provides restriction endonuclease data for 75 human light chains. Table 20 shows corresponding data for 79 human heavy chains. In each Table, the endonucleases are ordered by increasing frequency of cutting. In these Tables, Nch is the number of chains cut by the enzyme and Ns is the number of sites (some chains have more than one site).

From this analysis, SfiI, NotI, AflII, ApaLI, and AscI are very suitable. SfiI and NotI are preferably used in pCES1 to insert the heavy-chain display segment. ApaLI and AscI are preferably used in pCES1 to insert the light-chain display segment.

BstEII-sites occur in 97% of germ-line JH genes. In rearranged V genes, only 54/79 (68%) of heavy-chain genes contain a BstEII-Site and 7/61 of these contain two sites. Thus, 47/79 (59%) contain a single BstEII-Site. An alternative to using BstEII is to cleave via UREs at the end of JH and ligate to a synthetic oligonucleotide that encodes part of CH1.

One example of preparing a family of DNA sequences using the methods of this invention involves capturing human CDR 3 diversity. As described above, mRNAs from various autoimmune patients are reverse transcribed into lower strand cDNA. After the top strand RNA is degraded, the lower strand is immobilized and a short oligonucleotide used to cleave the cDNA upstream of CDR3. A partially duplexed synthetic DNA adapter is then annealed to the DNA and the DNA is amplified using a primer to the adapter and a primer to the constant region (after FR4). The DNA is then cleaved using BstEII (in FR4) and a restriction endonuclease appropriate to the partially double-stranded adapter (e.g., XbaI and AflII (in FR3)). The DNA is then ligated into a synthetic VH skeleton such as 3-23.

One example of preparing a single-stranded DNA that was cleaved using the URE method involves the human Kappa chain. The cleavage site in the sense strand of this chain is depicted in Table 17. The oligonucleotide kapextURE is annealed to the oligonucleotides (kaBR01UR, kaBR02UR, kaBR03UR, and kaBR04UR) to form a partially duplex DNA. This DNA is then ligated to the cleaved soluble kappa chains. The ligation product is then amplified using primers kapextUREPCR and CKForeAsc (which inserts a AscI site after the end of C kappa). This product is then cleaved with ApaLI and AscI and ligated to similarly cut recipient vector.

Another example involves the cleavage of lambda light chains, illustrated in Table 18. After cleavage, an extender (ON_LamEx133) and four bridge oligonucleotides (ON_LamB1-133, ON_LamB2-133, ON_LamB3-133, and ON_LamB4-133) are annealed to form a partially duplex. DNA. That DNA is ligated to the cleaved lambda-chain sense strands. After ligation, the DNA is amplified with ON_Lam133PCR and a forward primer specific to the lambda constant domain, such as CL2ForeAsc or CL7ForeAsc (Table 130).

In human heavy chains, one can cleave almost all genes in FR4 (downstream, i.e., toward the 3' end of the sense strand, of CDR3) at a BstEII-Site that occurs at a constant position in a very large fraction of human heavy-chain V genes. One then needs a site in FR3, if only CDR3 diversity is to be captured, in FR2, if CDR2 and CDR3 diversity is wanted, or in FR1, if all the CDR diversity is wanted. These sites are preferably inserted as part of the partially double-stranded adaptor.

The preferred process of this invention is to provide recipient vectors (e.g., for display and/or expression) having sites that allow cloning of either light or heavy chains. Such vectors are well known and widely used in the art. A preferred phage display vector in accordance with this invention is phage MALIA3. This displays in gene III. The sequence of the phage MALIA3 is shown in Table 21A (annotated) and Table 21B (condensed).

The DNA encoding the selected regions of the light or heavy chains can be transferred to the vectors using endonucleases that cut either light or heavy chains only very rarely. For example, light chains may be captured with ApaLI and AscI. Heavy-chain genes are preferably cloned into a recipient vector having SfiI, NcoI, XbaI, AflII, BstEII, ApaI, and NotI sites. The light chains are preferably moved into the library as ApaLI-AscI fragments. The heavy chains are preferably moved into the library as SfiI-NotI fragments.

Most preferably, the display is had on the surface of a derivative of M13 phage. The most preferred vector contains all the genes of M13, an antibiotic resistance gene, and the display cassette. The preferred vector is provided with restriction sites that allow introduction and excision of members of the diverse family of genes, as cassettes. The preferred vector is stable against rearrangement under the growth conditions used to amplify phage.

In another embodiment of this invention, the diversity captured by the methods of the present invention may be displayed and/or expressed in a phagemid vector (e.g., pCES1) that displays and/or expresses the peptide, polypeptide or protein. Such vectors may also be used to store the diversity for subsequent display and/or expression using other vectors or phage.

In another embodiment of this invention, the diversity captured by the methods of the present invention may be displayed and/or expressed in a yeast vector.

In another embodiment, the mode of display may be through a short linker to anchor domains—one possible anchor comprising the final portion of M13 III ("IIIstump") and a second possible anchor being the full length III mature protein.

The IIIstump fragment contains enough of M13 III to assemble into phage but not the domains involved in mediating infectivity. Because the w.t. III proteins are present the phage is unlikely to delete the antibody genes and phage that do delete these segments receive only a very small growth advantage. For each of the anchor domains, the DNA encodes the w.t. AA sequence, but differs from the w.t. DNA sequence to a very high extent. This will greatly reduce the potential for homologous recombination between the anchor and the w.t. gene that is also present (see Example 6).

Most preferably, the present invention uses a complete phage carrying an antibiotic-resistance gene (such as an ampicillin-resistance gene) and the display cassette. Because the w.t. iii and possibly viii genes are present, the w.t. proteins are also present. The display cassette is transcribed from a regulatable promoter (e.g., $P_{LacZ}$). Use of a regulatable promoter allows control of the ratio of the fusion display gene to the corresponding w.t. coat protein. This ratio determines the average number of copies of the display fusion per phage (or phagemid) particle.

Another aspect of the invention is a method of displaying peptides, polypeptides or proteins (and particularly Fabs) on filamentous phage. In the most preferred embodiment this method displays FABs and comprises:

a) obtaining a cassette capturing a diversity of segments of DNA encoding the elements:

$P_{reg}$::RBS1::SS1::VL::CL::stop::RBS2::SS2::VH::CH1::linker::anchor::stop::, where $P_{reg}$ is a regulatable promoter, RBS1 is a first ribosome binding site, SS1 is a signal sequence operable in the host strain, VL is a member of a diverse set of light-chain variable regions, CL is a light-chain constant region, stop is one or more stop codons, RBS2 is a second ribosome binding site, SS2 is a second signal sequence operable in the host strain, VH is a member of a diverse set of heavy-chain variable regions, CH1 is an antibody heavy-chain first constant domain, linker is a sequence of amino acids of one to about 50 residues, anchor is a protein that will assemble into the filamentous phage particle and stop is a second example of one or more stop codons; and b) positioning that cassette within the phage genome to maximize the viability of the phage and to minimize the potential for deletion of the cassette or parts thereof.

The DNA encoding the anchor protein in the above preferred cassette should be designed to encode the same (or a closely related) amino acid sequence as is found in one of the coat proteins of the phage, but with a distinct DNA sequence. This is to prevent unwanted homologous recombination with the w.t. gene. In addition, the cassette should be placed in the intergenic region. The positioning and orientation of the display cassette can influence the behavior of the phage.

In one embodiment of the invention, a transcription terminator may be placed after the second stop of the display cassette above (e.g., Trp). This will reduce interaction between the display cassette and other genes in the phage antibody display vector.

In another embodiment of the methods of this invention, the phage or phagemid can display and/or express proteins other than Fab, by replacing the Fab portions indicated above, with other protein genes.

Various hosts can be used the display and/or expression aspect of this invention. Such hosts are well known in the art. In the preferred embodiment, where Fabs are being displayed and/or expressed, the preferred host should grow at 30° C. and be RecA⁻ (to reduce unwanted genetic recombination) and EndA⁻ (to make recovery of RF DNA easier). It is also preferred that the host strain be easily transformed by electroporation.

XL1-Blue MRF' satisfies most of these preferences, but does not grow well at 30° C. XL1-Blue MRF' does grow slowly at 38° C. and thus is an acceptable host. TG-1 is also an acceptable host although it is RecA⁺ and EndA⁺. XL1-Blue MRF' is more preferred for the intermediate host used to accumulate diversity prior to final construction of the library.

After display and/or expression, the libraries of this invention may be screened using well known and conventionally used techniques. The selected peptides, polypeptides or proteins may then be used to treat disease. Generally, the peptides, polypeptides or proteins for use in therapy or in pharmaceutical compositions are produced by isolating the DNA encoding the desired peptide, polypeptide or protein from the member of the library selected. That DNA is then used in conventional methods to produce the peptide, polypeptides or protein it encodes in appropriate host cells, preferably mammalian host cells, e.g., CHO cells. After isolation, the peptide, polypeptide or protein is used alone or with pharmaceutically acceptable compositions in therapy to treat disease.

EXAMPLES

Example 1

RACE Amplification of Heavy and Light Chain Antibody Repertoires from Autoimmune Patients Total RNA was isolated from individual blood samples (50 ml) of 11 patients using a RNAzol™ kit (CINNA/Biotecx), as described by the manufacturer. The patients were diagnosed as follows:
1. SLE and phospholipid syndrome
2. limited systemic sclerosis
3. SLE and Sjogren syndrome
4. Limited Systemic sclerosis
5. Reumatoid Arthritis with active vasculitis
6. Limited systemic sclerosis and Sjogren Syndrome
7. Reumatoid Artritis and (not active) vasculitis
8. SLE and Sjogren syndrome
9. SLE
10. SLE and (active) glomerulonephritis
11. Polyarthritis/Raynauds Phenomen From these 11 samples of total RNA, Poly-A+ RNA was isolated using Promega PolyATtract® mRNA Isolation kit (Promega).

Figure 3:
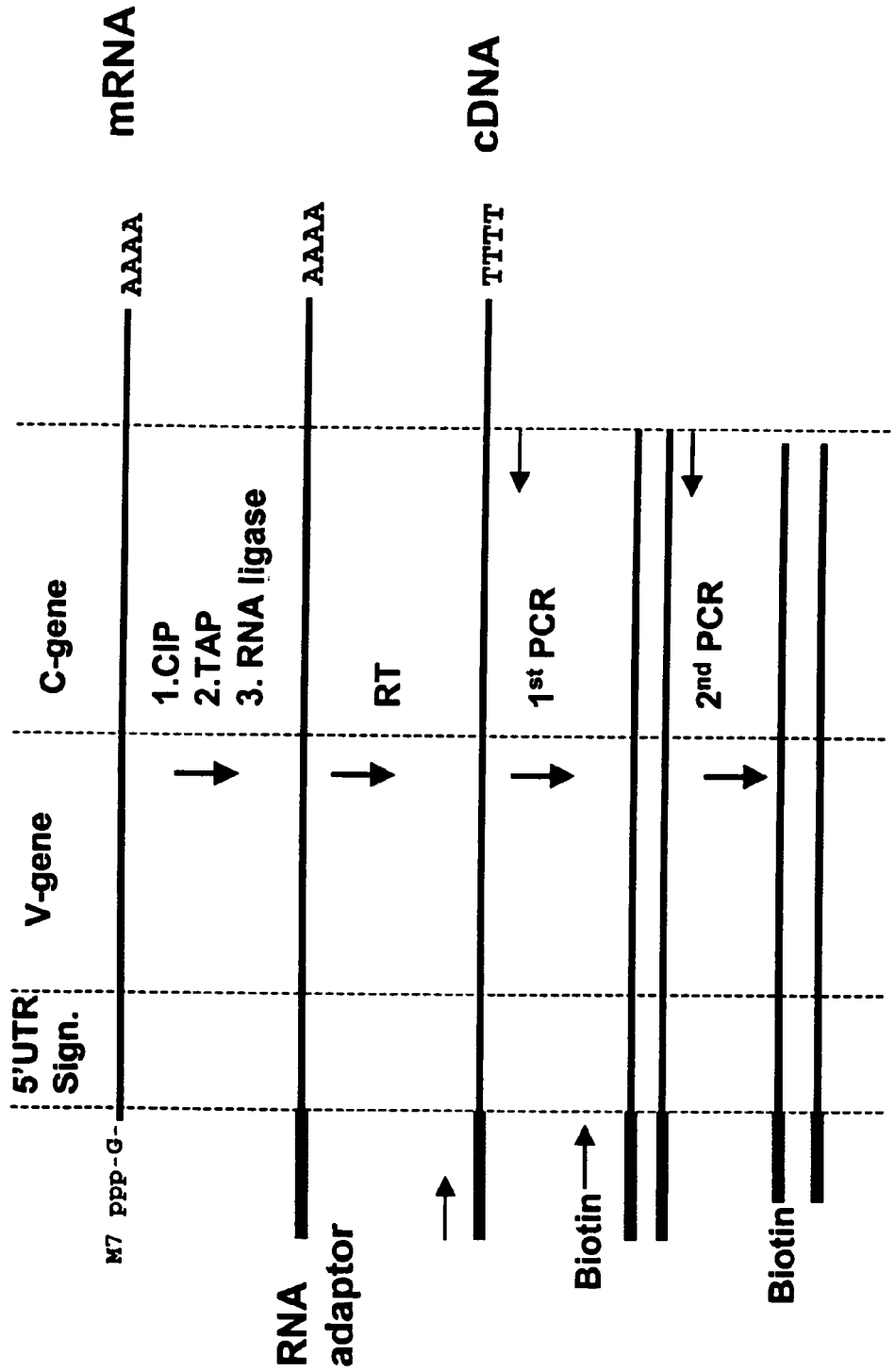
FIG. 3 is a schematic of RACE amplification of antibody heavy and light chains.

250 ng of each poly-A+ RNA sample was used to amplify antibody heavy and light chains with the GeneRAacer™ kit (Invitrogen cat no. L1500-01). A schematic overview of the RACE procedure is shown in FIG. 3.

Using the general protocol of the GeneRAacer™ kit, an RNA adaptor was ligated to the 5' end of all mRNAs. Next, a reverse transcriptase reaction was performed in the presence of oligo(dT15) specific primer under conditions described by the manufacturer in the GeneRAacer™ kit.

⅕ of the cDNA from the reverse transcriptase reaction was used in a 20 ul PCR reaction. For amplification of the heavy chain IgM repertoire, a forward primer based on the CH1 chain of IgM (HuCmFOR) and a backward primer based on the ligated synthetic adaptor sequence [5'A] were used. (See Table 22)

For amplification of the kappa and lambda light chains, a forward primer that contains the 3' coding-end of the cDNA [HuCkFor and HuCLFor2+HuCLfor7] and a backward primer based on the ligated synthetic adapter sequence [5'A] was used (See Table 22). Specific amplification products after 30 cycles of primary PCR were obtained.

Figure 4:
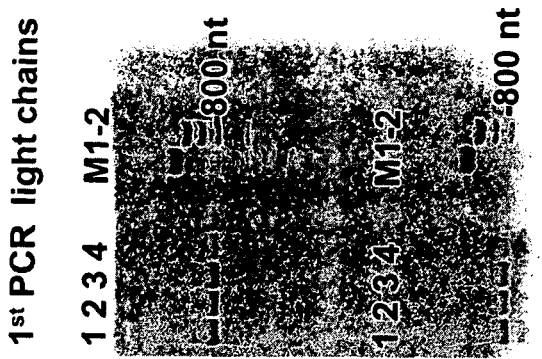
FIG. 4 depicts gel analysis of amplification products obtained after the primary PCR reaction from 4 different patient samples.
Figure 4:
Figure 4:
Figure 4:
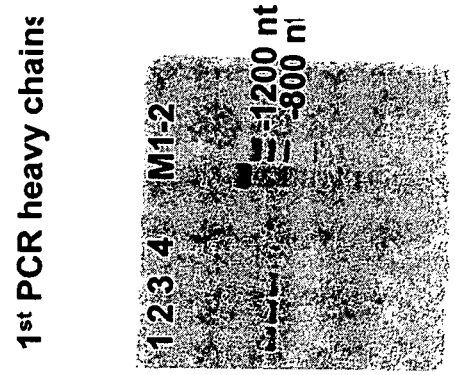

FIG. 4 shows the amplification products obtained after the primary PCR reaction from 4 different patient samples. 8 ul primary PCR product from 4 different patients was analyzed on a agarose gel [labeled 1, 2, 3 and 4]. For the heavy chain, a product of approximately 950 nt is obtained while for the kappa and lambda light chains the product is approximately 850 nt. M1-2 are molecular weight markers.

PCR products were also analyzed by DNA sequencing [10 clones from the lambda, kappa or heavy chain repertoires]. All sequenced antibody genes recovered contained the full coding sequence as well as the 5' leader sequence and the V gene diversity was the expected diversity (compared to literature data).

50 ng of all samples from all 11 individual amplified samples were mixed for heavy, lambda light or kappa light chains and used in secondary PCR reactions.

In all secondary PCRs approximately 1 ng template DNA from the primary PCR mixture was used in multiple 50 ul PCR reactions (25 cycles).

For the heavy chain, a nested biotinylated forward primer [HuCm-Nested] was used, and a nested 5' end backward primer located in the synthetic adapter-sequence [5'NA] was used. The 5' end lower-strand of the heavy chain was biotinylated.

For the light chains, a 5' end biotinylated nested primer in the synthetic adapter was used [5'NA] in combination with a 3' end primer in the constant region of Ckappa and Clambda, extended with a sequence coding for the AscI restriction site [kappa: HuCkForAscI, Lambda: HuCL2-FOR-ASC+ HuCL7-FOR-ASC]. [5' end Top strand DNA was biotinylated]. After gel-analysis the secondary PCR products were pooled and purified with Promega Wizzard PCR cleanup. Approximately 25 ug biotinylated heavy chain, lambda and kappa light chain DNA was isolated from the 11 patients.

Example 2

Capturing Kappa Chains with BsmAI

A repertoire of human-kappa chain mRNAs was prepared using the RACE method of Example 1 from a collection of patients having various autoimmune diseases.

This Example followed the protocol of Example 1. Approximately 2 micrograms (ug) of human kappa-chain (Igkappa) gene RACE material with biotin attached to 5'-end of upper strand was immobilized as in Example 1 on 200 microliters (μL) of Seradyn magnetic beads. The lower strand was removed by washing the DNA with 2 aliquots 200 μL of 0.1 M NaOH (pH 13) for 3 minutes for the first aliquot followed by 30 seconds for the second aliquot. The beads were neutralized with 200 μL of 10 mM Tris (pH 7.5) 100 mM NaCl. The short oligonucleotides shown in Table 23 were added in 40 fold molar excess in 100 μL of NEB buffer 2 (50 mM NaCl, 10 mM Tris-HCl, 10 mM $MgCl_2$, 1 mM dithiothreitol pH 7.9) to the dry beads. The mixture was incubated at 95° C. for 5 minutes then cooled down to 55° C. over 30 minutes. Excess oligonucleotide was washed away with 2 washes of NEB buffer 3 (100 mM NaCl, 50 mM Tris-HCl, 10 mM $MgCl_2$, 1 mM dithiothreitol pH 7.9). Ten units of BsmAI (NEB) were added in NEB: buffer 3 and incubated for 1 h at 55° C. The cleaved downstream DNA was collected and purified over a Qiagen PCR purification column (FIGS. 5 and 6).

Figure 5:
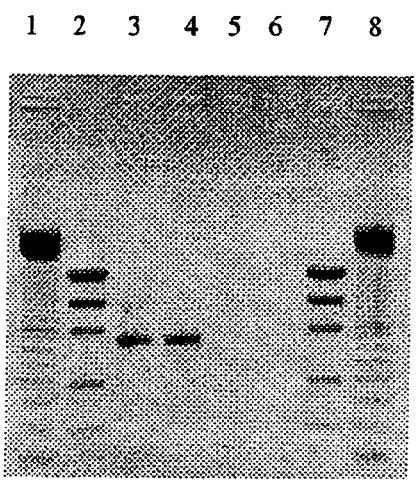
FIG. 5 depicts gel analysis of cleaved kappa DNA from Example 2.

FIG. 5 shows an analysis of digested kappa single-stranded DNA. Approximately 151.5 pmol of adapter was annealed to 3.79 pmol of immobilized kappa single-stranded DNA followed by digestion with 15 U of BsmAI. The supernatant containing the desired DNA was removed and analyzed by 5% polyacrylamide gel along with the remaining beads which contained uncleaved full length kappa DNA. 189 pmol of cleaved single-stranded DNA was purified for further analysis. Five percent of the original full length ssDNA remained on the beads.

Figure 6:
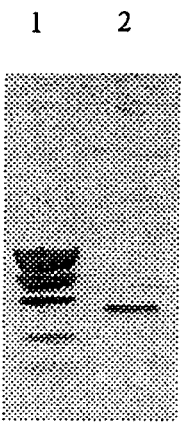
FIG. 6 depicts gel analysis of extender-cleaved kappa DNA from Example 2.

FIG. 6 shows an analysis of the extender-cleaved kappa ligation. 180 pmol of pre-annealed bridge/extender was ligated to 1.8 pmol of BsmAI digested single-stranded DNA. The ligated DNA was purified by Qiagen PCR purification column and analyzed on a 5% polyacrylamide gel. Results indicated that the ligation of extender to single-stranded DNA was 95% efficient.

A partially double-stranded adaptor was prepared using the oligonucleotide shown in Table 23. The adaptor was added to the single-stranded DNA in 100 fold molar excess along with 1000 units of T4 DNA ligase and incubated overnight at 16° C. The excess oligonucleotide was removed with a Qiagen PCR purification column. The ligated material was amplified by PCR using the primers kapPCRt1 and kapfor shown in Table 23 for 10 cycles with the program shown in Table 24.

Figure 7:
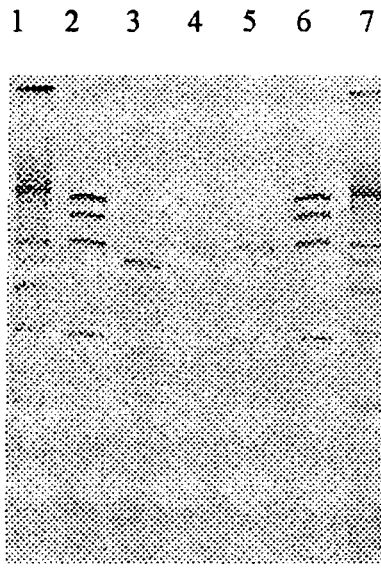
FIG. 7 depicts gel analysis of the PCR product from the extender-kappa amplification from Example 2.
Figure 8:
FIG. 8 depicts gel analysis of purified PCR product from the extender-kappa amplification from Example 2.

The soluble PCR product was run on a gel and showed a band of approximately 700 n, as expected (FIGS. 7 and 8). The DNA was cleaved with enzymes ApaLI and AscI, gel purified, and ligated to similarly cleaved vector pCES1.

FIG. 7 shows an analysis of the PCR product from the extender-kappa amplification. Ligated extender-kappa single-stranded DNA was amplified with primers specific to the extender and to the constant region of the light chain. Two different template concentrations, 10 ng versus 50 ng, were used as template and 13 cycles were used to generate approximately 1.5 ug of dsDNA as shown by 0.8% agarose gel analysis.

FIG. 8 shows an analysis of the purified PCR product from the extender-kappa amplification. Approximately 5 ug of PCR amplified extender-kappa double-stranded DNA was run out on a 0.8% agarose gel, cut out, and extracted with a GFX gel purification column. By gel analysis, 3.5 ug of double-stranded DNA was prepared.

Figure 9:
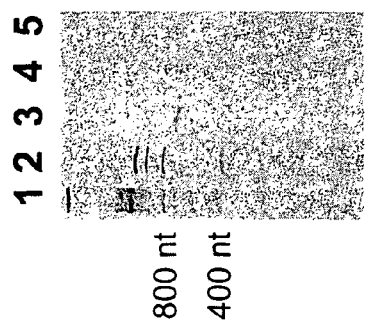
FIG. 9 depicts gel analysis of cleaved and ligated kappa light chains from Example 2.
Figure 9:
Figure 9:
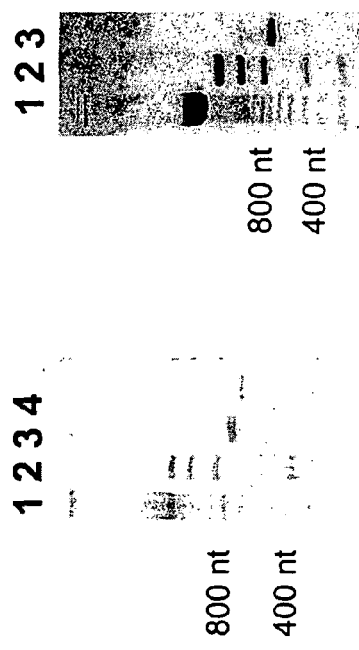

The assay for capturing kappa chains with BsmAI was repeated and produced similar results. FIG. 9A shows the DNA after it was cleaved and collected and purified over a Qiagen PCR purification column. FIG. 9B shows the partially double-stranded adaptor ligated to the single-stranded DNA. This ligated material was then amplified (FIG. 9C). The gel showed a band of approximately 700 n.

Table 25 shows the DNA sequence of a kappa light chain captured by this procedure. Table 26 shows a second sequence captured by this procedure. The closest bridge sequence was complementary to the sequence 5'-agccacc-3', but the sequence captured reads 5'-Tgccacc-3', showing that some mismatch in the overlapped region is tolerated.

Example 3

Construction of Synthetic CDR1 and CDR2 Diversity in V-3-23 VH Framework

Synthetic diversity in Complementary Determinant Region (CDR) 1 and 2 was created in the 3-23 VH framework in a two step process: first, a vector containing the 3-23 VH framework was constructed; and then, a synthetic CDR 1 and 2 was assembled and cloned into this vector.

For construction of the 3-23 VH framework, 8 oligonucleotides and two PCR primers (long oligonucleotides—TOPFR1A, BOTFR1B, BOTFR2, BOTFR3, F06, BOTFR4, ON-vgC1, and ON-vgC2 and primers—SFPRMET and BOTPCRFRIM, shown in Table 27) that overlap were designed based on the Genebank sequence of 3-23 VH framework region. The design incorporated at least one useful restriction site in each framework region, as shown in Table 27. In Table 27, the segments that were synthesized are shown as bold, the overlapping regions are underscored, and the PCR priming regions at each end are underscored.

A mixture of these 8 oligos was combined at a final concentration of 2.5 uM in a 20 ul PCR reaction. The PCR mixture contained 200 uM dNTPs, 2.5 mM $MgCl_2$, 0.02 U Pfu Turbo™ DNA Polymerase, 1 U Qiagen HotStart Taq DNA Polymerase, and 1× Qiagen PCR buffer. The PCR program consisted of 10 cycles of 94° C. for 30 s, 55° C. for 30 s, and 72° C. for 30 s.

The assembled 3-23 VH DNA sequence was then amplified, using 2.5 ul of a 10-fold dilution from the initial PCR in 100 ul PCR reaction. The PCR reaction contained 200 uM dNTPs, 2.5 mM $MgCl_2$, 0.02 U Pfu Turbo™ DNA Polymerase, 1 U Qiagen HotStart Taq DNA Polymerase, 1× Qiagen PCR Buffer and 2 outside primers (SFPRMET and BOTPCRPRIM) at a concentration of 1 uM. The PCR program consisted of 23 cycles at 94° C. for 30 s, 55° C. for 30 s, and 72° C. for 60 s. The 3-23 VH DNA sequence was digested and cloned into pCES1 (phagemid vector) using the SfiI and BstEII restriction endonuclease sites. All restriction enzymes mentioned herein were supplied by New England BioLabs, Beverly, Mass. and used as per the manufacturer's instructions.

Stuffer sequences (shown in Table 28 and Table 29) were introduced into pCES1 to replace CDR1/CDR2 sequences (900 bases between BspEI and XbaI RE sites) and CDR3 sequences (358 bases between AflII and BstEII) prior to cloning the CDR1/CDR2 diversity. This new vector was termed pCES5 and its sequence is given in Table 29.

Having stuffers in place of the CDRs avoids the risk that a parental sequence would be over-represented in the library. The stuffer sequences are fragments from the penicillase gene of *E. coli*. The CDR1-2 stuffer contains restriction sites for BglII, Bsu36I, BclI, XcmI, MluI, PvuII, HpaI, and HincII, the underscored sites being unique within the vector pCES5. The stuffer that replaces CDR3 contains the unique restriction endonuclease site RsrII.

A schematic representation of the design for CDR1 and CDR2 synthetic diversity is shown FIG. 10. The design was based on the presence of mutations in DP47/3-23 and related germline genes. Diversity was designed to be introduced at the positions within CDR1 and CDR2 indicated by the numbers in FIG. 10. The diversity at each position was chosen to be one of the three following schemes: 1=ADEFGHIKLM-NPQRSTVWY; 2=YRWVGS; 3=PS, in which letters encode equimolar mixes of the indicated amino acids.

For the construction of the CDR1 and CDR2 diversity, 4 overlapping oligonucleotides (oN-vgC1, ON_Br12, ON_CD2Xba, and ON-vgC2, shown in Table 27 and Table 30) encoding CDR1/2, plus flanking regions, were designed. A mixture of these 4 oligos was combined at a final concentration of 2.5 uM in a 40 ul PCR reaction. Two of the 4 oligos contained variegated sequences positioned at the CDR1 and the CDR2. The PCR mixture contained 200 uM dNTPs, 2.5 U Pwo DNA Polymerase (Roche), and 1× Pwo PCR buffer with 2 mM MgSO$_4$. The PCR program consisted of 10 cycles at 94° C. for 30 s, 60° C. for 30 s, and 72° C. for 60 s. This assembled CDR1/2 DNA sequence was amplified, using 2.5 ul of the mixture in 100 ul PCR reaction. The PCR reaction contained 200 uM dNTPs, 2.5 U Pwo DNA Polymerase, 1× Pwo PCR Buffer with 2 mM MgSO$_4$ and 2 outside primers at a concentration of 1 uM. The PCR program consisted of 10 cycles at 94° C. for 30 s, 60° C. for 30 s, and 72° C. for 60 s. These variegated sequences were digested and cloned into the 3-23 VH framework in place of the CDR1/2 stuffer.

We obtained approximately 7×10$^7$ independent transformants. CDR3 diversity either from donor populations or from synthetic DNA can be cloned into the vector containing synthetic CDR1 and CDR 2 diversity.

Figure 11:
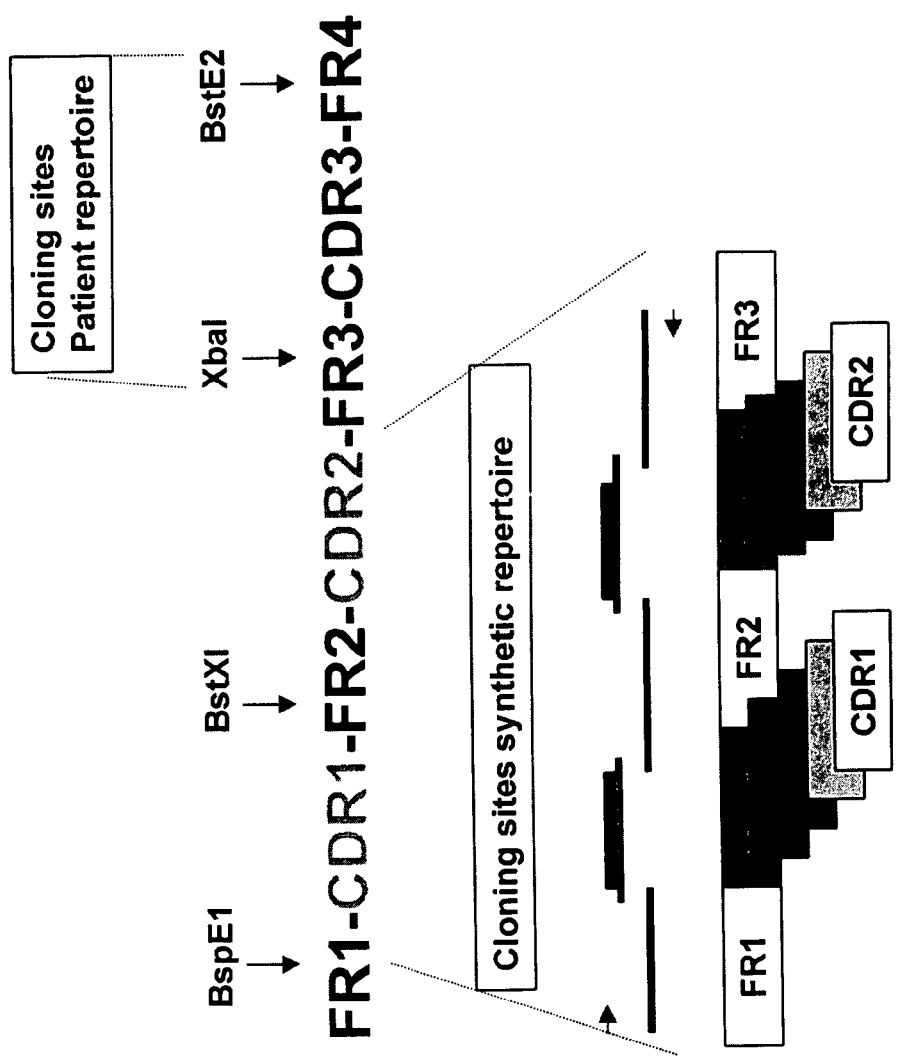
FIG. 11 is a schematic of the cloning schedule for construction of the heavy chain repertoire.

A schematic representation of this procedure is shown in FIG. 11. A sequence encoding the FR-regions of the human V3-23 gene segment and CDR regions with synthetic diversity was made by oligonucleotide assembly and cloning via BspE1 and XbaI sites into a vector that complements the FR1 and FR3 regions. Into this library of synthetic VH segments, the complementary VH-CDR3 sequence (top right) was cloned via XbaI an BstEII sites. The resulting cloned CH genes contain a combination of designed synthetic diversity and natural diversity (see FIG. 11).

Example 4

Cleavage and Ligation of the Lambda Light Chains with HinfI

Figure 12A:
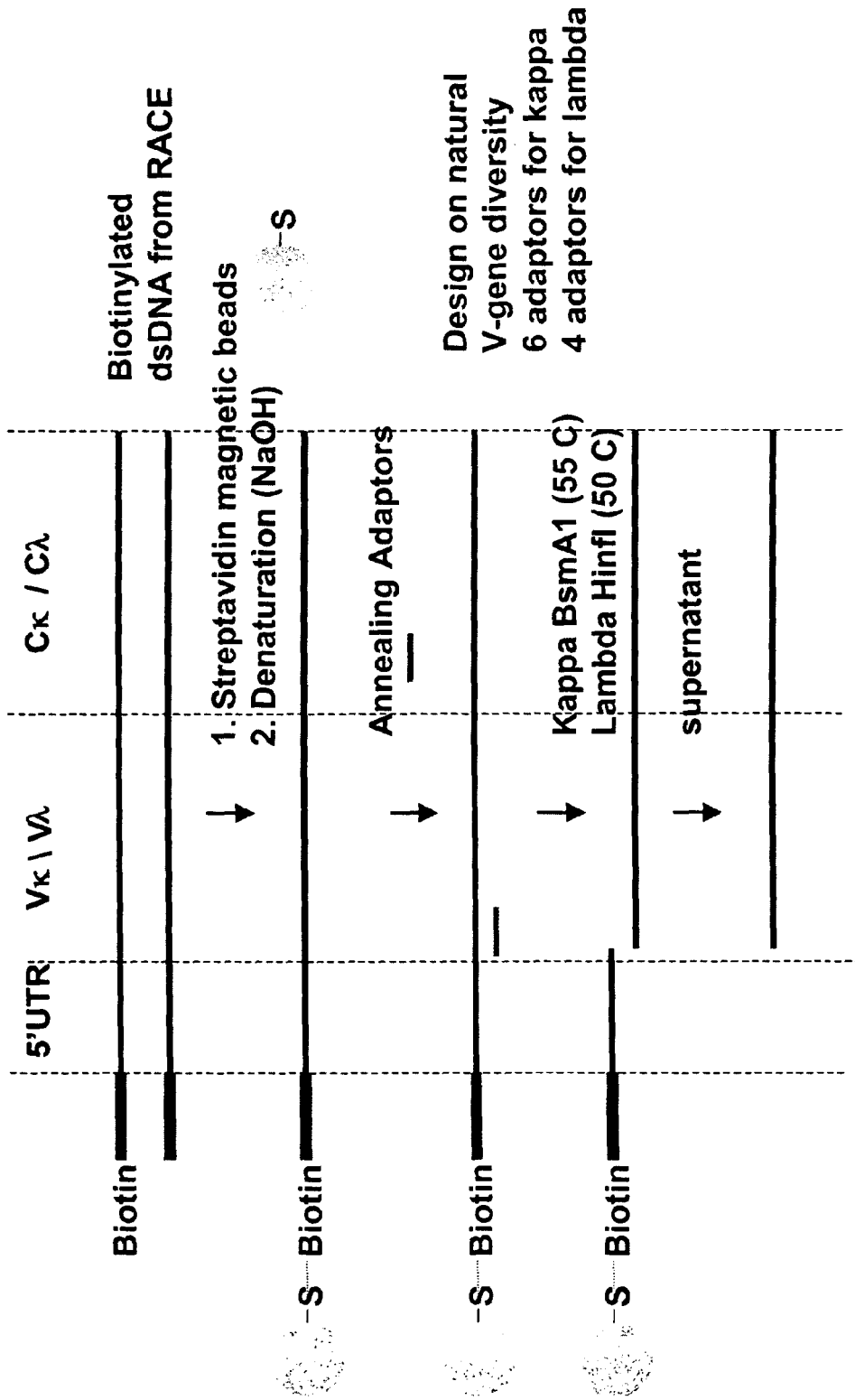
FIG. 12 is a schematic of the cleavage and ligation of the antibody light chain.
Figure 12B:
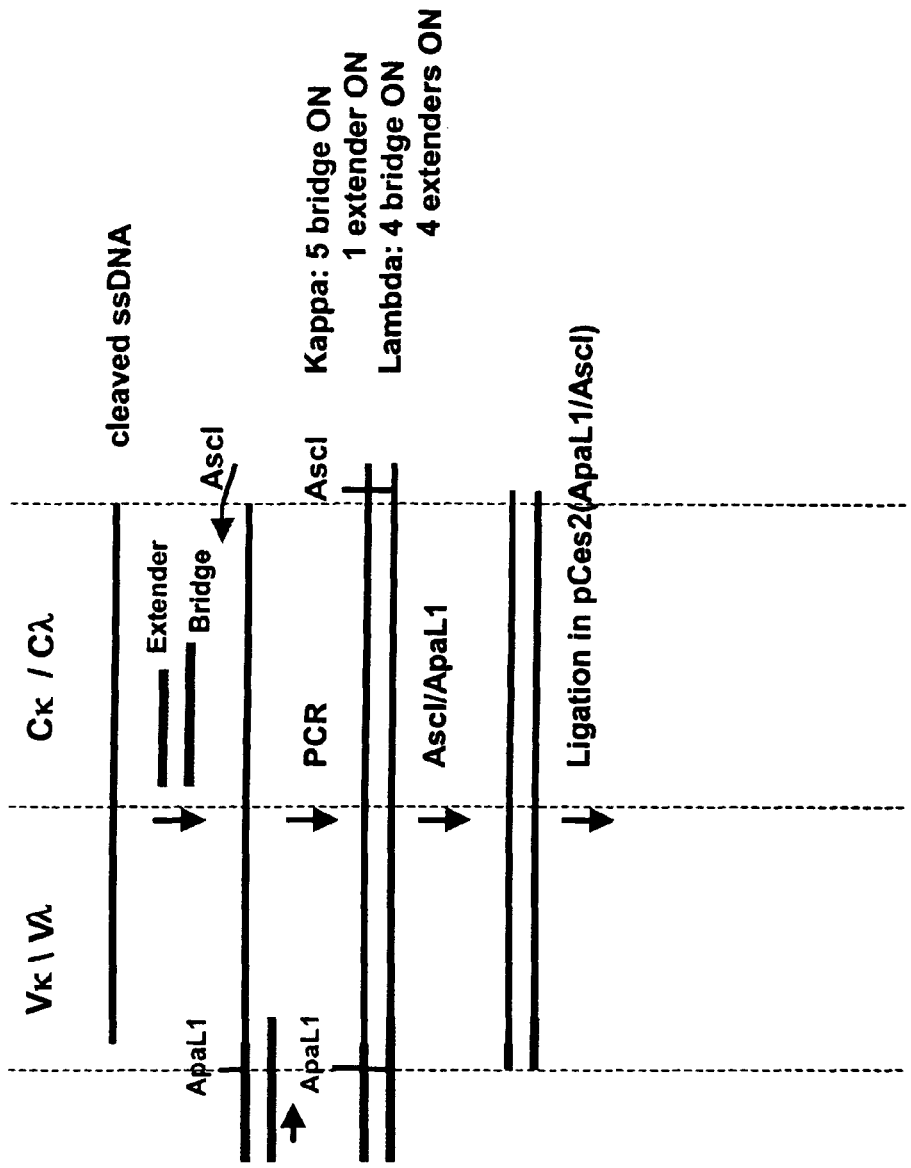

A schematic of the cleavage and ligation of antibody light chains is shown in FIGS. 12A and 12B. Approximately 2 ug of biotinylated human Lambda DNA prepared as described in Example 1 was immobilized on 200 ul Seradyn magnetic beads. The lower strand was removed by incubation of the DNA with 200 ul of 0.1 M NaOH (pH=13) for 3 minutes, the supernatant was removed and an additional washing of 30 seconds with 200 ul of 0.1 M NaOH was performed. Supernatant was removed and the beads were neutralized with 200 ul of 10 mM Tris (pH=7.5), 100 mM NaCl. 2 additional washes with 200 ul NEB2 buffer 2, containing 10 mM Tris (pH=7.9), 50 mM NaCl, 10 mM MgCl2 and 1 mM dithiothreitol, were performed. After immobilization, the amount of ssDNA was estimated on a 5% PAGE-UREA gel.

About 0.8 ug ssDNA was recovered and incubated in 100 ul NEB2 buffer 2 containing 80 molar fold excess of an equimolar mix of ON_Lam1aB7, ON_Lam2aB7, ON_Lam31B7 and ON_Lam3rB7 [each oligo in 20 fold molar excess] (see Table 31).

The mixture was incubated at 95° C. for 5 minutes and then slowly cooled down to 50° C. over a period of 30 minutes. Excess of oligonucleotide was washed away with 2 washes of 200 ul of NEB buffer 2. 4 U/ug of Hinf I was added and incubated for 1 hour at 50° C. Beads were mixed every 10 minutes.

Figure 13:
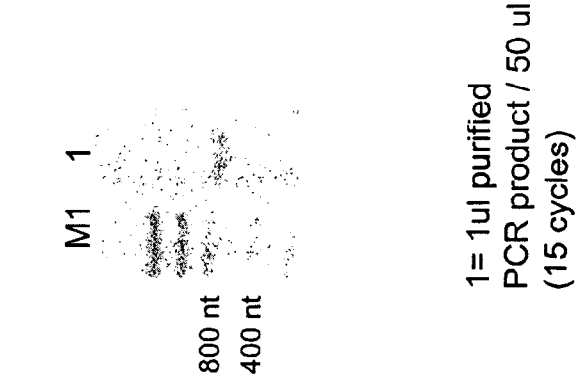
FIG. 13 depicts gel analysis of cleaved and ligated lambda light chains from Example 4.
Figure 13:
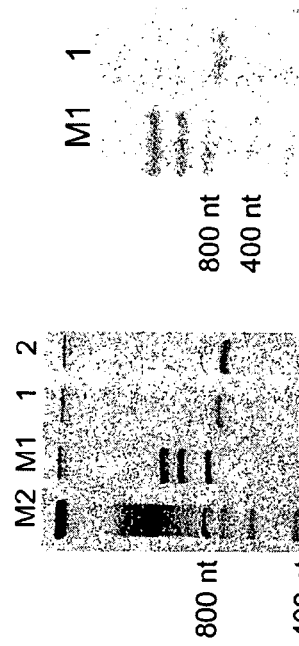
Figure 13:
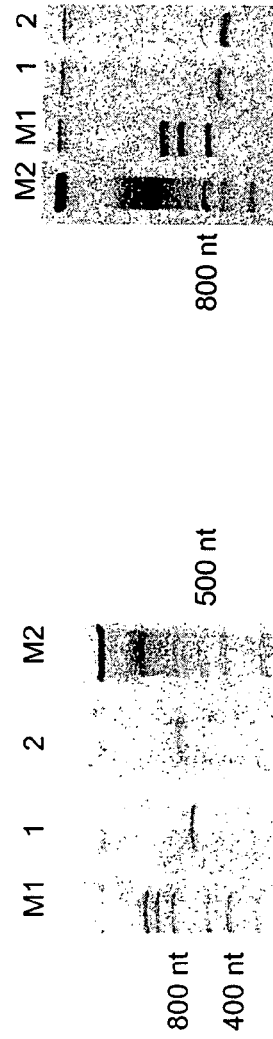

After incubation the sample was purified over a Qiagen PCR purification column and was subsequently analysed on a 5% PAGE-urea gel (see FIG. 13A, cleavage was more than 70% efficient).

A schematic of the ligation of the cleaved light chains is shown in FIG. 12B. A mix of bridge/extender pairs was prepared from the Brg/Ext oligo's listed in Table 31 (total molar excess 100 fold) in 1000 U of T4 DNA Ligase (NEB) and incubated overnight at 16° C. After ligation of the DNA, the excess oligonucleotide was removed with a Qiagen PCR purification column and ligation was checked on a Urea-PAGE gel (see FIG. 13B; ligation was more than 95% efficient).

Multiple PCRs were performed containing 10 ng of the ligated material in an 50 ul PCR reaction using 25 pMol ON lamPlePCR and 25 pmol of an equimolar mix of Hu-CL2AscI/HuCL7AscI primer (see Example 1).

PCR was performed at 60° C. for 15 cycles using Pfu polymerase. About 1 ug of dsDNA was recovered per PCR (see FIG. 13C) and cleaved with ApaL1 and AscI for cloning the lambda light chains in pCES2.

Example 5

Capture of Human Heavy-Chain CDR3 Population

Figure 14A:
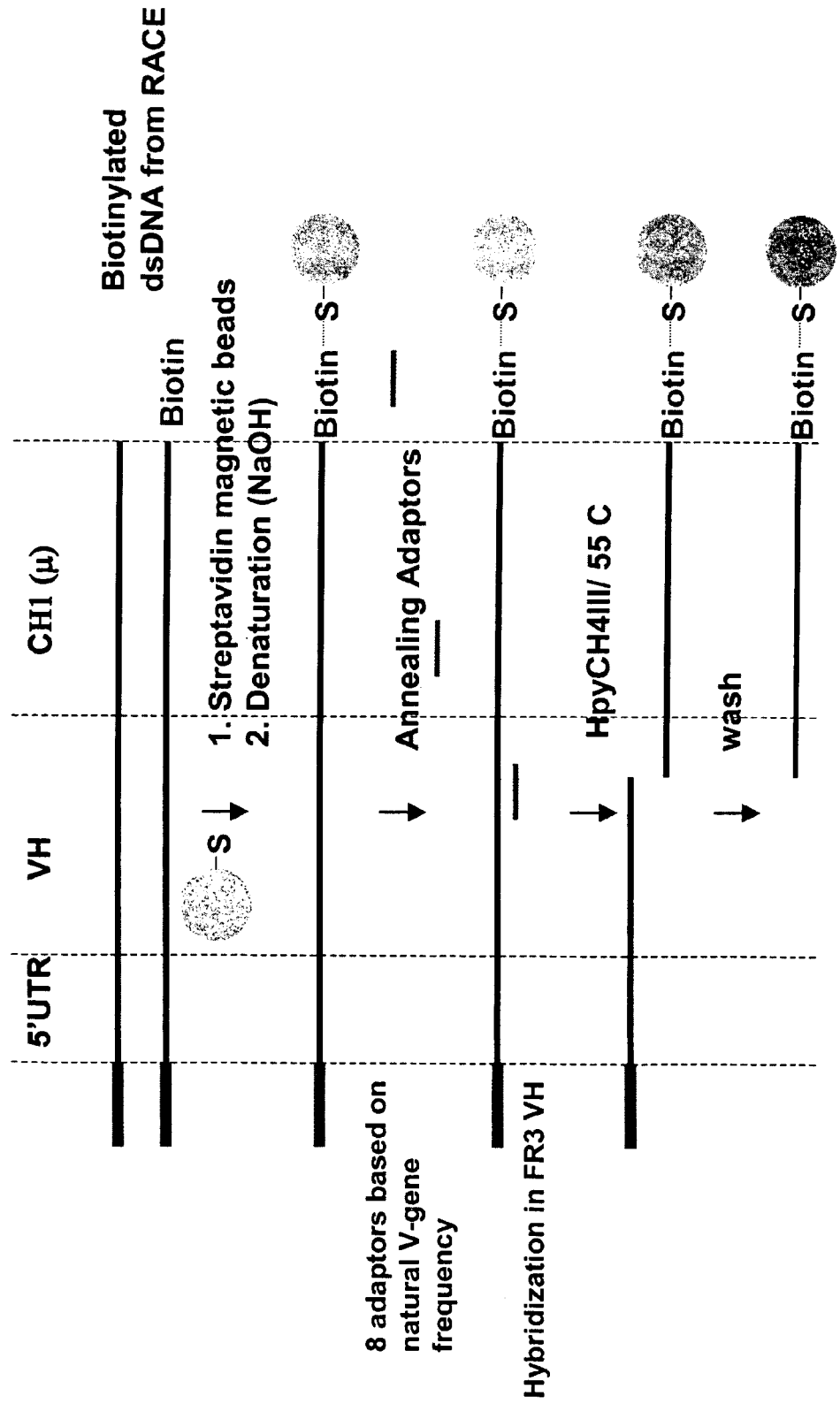
FIG. 14 is a schematic of the cleavage and ligation of the antibody heavy chain.
Figure 14B:
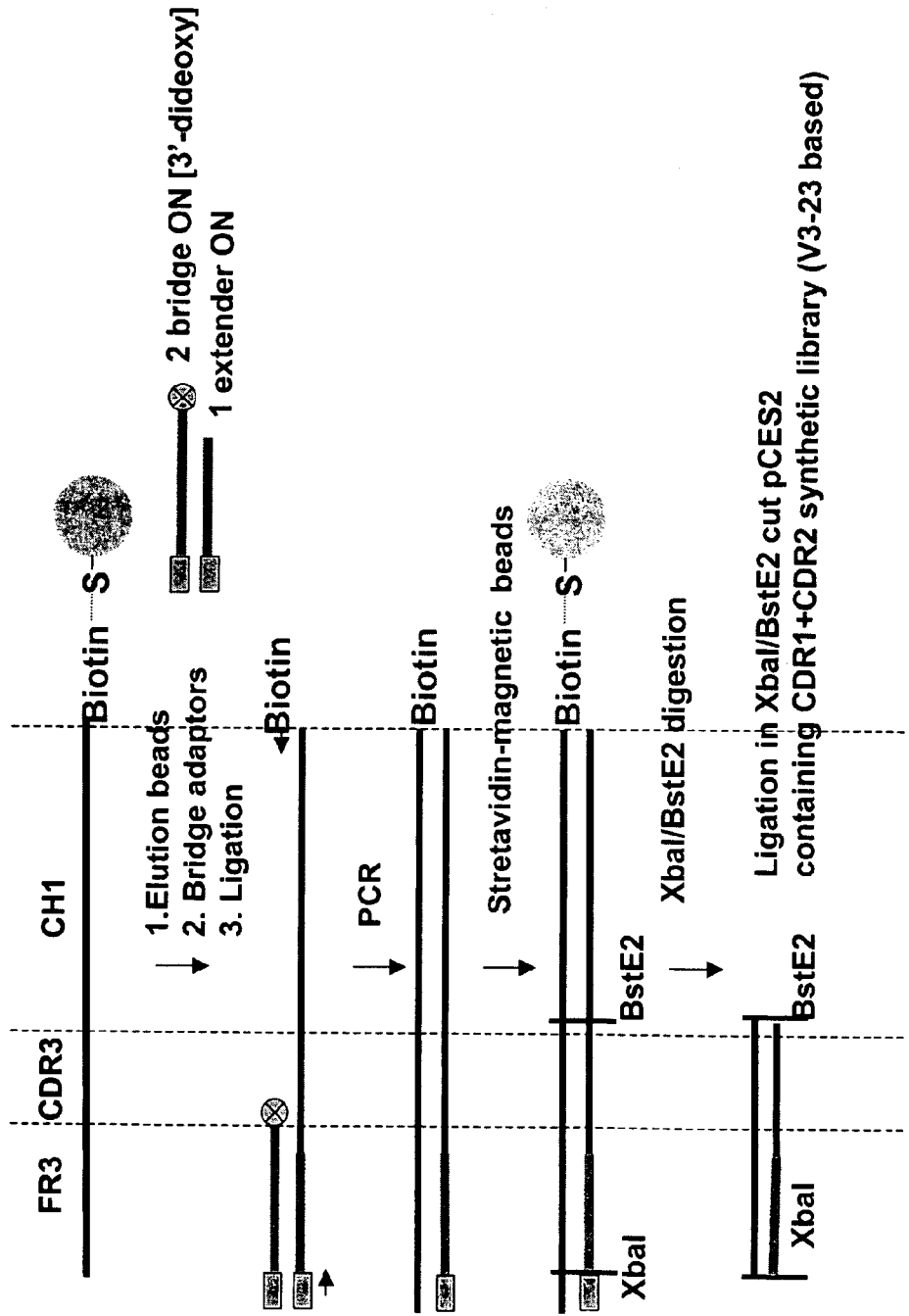

A schematic of the cleavage and ligation of antibody light chains is shown in FIGS. 14A and 14B.

Figure 15:
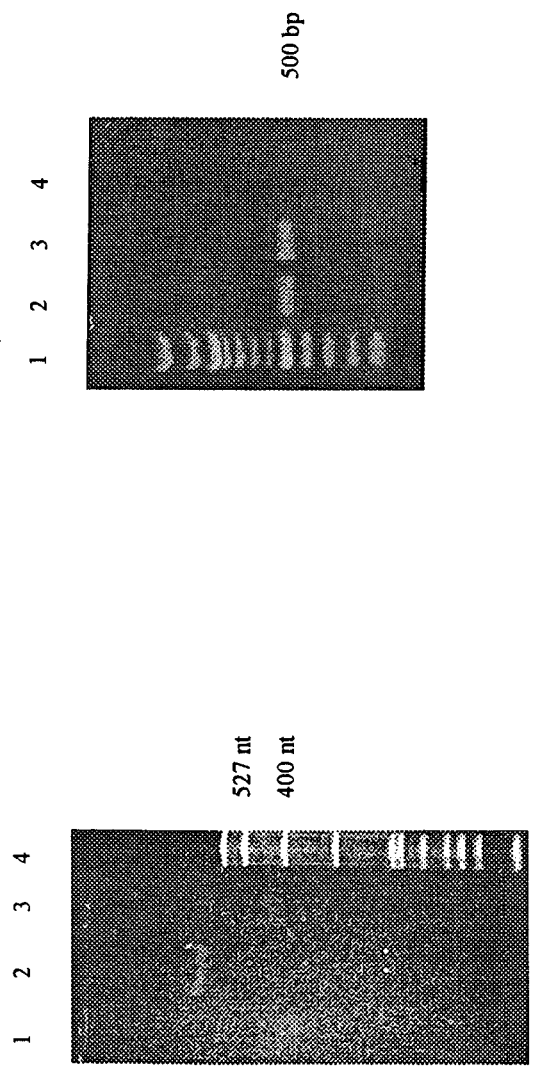
FIG. 15 depicts gel analysis of cleaved and ligated lambda light chains from Example 5.

Approximately 3 ug of human heavy-chain (IgM) gene RACE material with biotin attached to 5'-end of lower strand was immobilized on 300 uL of Seradyn magnetic beads. The upper strand was removed by washing the DNA with 2 aliquots 300 uL of 0.1 M NaOH (pH 13) for 3 minutes for the first aliquot followed by 30 seconds for the second aliquot. The beads were neutralized with 300 uL of 10 mM Tris (pH 7.5) 100 mM NaCl. The REadaptors (oligonucleotides used to make single-stranded DNA locally double-stranded) shown in Table 32 were added in 30 fold molar excess in 200 uL of NEB buffer 4 (50 mM Potassium Acetate, 20 mM Tris-Acetate, 10 mM Magnesuim Acetate, 1 mM dithiothreitol pH 7.9) to the dry beads. The REadaptors were incubated with the single-stranded DNA at 80° C. for 5 minutes then cooled down to 55° C. over 30 minutes. Excess REadaptors were washed away with 2 washes of NEB buffer 4. Fifteen units of HpyCH4III (NEB) were added in NEB buffer 4 and incubated for 1 hour at 55° C. The cleaved downstream DNA remaining on the beads was removed from the beads using a Qiagen Nucleotide removal column (see FIG. 15).

The Bridge/Extender pairs shown in Table 33 were added in 25 molar excess along with 1200 units of T4 DNA ligase and incubated overnight at 16° C. Excess Bridge/Extender was removed with a Qiagen PCR purification column. The ligated material was amplified by PCR using primers H43.XAExtPCR2 and Hucumnest shown in Table 34 for 10 cycles with the program shown in Table 35.

The soluble PCR product was run on a gel and showed a band of approximately 500 n, as expected (see FIG. 15B). The DNA was cleaved with enzymes SfiI and NotI, gel purified, and ligated to similarly cleaved vector PCES1.

Example 6

Description of Phage Display Vector CJRA05, a Member of the Library Built in Vector DY3F7

Figure 16:
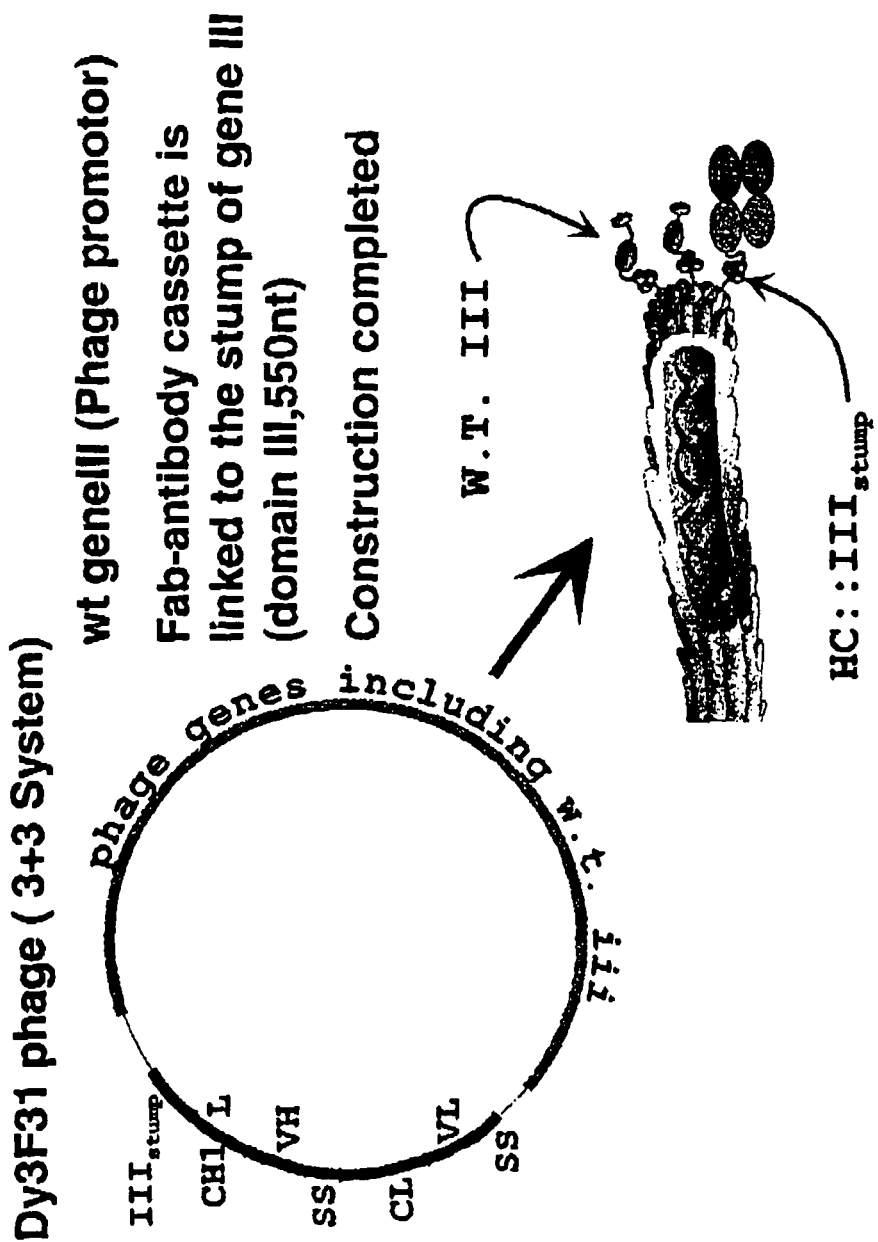
FIG. 16 is a schematic of a phage display vector.

Table 36 contains an annotated DNA sequence of a member of the library, CJRA05, see FIG. 16. Table 36 is to be read as follows: on each line everything that follows an exclamation mark "!" is a comment. All Occurrences of A, C, G, and T before "!" are the DNA sequence. Case is used only to show that certain bases constitute special features, such as restriction sites, ribosome binding sites, and the like, which are labeled below the DNA. CJRA05 is a derivative of phage DY3F7, obtained by cloning an ApaLI to NotI fragment into these sites in DY3F31. DY3F31 is like DY3F7 except that the light chain and heavy chain genes have been replaced by "stuffer" DNA that does not code for any antibody. DY3F7 contains an antibody that binds streptavidin, but did not come from the present library.

The phage genes start with gene ii and continue with genes x, v, vii, ix, viii, iii, vi, and iv. Gene iii has been slightly modified in that eight codons have been inserted between the signal sequence and the mature protein and the final amino acids of the signal sequence have been altered. This allows restriction enzyme recognition sites EagI and XbaI to be present. Following gene iv is the phage origin of replication (ori). After ori is bla which confers resistance to ampicillin (ApR). The phage genes and bla are transcribed in the same sense.

Figure 17:
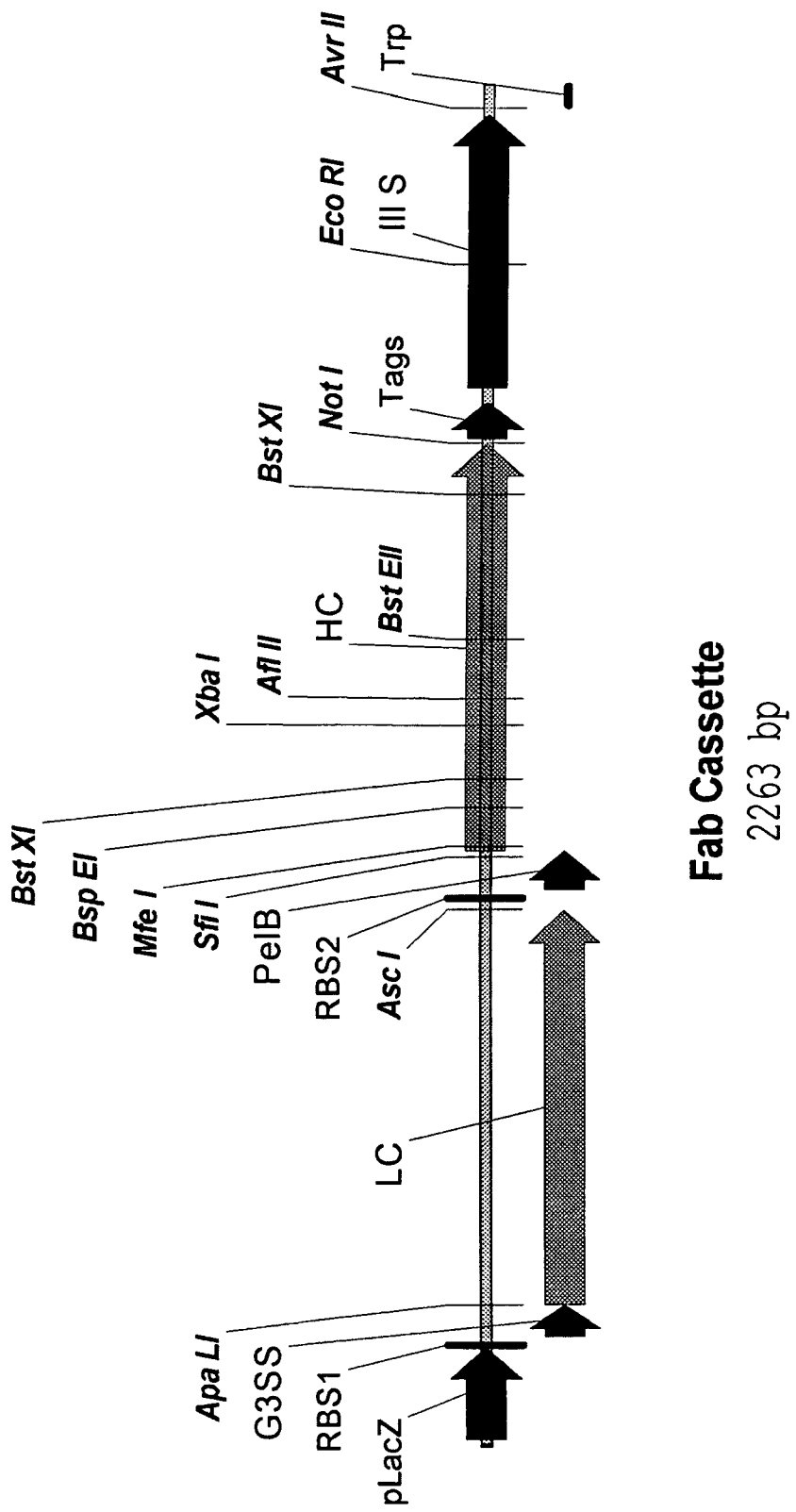
FIG. 17 is a schematic of a Fab cassette.

After bla, is the Fab cassette (illustrated in FIG. 17) comprising:
a) PlacZ promoter,
b) A first Ribosome Binding Site (RBS1),
c) The signal sequence form M13 iii,
d) An ApaLI RERS,
e) A light chain (a kappa L20::JK1 shortened by one codon at the V-J boundary in this case),
f) An AscI RERS,
g) A second Ribosome Binding Site (RBS2),
h) A signal sequence, preferably PelB, which contains,
i) An SfiI RERS,
j) A synthetic 3-23 V region with diversity in CDR1 and CDR2,
k) A captured CDR3,
l) A partially synthetic J region (FR4 after BstEII),
m) CH1,
n) A NotI RERS,
o) A His6 tag (SEQ ID NO: 12),
p) A cMyc tag,
q) An amber codon,
r) An anchor DNA that encodes the same amino-acid sequence as codons 273 to 424 of M13 iii (as shown in Table 37).
s) Two stop codons,
t) An AvrII RERS, and
u) A trp terminator.

The anchor (item r) encodes the same amino-acid sequence as do codons 273 to 424 of M13 iii but the DNA is approximately as different as possible from the wild-type DNA sequence. In Table 36, the III' stump runs from base 8997 to base 9455. Below the DNA, as comments, are the differences with wild-type iii for the comparable codons with "!W.T" at the ends of these lines. Note that Met and Trp have only a single codon and must be left as is. These AA types are rare. Ser codons can be changed at all three base, while Leu and Arg codons can be changed at two.

In most cases, one base change can be introduced per codon. This has three advantages: 1) recombination with the wild-type gene carried elsewhere on the phage is less likely, 2) new restriction sites can be introduced, facilitating construction; and 3) sequencing primers that bind in only one of the two regions can be designed.

The fragment of M13 III shown in CJRA05 is the preferred length for the anchor segment. Alternative longer or shorter anchor segments defined by reference to whole mature III protein may also be utilized.

The sequence of M13 III consists of the following elements: Signal Sequence:Domain 1 (D1)::Linker 1 (L1)::Domain 2 (D2)::Linker 2 (L2)::Domain 3 (D1)::Transmembrane Segment (TM):: Intracellular anchor (IC) (see Table 38).

The pIII anchor (also known as trpIII) preferably consists of D2::L2::D3::TM::IC. Another embodiment for the pIII anchor consists of D2'::L2::D3::TM::IC (where D2' comprises the last 21 residues of D2 with the first 109 residues deleted). A further embodiment of the pIII anchor consists of D2'(C>S)::L2::D3::TM::IC (where D2' (C>S) is D2' with the single C converted to S), and d) D3::TM::IC.

Table 38 shows a gene fragment comprising the NotI site, His6 tag (SEQ ID NO: 12), cMyc tag, an amber codon, a recombinant enterokinase cleavage site, and the whole of mature M13 III protein. The DNA used to encode this sequence is intentionally very different from the DNA of wild-type gene iii as shown by the lines denoted "W.T." containing the w.t. bases where these differ from this gene. III is divided into domains denoted "domain 1", "linker 1", "domain 2", "linker 2", "domain 3", "transmembrane segment", and "intracellular anchor".

Alternative preferred anchor segments (defined by reference to the sequence of Table 38) include:
codons 1-29 joined to codons 104-435, deleting domain 1 and retaining linker 1 to the end;
codons 1-38 joined to codons 104-435, deleting domain 1 and retaining the rEK cleavage site plus linker 1 to the end from III;
codons 1-29 joined to codons 236-435, deleting domain 1, linker 1, and most of domain 2 and retaining linker 2 to the end;
codons 1-38 joined to codons 236-435, deleting domain 1, linker 1, and most of domain 2 and retaining linker 2 to the end and the rEK cleavage site;
codons 1-29 joined to codons 236-935 and changing codon 240 to Ser (e.g., agc), deleting domain 1, linker 1, and most of domain 2 and retaining linker 2 to the end; and
codons 1-38 joined to codons 236-435 and changing codon 240 to Ser (e.g., agc), deleting domain 1, linker 1, and most of domain 2 and retaining linker 2 to the end and the rEK cleavage site.

The constructs would most readily be made by methods similar to those of Wang and Wilkinson (*Biotechniques* 2001: 31(4)722-724) in which PCR is used to copy the vector except the part to be deleted and matching restriction sites are introduced or retained at either end of the part to be kept. Table 39 shows the oligonucleotides to be used in deleting parts of the III anchor segment. The DNA shown in Table 38 has an NheI site before the DINDDRMA (residues 29-36 of SEQ ID NO: 594) recombinant enterokinase cleavage site (rEKCS). If NheI is used in the deletion process with this DNA, the rEKCS site would be lost. This site could be quite useful in cleaving Fabs from the phage and might facilitate capture of very high-afffinity antibodies. One could mutagenize this sequence so that the NheI site would follow the rEKCS site, an Ala Ser amino-acid sequence is already present. Alternatively, one could use SphI for the deletions. This would involve a slight change in amino acid sequence but would be of no consequence.

Example 7

Selection of Antigen Binders from an Enriched Library of Human Antibodies Using Phage Vector DY3F31

In this example the human antibody library used is described in de Haard et al., (*Journal of Biological Chemistry*, 274 (26): 18218-30 (1999). This library, consisting of a large non-immune human Fab phagemid library, was first enriched on antigen, either on streptavidin or on phenyl-oxazolone (phOx). The methods for this are well known in the art. Two preselected Fab libraries, the first one selected once on immobilized phOx-BSA (R1-ox) and the second one selected twice on streptavidin (R2-strep), were chosen for recloning.

These enriched repertoires of phage antibodies, in which only a very low percentage have binding activity to the antigen used in selection, were confirmed by screening clones in an ELISA for antigen binding. The selected Fab genes were transferred from the phagemid vector of this library to the DY3F31 vector via ApaL1-Not1 restriction sites.

DNA from the DY3F31 phage vector was pretreated with ATP dependent DNAse to remove chromosomal DNA and then digested with ApaL1 and Not1. An extra digestion with AscI was performed in between to prevent self-ligation of the vector. The ApaL1/NotI Fab fragment from the preselected libraries was subsequently ligated to the vector DNA and transformed into competent XL1-blue MRF' cells.

Libraries were made using vector:insert ratios of 1:2 for phOx-library and 1:3 for STREP library, and using 100 ng ligated DNA per 50 µl of electroporation-competent cells (electroporation conditions: one shock of 1700 V, 1 hour recovery of cells in rich SOC medium, plating on amplicillin-containing agar plates).

This transformation resulted in a library size of $1.6 \times 10^6$ for R1-ox in DY3F31 and $2.1 \times 10^6$ for R2-strep in DY3F31. Sixteen colonies from each library were screened for insert, and all showed the correct size insert (±1400 bp) (for both libraries).

Phage was prepared from these Fab libraries as follows. A representative sample of the library was inoculated in medium with ampicillin and glucose, and at OD 0.5, the medium exchanged for ampicillin and 1 mM IPTG. After overnight growth at 37° C., phage was harvested from the supernatant by PEG-NaCl precipitation. Phage was used for selection on antigen. R1-ox was selected on phOx-BSA coated by passive adsorption onto immunotubes and R2-strep on streptavidin coated paramagnetic beads (Dynal, Norway), in procedures described in de Haard et. al. and Marks et. al., *Journal of Molecular Biology*, 222(3): 581-97 (1991). Phage titers and enrichments are given in Table 40.

Clones from these selected libraries, dubbed R2-ox and R3-strep respectively, were screened for binding to their antigens in ELISA. 44 clones from each selection were picked randomly and screened as phage or soluble Fab for binding in ELISA. For the libraries in DY3F31, clones were first grown in 2TY-2% glucose-50 µg/ml AMP to an OD600 of approximately 0.5, and then grown overnight in 2TY-50 µg/ml AMP+/−1 mM IPTG. Induction with IPTG may result in the production of both phage-Fab and soluble Fab. Therefore the (same) clones were also grown without IPTG. Table 41 shows the results of an ELISA screening of the resulting supernatant, either for the detection of phage particles with antigen binding (Anti-M13 HRP=anti-phage antibody), or for the detection of human Fabs, be it on phage or as soluble fragments, either with using the anti-myc antibody 9E10 which detects the myc-tag that every Fab carries at the C-terminal end of the heavy chain followed by a HRP-labeled rabbit-anti-Mouse serum (column 9E10/RAM-HRP), or with anti-light chain reagent followed by a HRP-labeled goat-anti-rabbit antiserum(anti-CK/CL Gar-HRP).

The results shows that in both cases antigen-binders are identified in the library, with as Fabs on phage or with the anti-Fab reagents (Table 41). IPTG induction yields an increase in the number of positives. Also it can be seen that for the phOx-clones, the phage ELISA yields more positives than the soluble Fab ELISA, most likely due to the avid binding of phage. Twenty four of the ELISA-positive clones were screened using PCR of the Fab-insert from the vector, followed by digestion with BstNI. This yielded 17 different patterns for the phOx-binding Fab's in 23 samples that were correctly analyzed, and 6 out of 24 for the streptavidin binding clones. Thus, the data from the selection and screening from this pre-enriched non-immune Fab library show that the DY3F31 vector is suitable for display and selection of Fab fragments, and provides both soluble Fab and Fab on phage for screening experiments after selection.

Example 8

Selection of Phage-Antibody Libraries on Streptavidin Magnetic-Beads

The following example describes a selection in which one first depletes a sample of the library of binders to streptavidin and optionally of binders to a non-target (i.e., a molecule other than the target that one does not want the selected Fab to bind). It is hypothesized that one has a molecule, termed a "competitive ligand", which binds the target and that an antibody which binds at the same site would be especially useful.

For this procedure Streptavidin Magnetic Beads (Dynal) were blocked once with blocking solution (2% Marvel Milk, PBS (pH 7.4), 0.01% Tween-20 ("2% MPBST")) for 60 minutes at room temperature and then washed five times with 2% MPBST. 450 µL of beads were blocked for each depletion and subsequent selection set.

Per selection, 6.25 µL of biotinylated depletion target (1 mg/mL stock in PEST) was added to 0.250 mL of washed, blocked beads (from step 1). The target was allowed to bind overnight, with tumbling, at 4° C. The next day, the beads are washed 5 times with PBST.

Per selection, 0.010 mL of biotinylated target antigen (1 mg/mL stock in PBST) was added to 0.100 mL of blocked and washed beads (from step 1). The antigen was allowed to bind overnight, with tumbling, at 4° C. The next day, the beads were washed 5 times with PBST.

In round 1, $2 \times 10^{12}$ up to $10^{13}$ plaque forming units (pfu) per selection were blocked against non-specific binding by adding to 0.500 mL of 2% MPBS (=2% MPBST without Tween) for 1 hr at RT (tumble). In later rounds, 1011 pfu per selection were blocked as done in round 1.

Each phage pool was incubated with 50 µL of depletion target beads (final wash supernatant removed just before use) on a Labquake rotator for 10 min at room temperature. After incubation, the phage supernatant was removed and incubated with another 50 µL of depletion target beads. This was repeated 3 more times using depletion target beads and twice using blocked streptavidin beads for a total of 7 rounds of depletion, so each phage pool required 350 µL of depletion beads.

A small sample of each depleted library pool was taken for titering. Each library pool was added to 0.100 mL of target beads (final wash supernatant was removed just before use) and allowed to incubate for 2 hours at room temperature (tumble).

Beads were then washed as rapidly as possible (e.g., 3 minutes total) with 5×0.500 mL PBST and then 2× with PBS. Phage still bound to beads after the washing were eluted once with 0.250 mL of competitive ligand (~1 µµM) in PBST for 1 hour at room temperature on a Labquake rotator. The eluate was removed, mixed with 0.500 mL Minimal A salts solution and saved. For a second selection, 0.500 mL 100 mM TEA was used for elution for 10 min at RT, then neutralized in a mix of 0.250 mL of 1 M Tris, pH 7.4+0.500 mL Min A salts.

After the first selection elution, the beads can be eluted again with 0.300 mL of non-biotinylated target. (1 mg/mL) for 1 hr at RT on a Labquake rotator. Eluted phage are added to 0.450 mL Minimal A salts.

Three eluates (competitor from 1st selection, target from 1st selection and neutralized TEA elution from 2nd selection) were kept separate and a small aliquot taken from each for titering. 0.500 mL Minimal A salts were added to the remaining bead aliquots after competitor and target elution and after. TEA elution. Take a small aliquot from each was taken for tittering.

Each elution and each set of eluted beads was mixed with 2XYT and an aliquot (e.g., 1 mL with 1. E 10/mL) of XL1-Blue MRF' $E.$ $coli$ cells (or other F' cell line) which had been chilled on ice after having been grown to mid-logarithmic phase, starved and concentrated (see procedure below—"Mid-Log prep of XL-1 blue MRF' cells for infection").

After approximately 30 minutes at room temperature, the phage/cell mixtures were spread onto Bio-Assay Dishes (243×243×18 mm, Nalge Nunc) containing 2XYT, 1 mM IPTG agar. The plates were incubated overnight at 30° C. The next day, each amplified phage culture was harvested from its respective plate. The plate was flooded with 35 mL TBS or LB, and cells were scraped from the plate. The resuspended cells were transferred to a centrifuge bottle. An additional 20 mL TBS or LB was used to remove any cells from the plate and pooled with the cells in the centrifuge bottle. The cells were centrifuged out, and phage in the supernatant was recovered by PEG precipitation. Over the next day, the amplified phage preps were titered.

In the first round, two selections yielded five amplified eluates. These amplified eluates were panned for 2-3 more additional rounds of selection using ~1. E 12 input phage/round. For each additional round, the depletion and target beads were prepared the night before the round was initiated.

For the elution steps in subsequent rounds, all elutions up to the elution step from which the amplified elution came from were done, and the previous elutions were treated as washes. For the bead infection amplified phage, for example, the competitive ligand and target elutions were done and then tossed as washes (see below). Then the beads were used to infect $E.$ $coli$. Two pools, therefore, yielded a total of 5 final elutions at the end of the selection.

1st Selection Set

A. Ligand amplified elution: elute w/ ligand for 1 hr, keep as elution

B. Target amplified elution: elute w/ ligand for 1 hr, toss as wash elute w/ target for 1 hr, keep as elution C. Bead infect, amp. elution: elute w/ ligand for 1 hr, toss as wash elute w/ target for 1 hr, toss as wash elute w/ cell infection, keep as elution 2nd Selection Set A. TEA amplified elution; elute w/ TEA 10 min, keep as elution B. Bead infect. amp. elution; elute w/ TEA 10 mm, toss as wash elute w/ cell infection, keep as elution Mid-Log Prep of XL1 Blue MRF' Cells for Infection (Based on Barbas et al. Phage Display Manual Procedure)

Culture XL1 blue MRF' in NZCYM (12.5 mg/mL tet) at 37° C. and 250 rpm overnight. Started at 500 mL culture in 2 liter flask by diluting cells 1/50 in NZCYM/tet (10 mL overnight culture added) and incubated at 37° C. at rpm until OD606 of 0.45 (1.5-2 hrs) was reached. Shaking was reduced to 100 rpm for 10 min. When OD600 reached between 0.55-0.65, cells were transferred to 2×250 mL centrifuge bottles, centrifuged at 600 g for 15 min at 4° C. Supernatant was poured off. Residual liquid was removed with a pipette.

The pellets were gently resuspended (not pipetting up and down) in the original volume of 1× Minimal A salts at room temp. The resuspended cells were transferred back into 2-liter flask, shaken at 100 rpm for 45 min at 37° C. This process was performed in order to starve the cells and restore pili. The cells were transferred to 2×250 mL centrifuge bottles, and centrifuged as earlier.

The cells were gently resuspended in ice cold Minimal A salts (5 mL per 500 mL original culture). The cells were put on ice for use in infections as soon as possible.

The phage eluates were brought up to 7.5 mL with 2XYT medium and 2.5 mL of cells were added. Beads were brought up to 3 mL with 2XYT and 1 mL of cells were added. Incubated at 37° C. for 30 min. The cells were plated on 2XYT, 1 mM IPTG agar large NUNC plates and incubated for 18 hr at 30° C.

Example 9

Incorporation of Synthetic Region in FR1/3 Region

Described below are examples for incorporating of fixed residues in antibody sequences for light chain kappa and lambda genes, and for heavy chains. The experimental conditions and oligonucleotides used for the examples below have been described in previous examples (e.g., Examples 3 & 4).

Figure 18:
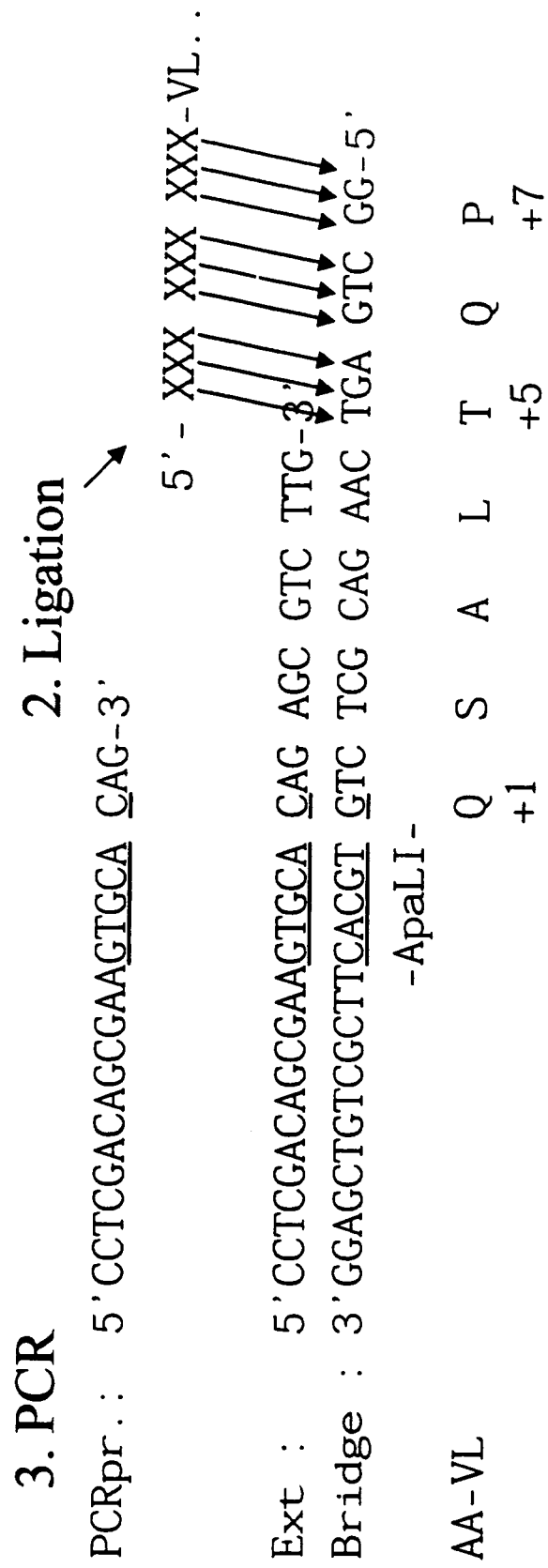
FIG. 18 is a schematic of a process for incorporating fixed FR1 residues in an antibody lambda sequence. The PCRpr oligonucleotide is shown in SEQ ID NO: 605 while the Bridge oligonucleotide and encoded peptide are shown in SEQ ID NOS 606-607, respectively.

The process for incorporating fixed FR1 residues in an antibody lambda sequence consists of 3 steps (see FIG. 18): (1) annealing of single-stranded DNA material encoding VL genes to a partially complementary oligonucleotide mix (indicated with Ext and Bridge), to anneal in this example to the region encoding residues 5-7 of the FR1 of the lambda genes (indicated with X..X; within the lambda genes the overlap may sometimes not be perfect); (2) ligation of this complex; (3) PCR of the ligated material with the indicated primer ('PCRpr') and for example one primer based within the VL gene. In this process the first few residues of all lambda genes will be encoded by the sequences present in the oligonucleotides (Ext., Bridge or PCRpr). After the PCR, the lambda genes can be cloned using the indicated restriction site for ApaLI.

Figure 19:
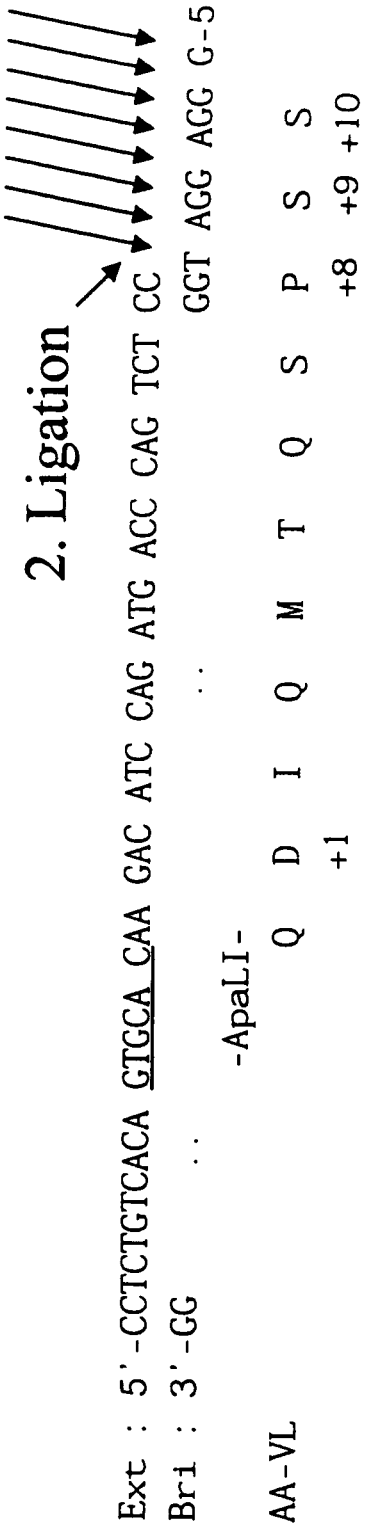
FIG. 19 is a schematic of a process for incorporating fixed FR1 residues in an antibody kappa sequence (see SEQ) ID NOS 608-611, respectively, in order of appearance).

The process for incorporating fixed FR1 residues in an antibody kappa-sequence (FIG. 19) consists of 3 steps: (1) annealing of single-stranded DNA material encoding VK genes to a partially complementary oligonucleotide mix (indicated with Ext and Bri), to anneal in this example to the region encoding residues 8-10 of the FR1 of the kappa genes (indicated with X..X; within the kappa genes the overlap may sometimes not be perfect); (2) ligation of this complex; (3) PCR of the ligated material with the indicated primer ('PCRpr') and for example one primer based within the VK gene. In this process the first few (8) residues of all kappa genes will be encode by the sequences present in the oligonucleotides (Ext., Bridge or PCRpr.). After the PCR, the kappa genes can be cloned using the indicated restriction site for ApaLI.

The process of incorporating fixed FR3 residues in a antibody heavy chain sequence (FIG. 20) consists of 3 steps: (1) annealing of single-stranded DNA material encoding part of the VH genes (for example encoding FR3, CDR3 and FR4 regions) to a partially complementary oligonucleotide mix (indicated with Ext and Bridge), to anneal in this example to the region encoding residues 92-94 (within the FR3 region) of VH genes (indicated with X..X; within the VH genes the overlap may sometimes not be perfect); (2) ligation of this complex; (3) PCR of the ligated material with the indicated primer ('PCRpr') and for example one primer based within the VH gene (such as in the FR4 region). In this process certain residues of all VH genes will be encoded by the sequences present in the oligonucleotides used here, in particular from PCRpr (for residues 70-73), or from Ext/Bridge oligonucleotides (residues 74-91). After the PCR, the partial VH genes can be cloned using the indicated restriction site for XbaI.

It will be understood that the foregoing is only illustrative of the principles of this invention and that various modifications can be made by those skilled in the art without departing from the scope of and spirit of the invention.

TABLE 1

Human GLG FR3 sequences

! VH1

```
! 66  67  68  69  70  71  72  73  74  75  76  77  78  79  80
  agg gtc acc atg acc agg gac acg tcc atc agc aca gcc tac atg
! 81  82  82a 82b 82c 83  84  85  86  87  88  89  90  91  92
  gag ctg agc agg ctg aga tct gac gac acg gcc gtg tat tac tgt
! 93  94  95
  gcg aga ga ! 1-02# 1 (SEQ ID NO: 34)

aga gtc acc att acc agg gac aca tcc gcg agc aca gcc tac atg
  gag ctg agc agc ctg aga tct gaa gac acg gct gtg tat tac tgt
  gcg aga ga ! 1-03# 2 (SEQ ID NO: 35)

aga gtc acc atg acc agg aac acc tcc ata agc aca gcc tac atg
  gag ctg agc agc ctg aga tct gag gac acg gcc gtg tat tac tgt
  gcg aga gg ! 1-08# 3 (SEQ ID NO: 36)

aga gtc acc atg acc aca gac aca tcc acg agc aca gcc tac atg
  gag ctg agg agc ctg aga tct gac gac acg gcc gtg tat tac tgt
  gcg aga ga ! 1-18# 4 (SEQ ID NO: 37)

aga gtc acc atg acc gag gac aca tct aca gac aca gcc tac atg
  gag ctg agc agc ctg aga tct gag gac acg gcc gtg tat tac tgt
  gca aca ga ! 1-24# 5 (SEQ ID NO: 38)

aga gtc acc att acc agg gac agg tct atg agc aca gcc tac atg
  gag ctg agc agc ctg aga tct gag gac aca gcc atg tat tac tgt
  gca aga ta ! 1-45# 6 (SEQ ID NO: 39)

aga gtc acc atg acc agg gac acg tcc acg agc aca gtc tac atg
  gag ctg agc agc ctg aga tct gag gac acg gcc gtg tat tac tgt
  gcg aga ga ! 1-46# 7 (SEQ ID NO: 40)

aga gtc acc att acc agg gac atg tcc aca agc aca gcc tac atg
  gag ctg agc agc ctg aga tcc gag gac acg gcc gtg tat tac tgt
  gcg gca ga ! 1-58# 8 (SEQ ID NO: 41)

aga gtc acg att acc gcg gac gaa tcc acg agc aca gcc tac atg
  gag ctg agc agc ctg aga tct gag gac acg gcc gtg tat tac tgt
  gcg aga ga ! 1-69# 9 (SEQ ID NO: 42)

aga gtc acg att acc gcg gac aaa tcc acg agc aca gcc tac atg
  gag ctg agc agc ctg aga tct gag gac acg gcc gtg tat tac tgt
  gcg aga ga ! 1-e# 10 (SEQ ID NO: 43)

aga gtc acc ata acc gcg gac acg tct aca gac aca gcc tac atg
  gag ctg agc agc ctg aga tct gag gac acg gcc gtg tat tac tgt
  gca aca ga ! 1-f# 11 (SEQ ID NO: 44)
```

! VH2

```
  agg ctc acc atc acc aag gac acc tcc aaa aac cag gtg gtc ctt
  aca atg acc aac atg gac cct gtg gac aca gcc aca tat tac tgt
  gca cac aga c! 2-05# 12 (SEQ ID NO: 45)

agg ctc acc atc tcc aag gac acc tcc aaa agc cag gtg gtc ctt
  acc atg acc aac atg gac cct gtg gac aca gcc aca tat tac tgt
```

TABLE 1-continued

Human GLG FR3 sequences gca cgg ata c! 2-26# 13 (SEQ ID NO: 46)

agg ctc acc atc tcc aag gac acc tcc aaa aac cag gtg gtc ctt
aca atg acc aac atg gac cct gtg gac aca gcc acg tat tac tgt
gca cgg ata c! 2-70# 14 (SEQ ID NO: 47)

! VH3 cga ttc acc atc tcc aga gac aac gcc aag aac tca ctg tat ctg
caa atg aac agc ctg aga gcc gag gac acg gct gtg tat tac tgt
gcg aga ga ! 3-07# 15 (SEQ ID NO: 48)

cga ttc acc atc tcc aga gac aac gcc aag aac tcc ctg tat ctg
caa atg aac agt ctg aga gct gag gac acg gcc ttg tat tac tgt
gca aaa gat a! 3-09# 16 (SEQ ID NO: 49)

cga ttc acc atc tcc agg gac aac gcc aag aac tca ctg tat ctg
caa atg aac agc ctg aga gcc gag gac acg gcc gtg tat tac tgt
gcg aga ga ! 3-11# 17 (SEQ ID NO: 50)

cga ttc acc atc tcc aga gaa aat gcc aag aac tcc ttg tat ctt
caa atg aac agc ctg aga gcc ggg gac acg gct gtg tat tac tgt
gca aga ga ! 3-13# 18 (SEQ ID NO: 51)

aga ttc acc atc tca aga gat gat tca aaa aac acg ctg tat ctg
caa atg aac agc ctg aaa acc gag gac aca gcc gtg tat tac tgt
acc aca ga ! 3-15# 19 (SEQ ID NO: 52)

cga ttc acc atc tcc aga gac aac gcc aag aac tcc ctg tat ctg
caa atg aac agt ctg aga gcc gag gac acg gcc ttg tat cac tgt
gcg aga ga ! 3-20# 20 (SEQ ID NO: 53)

cga ttc acc atc tcc aga gac aac gcc aag aac tca ctg tat ctg
caa atg aac agc ctg aga gcc gag gac acg gct gtg tat tac tgt
gcg aga ga ! 3-21# 21 (SEQ ID NO: 54)

cgg ttc acc atc tcc aga gac aat tcc aag aac acg ctg tat ctg
caa atg aac agc ctg aga gcc gag gac acg gcc gta tat tac tgt
gcg aaa ga ! 3-23# 22 (SEQ ID NO: 55)

cga ttc acc atc tcc aga gac aat tcc aag aac acg ctg tat ctg
caa atg aac agc ctg aga gct gag gac acg gct gtg tat tac tgt
gcg aaa ga ! 3-30# 23 (SEQ ID NO: 56)

cga ttc acc atc tcc aga gac aat tcc aag aac acg ctg tat ctg
caa atg aac agc ctg aga gct gag gac acg gct gtg tat tac tgt
gcg aga ga ! 3303# 24 (SEQ ID NO: 57)

cga ttc acc atc tcc aga gac aat tcc aag aac acg ctg tat ctg
caa atg aac agc ctg aga gct gag gac acg gct gtg tat tac tgt
gcg aaa ga ! 3305# 25 (SEQ ID NO: 58)

cga ttc acc atc tcc aga gac aat tcc aag aac acg ctg tat ctg
caa atg aac agc ctg aga gcc gag gac acg gct gtg tat tac tgt
gca aga ga ! 3-33# 26 (SEQ ID NO: 59)

cga ttc acc atc tcc aga gac aac agc aaa aac tcc ctg tat ctg
caa atg aac agt ctg aga act gag gac acc gcc ttg tat tac tgt
gca aaa gat a! 3-43#27 (SEQ ID NO: 60)

cga ttc acc atc tcc aga gac aat gcc aag aac tca ctg tat ctg
caa atg aac agc ctg aga gac gag gac acg gct gtg tat tac tgt
gcg aga ga ! 3-48# 28 (SEQ ID NO: 61)

aga ttc acc atc tca aga gat ggt tcc aaa agc atc gcc tat ctg
caa atg aac agc ctg aaa acc gag gac aca gcc gtg tat tac tgt
act aga ga ! 3-49# 29 (SEQ ID NO: 62)

cga ttc acc atc tcc aga gac aat tcc aag aac acg ctg tat ctt
caa atg aac agc ctg aga gcc gag gac acg gcc gtg tat tac tgt
gcg aga ga ! 3-53# 30 (SEQ ID NO: 63)

aga ttc acc atc tcc aga gac aat tcc aag aac acg ctg tat ctt
caa atg ggc agc ctg aga gct gag gac atg gct gtg tat tac tgt
gcg aga ga ! 3-64# 31 (SEQ ID NO: 64)

aga ttc acc atc tcc aga gac aat tcc aag aac acg ctg tat ctt
caa atg aac agc ctg aga gct gag gac acg gct gtg tat tac tgt TABLE 1-continued Human GLG FR3 sequences gcg aga ga ! 3-66# 32 (SEQ ID NO: 65)

aga ttc acc atc tca aga gat gat tca aag aac tca ctg tat ctg
caa atg aac agc ctg aaa acc gag gac acg gcc gtg tat tac tgt
gct aga ga ! 3-72# 33 (SEQ ID NO: 66)

agg ttc acc atc tcc aga gat gat tca aag aac acg gcg tat ctg
caa atg aac agc ctg aaa acc gag gac acg gcc gtg tat tac tgt
act aga ca ! 3-73# 34 (SEQ ID NO: 67)

cga ttc acc atc tcc aga gac aac gcc aag aac acg ctg tat ctg
caa atg aac agt ctg aga gcc gag gac acg gct gtg tat tac tgt
gca aga ga ! 3-74# 35 (SEQ ID NO: 68)

aga ttc acc atc tcc aga gac aat tcc aag aac acg ctg cat ctt
caa atg aac agc ctg aga gct gag gac acg gct gtg tat tac tgt
aag aaa ga ! 3-d# 36 (SEQ ID NO: 69)

! VH4 cga gtc acc ata tca gta gac aag tcc aag aac cag ttc tcc ctg
aag ctg agc tct gtg acc gcc gcg gac acg gcc gtg tat tac tgt
gcg aga ga ! 4-04# 37 (SEQ ID NO: 70)

cga gtc acc atg tca gta gac acg tcc aag aac cag ttc tcc ctg
aag ctg agc tct gtg acc gcc gtg gac acg gcc gtg tat tac tgt
gcg aga aa ! 4-28# 38 (SEQ ID NO: 71)

cga gtt acc ata tca gta gac acg tct aag aac cag ttc tcc ctg
aag ctg agc tct gtg act gcc gcg gac acg gcc gtg tat tac tgt
gcg aga ga ! 4301# 39 (SEQ ID NO: 72)

cga gtc acc ata tca gta gac agg tcc aag aac cag ttc tcc ctg
aag ctg agc tct gtg acc gcc gcg gac acg gcc gtg tat tac tgt
gcc aga ga ! 4302# 40 (SEQ ID NO: 73)

cga gtt acc ata tca gta gac acg tcc aag aac cag ttc tcc ctg
aag ctg agc tct gtg act gcc gca gac acg gcc gtg tat tac tgt
gcc aga ga ! 4304# 41 (SEQ ID NO: 74)

cga gtt acc ata tca gta gac acg tct aag aac cag ttc tcc ctg
aag ctg agc tct gtg act gcc gcg gac acg gcc gtg tat tac tgt
gcg aga ga ! 4-31# 42 (SEQ ID NO: 75)

cga gtc acc ata tca gta gac acg tcc aag aac cag ttc tcc ctg
aag ctg agc tct gtg acc gcc gcg gac acg gct tat tac tgt
gcg aga ga ! 4-34# 43 (SEQ ID NO: 76)

cga gtc acc ata tcc gta gac acg tcc aag aac cag ttc tcc ctg
aag ctg agc tct gtg acc gcc gca gac acg gct gtg tat tac tgt
gcg aga ca ! 4-39# 44 (SEQ ID NO: 77)

cga gtc acc ata tca gta gac acg tcc aag aac cag ttc tcc ctg
aag ctg agc tct gtg acc gct gcg gac acg gcc gtg tat tac tgt
gcg aga ga ! 4-59# 45 (SEQ ID NO: 78)

cga gtc acc ata tca gta gac acg tcc aag aac cag ttc tcc ctg
aag ctg agc tct gtg acc gct gcg gac acg gcc gtg tat tac tgt
gcg aga ga ! 4-61# 46 (SEQ ID NO: 79)

cga gtc acc ata tca gta gac acg tcc aag aac cag ttc tcc ctg
aag ctg agc tct gtg acc gcc gca gac acg gcc gtg tat tac tgt
gcg aga ga ! 4-b# 47 (SEQ ID NO: 80)

! VH5 cag gtc acc atc tca gcc gac aag tcc atc agc acc gcc tac ctg
cag tgg agc agc ctg aag gcc tcg gac acc gcc atg tat tac tgt
gcg aga ca ! 5-51# 48 (SEQ ID NO: 81)

cac gtc acc atc tca gct gac aag tcc atc agc act gcc tac ctg
cag tgg agc agc ctg aag gcc tcg gac acc gcc atg tat tac tgt
gcg aga ! 5-a# 49 (SEQ ID NO: 82)

TABLE 1-continued

Human GLG FR3 sequences

! VH6 cga ata acc atc aac cca gac aca tcc aag aac cag ttc tcc ctg
cag ctg aac tct gtg act ccc gag gac acg gct gtg tat tac tgt
gca aga ga ! 6-1# 50 (SEQ ID NO: 83)

! VH7 cgg ttt gtc ttc tcc ttg gac acc tct gtc agc acg gca tat ctg
cag atc tgc agc cta aag gct gag gac act gcc gtg tat tac tgt
gcg aga ga ! 74.1# 51 (SEQ ID NO: 84)

TABLE 2

Enzymes that either cut 15 or more human GLGs or have 5+-base recognition in FR3

Typical entry:
REname     Recognition     #sites
GLGid#: base# GLGid#: base# GLGid#: base# ...

BstEII     Ggtnacc        2
1: 3       48: 3
There are 2 hits at base# 3
MaeIII     gtnac          36
1: 4    2: 4    3: 4    4: 4    5: 4    6: 4
7: 4    8: 4    9: 4    10: 4   11: 4   37: 4
37: 58  38: 4   38: 58  39: 4   39: 58  40: 4
40: 58  41: 4   41: 58  42: 4   42: 58  43: 4
43: 58  44: 4   44: 58  45: 4   45: 58  46: 4
46: 58  47: 4   47: 58  48: 4   49: 4   50: 58
There are 24 hits at base# 4
Tsp45I     gtsac          33
1: 4    2: 4    3: 4    4: 4    5: 4    6: 4
7: 4    8: 4    9: 4    10: 4   11: 4   37: 4
37: 58  38: 4   38: 58  39: 58  40: 4   40: 58
41: 4   42: 58  43: 4   43: 58  44: 4   44: 58
45: 4   45: 58  46: 4   46: 58  47: 4   47: 58
48: 4   49: 4   50: 58
There are 21 hits at base# 4
HphI       tcacc          45
1: 5    2: 5    3: 5    4: 5    5: 5    6: 5
7: 5    8: 5    11: 5   12: 5   12: 11  13: 5
14: 5   15: 5   16: 5   17: 5   18: 5   19: 5
20: 5   21: 5   22: 5   23: 5   24: 5   25: 5
26: 5   27: 5   28: 5   29: 5   30: 5   31: 5
32: 5   33: 5   34: 5   35: 5   36: 5   37: 5
38: 5   40: 5   43: 5   44: 5   45: 5   46: 5
47: 5   48: 5   49: 5
There are 44 hits at base# 5
NlaIII     CATG           26
1: 9    1: 42   2: 42   3: 9    3: 42   4: 9
4: 42   5: 9    5: 42   6: 42   6: 78   7: 9
7: 42   8: 21   8: 42   9: 42   10: 42  11: 42
12: 57  13: 48  13: 57  14: 57  31: 72  38: 9
48: 78  49: 78
There are 11 hits at base# 42
There are 1 hits at base# 48 Could cause raggedness.
BsaJI      Ccnngg         37
1: 14   2: 14   5: 14   6: 14   7: 14   8: 14
8: 65   9: 14   10: 14  11: 14  12: 14  13: 14
14: 14  15: 65  17: 14  17: 65  18: 65  19: 65
20: 65  21: 65  22: 65  26: 65  29: 65  30: 65
33: 65  34: 65  35: 65  37: 65  38: 65  39: 65
40: 65  42: 65  43: 65  48: 65  49: 65  50: 65
51: 14
There are 23 hits at base# 65
There are 14 hits at base# 14
AluI       AGct           42
1: 47   2: 47   3: 47   4: 47   5: 47   6: 47
7: 47   8: 47   9: 47   10: 47  11: 47  16: 63
23: 63  24: 63  25: 63  31: 63  32: 63  36: 63
<u>37: 47</u>  <u>37: 52</u>  <u>38: 47</u>  <u>38: 52</u>  <u>39: 47</u>  <u>39: 52</u>
<u>40: 47</u>  <u>40: 52</u>  <u>41: 47</u>  <u>41: 52</u>  <u>42: 47</u>  <u>42: 52</u>
<u>43: 47</u>  <u>43: 52</u>  <u>44: 47</u>  <u>44: 52</u>  <u>45: 47</u>  <u>45: 52</u>
<u>46: 47</u>  <u>46: 52</u>  <u>47: 47</u>  <u>47: 52</u>  49: 15  50: 47
There are 23 hits at base# 47
There are 11 hits at base# 52 Only 5 bases from 47
BlpI       GCtnagc        21
1: 48   2: 48   3: 48   5: 48   6: 48   7: 48
8: 48   9: 48   10: 48  11: 48  37: 48  38: 48
39: 48  40: 48  41: 48  42: 48  43: 48  44: 48
45: 48  46: 48  47: 48
There are 21 hits at base# 48
MwoI       GCNNNNNnngc    19
           (SEQ ID NO: 85)
1: 48   2: 28   19: 36  22: 36  23: 36  24: 36
25: 36  26: 36  35: 36  37: 67  39: 67  40: 67
41: 67  42: 67  43: 67  44: 67  45: 67  46: 67
47: 67
There are 10 hits at base# 67
There are 7 hits at base# 36
DdeI       Ctnag          71
1: 49   1: 58   2: 49   2: 58   3: 49   3: 58
3: 65   4: 49   4: 58   5: 49   5: 58   5: 65
6: 49   <u>6: 58</u>   <u>6: 65</u>   7: 49   <u>7: 58</u>   <u>7: 65</u>
8: 49   8: 58   9: 49   <u>9: 58</u>   <u>9: 65</u>   10: 49
<u>10: 58</u>  <u>10: 65</u>  11: 58  <u>11: 58</u>  <u>11: 65</u>  15: 58
<u>16: 58</u>  <u>16: 65</u>  17: 58  18: 58  20: 58  21: 58
22: 58  <u>23: 58</u>  <u>23: 65</u>  <u>24: 58</u>  <u>24: 65</u>  <u>25: 58</u>
<u>25: 65</u>  26: 58  <u>27: 58</u>  <u>27: 65</u>  28: 58  30: 58
<u>31: 58</u>  <u>31: 65</u>  <u>32: 58</u>  <u>32: 65</u>  35: 58  <u>36: 58</u>
<u>36: 65</u>  37: 49  38: 49  39: 26  39: 49  40: 49
41: 49  42: 26  42: 49  43: 49  44: 49  45: 49
46: 49  47: 49  48: 12  49: 12  51: 65
There are 29 hits at base# 58
There are 22 hits at base# 49 Only nine base from 58
There are 16 hits at base# 65 Only seven bases from 58
BglII      Agatct         11
1: 61   2: 61   3: 61   4: 61   5: 61   6: 61
7: 61   9: 61   10: 61  11: 61  51: 47
There are 10 hits at base# 61
BstYI      Rgatcy         12
1: 61   2: 61   3: 61   4: 61   5: 61   6: 61
7: 61   8: 61   9: 61   10: 61  11: 61  51: 47
There are 11 hits at base# 61
Hpy188I    TCNga          17
1: 64   2: 64   3: 64   4: 64   5: 64   6: 64
7: 64   8: 64   9: 64   10: 64  11: 64  16: 57
20: 57  27: 57  35: 57  48: 67  49: 67
There are 11 hits at base# 64
There are 4 hits at base# 57
There are 2 hits at base# 67 Could be ragged.
MslI       CAYNNnnRTG     44
           (SEQ ID NO: 86)
1: 72   2: 72   3: 72   4: 72   5: 72   6: 72
7: 72   8: 72   9: 72   10: 72  11: 72  15: 72
17: 72  18: 72  19: 72  21: 72  23: 72  24: 72
25: 72  26: 72  28: 72  29: 72  30: 72  31: 72
32: 72  33: 72  34: 72  35: 72  36: 72  37: 72
38: 72  39: 72  40: 72  41: 72  42: 72  43: 72
44: 72  45: 72  46: 72  47: 72  48: 72  49: 72
50: 72  51: 72

TABLE 2-continued

| | | | | | |
|---|---|---|---|---|---|
| There are 44 hits at base# 72 | | | | | |
| BsiEI | CGRYcg | 23 | | | |
| 1: 74 | 3: 74 | 4: 74 | 5: 74 | 7: 74 | 8: 74 |
| 9: 74 | 10: 74 | 11: 74 | 17: 74 | 22: 74 | 30: 74 |
| 33: 74 | 34: 74 | 37: 74 | 38: 74 | 39: 74 | 40: 74 |
| 41: 74 | 42: 74 | 45: 74 | 46: 74 | 47: 74 | |
| There are 23 hits at base# 74 | | | | | |
| EaeI | Yggccr | 23 | | | |
| 1: 74 | 3: 74 | 4: 74 | 5: 74 | 7: 74 | 8: 74 |
| 9: 74 | 10: 74 | 11: 74 | 17: 74 | 22: 74 | 30: 74 |
| 33: 74 | 34: 74 | 37: 74 | 38: 74 | 39: 74 | 40: 74 |
| 41: 74 | 42: 74 | 45: 74 | 46: 74 | 47: 74 | |
| There are 23 hits at base# 74 | | | | | |
| EagI | Cggccg | 23 | | | |
| 1: 74 | 3: 74 | 4: 74 | 5: 74 | 7: 74 | 8: 74 |
| 9: 74 | 10: 74 | 11: 74 | 17: 74 | 22: 74 | 30: 74 |
| 33: 74 | 34: 74 | 37: 74 | 38: 74 | 39: 74 | 40: 74 |
| 41: 74 | 42: 74 | 45: 74 | 46: 74 | 47: 74 | |
| There are 23 hits at base# 74 | | | | | |
| HaeIII | GGcc | 27 | | | |
| 1: 75 | 3: 75 | 4: 75 | 5: 75 | 7: 75 | 8: 75 |
| 9: 75 | 10: 75 | 11: 75 | 16: 75 | 17: 75 | 20: 75 |
| 22: 75 | 30: 75 | 33: 75 | 34: 75 | 37: 75 | 38: 75 |
| 39: 75 | 40: 75 | 41: 75 | 42: 75 | 45: 75 | 46: 75 |
| 47: 75 | 48: 63 | 49: 63 | | | |
| There are 25 hits at base# 75 | | | | | |
| Bst4CI | ACNgt 65° C. | | 63 Sites There is a third isoschismer | | |
| 1: 86 | 2: 86 | 3: 86 | 4: 86 | 5: 86 | 6: 86 |
| 7: 34 | 7: 86 | 8: 86 | 9: 86 | 10: 86 | 11: 86 |
| 12: 86 | 13: 86 | 14: 86 | 15: 36 | 15: 86 | 16: 53 |
| 16: 86 | 17: 36 | 17: 86 | 18: 86 | 19: 86 | 20: 53 |
| 20: 86 | 21: 36 | 21: 86 | 22: 0 | 22: 86 | 23: 86 |
| 24: 86 | 25: 86 | 26: 86 | 27: 53 | 27: 86 | 28: 36 |
| 28: 86 | 29: 86 | 30: 86 | 31: 86 | 32: 86 | 33: 36 |
| 33: 86 | 34: 86 | 35: 53 | 35: 86 | 36: 86 | 37: 86 |
| 38: 86 | 39: 86 | 40: 86 | 41: 86 | 42: 86 | 43: 86 |
| 44: 86 | 45: 86 | 46: 86 | 47: 86 | 48: 86 | 49: 86 |
| 50: 86 | 51: 0 | 51: 86 | | | |
| There are 51 hits at base# 86 All the other sites are well away | | | | | |
| HpyCH4III | ACNgt | 63 | | | |
| 1: 86 | 2: 86 | 3: 86 | 4: 86 | 5: 86 | 6: 86 |
| 7: 34 | 7: 86 | 8: 86 | 9: 86 | 10: 86 | 11: 86 |
| 12: 86 | 13: 86 | 14: 86 | 15: 36 | 15: 86 | 16: 53 |
| 16: 86 | 17: 36 | 17: 86 | 18: 86 | 19: 86 | 20: 53 |
| 20: 86 | 21: 36 | 21: 86 | 22: 0 | 22: 86 | 23: 86 |
| 24: 86 | 25: 86 | 26: 86 | 27: 53 | 27: 86 | 28: 36 |
| 28: 86 | 29: 86 | 30: 86 | 31: 86 | 32: 86 | 33: 36 |
| 33: 86 | 34: 86 | 35: 53 | 35: 86 | 36: 86 | 37: 86 |
| 38: 86 | 39: 86 | 40: 86 | 41: 86 | 42: 86 | 43: 86 |
| 44: 86 | 45: 86 | 46: 86 | 47: 86 | 48: 86 | 49: 86 |
| 50: 86 | 51: 0 | 51: 86 | | | |
| There are 51 hits at base# 86 | | | | | |
| HinfI | Gantc | 43 | | | |
| 2: 2 | 3: 2 | 4: 2 | 5: 2 | 6: 2 | 7: 2 |
| 8: 2 | 9: 2 | 9: 22 | 10: 2 | 11: 2 | 15: 2 |
| 16: 2 | 17: 2 | 18: 2 | 19: 2 | 19: 22 | 20: 2 |
| 21: 2 | 23: 2 | 24: 2 | 25: 2 | 26: 2 | 27: 2 |
| 28: 2 | 29: 2 | 30: 2 | 31: 2 | 32: 2 | 33: 2 |
| 33: 22 | 34: 22 | 35: 2 | 36: 2 | 37: 2 | 38: 2 |
| 40: 2 | 43: 2 | 44: 2 | 45: 2 | 46: 2 | 47: 2 |
| 50: 60 | | | | | |
| There are 38 hits at base# 2 | | | | | |
| MlyI | GAGTCNNNNNn (SEQ ID NO: 87) | 18 | | | |
| 2: 2 | 3: 2 | 4: 2 | 5: 2 | 6: 2 | 7: 2 |
| 8: 2 | 9: 2 | 10: 2 | 11: 2 | 37: 2 | 38: 2 |
| 40: 2 | 43: 2 | 44: 2 | 45: 2 | 46: 2 | 47: 2 |
| There are 18 hits at base# 2 | | | | | |
| PleI | gagtc | 18 | | | |
| 2: 2 | 3: 2 | 4: 2 | 5: 2 | 6: 2 | 7: 2 |
| 8: 2 | 9: 2 | 10: 2 | 11: 2 | 37: 2 | 38: 2 |
| 40: 2 | 43: 2 | 44: 2 | 45: 2 | 46: 2 | 47: 2 |
| There are 18 hits at base# 2 | | | | | |
| AciI | Ccgc | 24 | | | |
| 2: 26 | 9: 14 | 10: 14 | 11: 14 | 27: 74 | 37: 62 |
| 37: 65 | 38: 62 | 39: 65 | 40: 62 | 40: 65 | 41: 65 |
| 42: 65 | 43: 62 | 43: 65 | 44: 62 | 44: 65 | 45: 62 |
| 46: 62 | 47: 62 | 47: 65 | 48: 35 | 48: 74 | 49: 74 |
| There are 8 hits at base# 62 | | | | | |
| There are 8 hits at base# 65 | | | | | |
| There are 3 hits at base# 14 | | | | | |
| There are 3 hits at base# 74 | | | | | |
| There are 1 hits at base# 26 | | | | | |
| There are 1 hits at base# 35 | | | | | |
| -"- | Gcgg | 11 | | | |
| 8: 91 | 9: 16 | 10: 16 | 11: 16 | 37: 67 | 39: 67 |
| 40: 67 | 42: 67 | 43: 67 | 45: 67 | 46: 67 | |
| There are 7 hits at base# 67 | | | | | |
| There are 3 hits at base# 16 | | | | | |
| There are 1 hits at base# 91 | | | | | |
| BsiHKAI | GWGCWc | 20 | | | |
| 2: 30 | 4: 30 | 6: 30 | 7: 30 | 9: 30 | 10: 30 |
| 12: 89 | 13: 89 | 14: 89 | 37: 51 | 38: 51 | 39: 51 |
| 40: 51 | 41: 51 | 42: 51 | 43: 51 | 44: 51 | 45: 51 |
| 46: 51 | 47: 51 | | | | |
| There are 11 hits at base# 51 | | | | | |
| Bsp1286I | GDGCHc | 20 | | | |
| 2: 30 | 4: 30 | 6: 30 | 7: 30 | 9: 30 | 10: 30 |
| 12: 89 | 13: 89 | 14: 89 | 37: 51 | 38: 51 | 39: 51 |
| 40: 51 | 41: 51 | 42: 51 | 43: 51 | 44: 51 | 45: 51 |
| 46: 51 | 47: 51 | | | | |
| There are 11 hits at base# 51 | | | | | |
| HgiAI | GWGCWc | 20 | | | |
| 2: 30 | 4: 30 | 6: 30 | 7: 30 | 9: 30 | 10: 30 |
| 12: 89 | 13: 89 | 14: 89 | 37: 51 | 38: 51 | 39: 51 |
| 40: 51 | 41: 51 | 42: 51 | 43: 51 | 44: 51 | 45: 51 |
| 46: 51 | 47: 51 | | | | |
| There are 11 hits at base# 51 | | | | | |
| BsoFI | GCngc | 26 | | | |
| 2: 53 | 3: 53 | 5: 53 | 6: 53 | 7: 53 | 8: 53 |
| 8: 91 | 9: 53 | 10: 53 | 11: 53 | 31: 53 | 36: 36 |
| 37: 64 | 39: 64 | 40: 64 | 41: 64 | 42: 64 | 43: 64 |
| 44: 64 | 45: 64 | 46: 64 | 47: 64 | 48: 53 | 49: 53 |
| 50: 45 | 51: 53 | | | | |
| There are 13 hits at base# 53 | | | | | |
| There are 10 hits at base# 64 | | | | | |
| TseI | Gcwgc | 17 | | | |
| 2: 53 | 3: 53 | 5: 53 | 6: 53 | 7: 53 | 8: 53 |
| 9: 53 | 10: 53 | 11: 53 | 31: 53 | 36: 36 | 45: 64 |
| 46: 64 | 48: 53 | 49: 53 | 50: 45 | 51: 53 | |
| There are 13 hits at base# 53 | | | | | |
| MnlI | gagg | 34 | | | |
| 3: 67 | 3: 95 | 4: 51 | 5: 16 | 5: 67 | 6: 67 |
| 7: 67 | 8: 67 | 9: 67 | 10: 67 | 11: 67 | 15: 67 |
| 16: 67 | 17: 67 | 19: 67 | 20: 67 | 21: 67 | 22: 67 |
| 23: 67 | 24: 67 | 25: 67 | 26: 67 | 27: 67 | 28: 67 |
| 29: 67 | 30: 67 | 31: 67 | 32: 67 | 33: 67 | 34: 67 |
| 35: 67 | 36: 67 | 50: 67 | 51: 67 | | |
| There are 31 hits at base# 67 | | | | | |
| HpyCH4V | TGca | 34 | | | |
| 5: 90 | 6: 90 | 11: 90 | 12: 90 | 13: 90 | 14: 90 |
| 15: 44 | 16: 44 | 16: 90 | 17: 44 | 18: 90 | 19: 44 |
| 20: 44 | 21: 44 | 22: 44 | 23: 44 | 24: 44 | 25: 44 |
| 26: 44 | 27: 44 | 27: 90 | 28: 44 | 29: 44 | 33: 44 |
| 34: 44 | 35: 44 | 35: 90 | 36: 38 | 48: 44 | 49: 44 |
| 50: 44 | 50: 90 | 51: 44 | 51: 52 | | |
| There are 21 hits at base# 44 | | | | | |
| There are 1 hits at base# 52 | | | | | |
| AccI | GTmkac | | 13 5-base recognition | | |
| 7: 37 | 11: 24 | 37: 16 | 38: 16 | 39: 16 | 40: 16 |
| 41: 16 | 42: 16 | 43: 16 | 44: 16 | 45: 16 | 46: 16 |
| 47: 16 | | | | | |
| There are 11 hits at base# 16 | | | | | |
| SacII | CCGCgg | | 8 6-base recognition | | |
| 9: 14 | 10: 14 | 11: 14 | 37: 65 | 39: 65 | 40: 65 |
| 42: 65 | 43: 65 | | | | |
| There are 5 hits at base# 65 | | | | | |
| There are 3 hits at base# 14 | | | | | |
| TfiI | Gawtc | 24 | | | |
| 9: 22 | 15: 2 | 16: 2 | 17: 2 | 18: 2 | 19: 2 |
| 19: 22 | 20: 2 | 21: 2 | 23: 2 | 24: 2 | 28: 2 |
| 26: 2 | 27: 2 | 28: 2 | 29: 2 | 30: 2 | 31: 2 |
| 32: 2 | 33: 2 | 33: 22 | 34: 22 | 35: 2 | 36: 2 |
| There are 20 hits at base# 2 | | | | | |
| BsmAI | Nnnnnngagac (SEQ ID NO: 88) | 19 | | | |
| 15: 11 | 16: 11 | 20: 11 | 21: 11 | 22: 11 | 23: 11 |
| 24: 11 | 25: 11 | 26: 11 | 27: 11 | 28: 11 | 28: 56 |
| 30: 11 | 31: 11 | 32: 11 | 35: 11 | 36: 11 | 44: 87 |
| 48: 87 | | | | | |

TABLE 2-continued

| | | | | | | |
|---|---|---|---|---|---|---|
| There are 16 hits at base# 11 | | | | | | |
| BpmI | ctccag | | 19 | | | |
| 15: 12 | 16: 12 | 17: 12 | 18: 12 | 20: 12 | 21: 12 | |
| 22: 12 | 23: 12 | 24: 12 | 25: 12 | 26: 12 | 27: 12 | |
| 28: 12 | 30: 12 | 31: 12 | 32: 12 | 34: 12 | 35: 12 | |
| 36: 12 | | | | | | |
| There are 19 hits at base# 12 | | | | | | |
| XmnI | GAANNnnttc | | 12 | | | |
| | (SEQ ID NO: 89) | | | | | |
| 37: 30 | 38: 30 | 39: 30 | 40: 30 | 41: 30 | 42: 30 | |
| 43: 30 | 44: 30 | 45: 30 | 46: 30 | 47: 30 | 50: 30 | |
| There are 12 hits at base# 30 | | | | | | |
| BsrI | NCcagt | | 12 | | | |
| 37: 32 | 38: 32 | 39: 32 | 40: 32 | 41: 32 | 42: 32 | |
| 43: 32 | 44: 32 | 45: 32 | 46: 32 | 47: 32 | 50: 32 | |

TABLE 2-continued

| | | | | | |
|---|---|---|---|---|---|
| There are 12 hits at base# 32 | | | | | |
| BanII | GRGCYc | | 11 | | |
| 37: 51 | 38: 51 | 39: 51 | 40: 51 | 41: 51 | 42: 51 |
| 43: 51 | 44: 51 | 45: 51 | 46: 51 | 47: 51 | |
| There are 11 hits at base# 51 | | | | | |
| Ec1136I | GAGctc | | 11 | | |
| 37: 51 | 38: 51 | 39: 51 | 40: 51 | 41: 51 | 42: 51 |
| 43: 51 | 44: 51 | 45: 51 | 46: 51 | 47: 51 | |
| There are 11 hits at base# 51 | | | | | |
| SacI | GAGCTc | | 11 | | |
| 37: 51 | 38: 51 | 39: 51 | 40: 51 | 41: 51 | 42: 51 |
| 43: 51 | 44: 51 | 45: 51 | 46: 51 | 47: 51 | |
| There are 11 hits at base# 51 | | | | | |

TABLE 3

Synthetic 3-23 FR3 of human heavy chains showning positions of possible cleavage sites

```
! Sites engineered into the synthetic gene are shown in upper case
! DNA
! with the RE name between vertical bars (as in | XbaI |).
! RERSs frequently found in GLGs are shown below the synthetic
! sequence
! with the name to the right (as in gtn ac=MaeIII(24), indicating
! that
! 24 of the 51 GLGs contain the site).
!                                            |---FR3---
!                                             89  90  (codon # in
!                                              R   F   synthetic 3-23)
!                                             |cgc|ttc|  6
! Allowed DNA                                 |cgn|tty|
!                                             |agr|
!                                              ga ntc = HinfI(38)
!                                              ga gtc = PleI(16)
!                                              ga wtc = TfiI(20)
!                                                 gtn ac = MaeIII(24)
!                                                 gts ac = Tsp45I(21)
!                                                 tc acc = HphI(44)
!        --------FR3-----------------------------------------------
!          91  92  93  94  95  96  97  98  99 100 101 102 103 104 105
!           T   I   S   R   D   N   S   K   N   T   L   Y   L   Q   M
(SEQ ID NO: 91)
         |act|atc|TCT|AGA|gac|aac|tct|aag|aat|act|ctc|tac|ttg|cag|atg| 51
! allowed|acn|ath|tcn|cgn|gay|aay|tcn|aar|aay|acn|ttr|tay|ttr|car|atg|
(SEQ ID NO: 90)
!            |agy|agr|       |agy|               |ctn|   |ctn|
!            |    ga|gac =BsmAI(16)                       ag ct = AluI(23)
!          c|ttc ag = BpmI(19)                       g ctn agc = BlpI
      (21)
!             |   |           g aan nnn ttc = XmnI(12)
!             | XbaI |                               tg ca = HpyCH4V(21)
!
!       ---FR3-----------------------------------------------------> |
!         106 107 108 109 110 111 112 113 114 115 116 117 118 119 120
!           N   S   L   R   A   E   D   T   A   V   Y   Y   C   A   K
         |aac|agC|TTA|AGg|gct|gag|gac|aCT|GCA|Gtc|tac|tat|tgc|gct|aaa| 96
! allowed|aay|tcn|tcr|cgn|gcn|gar|gay|acn|gcn|gtn|tay|tgy|gcn|aar|
!            |agy|ctn|agr|       |       |
!            |   |   | cc nng g = BsaJI(23)       ac ngt = Bst4CI(51)
!            |   |  aga tct = BglII(10)    |     ac ngt = HpyCH4III(51)
!            |   |  Rga tcY = BstYI(11)    |     ac ngt = TaaI(51)
!            |   |   |     c ayn nnn rtc = MslI(44)
!            |   |   |         cg ryc g = BsiEI(23)
!            |   |   |           yg gcc r = EaeI(23)
!            |   |   |           cg gcc g = EagI(23)
!            |   |   |            lg gcc = HaeIII(25)
!            |   |   |     gag g = MnlI(32)|
!            |AflII |        | FstI |
```

TABLE 4

REdaptors, Extenders, and Bridges used for Cleavage and Capture of Human Heavy Chains in FR3.

A: HpyCH4V Probes of actual human HC genes (SEQ ID NOS 92-100, respectively, in order of appearance)

```
!HpyCH4V in FR3 of human HC, bases 35-56; only those with TGca site
TGca; 10,
RE recognition: tgca of length 4 is expected at 10
 1                                            6-1  agttctccctgcagatgaactc
 2                      3-11, 3-07, 3-21, 3-72, 3-48 cactgtatctgcaaatgaacag
 3                              3-09, 3-43, 3-20 ccctgtatctgcaaatgaacag
 4                                           5-51 ccgcctacctgcagtggagcag
 5  3-15, 3-30, 3-30.5, 3-30.3, 3-74, 3-23, 3-33 cgctgtatctgcaaatgaacag
 6                                          7-4.1 cggcatatctgcagatctgcag
 7                                           3-73 cggcgtatctgcaaatgaacag
 8                                            5-a ctgcctacctgcagtggagcag
 9                                           3-49 tcgcctatctgcaaatgaacag
```

B: HpyCH4V REdaptors, Extenders, and Bridges
B.1 REdaptors

```
! Cutting HC lower strand:
! TmKeller for 100 mM NaCl, zero formamide
! Edapters for cleavage
```

| | | $T_m^W$ | $T_m^K$ | SEQ ID NO: |
|---|---|---|---|---|
| (ON_HCFR36-1) | 5'-agttctcccTGCAgctgaactc-3' | 68.0 | 64.5 | 92 |
| (ON_HCFR36-1A) | 5'-ttctcccTGCAgctgaactc-3' | 62.0 | 62.5 | residues 3-22 of 92 |
| (ON_HCFR36-1B) | 5'-ttctcccTGCAgctgaac-3' | 56.0 | 59.9 | residues 3-20 of 92 |
| (ON_HCFR33-15) | 5'-cgctgtatcTGCAaatgaacag-3' | 64.0 | 60.8 | 96 |
| (ON_HCFR33-15A) | 5'-ctgtatcTGCAaatgaacag-3' | 56.0 | 56.3 | residues 3-22 of 96 |
| (ON_HCFR33-15B) | 5'-ctgtatcTGCAaatgaac-3' | 50.0 | 53.1 | residues 3-20 of 96 |
| (ON_HCFR33-11) | 5'-cactgtatcTGCAaatgaacag-3' | 62.0 | 56.9 | 93 |
| (ON_HCFR35-51) | 5'-ccgcctaccTGCAgtggagcag-3' | 74.0 | 70.1 | 95 |

B.2 Segment of synthetic 3-23 gene into which captured CDR3 is to be cloned

```
!           XbaI... (SEQ ID NO: 101)
!D323* cgCttcacTaag tcT aga gac aaC tcT aag aaT acT ctC taC
!     scab........ designed gene 3-23 gene.................
!     HpyCH4V
!      .. ..           AflII...
!     Ttg caG atg aac agc TtA agG . . .
!     ........................... . . .
```

B.3 Extender and Bridges

```
! Extender (bottom strand):
! (SEQ ID NO: 102)
(ON_HCHpyEx01) 5'-cAAgTAgAgAgTATTcTTAgAgTTgTcTcTAgAcTTAgTgAAgcg-3'
! ON_HCHpyEx01 is the reverse complement of
! 5'-cgCttcacTaag tcT aga gac aaC tcT aag aaT acT ctC taC Ttg -3'
!
! Bridges (top strand, 9-base overlap):
!(SEQ ID NO: 103)
!(ON_HCBpyBr016-1)  5'-cgCttcacTaag tcT aga gac aaC tcT aag-
                      aaT acT ctC taC Ttg CAgotgaac-3' (3'-term C is blocked)
!
! 3-15 et al. + 3-11 (SEQ ID NO: 104)
(ON_HCHpyBr023-15) 5'-cgCttcacTaag tcT aga gac aaC tcT aag-
                      aaT acT ctC taC Ttg CAaatgaac-3' (3'-term C is blocked)
!
!    5-51 (SEQ ID NO: 105)
(ON_HCHpyBr045-51) 5'-cgCttcacTaag tcT aga gac aaC tcT aag-
                      aaT acT ctC taC Ttg CAgtggagc-3' (3'-term C is blocked)
!
! PCR primer (top strand)
!
(ON_HCHpyPCR)      5'-cgCttcacTaag tcT aga gac-3' (SEQ ID NO: 106)
!
```

C: BlpI Probes from human HC GLGs

```
 1   1-58, 1-03, 1-08, 1-69, 1-24, 1-45, 1-46, acatggaGCTGAGCagcctgag
     1-f, 1-e (SEQ ID NO: 107)
```

TABLE 4-continued

REdaptors, Extenders, and Bridges used for Cleavage
and Capture of Human Heavy Chains in FR3.

| | | |
|---|---|---|
| 2 | 1-02 | acatggaGCTGAGCaggctgag (SEQ ID NO: 108) |
| 3 | 1-18 | acatggagctgaggagcctgag (SEQ ID NO: 109) |
| 4 | 5-51, 5-a | acctgcagtggagcagcctgaa (SEQ ID NO: 110) |
| 5 | 3-15, 3-73, 3-49, 3-72 | atctgcaaatgaacagcctgaa (SEQ ID NO: 111) |
| 6 | 3303, 3-33, 3-07, 3-11, 3-30, 3-21, 3-23, 3305, 3-48 | atctgcaaatgaacagcctgag (SEQ ID NO: 112) |
| 7 | 3-20, 3-74, 3-09, 3-43 | atctgcaaatgaacagtctgag (SEQ ID NO: 113) |
| 8 | 74.1 | atctgcagatctgcagcctaaa (SEQ ID NO: 114) |
| 9 | 3-66, 3-13, 3-53, 3-d | atcttcaaatgaacagcctgag (SEQ ID NO: 115) |
| 10 | 3-64 | atcttcaaatgggcagcctgag (SEQ ID NO: 116) |
| 11 | 4301, 4-28, 4302, 4-04, 4304, 4-31, 4-34, 4-39, 4-59, 4-61, 4-b | ccctgaaGCTGAGCtctgtgac (SEQ ID NO: 117) |
| 12 | 6-1 | ccctgcagctgaactctgtgac (SEQ ID NO: 118) |
| 13 | 2-70, 2-05 | tccttacaatgaccaacatgga (SEQ ID NO: 119) |
| 14 | 2-26 | tccttaccatgaccaacatgga (SEQ ID NO: 120) |

D: BlpI REdaptors, Extenders, and Bridges
D.1 REdaptors

| | | $T_m^W$ | $T_m K$ |
|---|---|---|---|
| (B1pF3HC1-58) | (SEQ ID NO: 121) 5'-ac atg gaG CTG AGC agc ctg ag-3' | 70 | 66.4 |
| (B1pF3HC6-1) | (SEQ ID NO: 122) 5'-cc ctg aag ctg agc tct gtg ac-3' | 70 | 66.4 |

!B1pF3HC6-1 matches 4-30.1, not 6-1.

D.2 Segment of synthetic 3-23 gene into
which captured CDR3 is to be cloned

```
!
BlpI
!                    XbaI...
... ...
!D323* cgCttcacTaag TCT AGA gac aaC tcT aag aaT acT ctC taC Ttg
caG atg aac
(SEQ ID NO: 123)!
!                    AflII...
!                    agC TTA AGG
```

D.3 Extender and Bridges

```
!Bridges
(B1pF3Br1) 5'-cgCttcacTcag tcT aga gaT aaC AGT aaA aaT acT TtG-
taC Ttg caG Ctg a|GC agc ctg-3' (SEQ ID NO: 124)
(B1pF3Br2) 5'-cgCttcacTcag tcT aga gaT aaC AGT aaA aaT acT TtG-
taC Ttg caG Ctg a|gc tct gtg-3' (SEQ ID NO: 125)
!              | lower strand is cut here
!Extender
(B1pF3Ext) 5'-
TcAgcTgcAAgTAcAAAgTATTTTTAcTgTTATcTCTAgAcTgAgTgAAgcg-3' (SEQ ID NO: 126)
!B1pF3Ext is the reverse complement of:
!5'-cgCttcacTcag tcT aga gaT aaC AGT aaA aaT acT TtG taC Ttg caG Ctg a-3'
!
(B1pF3PCR) 5'-cgCttcacTcag tcT aga gaT aaC-3' (SEQ ID NO: 127)
```

E: HpyCH4III Distinct GLG sequences surrounding site, bases 77-98

| | | |
|---|---|---|
| 1 | 102#1, 118#4, 146#7, 169#9, 1e#10, 311#17, 353#30, 404#37, 4301 | ccgtgtattactgtgcgagaga (SEQ ID NO: 128) |
| 2 | 103#2, 307#15, 321#21, 3303#24, 333#26, 348#28, 364#31, 366#32 | ctgtgtattactgtgcgagaga (SEQ ID NO: 129) |
| 3 | 108#3 | ccgtgtattactgtgcgagagg (SEQ ID NO: 130) |
| 4 | 124#5, 1f#11 | ccgtgtattactgtgcaacaga (SEQ ID NO: 131) |
| 5 | 145#6 | ccatgtattactgtgcaagata (SEQ ID NO: 132) |

TABLE 4-continued

REdaptors, Extenders, and Bridges used for Cleavage
and Capture of Human Heavy Chains in FR3.

| | | |
|---|---|---|
| 6 | 158#8 | ccgtgtattactgtgcggcaga (SEQ ID NO: 133) |
| 7 | 205#12 | ccacatattactgtgcacacag (SEQ ID NO: 134) |
| 8 | 226#13 | ccacatattactgtgcacggat (SEQ ID NO: 135) |
| 9 | 270#14 | ccacgtattactgtgcacggat (SEQ ID NO: 136) |
| 10 | 309#16, 343#27 | ccttgtattactgtgcaaaaga (SEQ ID NO: 137) |
| 11 | 313#18, 374#35, 61#50 | ctctgtattactgtccaagaga (SEQ ID NO: 138) |
| 12 | 315#19 | ccgtgtattactgtaccacaga (SEQ ID NO: 139) |
| 13 | 320#20 | acttgtatcactgtgcgagaga (SEQ ID NO: 140) |
| 14 | 323#22 | ccgtatattactgtgcgaaaga (SEQ ID NO: 141) |
| 15 | 330#23, 3305#25 | ctgtgtattactgtgcgaaaga (SEQ ID NO: 142) |
| 16 | 349#29 | ccgtgtattactgtactagaga (SEQ ID NO: 143) |
| 17 | 372#33 | ccgtgtattactgtgctagaga (SEQ ID NO: 144) |
| 18 | 373#34 | ccgtgtattactgtactagaca (SEQ ID NO: 145) |
| 19 | 3d#36 | ctgtgtattactgtaagaaaga (SEQ ID NO: 146) |
| 20 | 428#38 | ccgtgtattactgtgcgagaaa (SEQ ID NO: 147) |
| 21 | 4302#40, 4304#41 | ccgtgtattactgtgccagaga (SEQ ID NO: 148) |
| 22 | 439#44 | ctgtgtattactgtgcgagaca (SEQ ID NO: 149) |
| 23 | 551#48 | ccatgtattactgtgcgagaca (SEQ ID NO: 150) |
| 24 | 5a#49 | ccatgtattactgtgcgaga (SEQ ID NO: 151) |

F: HpyCH4III REdaptors, Extenders, and Bridges
F.1 REdaptors
(SEQ ID NOS 152-159, respectively, in order of appearance)

```
!ONs for cleavage of HC(lower) in FR3(bases 77-97)
!For cleavage with HpyCE4III, Bst4CI, or TaaI
!cleavage is in lower chain before base 88.
!                   77 788 888 888 889 999 999 9
!                   78 901 234 567 890 123 456 7       T_m^W
```

| | | |
|---|---|---|
| (H43.77.97.1-02#1) | 5'-cc gtg tat tAC TGT gcg aga g-3' | 6462.6 |
| (H43.77.97.1-03#2) | 5'-ct gtg tat tAC TGT gcg aga g-3' | 6260.6 |
| (H43.77.97.108#3) | 5'-cc gtg tat tAC TGT gcg aga g-3' | 6462.6 |
| (H43.77.97.323#22) | 5'-cc gta tat tac tgt gcg aaa g-3' | 6058.7 |
| (H43.77.97.330#23) | 5'-ct gtg tat tac tgt gcg aaa g-3' | 6058.7 |
| (H43.77.97.439#44) | 5'-ct gtg tat tac tgt gcg aga c-3' | 6260.6 |
| (H43.77.97.551#48) | 5'-cc atg tat tac tgt gcg aga c-3' | 6260.6 |
| (H43.77.97.5a#49) | 5'-cc atg tat tAC TGT gcg aga c-3' | 5858.3 |

F.2 Extender and Bridges

```
!XbaI and AflII sites in bridges are bunged
(H43.XABr1) 5'-ggtgtagtga-
|TCT|AGt|gac|aac|tct|aag|aat|act|ctc|tac|ttg|cag|atg|-
|aac|agC|TTt|AGg|gct|gag|gac|aCT|GCA|Gtc|tac|tat tgt gcg aga-3' (SEQ ID NO: 160)
(H43.XAEr2) 5'-ggtgtagtga-
|TCT|AGt|gac|aac|tct|aag|aat|act|ctc|tac|ttg|cag|atg|-
|aac|agC|TTt|AGg|gct|gag|gac|aCT|GCA|Gtc|tac|tat tgt gcg aaa-3' (SEQ ID NO: 161)
(H43.XAExt) 5'-ATAgTAgAcT gcAgTgTccT cAgcccTTAA gcTgTTcATc TgcAAgTAgA-
```

TABLE 4-continued

REdaptors, Extenders, and Bridges used for Cleavage
and Capture of Human Heavy Chains in FR3.

gAgTATTcTT AgAgTTgTcT cTAgATcAcT AcAcc-3' (SEQ ID NO: 162)
H43.XAExt is the reverse complement of
!5'-ggtgtactga-
!|TCT|AGA|gac|aac|tct|aag|aat|act|ctc|tac|ttg|cag|atg|-
!|aac|agC|TTA|AGg|gct|gag|gac|aCT|GCA|Gtc|tac|tat -3' (SEQ ID NO: 638)
(H43.XAPCR) 5'-ggtgtagtga |TCT|AGA|gac|aac-3' (SEQ ID NO: 163)
!XbaI and AflII sites in bridges are bunged
(H43.ABr1) 5'-ggtgtagtga-
|aac|agC|TTt|AGg|gct|gag|gac|aCT|GCA|Gtc|tac|tat tgt gcg aga-3' (SEQ ID NO: 164)
(H43.ABr2) 5'-ggtgtagtga-
|aac|agC|TTt|AGg|gct|gag|gac|aCT|GCA|Gtc|tac|tat tgt gcg aaa-3' (SEQ ID NO: 165)
(H43.AExt) 5'-ATAgTAgAcTgcAgTgTccTcAgcccTTAAgcTgTTTcAcTAcAcc-3' (SEQ ID NO: 166)
!(H43.AExt) is the reverse complement of 5'-ggtgtagtga-
!|aac|agC|TTA|AGg|gct|gag|gac|aCT|GCA|Gtc|tac|tat -3' (SEQ ID NO: 167)
(H43.APCR) 5'-ggtgtagtga |aac|agC|TTA|AGg|gct|g-3' (SEQ ID NO: 168)

TABLE 5

Analysis of frequency of matching REdaptors in actual V genes

A: HpyCH4V in HC at bases 35-56

| Id | Ntot | \multicolumn{11}{c}{Number of mismatches} | Number Cut | Id | Probe |
|----|------|---|---|---|---|---|---|---|---|---|---|---|------|----|-------|
|    |      | 0 | 1 | 2 | 3 | 4 | 5 | 6 | 7 | 8 | 9 | 10 |  |  |  |
| 1 | 510 | 5 | 11 | 274 | 92 | 61 | 25 | 22 | 11 | 1 | 3 | 5 | 443 | 6-1 | agttctcccTG CAgctgaactc |
| 2 | 192 | 54 | 42 | 32 | 24 | 15 | 2 | 3 | 10 | 3 | 1 | 6 | 167 | 3-11 | cactgtatcTG CAaatgaacag |
| 3 | 58 | 19 | 7 | 17 | 6 | 5 | 1 | 0 | 1 | 0 | 2 | 0 | 54 | 3-09 | ccctgtatcTG CAaatgaacag |
| 4 | 267 | 42 | 33 | 9 | 8 | 8 | 82 | 43 | 22 | 8 | 11 | 1 | 100 | 5-51 | ccgcctaccTG CAgtggagcag |
| 5 | 250 | 111 | 59 | 41 | 24 | 7 | 5 | 1 | 0 | 0 | 2 | 0 | 242 | 3-15 | cgctgtatcTG CAaatgaacag |
| 6 | 7 | 0 | 2 | 0 | 1 | 0 | 0 | 0 | 0 | 0 | 4 | 0 | 3 | 7-4.1 | cggcatatcTG CAgatctgcag |
| 7 | 7 | 0 | 2 | 2 | 0 | 0 | 2 | 1 | 0 | 0 | 0 | 0 | 4 | 3-73 | cggcgtatcTG CAaatgaacag |
| 8 | 26 | 10 | 4 | 1 | 3 | 1 | 2 | 1 | 3 | 1 | 0 | 0 | 19 | 5-a | ctgcctaccTG CAgtggagcag |
| 9 | 21 | 8 | 2 | 3 | 1 | 6 | 1 | 0 | 0 | 0 | 0 | 0 | 20 | 3-49 | tcgcctatcTG CAaatgaacag |
|  | 1338 | 249 | 162 | 379 | 149 | 103 | 120 | 71 | 47 | 13 | 23 | 12 | 1052 |  | (SEQ ID NOS 169-177 respectively in order of appearance) |
|  |  | 249 | 411 | 790 | 939 | 1042 | 1162 | 1233 | 1280 | 1293 | 1316 | 1338 |  |  |  |

| Id | Probe | dotted probe |
|----|-------|--------------|
| 6-1 | agttctcccTGCAgctgaactc | agttctcccTGCAgctgaactc |
| 3-11 | cactgtatcTGCAaatgaacag | cac.g.at.....aa.....ag |
| 3-09 | ccctgtatcTGCAaatgaacag | ccc.g.at.....aa.....ag |
| 5-51 | ccgcctaccTGCAgtggagcag | ccgc...a........tg...g.ag |
| 3-15 | cgctgtatcTGCAaatgaacag | c.c.g.at.....aa.....ag |
| 7-4.1 | cggcatatcTGCAgatctgcag | c.gca.at......a.ctg..ag |
| 3-73 | cggcgtatcTGCAaatgaacag | c.gcg.at.....aa.....ag |
| 5-a | ctgcctaccTGCAgtggagcag | ctgc...a........tg...g.ag |
| 3-49 | tcgcctatcTGCAaatgaacag | tcgc..at.....aa.....ag |

(SEQ ID NOS 169-177, respectively in order of appearance)

Seqs with the expected RE site only....... 1004
(Counts only cases with 4 or fewer mismatches)
Seqs with only an unexpected site......... 0

TABLE 5-continued

Analysis of frequency of matching REdaptors in actual V genes

Seqs with both expected and unexpected                48
(Counts only cases with 4 or fewer mismatches)
Seqs with no sites........................             0

B: BlpI in HC

| Id | Ntot | 0 | 1 | 2 | 3 | 4 | 5 | 6 | 7 | 8 | NCut | Name | |
|----|------|---|---|---|---|---|---|---|---|---|------|------|---|
| 1 | 133 | 73 | 16 | 11 | 13 | 6 | 9 | 1 | 4 | 0 | 119 | 1-58 | acatggaGCTG AGCagcctgag |
| 2 | 14 | 11 | 1 | 0 | 0 | 0 | 0 | 1 | 0 | 1 | 12 | 1-02 | acatggagctg agcaggctgag |
| 3 | 34 | 17 | 8 | 2 | 6 | 1 | 0 | 0 | 0 | 0 | 0 | 1-18 | acatggagctg aggagcctgag |
| 4 | 120 | 50 | 32 | 16 | 10 | 9 | 1 | 1 | 1 | 0 | 2 | 5-51 | acctgcagtgg agcagcctgaa |
| 5 | 55 | 13 | 11 | 10 | 17 | 3 | 1 | 0 | 0 | 0 | 0 | 3-15 | atctgcaaatg aacagcctgaa |
| 6 | 340 | 186 | 88 | 41 | 15 | 6 | 3 | 0 | 1 | 0 | 0 | 3303 | atctgcaaatg aacagcctgag |
| 7 | 82 | 25 | 16 | 25 | 12 | 1 | 3 | 0 | 0 | 0 | 0 | 3-20 | atctgcaaatg aacagtctgag |
| 8 | 3 | 0 | 2 | 0 | 1 | 0 | 0 | 0 | 0 | 0 | 0 | 74.1 | atctgcagatc tgcagcctaaa |
| 9 | 23 | 18 | 2 | 2 | 1 | 0 | 0 | 0 | 0 | 0 | 0 | 3-66 | atcttcaaatg aacagcctgag |
| 10 | 2 | 1 | 0 | 1 | 0 | 0 | 0 | 0 | 0 | 0 | 0 | 3-64 | atcttcaaatg ggcagcctgag |
| 11 | 486 | 249 | 78 | 81 | 38 | 21 | 10 | 4 | 4 | 1 | 467 | 4301 | ccctgaagctg agctctgtgac |
| 12 | 16 | 6 | 3 | 1 | 0 | 1 | 1 | 3 | 1 | 0 | 1 | 6-1 | ccctgcagctg aactctgtgac |
| 13 | 28 | 15 | 8 | 2 | 2 | 1 | 0 | 0 | 0 | 0 | 0 | 2-70 | tccttacaatg accaacatgga |
| 14 | 2 | 0 | 2 | 0 | 0 | 0 | 0 | 0 | 0 | 0 | 0 | 2-26 | tccttaccatg accaacatgga |
|  |  |  |  |  |  |  |  |  |  |  | 601 | | (SEQ ID NOS 178-191), respectively in order of appearance) |

| Name | Full sequence | Dot mode |
|------|---------------|----------|
| 1-58 | acatggaGCTGAGCagcctgag | acatggaGCTGAGCagcctgag |
| 1-02 | acatggagctgagcaggctgag | ................g..... |
| 1-18 | acatggagctgaggagcctgag | ..............g........ |
| 5-51 | acctgcagtggagcagcctgaa | ..c..c..tg...........a |
| 3-15 | atctgcaaatgaacagcctgaa | .tc..c..aa..........a |
| 3-30.3 | atctgcaaatgaacagcctgag | .tc..c..aa....a........ |
| 3-20 | atctgcaaatgaacagtctgag | .tc..c..aa....a...t..... |
| 7-4.1 | atctgcagatctgcagcctaaa | .tc..c..a.ct.......a.a |
| 3-66 | atcttcaaatgaacagcctgag | .tc.tc..aa..a.......... |
| 3-64 | atcttcaaatgggcagcctgag | .tc.tc.aa..g.......... |
| 4-30.1 | ccctgaagctgagctctgtgac | c.c..a........tctg...c |
| 6-1 | ccctgcagctgaactctgtgac | c.c..c......a.tctg...c |
| 2-70 | tccttaccatgaccaacatgga | t.c.tacca...c..a.a..ga |
| 2-26 | tccttaccatgaccaacatgga | t.c.tacca...c..a.a..ga |

(SEQ ID NOS 178-191, respectively in order of appearance)

Seqs with the expected RE site only....... 597 (counting sequences with 4 or fewer mismatches)
Seqs with only an unexpected site.........   2
Seqs with both expected and unexpected....   2
Seqs with no sites........................ 686

C: HpyCH4III, Bat4CI, or TaaI in HC

In scoring whether the RE site of interest is present, only one that have 4 or fewer mismatches are counted.
Number of sequences.......... 1617

| Id | Ntot | 0 | 1 | 2 | 3 | 4 | 5 | 6 | 7 | 8 | Ncut | acngt | acngt |
|----|------|---|---|---|---|---|---|---|---|---|------|-------|-------|
| 1 | 244 | 78 | 92 | 43 | 18 | 10 | 1 | 2 | 0 | 0 | 241 | 102#1,1 | ccgtgtattAC TGTgcgagaga | ccgtgtattactgtgcgagaga |
| 2 | 457 | 69 | 150 | 115 | 66 | 34 | 11 | 8 | 3 | 1 | 434 | 103#2,3 | ctgtgtattac tgtgcgagaga | .t.................... |
| 3 | 173 | 52 | 45 | 36 | 22 | 14 | 3 | 0 | 0 | 1 | 169 | 108#3 | ccgtgtattac tgtgcgagagg | ....................g |

TABLE 5-continued

Analysis of frequency of matching REdaptors in actual V genes

| | | | | | | | | | | | | | |
|---|---|---|---|---|---|---|---|---|---|---|---|---|---|
| 4 | 16 | 0 | 3 | 2 | 2 | 1 | 6 0 | 1 1 | 8 | 124#5,1 | ccgtgtattac tgtgcaacaga | ................a.c... |
| 5 | 4 | 0 | 0 | 1 | 0 | 1 | 1 0 | 1 0 | 2 | 145#6 | ccatgtattac tgtgcaagata | ...a............a...t. |
| 6 | 15 | 1 | 0 | 1 | 0 | 6 | 4 1 | 1 1 | 8 | 158#8 | ccgtgtattac tgtgcggcaga | ................gc... |
| 7 | 23 | 4 | 8 | 5 | 2 | 2 | 1 1 | 0 0 | 21 | 205#12 | ccacatattac tgtgcacacag | ...aca............acacag |
| 8 | 9 | 1 | 1 | 1 | 0 | 3 | 2 1 | 0 0 | 6 | 226#13 | ccacatattac tgtgcacggat | ...aca............ac.gat |
| 9 | 7 | 1 | 3 | 1 | 1 | 0 | 0 1 | 0 0 | 6 | 270#14 | ccacgtattac tgtgcacggat | ...ac.............ac.gat |
| 10 | 23 | 7 | 3 | 5 | 5 | 2 | 1 0 | 0 0 | 22 | 309#16, | ccttgtattac tgtgcaaaaga | ...t.............a.a... |
| 11 | 35 | 5 | 10 | 7 | 6 | 3 | 3 0 | 1 0 | 31 | 313#18, | ctgtgtattac tgtgcaagaga | .t..............a...... |
| 12 | 18 | 2 | 3 | 2 | 2 | 6 | 1 0 | 2 0 | 15 | 315#19 | ccgtgtattac tgtaccacaga | ..............a.c.c... |
| 13 | 3 | 1 | 2 | 0 | 0 | 0 | 0 0 | 0 0 | 3 | 320#20 | ccttgtatcac tgtgcgagaga | ..t......c........... |
| 14 | 117 | 29 | 23 | 28 | 22 | 8 | 4 2 | 1 0 | 110 | 323#22 | ccgtatattac tgtgcgaaaga | .....a.............a... |
| 15 | 75 | 21 | 25 | 13 | 9 | 1 | 4 2 | 0 0 | 69 | 330#23, | ctgtgtattac tgtgcgaaaga | .t.................a... |
| 16 | 14 | 2 | 2 | 2 | 3 | 0 | 3 1 | 1 0 | 9 | 349#29 | ccgtgtattac tgtactagaga | ..............a.t..... |
| 17 | 2 | 0 | 0 | 1 | 0 | 0 | 1 0 | 0 0 | 1 | 372#33 | ccgtgtattac tgtgctagaga | ................t..... |
| 18 | 1 | 0 | 0 | 1 | 0 | 0 | 0 0 | 0 0 | 1 | 373#34 | ccgtgtattac tgtactagaca | ..............a.t...c. |
| 19 | 2 | 0 | 0 | 0 | 0 | 0 | 0 0 | 0 2 | 0 | 3d#36 | ctgtgtattac tgtaagaaaga | .t............aa..a... |
| 20 | 34 | 4 | 9 | 9 | 4 | 5 | 3 0 | 0 0 | 31 | 428#38 | ccgtgtattac tgtgcgagaaa | ....................a. |
| 21 | 17 | 5 | 4 | 2 | 2 | 3 | 1 0 | 0 0 | 16 | 4302#40 | ccgtgtattac tgtgccagaga | ..................c..... |
| 22 | 75 | 15 | 17 | 24 | 7 | 10 | 1 1 | 0 0 | 73 | 439#44 | ctgtgtattac tgtgcgagaca | .t.................c. |
| 23 | 40 | 14 | 15 | 4 | 5 | 1 | 0 1 | 0 0 | 39 | 551#48 | ccatgtattac tgtgcgagaca | ...a...............c. |
| 24 | 213 | 26 | 56 | 60 | 42 | 20 | 7 2 | 0 0 | 204 | 5a#49 | ccatgtattac tgtgcgagaAA | ...a................AA |

| Group | 337 | 471 | 363 | 218 | 130 | 58 | 23 | 11 | 6 | (SEQ ID NOS 192-215, |
| Cumulative | 337 | 806 | 1171 | 1389 | 1519 | 1577 | 1600 | 1611 | 1617 | respectively in order of appearance) |

Seqs with the expected RE site only.......1511
Seqs with only unexpected site............ 0
Seqs with both expected and unexpected.... 8
Seqs with no sites........................ 0

Table 5D

Analysis repeated using only 8 best REdaptors

| Id | Ntot | 0 | 1 | 2 | 3 | 4 | 5 | 6 | 7 | 8+ | | | |
|---|---|---|---|---|---|---|---|---|---|---|---|---|---|
| 1 | 301 | 78 | 101 | 54 | 32 | 16 | 9 | 10 | 1 | 0 | 281 | 102#1 | ccgtgtattac tgtgcgagaga (SEQ ID NO: 267) |
| 2 | 493 | 69 | 155 | 125 | 73 | 37 | 14 | 11 | 3 | 6 | 459 | 103#2 | ctgtgtattac tgtgcgagaga (SEQ ID NO: 268) |
| 3 | 189 | 52 | 45 | 38 | 23 | 18 | 5 | 4 | 1 | 3 | 176 | 108#3 | ccgtgtattac tgtgcgagagg (SEQ ID NO: 269) |
| 4 | 127 | 29 | 23 | 26 | 24 | 10 | 6 | 5 | 2 | 0 | 114 | 323#22 | ccgtatattac tgtgcgaaaga (SEQ ID NO: 270) |

TABLE 5-continued

Analysis of frequency of matching REdaptors in actual V genes

| | | | | | | | | | | | | | |
|---|---|---|---|---|---|---|---|---|---|---|---|---|---|
| 5 | 78 | 21 | 25 | 14 | 11 | 1 | 4 | 2 | 0 | 0 | 72 | 330#23 | ctgtgtattac tgtgcgaaaga (SEQ ID NO: 639) |
| 6 | 79 | 15 | 17 | 25 | 8 | 11 | 1 | 2 | 0 | 0 | 76 | 439#44 | ctgtgtattac tgtgcgagaca (SEQ ID NO: 272) |
| 7 | 43 | 14 | 15 | 5 | 5 | 3 | 0 | 1 | 0 | 0 | 42 | 551#48 | ccatgtattac tgtgcgagaca (SEQ ID NO: 273) |
| 8 | 307 | 26 | 63 | 72 | 51 | 38 | 24 | 14 | 13 | 6 | 250 | 5a#49 | ccatgtattac tgtgcgaga (residues 1-20 of SEQ ID NO: 274) |

| | | | |
|---|---|---|---|
| 1 | 102#1 | ccgtgtattactgtgcgagaga | ccgtgtattactgtgcgagaga |
| 2 | 103#2 | ctgtgtattactgtgcgagaga | .t..................... |
| 3 | 108#3 | ccgtgtattactgtgcgagagg | ......................g |
| 4 | 323#22 | ccgtatattactgtgcgaaaga | ....a............a... |
| 5 | 330#23 | ctgtgtattactgtgcgaaaga | .t...............a... |
| 6 | 438#44 | ctgtgtattactgtgcgagaca | .t...............c. |
| 7 | 551#48 | ccatgtattactgtgcgagaca | ...a.............c. |
| 8 | 5a#49 | ccatgtattactgtgcgagaAA | ...a..............AA |

(SEQ ID NOS 267-274, respectively in order of appearance)

Seqs with the expected RE site only.......1463/1617
Seqs with only an unexpected site.........  0
Seqs with both expected and unexpected....  7
Seqs with no sites........................  0

TABLE 6

Human HC GLG FR1 Sequences
VH Exon - Nucleotide sequence alignment

VH1

1-02   CAG GTG CAG CTG GTG CAG TCT GGG GCT GAG GTG AAG AAG CCT GGG GCC TCA GTG AAG
       GTC TCC TGC AAG GCT TCT GGA TAC ACC TTC ACC (SEQ ID NO: 216)

1-03   cag gtC cag ctT gtg cag tct ggg gct gag gtg aag aag cct ggg gcc tca gtg aag
       gtT tcc tgc aag gct tct gga tac acc ctc acT (SEQ ID NO: 217)

1-08   cag gtg cag ctg gtg cag tct ggg gct gag gtg aag aag cct ggg gcc tca gtg aag
       gtc tcc tgc aag gct tct gga tac acc ctc acc (SEQ ID NO: 218)

1-18   cag gtT cag ctg gtg cag tct ggA gct gag gtg aag aag cct ggg gcc tca gtg aag
       gtc tcc tgc aag gct tct ggT tac acc ttT acc (SEQ ID NO: 219)

1-24   cag gtC cag ctg gtA cag tct ggg gct gag gtg aag aag cct ggg gcc tca gtg aag
       gtc tcc tgc aag gTt tcC gga tac acc Ctc acT (SEQ ID NO: 220)

1-45   cag Atg cag ctg gtg cag tct ggg gct gag gtg aag aag Act ggg Tcc tca gtg aag
       gtT tcc tgc aag gct tcC gga tac acc ttc acc (SEQ ID NO: 221)

1-46   cag gtg cag ctg gtg cag tct ggg gct gag gtg aag aag cct ggg gcc tca gtg aag
       gtT tcc tgc aag gcA tct gga tac acc ttc acc (SEQ ID NO: 222)

1-58   caA Atg cag ctg gtg cag tct ggg Cct gag gtg aag aag cct ggg Acc tca gtg aag
       gtc tcc tgc aag gct tct gga tTc acc ttT acT (SEQ ID NO: 223)

1-69   cag gtg cag ctg gtg cag tct ggg gct cag gtg aag aag cct ggg Tcc tcG gtg aag
       gtc tcc tgc aag gct tct gga GGc acc ttc aGc (SEQ ID NO: 224)

1-e    cag gtg cag ctg gtg cag tct ggg gct gag gtg aag aag cct ggg Tcc tcG gtg aag
       gtc tcc tgc aag gct tct gga GGc acc ttc aGc (SEQ ID NO: 225)

1-f    Gag gtC cag ctg gtA cag tct ggg gct gag gtg aag aag cct ggg gcT Aca gtg aaA
       Atc tcc tgc aag gTt tct gga tac acc ttc acc (SEQ ID NO: 226)

TABLE 6-continued

Human HC GLG FR1 Sequences
VH Exon - Nucleotide sequence alignment

VH2

2-05    CAG ATC ACC TTG AAG GAG TCT GGT CCT ACG CTG GTG AAA CCC ACA CAG ACC CTC ACG
        CTG ACC TGC ACC TTC TCT GGG TTC TCA CTC AGC (SEQ ID NO: 227)

2-26    cag Gtc acc ttg aag gag tct ggt cct GTg ctg gtg aaa ccc aca Gag acc ctc acg
        ctg acc tgc acc Gtc tct ggg ttc tca ctc agc (SEQ ID NO: 228)

2-70    cag Gtc acc ttg aag gag tct ggt cct Gcg ctg gtg aaa ccc aca cag acc ctc acA
        ctg acc tgc acc ttc tct ggg ttc tca ctc agc (SEQ ID NO: 229)

VH3

3-07    GAG GTG CAG CTG GTG GAG TCT GGG GGA GGC TTG GTC CAG CCT GGG GGG TCC CTG AGA
        CTC TCC TGT GCA GCC TCT GGA TTC ACC TTT AGT (SEQ ID NO: 230)

3-09    gaA gtg cag ctg gtg gag tct ggg gga ggc ttg gtA cag cct ggC Agg tcc ctg aga
        ctc tcc tgt gca gcc tct gga ttc acc ttt GAt (SEQ ID NO: 231)

3-11    Cag gtg cag ctg gtg gag tct ggg gga ggc ttg gtc Aag cct ggA ggg tcc ctg aga
        ctc tcc tgt gca gcc tct gga ttc acc ttC agt (SEQ ID NO: 232)

3-13    gag gtg cag ctg gtg gag tct ggg gga ggc ttg gtA cag cct ggg ggg tcc ctg aga
        ctc tcc tgt gca gcc tct gga ttc acc ttC agt (SEQ ID NO: 233)

3-15    gag gtg cag ctg gtg gag tct ggg gga ggc ttg gtA Aag cct ggg ggg tcc ctT aga
        ctc tcc tgt gca gcc tct gga ttc acT ttC agt (SEQ ID NO: 234)

3-20    gag gtg cag ctg gtg gag tct ggg gga ggT Gtg gtA cGg cct ggg ggg tcc ctg aga
        ctc ccc tgt gca gcc tct gga ttc acc ttt GAt (SEQ ID NO: 235)

3-21    gag gtg cag ctg gtg gag tct ggg gga ggc Ctg gtc Aag cct ggg ggg tcc ctg aga
        ctc tcc tgt gca gcc tct gga ttc acc ttc agt (SEQ ID NO: 236)

3-23    gag gtg cag ctg Ttg gag tct ggg gga ggc ttg gtA cag cct ggg ggg tcc ctg aga
        ctc tcc tgt gca gcc tct gga ttc acc ttt agC (SEQ ID NO: 237)

3-30    Cag gtg cag ctg gtg gag tct ggg gga ggc Gtg gtc cag cct ggg Agg tcc ctg aga
        ctc tcc tgt gca gcc tct gga ttc acc ttC agt (SEQ ID NO: 238)

3-30.3  Cag gtg cag ctg gtg gag tct ggg gga ggc Gtg gtc cag cct ggg Agg tcc ctg aga
        ctc tcc tgt gca gcc tct gga ttc acc ttC agt (SEQ ID NO: 239)

3-30.5  Cag gtg cag ctg gtg gag tct ggg gga ggc Gtg gtc cag cct ggg Agg tcc ctg aga
        ctc tcc tgt gca gcc tct gga ttc acc ttC agt (SEQ ID NO: 240)

3-33    Cag gtg cag ctg gtg gag tct ggg gga ggc Gtg gtc cag cct ggg Agg tcc ctg aga
        ctc tcc tgt gca gcG tct gga ttc acc ttC agt (SEQ ID NO: 241)

3-43    gaA gtg cag ctg gtg gag tct ggg gga gTc Gtg gtA cag cct ggg ggg tcc ctg aga
        ctc tcc tgt gca gcc tct gga ttc acc ttt GAt (SEQ ID NO: 242)

3-48    gag gtg cag ctg gtg gag tct ggg gga ggc ttg gtA cag cct ggg ggg tcc ctg aga
        ctc tcc tgt gca gcc tct gga ttc acc ttC agt (SEQ ID NO: 243)

3-49    gag gtg cag ctg gtg gag tct ggg gga ggc ttg gtA cag ccA ggg Cgg tcc ctg aga
        ctc tcc tgt Aca gcT tct gga ttc acc ttt Ggt (SEQ ID NO: 244)

3-53    gag gtg cag ctg gtg gag Act ggA gga ggc ttg Atc cag cct ggg ggg tcc ctg aga
        ctc tcc tgt gca gcc tct ggG ttc acc GtC agt (SEQ ID NO: 245)

3-64    gag gtg cag ctg gtg gag tct ggg gga ggc ttg gtc cag cct ggg ggg tcc ctg aga
        ctc tcc tgt gca gcc tct gga ttc acc ttC agt (SEQ ID NO: 246)

3-66    gag gtg cag ctg gtg gag tct ggg gga ggc ttg gtc cag cct ggg ggg tcc ctg aga
        ctc tcc tgt gca gcc tct gga ttc acc GtC agt (SEQ ID NO: 247)

3-72    gag gtg cag ctg gtg gag tct ggg gga ggc ttg gtc cag cct ggA ggg tcc ctg aga
        ctc tcc tgt gca gcc tct gga ttc acc ttC act (SEQ ID NO: 248)

3-73    gag gtg cag ctg gtg gag tct ggg gga ggc ttg gtc cag cct ggg ggg tcc ctg aAa
        ctc tcc tgt gca gcc tct ggG ttc acc ttC agt (SEQ ID NO: 249)

3-74    gag gtg cag ctg gtg gag tcC ggg gga ggc ttA gtT cag cct ggg ggg tcc ctg aga
        ctc tcc tgt gca gcc tct gga ttc acc ttC agt (SEQ ID NO: 250)

TABLE 6-continued

Human HC GLG FR1 Sequences
VH Exon - Nucleotide sequence alignment

```
3-d     gag gtg cag ctg gtg gag tct Cgg gga gTc ttg gtA cag cct ggg ggg tcc ctg aga
        ctc tcc tgt gca gcc tct gga ttc acc GtC agt (SEQ ID NO: 251)
```

VH4

```
4-04    CAG GTG CAG CTG CAG GAG TCG GGC CCA GGA CTG GTG AAG CCT TCG GGG ACC CTG TCC
        CTC ACC TGC GCT GTC TCT GGT GGC TCC ATC AGC (SEQ ID NO: 252)

4-28    cag gtg cag ctg cag gag tcg ggc cca gga ctg gtg aag cct tcg gAC acc ctg tcc
        ctc acc tgc gct gtc tct ggt TAc tcc atc agc (SEQ ID NO: 253)

4-30.1  cag gtg cag ctg cag gag tcg ggc cca gga ctg gtg aag cct tcA CAg acc ctg tcc
        ctc acc tgc Act gtc tct ggt ggc tcc atc agc (SEQ ID NO: 254)

4-30.2  cag Ctg cag ctg cag gag tcC ggc Tca gga ctg gtg aag cct tcA CAg acc ctg tcc
        ctc Acc tgc gct gtc tct ggt ggc tcc atc agc (SEQ ID NO: 255)

4-30.4  cag gtg cag ctg cag gag tcg ggc cca gga ctg gtg aag cct tcA CAg acc ctg tcc
        ctc acc tgc Act gtc tct ggt ggc tcc atc agc (SEQ ID NO: 256)

4-31    cag gtg cag ctg cag gag tcg ggc cca gga ctg gtg aag cct tcA CAg acc ctg tcc
        ctc acc tgc Act gtc tct ggt ggc tcc atc agc (SEQ ID NO: 257)

4-34    cag gtg cag ctA cag Cag tGg ggc Gca gga ctg Ttg aag cct tcg gAg acc ctg tcc
        ctc acc tgc gct gtc tAt ggt ggG tcc Ttc agT (SEQ ID NO: 258)

4-39    cag Ctg cag ctg gtc tcg ggc cca gga ctg gtg aag cct tcg gAg acc ctg tcc
        ctc acc tgc Act gtc tct ggt ggc tcc atc agc (SEQ ID NO: 259)

4-59    cag gtg cag ctg cag gag tcg ggc cca gga ctg gtg aag cct tcg gAg acc ctg tcc
        ctc acc tgc Act gtc tct ggt ggc tcc atc agT (SEQ ID NO: 260)

4-61    cag gtg cag ctg cag gag tcg ggc cca gga ctg gtg aag cct tcg gAg acc ctg tcc
        ctc acc tgc Act gtc tct ggt ggc tcc Gtc agc (SEQ ID NO: 261)

4-b     cag gtg cag ctg cag gag tcg ggc cca gga ctg gtg aag cct tcg gAg acc ctg tcc
        ctc acc tgc gct gtc tct ggt TAc tcc atc agc (SEQ ID NO: 262)
```

VH5

```
5-51    GAG GTG CAG CTG GTG CAG TCT GGA GCA GAG GTG AAA AAG CCC GGG GAG TCT CTG AAG
        ATC TCC TGT AAG GGT TCT GGA TAC AGC TTT ACC (SEQ ID NO: 263)

5-a     gaA gtg cag ctg gtg cag tct gga gca gag gtg aaa aag ccc ggg gag tct ctg aGg
        atc tcc tgt aag ggt tct gga tac agc ttt acc (SEQ ID NO: 264)
```

VH6

```
6-1     CAG GTA CAG CTG CAG CAG TCA GGT CCA GGA CTG GTG AAG CCC TCG CAG ACC CTC TCA
        CTC ACC TGT GCC ATC TCC GGG GAC AGT GTC TCT (SEQ ID NO: 265)
```

VH7

```
7-4.1   CAG GTG CAG CTG GTG CAA TCT GGG TCT GAG TTG AAG AAG CCT GGG GCC TCA GTG AAG
        GTT TCC TGC AAG GCT TCT GGA TAC ACC TTC ACT (SEQ ID NO: 266)
```

TABLE 7

RERS sites in Human HC GLG FR1s where there are at least 20 GLGs cut

| BsgI | | GTGCAG | 71 (cuts 16/14 bases to right) |  |  |
|---|---|---|---|---|---|
| 1:4 | 1:13 | 2:13 | 3:4 | 3:13 | 4:13 |
| 6:13 | 7:4 | 7:13 | 8:13 | 9:4 | 9:13 |
| 10:4 | 10:13 | 15:4 | 15:65 | 16:4 | 16:65 |
| 17:4 | 17:65 | 18:4 | 18:65 | 19:4 | 19:65 |
| 20:4 | 20:65 | 21:4 | 21:65 | 22:4 | 22:65 |
| 23:65 | 23:65 | 24:4 | 24:65 | 25:4 | 25:65 |
| 26:4 | 26:65 | 27:4 | 27:65 | 28:4 | 28:65 |
| 29:4 | 30:4 | 30:65 | 31:4 | 31:65 | 32:4 |
| 32:65 | 33:4 | 33:65 | 34:4 | 34:65 | 35:4 |
| 35:65 | 36:4 | 36:65 | 37:4 | 38:4 | 39:4 |
| 41:4 | 42:4 | 43:4 | 45:4 | 46:4 | 47:4 |
| 48:4 | 48:13 | 49:4 | 49:13 | 51:4 | |

RERS sites in Human HC GLG FR1s where there are at least 20 GLGs cut

| There are 39 hits at base# 4 | | | | | |
|---|---|---|---|---|---|
| There are 21 hits at base# 65 | | | | | |
| -"- | | ctgcac | 9 | | |
| 12:63 | 13:63 | 14:63 | 39:63 | 41:63 | 42:63 |
| 44:63 | 45:63 | 46:63 | | | |
| BbvI | | GCAGC | 65 | | |
| 1:6 | 3:6 | 6:6 | 7:6 | 8:6 | 9:6 |
| 10:6 | 15:6 | 15:67 | 16:6 | 16:67 | 17:6 |
| 17:67 | 18:6 | 18:67 | 19:6 | 19:67 | 20:6 |
| 20:67 | 21:6 | 21:67 | 22:6 | 22:67 | 23:6 |
| 23:67 | 24:6 | 24:67 | 25:6 | 25:67 | 26:6 |
| 26:67 | 27:6 | 27:67 | 28:6 | 28:67 | 29:6 |
| 30:6 | 30:67 | 31:6 | 31:67 | 32:6 | 32:67 |

TABLE 7-continued

RERS sites in Human HC GLG FR1s where there are at least 20 GLGs cut

| | | | | | |
|---|---|---|---|---|---|
| 33: 6 | 33: 67 | 34: 6 | 34: 67 | 35: 6 | 35: 67 |
| 36: 6 | 36: 67 | 37: 6 | 38: 6 | 39: 6 | 40: 6 |
| 41: 6 | 42: 6 | 43: 6 | 44: 6 | 45: 6 | 46: 6 |
| 47: 6 | 48: 6 | 49: 6 | 50: 12 | 51: 6 | |

There are 43 hits at base# 6 Bolded sites very near sites listed below
There are 21 hits at base# 67
-"-  gctgc  13

| | | | | | |
|---|---|---|---|---|---|
| 37: 9 | 38: 9 | 39: 9 | 40: 3 | 40: 9 | 41: 9 |
| 42: 9 | 44: 3 | 44: 9 | 45: 9 | 46: 9 | 47: 9 |
| 50: 9 | | | | | |

There are 11 hits at base# 9

BsoFI  GCngc  78

| | | | | | |
|---|---|---|---|---|---|
| 1: 6 | 3: 6 | 6: 6 | 7: 6 | 8: 6 | 9: 6 |
| 10: 6 | 15: 6 | 15: 67 | 16: 6 | 16: 67 | 17: 6 |
| 17: 67 | 18: 6 | 18: 67 | 19: 6 | 19: 67 | 20: 6 |
| 20: 67 | 21: 6 | 21: 67 | 22: 6 | 22: 67 | 23: 6 |
| 23: 67 | 24: 6 | 24: 67 | 25: 6 | 25: 67 | 26: 6 |
| 26: 67 | 27: 6 | 27: 67 | 28: 6 | 28: 67 | 29: 6 |
| 30: 6 | 30: 67 | 31: 6 | 31: 67 | 32: 6 | 32: 67 |
| 33: 6 | 33: 67 | 34: 6 | 34: 67 | 35: 6 | 35: 67 |
| 36: 6 | 36: 67 | <u>37: 6</u> | <u>37: 9</u> | <u>38: 6</u> | <u>38: 9</u> |
| 39: 6 | 39: 9 | <u>40: 3</u> | <u>40: 6</u> | <u>40: 9</u> | 41: 6 |
| 41: 9 | 42: 6 | 42: 9 | 43: 6 | <u>44: 3</u> | <u>44: 6</u> |
| <u>44: 9</u> | <u>45: 6</u> | <u>45: 9</u> | <u>46: 6</u> | <u>46: 9</u> | <u>47: 6</u> |
| <u>47: 9</u> | 48: 6 | 49: 6 | 50: 9 | 50: 12 | 51: 6 |

There are 43 hits at base# 6 These often occur together.
There are 11 hits at base# 9
There are 2 hits at base# 3
There are 21 hits at base# 67

TseI  Gcwgc  78

| | | | | | |
|---|---|---|---|---|---|
| 1: 6 | 3: 6 | 6: 6 | 7: 6 | 8: 6 | 9: 6 |
| 10: 6 | 15: 6 | 15: 67 | 16: 6 | 16: 67 | 17: 6 |
| 17: 67 | 18: 6 | 18: 67 | 19: 6 | 19: 67 | 20: 6 |
| 20: 67 | 21: 6 | 21: 67 | 22: 6 | 22: 67 | 23: 6 |
| 23: 67 | 24: 6 | 24: 67 | 25: 6 | 25: 67 | 26: 6 |
| 26: 67 | 27: 6 | 27: 67 | 28: 6 | 28: 67 | 29: 6 |
| 30: 6 | 30: 67 | 31: 6 | 31: 67 | 32: 6 | 32: 67 |
| 33: 6 | 33: 67 | 34: 6 | 34: 67 | 35: 6 | 35: 67 |
| 36: 6 | 36: 67 | <u>37: 6</u> | 37: 9 | <u>38: 6</u> | 38: 9 |
| <u>39: 6</u> | 39: 9 | <u>40: 3</u> | <u>40: 6</u> | <u>40: 9</u> | <u>41: 6</u> |
| <u>41: 9</u> | <u>42: 6</u> | <u>42: 9</u> | 43: 6 | <u>44: 3</u> | <u>44: 6</u> |
| <u>44: 9</u> | <u>45: 6</u> | <u>45: 9</u> | <u>46: 6</u> | <u>46: 9</u> | <u>47: 6</u> |
| <u>47: 9</u> | 48: 6 | 49: 6 | <u>50: 9</u> | <u>50: 12</u> | 51: 6 |

There are 43 hits at base# 6 Often together.
There are 11 hits at base# 9
There are 2 hits at base# 3
There are 1 hits at base# 12
There are 21 hits at base# 67

MspAlI  CMGckg  48

| | | | | | |
|---|---|---|---|---|---|
| 1: 7 | 3: 7 | 4: 7 | 5: 7 | 6: 7 | 7: 7 |
| 8: 7 | 9: 7 | 10: 7 | 11: 7 | 15: 7 | 16: 7 |
| 17: 7 | 18: 7 | 19: 7 | 20: 7 | 21: 7 | 22: 7 |
| 23: 7 | 24: 7 | 25: 7 | 26: 7 | 27: 7 | 28: 7 |
| 29: 7 | 30: 7 | 31: 7 | 32: 7 | 33: 7 | 34: 7 |
| 35: 7 | 36: 7 | 37: 7 | 38: 7 | 39: 7 | <u>40: 1</u> |
| <u>40: 7</u> | 41: 7 | 42: 7 | <u>44: 1</u> | <u>44: 7</u> | 45: 7 |
| 46: 7 | 47: 7 | 48: 7 | 49: 7 | 50: 7 | 51: 7 |

There are 46 hits at base# 7

PvuII  CAGctg  48

| | | | | | |
|---|---|---|---|---|---|
| 1: 7 | 3: 7 | 4: 7 | 5: 7 | 6: 7 | 7: 7 |
| 8: 7 | 9: 7 | 10: 7 | 11: 7 | 15: 7 | 16: 7 |
| 17: 7 | 18: 7 | 19: 7 | 20: 7 | 21: 7 | 22: 7 |
| 23: 7 | 24: 7 | 25: 7 | 26: 7 | 27: 7 | 28: 7 |
| 29: 7 | 30: 7 | 31: 7 | 32: 7 | 33: 7 | 34: 7 |
| 35: 7 | 36: 7 | 37: 7 | 38: 7 | 39: 7 | <u>40: 1</u> |
| <u>40: 7</u> | 41: 7 | 42: 7 | <u>44: 1</u> | <u>44: 7</u> | 45: 7 |
| 46: 7 | 47: 7 | 48: 7 | 49: 7 | 50: 7 | 51: 7 |

There are 46 hits at base# 7
There are 2 hits at base# 1

AluI  AGct  54

| | | | | | |
|---|---|---|---|---|---|
| 1: 8 | 2: 8 | 3: 8 | 4: 8 | 4: 24 | 5: 8 |
| 6: 8 | 7: 8 | 8: 8 | 9: 8 | 10: 8 | 11: 8 |
| 15: 8 | 16: 8 | 17: 8 | 18: 8 | 19: 8 | 20: 8 |
| 21: 8 | 22: 8 | 23: 8 | 24: 8 | 25: 8 | 26: 8 |
| 27: 8 | 28: 8 | 29: 8 | 29: 69 | 30: 8 | 31: 8 |
| 32: 8 | 33: 8 | 34: 8 | 35: 8 | 36: 8 | 37: 8 |
| 38: 8 | 39: 8 | <u>40: 2</u> | <u>40: 8</u> | 41: 8 | 42: 8 |
| 43: 8 | <u>44: 2</u> | <u>44: 8</u> | 45: 8 | 46: 8 | 47: 8 |
| 48: 8 | 48: 82 | 49: 8 | 49: 82 | 50: 8 | 51: 8 |

There are 48 hits at base# 8
There are 2 hits at base# 2

DdeI  Ctnag  48

| | | | | | |
|---|---|---|---|---|---|
| 1: 26 | 1: 48 | 2: 26 | 2: 48 | 3: 26 | 3: 48 |
| 4: 26 | 4: 48 | 5: 26 | 5: 48 | 6: 26 | 6: 48 |
| 7: 26 | 7: 48 | 8: 26 | 8: 48 | 9: 26 | 10: 26 |
| 11: 26 | 12: 85 | 13: 85 | 14: 85 | 15: 52 | 16: 52 |
| 17: 52 | 18: 52 | 19: 52 | 20: 52 | 21: 52 | 22: 52 |
| 23: 52 | 24: 52 | 25: 52 | 26: 52 | 27: 52 | 28: 52 |
| 29: 52 | 30: 52 | 31: 52 | 32: 52 | 33: 52 | 35: 30 |
| 35: 52 | 36: 52 | 37: 52 | 40: 24 | 42: 52 | 51: 26 |
| 47: 52 | 48: 52 | 49: 52 | 51: 52 | | 51: 48 |

There are 22 hits at base# 52 52 and 48 never together.
There are 9 hits at base# 48
There are 12 hits at base# 26 26 and 24 never together.

HphI  tcacc  42

| | | | | | |
|---|---|---|---|---|---|
| 1: 86 | 3: 86 | 6: 86 | 7: 86 | 8: 80 | 11: 86 |
| 12: 5 | 13: 5 | 14: 5 | 15: 80 | 16: 80 | 17: 80 |
| 18: 80 | 20: 80 | 21: 80 | 22: 80 | 23: 80 | 24: 80 |
| 25: 80 | 26: 80 | 27: 80 | 28: 80 | 29: 80 | 30: 80 |
| 31: 80 | 32: 80 | 33: 80 | 34: 80 | 35: 80 | 36: 80 |
| 37: 59 | 38: 59 | 39: 59 | 40: 59 | 41: 59 | 42: 59 |
| 43: 59 | 44: 59 | 45: 59 | 46: 59 | 47: 59 | 50: 59 |

There are 22 hits at base# 80 80 and 86 never together.
There are 5 hits at base# 86
There are 12 hits at base# 59

BssKI  Nccngg  50

| | | | | | |
|---|---|---|---|---|---|
| 1: 39 | 2: 39 | 3: 39 | 4: 39 | 5: 39 | 7: 39 |
| 8: 39 | 9: 39 | 10: 39 | 11: 39 | 15: 39 | 16: 39 |
| 17: 39 | 18: 39 | 19: 39 | 20: 39 | 21: 29 | 21: 39 |
| 22: 39 | 23: 39 | 24: 39 | 25: 39 | 26: 39 | 27: 39 |
| 28: 39 | 29: 39 | 30: 39 | 31: 39 | 32: 39 | 33: 39 |
| 34: 39 | 35: 19 | 35: 39 | 36: 39 | 37: 24 | 38: 24 |
| 39: 24 | 41: 24 | 42: 24 | 44: 24 | 45: 24 | 46: 24 |
| 47: 24 | <u>48: 39</u> | <u>48: 40</u> | <u>49: 39</u> | <u>49: 40</u> | 50: 24 |
| 50: 73 | 51: 39 | | | | |

There are 35 hits at base# 39 39 and 40 together twice.
There are 2 hits at base# 40

BsaJI  Ccnngg  47

| | | | | | |
|---|---|---|---|---|---|
| 1: 40 | 2: 40 | 3: 40 | 4: 40 | 5: 40 | 7: 40 |
| 8: 40 | 9: 40 | 9: 47 | 10: 40 | 10: 47 | 11: 40 |
| 15: 40 | 18: 40 | 19: 40 | 20: 40 | 21: 40 | 22: 40 |
| 23: 40 | 24: 40 | 25: 40 | 26: 40 | 27: 40 | 28: 40 |
| 29: 40 | 30: 40 | 31: 40 | 32: 40 | 34: 40 | 35: 20 |
| 35: 40 | 36: 40 | 37: 24 | 38: 24 | 39: 24 | 41: 24 |
| 42: 24 | 44: 24 | 45: 24 | 46: 24 | 47: 24 | <u>48: 40</u> |
| <u>48: 41</u> | <u>49: 40</u> | <u>49: 41</u> | 50: 74 | 51: 40 | |

There are 32 hits at base# 40 40 and 41 together twice.
There are 2 hits at base# 41
There are 9 hits at base# 24
There are 2 hits at base# 47

BstNI  CCwgg  44
PspGI  ccwgg
ScrFI($M, HpaII)  CCwgg

| | | | | | |
|---|---|---|---|---|---|
| 1: 40 | 2: 40 | 3: 40 | 4: 40 | 5: 40 | 7: 40 |
| 8: 40 | 9: 40 | 10: 40 | 11: 40 | 15: 40 | 16: 40 |
| 17: 40 | 18: 40 | 19: 40 | 20: 40 | 21: 30 | 21: 40 |
| 22: 40 | 23: 40 | 24: 40 | 25: 40 | 26: 40 | 27: 40 |
| 28: 40 | 29: 40 | 30: 40 | 31: 40 | 32: 40 | 33: 40 |
| 34: 40 | 35: 40 | 36: 40 | 37: 25 | 38: 25 | 39: 25 |
| 41: 25 | 42: 25 | 44: 25 | 45: 25 | 46: 25 | 47: 25 |
| 50: 25 | 51: 40 | | | | |

There are 33 hits at base# 40

ScrFI  CCngg  50

| | | | | | |
|---|---|---|---|---|---|
| 1: 40 | 2: 40 | 3: 40 | 4: 40 | 5: 40 | 7: 40 |
| 8: 40 | 9: 40 | 10: 40 | 11: 40 | 15: 40 | 16: 40 |
| 17: 40 | 18: 40 | 19: 40 | 20: 40 | 21: 30 | 21: 40 |
| 22: 40 | 23: 40 | 24: 40 | 25: 40 | 26: 40 | 27: 40 |
| 28: 40 | 29: 40 | 30: 40 | 31: 40 | 32: 40 | 33: 40 |
| 34: 40 | 35: 20 | 35: 40 | 36: 40 | 37: 25 | 38: 25 |
| 39: 25 | 41: 25 | 42: 25 | 44: 25 | 45: 25 | 46: 25 |
| 47: 25 | 48: 40 | 48: 41 | 49: 40 | 49: 41 | 50: 25 |
| 50: 74 | 51: 40 | | | | |

TABLE 7-continued

RERS sites in Human HC GLG FR1s where there are at least 20 GLGs cut

There are 35 hits at base# 40
There are 2 hits at base# 41

EcoO109I  RGgnccy  34
| | | | | | |
|---|---|---|---|---|---|
| 1: 43 | 2: 43 | 3: 43 | 4: 43 | 5: 43 | 6: 43 |
| 7: 43 | 8: 43 | 9: 43 | 10: 43 | 15: 46 | 16: 46 |
| 17: 46 | 18: 46 | 19: 46 | 20: 46 | 21: 46 | 22: 46 |
| 23: 46 | 24: 46 | 25: 46 | 26: 46 | 27: 46 | 28: 46 |
| 30: 46 | 31: 46 | 32: 46 | 33: 46 | 34: 46 | 35: 46 |
| 36: 46 | 37: 46 | 43: 79 | 51: 43 | | |

There are 22 hits at base# 46 46 and 43 never together
There are 11 hits at base# 43

NlaIV  GGNncc  71
| | | | | | |
|---|---|---|---|---|---|
| 1: 43 | 2: 43 | 3: 43 | 4: 43 | 5: 43 | 6: 43 |
| 7: 43 | 8: 43 | 9: 43 | 9: 79 | 10: 43 | 10: 79 |
| _15: 46_ | _15: 47_ | 16: 47 | _17: 46_ | _17: 47_ | _18: 46_ |
| _18: 47_ | _19: 46_ | _19: 47_ | _20: 46_ | _20: 47_ | _21: 46_ |
| _21: 47_ | _22: 46_ | _22: 47_ | 23: 47 | 24: 47 | 25: 47 |
| 26: 47 | _27: 46_ | _27: 47_ | _28: 46_ | _28: 47_ | 29: 47 |
| _30: 46_ | _30: 47_ | _31: 46_ | _31: 47_ | _32: 46_ | _32: 47_ |
| _33: 46_ | _33: 47_ | _34: 46_ | _34: 47_ | _35: 46_ | _35: 47_ |
| _36: 46_ | _36: 47_ | 37: 21 | _37: 46_ | _37: 47_ | 37: 79 |
| 38: 21 | 39: 21 | 39: 79 | 40: 79 | 41: 21 | 41: 79 |
| 42: 21 | 42: 79 | 43: 79 | 44: 21 | 44: 79 | 45: 21 |
| 45: 79 | 46: 21 | 46: 79 | 47: 21 | 51: 43 | |

There are 23 hits at base# 47 46 & 47 often together
There are 17 hits at base# 46 There are 11 hits at base# 43

Sau96I  Ggncc  70
| | | | | | | |
|---|---|---|---|---|---|---|
| 1: 44 | 2: 3 | 2: 44 | 3: 44 | 4: 44 | 5: 3 | 5: 44 | 6: 44 |
| 7: 44 | 8: 22 | 8: 44 | 9: 44 | 10: 44 | 11: 3 | 12: 22 | 13: 22 |
| 14: 22 | 15: 33 | 15: 47 | 16: 47 | 17: 47 | 18: 47 | 19: 47 | 20: 47 |
| 21: 47 | 22: 47 | 23: 33 | 23: 47 | 24: 33 | 24: 47 | 25: 33 | 25: 47 |
| 26: 33 | 26: 47 | 27: 47 | 28: 47 | 29: 47 | 30: 47 | 31: 33 | 31: 47 |
| 32: 33 | 32: 47 | 33: 33 | 33: 47 | 34: 33 | 34: 47 | 35: 47 | 36: 47 |
| _37: 21_ | _37: 22_ | 37: 47 | _38: 21_ | _38: 22_ | 39: 21 | 39: 22 | 41: 21 |
| 41: 22 | 42: 21 | 42: 22 | 43: 80 | 44: 21 | 44: 22 | 45: 21 | 45: 22 |
| 46: 21 | 46: 22 | 47: 21 | 47: 22 | 50: 22 | 51: 44 | | |

There are 23 hits at base# 47 These do not occur together.
There are 11 hits at base# 44
There are 14 hits at base# 22 These do occur together.
There are 9 hits at base# 21
(SEQ ID NO: 13)

BsmAI  GTCTCNnnnn  22
| | | | | |
|---|---|---|---|---|
| 1: 58 | 3: 58 | 4: 58 | 5: 58 | 8: 58 | 9: 58 |
| 10: 58 | 13: 70 | 36: 18 | 37: 70 | 38: 70 | 39: 70 |
| 40: 70 | 41: 70 | 42: 70 | 44: 70 | 45: 70 | 46: 70 |
| 47: 70 | 48: 48 | 49: 48 | 50: 85 | | |

There are 11 hits at base# 70
(SEQ ID NO: 14)

-"-  Nnnnnngagac  27
| | | | | | |
|---|---|---|---|---|---|
| 13: 40 | 15: 48 | 16: 48 | 17: 48 | 18: 48 | 20: 48 |
| 21: 48 | 22: 48 | 23: 48 | 24: 48 | 25: 48 | 26: 48 |
| 27: 48 | 28: 48 | 29: 48 | 30: 10 | 30: 48 | 31: 48 |
| 32: 48 | 33: 48 | 35: 48 | 36: 48 | 43: 40 | 44: 40 |
| 45: 40 | 46: 40 | 47: 40 | | | |

There are 20 hits at base# 48

AvaII  Ggwcc  44
Sau96I($M.HaeIII)  Ggwcc  44
| | | | | | |
|---|---|---|---|---|---|
| 2: 3 | 5: 3 | 6: 44 | 8: 44 | 9: 44 | 10: 44 |
| 11: 3 | 12: 22 | 13: 22 | 14: 22 | 15: 33 | 15: 47 |
| 16: 47 | 17: 47 | 18: 47 | 19: 47 | 20: 47 | 21: 47 |
| 22: 47 | 23: 33 | 23: 47 | 24: 33 | 24: 47 | 25: 33 |
| 25: 47 | 26: 33 | 26: 47 | 27: 47 | 28: 47 | 29: 47 |
| 30: 47 | 31: 33 | 31: 47 | 32: 33 | 32: 47 | 33: 33 |
| 33: 47 | 34: 33 | 34: 47 | 35: 47 | 36: 47 | 37: 47 |
| 43: 80 | 50: 22 | | | | |

There are 23 hits at base# 47 44 & 47 never together
There are 4 hits at base# 44

PpuMI  RGgwccy  27
| | | | | |
|---|---|---|---|---|
| 6: 43 | 8: 43 | 9: 43 | 10: 43 | 15: 46 | 16: 46 |
| 17: 46 | 18: 46 | 19: 46 | 20: 46 | 21: 46 | 22: 46 |
| 23: 46 | 24: 46 | 25: 46 | 26: 46 | 27: 46 | 28: 46 |
| 30: 46 | 31: 46 | 32: 46 | 33: 46 | 34: 46 | 35: 46 |
| 36: 46 | 37: 46 | 43: 79 | | | |

There are 22 hits at base# 46 43 and 46 never occur together.
There are 4 hits at base# 43

BsmFI  GGGAC  3
| | | | | |
|---|---|---|---|---|
| 8: 43 | 37: 46 | 50: 77 | | | |

-"-  gtccc  33
| | | | | |
|---|---|---|---|---|
| 15: 48 | 16: 48 | 17: 48 | 1: 0 | 1: 0 | 20: 48 |
| 21: 48 | 22: 48 | 23: 48 | 24: 48 | 25: 48 | 26: 48 |
| 27: 48 | 28: 48 | 29: 48 | 30: 48 | 31: 48 | 32: 48 |
| 33: 48 | 34: 48 | 35: 48 | 36: 48 | 37: 54 | 38: 54 |
| 39: 54 | 40: 54 | 41: 54 | 42: 54 | 43: 54 | 44: 54 |
| 45: 54 | 46: 54 | 47: 54 | | | |

There are 20 hits at base# 48
There are 11 hits at base# 54

HinfI  Gantc  80
| | | | | | |
|---|---|---|---|---|---|
| 8: 77 | 12: 16 | 13: 16 | 14: 16 | 15: 16 | 15: 56 |
| 15: 77 | 16: 16 | 16: 56 | 16: 77 | 17: 16 | 17: 56 |
| 17: 77 | 18: 16 | 18: 56 | 18: 77 | 19: 16 | 19: 56 |
| 19: 77 | 20: 16 | 20: 56 | 20: 77 | 21: 16 | 21: 56 |
| 21: 77 | 22: 16 | 22: 56 | 22: 77 | 23: 16 | 23: 56 |
| 23: 77 | 24: 16 | 24: 56 | 24: 77 | 25: 16 | 25: 56 |
| 25: 77 | 26: 16 | 26: 56 | 26: 77 | 27: 16 | 27: 26 |
| 27: 56 | 27: 77 | 28: 16 | 28: 56 | 28: 77 | 29: 16 |
| 29: 56 | 29: 77 | 30: 56 | 31: 16 | 31: 56 | 31: 77 |
| 32: 16 | 32: 56 | 32: 77 | 33: 16 | 33: 56 | 33: 77 |
| 34: 16 | 35: 16 | 35: 56 | 35: 77 | 36: 16 | 36: 26 |
| 36: 56 | 36: 77 | 37: 16 | 38: 16 | 39: 16 | 40: 16 |
| 41: 16 | 42: 16 | 44: 16 | 45: 16 | 46: 16 | 47: 16 |
| 48: 46 | 49: 46 | | | | |

There are 34 hits at base# 16

TfiI  Gawtc  21
| | | | | | |
|---|---|---|---|---|---|
| 8: 77 | 15: 77 | 16: 77 | 17: 77 | 18: 77 | 19: 77 |
| 20: 77 | 21: 77 | 22: 77 | 23: 77 | 24: 77 | 25: 77 |
| 26: 77 | 27: 77 | 28: 77 | 29: 77 | 31: 77 | 32: 77 |
| 33: 77 | 35: 77 | 36: 77 | | | |

There are 21 hits at base# 77

MlyI  GAGTC  38
| | | | | | |
|---|---|---|---|---|---|
| 12: 16 | 13: 16 | 14: 16 | 15: 16 | 16: 16 | 17: 16 |
| 18: 16 | 19: 16 | 20: 16 | 21: 16 | 22: 16 | 23: 16 |
| 24: 16 | 25: 16 | 26: 16 | 27: 16 | 27: 26 | 28: 16 |
| 29: 16 | 31: 16 | 32: 16 | 33: 16 | 34: 16 | 35: 16 |
| 36: 16 | 36: 26 | 37: 16 | 38: 16 | 39: 16 | 40: 16 |
| 41: 16 | 42: 16 | 44: 16 | 45: 16 | 46: 16 | 47: 16 |
| 48: 46 | 49: 46 | | | | |

There are 34 hits at base# 16

-"-  GACTC  21
| | | | | | |
|---|---|---|---|---|---|
| 15: 56 | 16: 56 | 17: 56 | 18: 56 | 19: 56 | 20: 56 |
| 21: 56 | 22: 56 | 23: 56 | 24: 56 | 25: 56 | 26: 56 |
| 27: 56 | 28: 56 | 29: 56 | 30: 56 | 31: 56 | 32: 56 |
| 33: 56 | 35: 56 | 36: 56 | | | |

There are 21 hits at base# 56

PleI  gagtc  38
| | | | | | |
|---|---|---|---|---|---|
| 12: 16 | 13: 16 | 14: 16 | 15: 16 | 16: 16 | 17: 16 |
| 18: 16 | 19: 16 | 20: 16 | 21: 16 | 22: 16 | 23: 16 |
| 24: 16 | 25: 16 | 26: 16 | 27: 16 | 27: 26 | 28: 16 |
| 29: 16 | 31: 16 | 32: 16 | 33: 16 | 34: 16 | 35: 16 |
| 36: 16 | 36: 26 | 37: 16 | 38: 16 | 39: 16 | 40: 16 |
| 41: 16 | 42: 16 | 44: 16 | 45: 16 | 46: 16 | 47: 16 |
| 48: 46 | 49: 46 | | | | |

There are 34 hits at base# 16

-"-  gactc  21
| | | | | | |
|---|---|---|---|---|---|
| 15: 56 | 16: 56 | 17: 56 | 18: 56 | 19: 56 | 20: 56 |
| 21: 56 | 22: 56 | 23: 56 | 24: 56 | 25: 56 | 26: 56 |
| 27: 56 | 28: 56 | 29: 56 | 30: 56 | 31: 56 | 32: 56 |
| 33: 56 | 35: 56 | 36: 56 | | | |

TABLE 7-continued

RERS sites in Human HC GLG FR1s where there are at least 20 GLGs cut

There are 21 hits at base# 56

| AlwNI | | CAGNNNctg | 26 | | |
|---|---|---|---|---|---|
| 15: 68 | 16: 68 | 17: 68 | 18: 68 | 19: 68 | 20: 68 |
| 21: 68 | 22: 68 | 23: 68 | 24: 68 | 25: 68 | 26: 68 |
| 27: 68 | 28: 68 | 29: 68 | 30: 68 | 31: 68 | 32: 68 |
| 33: 68 | 34: 68 | 35: 68 | 36: 68 | 39: 46 | 40: 46 |
| 41: 46 | 42: 46 | | | | |

There are 22 hits at base# 68

TABLE 8

Kappa FR1 GLGs

```
 1   2   3   4   5   6   7   8   9   10  11  12
GAC ATC CAG ATG ACC CAG TCT CCA TCC TCC CTG TCT
 13  14  15  16  17  18  19  20  21  22  23
GCA TCT GTA GGA GAC AGA GTC ACC ATC ACT TGC !   O12  (SEQ ID NO: 275)
GAC ATC CAG ATG ACC CAG TCT CCA TCC TCC CTG TCT

GCA TCT GTA GGA GAC AGA GTC ACC ATC ACT TGC !   O2   (SEQ ID NO: 276)
GAC ATC CAG ATG ACC CAG TCT CCA TCC TCC CTG TCT

GCA TCT GTA GGA GAC AGA GTC ACC ATC ACT TGC !   O18  (SEQ ID NO: 277)
GAC ATC CAG ATG ACC CAG TCT CCA TCC TCC CTG TCT

GCA TCT GTA GGA GAC AGA GTC ACC ATC ACT TGC !   O8   (SEQ ID NO: 278)
GAC ATC CAG ATG ACC CAG TCT CCA TCC TCC CTG TCT

GCA TCT GTA GGA GAC AGA GTC ACC ATC ACT TGC !   A20  (SEQ ID NO: 279)
GAC ATC CAG ATG ACC CAG TCT CCA TCC TCC CTG TCT

GCA TCT GTA GGA GAC AGA GTC ACC ATC ACT TGC !   A30  (SEQ ID NO: 280)
AAC ATC CAG ATG ACC CAG TCT CCA TCT GCC ATG TCT

GCA TCT GTA GGA GAC AGA GTC ACC ATC ACT TGT !   L14  (SEQ ID NO: 281)
GAC ATC CAG ATG ACC CAG TCT CCA TCC TCA CTG TCT

GCA TCT GTA GGA GAC AGA GTC ACC ATC ACT TGT !   L1   (SEQ ID NO: 282)
GAC ATC CAG ATG ACC CAG TCT CCA TCC TCA CTG TCT

GCA TCT GTA GGA GAC AGA GTC ACC ATC ACT TGT !   L15  (SEQ ID NO: 283)
GCC ATC CAG TTG ACC CAG TCT CCA TCC TCC CTG TCT

GCA TCT GTA GGA GAC AGA GTC ACC ATC ACT TGC !   L4   (SEQ ID NO: 284)
GCC ATC CAG TTG ACC CAG TCT CCA TCC TCC CTG TCT

GCA TCT GTA GGA GAC AGA GTC ACC ATC ACT TGC !   L18  (SEQ ID NO: 285)
GAC ATC CAG ATG ACC CAG TCT CCA TCT TCC GTG TCT

GCA TCT GTA GGA GAC AGA GTC ACC ATC ACT TGT !   L5   (SEQ ID NO: 286)
GAC ATC CAG ATG ACC CAG TCT CCA TCT TCT GTG TCT

GCA TCT GTA GGA GAC AGA GTC ACC ATC ACT TGT !   L19  (SEQ ID NO: 287)
GAC ATC CAG TTG ACC CAG TCT CCA TCC TTC CTG TCT

GCA TCT GTA GGA GAC AGA GTC ACC ATC ACT TGC !   L8   (SEQ ID NO: 288)
GCC ATC CGG ATG ACC CAG TCT CCA TTC TCC CTG TCT

GCA TCT GTA GGA GAC AGA GTC ACC ATC ACT TGC !   L23  (SEQ ID NO: 289)
GCC ATC CGG ATG ACC CAG TCT CCA TCC TCA TTC TCT

GCA TCT ACA GGA GAC AGA GTC ACC ATC ACT TGT !   L9   (SEQ ID NO: 290)
GTC ATC TGG ATG ACC CAG TCT CCA TCC TTA CTC TCT

GCA TCT ACA GGA GAC AGA GTC ACC ATC AGT TGT !   L24  (SEQ ID NO: 291)
GCC ATC CAG ATG ACC CAG TCT CCA TCC TCC CTG TCT

GCA TCT GTA GGA GAC AGA GTC ACC ATC ACT TGC !   L11  (SEQ ID NO: 292)
GAC ATC CAG ATG ACC CAG TCT CCT TCC ACC CTG TCT

GCA TCT GTA GGA GAC AGA GTC ACC ATC ACT TGC !   L12  (SEQ ID NO: 293)
GAT ATT GTG ATG ACC CAG ACT CCA CTC TCC CTG CCC

GTC ACC CCT GGA GAG CCG GCC TCC ATC TCC TGC !   O11  (SEQ ID NO: 294)
GAT ATT GTG ATG ACC CAG ACT CCA CTC TCC CTG CCC
```

TABLE 8-continued

Kappa FR1 GLGs

```
GTC ACC CCT GGA GAG CCG GCC TCC ATC TCC TGC !  O1   (SEQ ID NO: 295)
GAT GTT GTG ATG ACT CAG TCT CCA CTC TCC CTG CCC

GTC ACC CTT GGA CAG CCG GCC TCC ATC TCC TGC !  A17  (SEQ ID NO: 296)
GAT GTT GTG ATG ACT CAG TCT CCA CTC TCC CTG CCC

GTC ACC CTT GGA CAG CCG GCC TCC ATC TCC TGC !  A1   (SEQ ID NO: 297)
GAT ATT GTG ATG ACC CAG ACT CCA CTC TCT CTG TCC

GTC ACC CCT GGA CAG CCG GCC TCC ATC TCC TGC !  A18  (SEQ ID NO: 298)
GAT ATT GTG ATG ACC CAG ACT CCA CTC TCT CTG TCC

GTC ACC CCT GGA CAG CCG GCC TCC ATC TCC TGC !  A2   (SEQ ID NO: 299)
GAT ATT GTG ATG ACT CAG TCT CCA CTC TCC CTG CCC

GTC ACC CCT GGA GAG CCG GCC TCC ATC TCC TGC !  A19  (SEQ ID NO: 300)
GAT ATT GTG ATG ACT CAG TCT CCA CTC TCC CTG CCC

GTC ACC CCT GGA GAG CCG GCC TCC ATC TCC TGC !  A3   (SEQ ID NO: 301)
GAT ATT GTG ATG ACC CAG ACT CCA CTC TCC TCA CCT

GTC ACC CTT GGA CAG CCG GCC TCC ATC TCC TGC !  A23  (SEQ ID NO: 302)
GAA ATT GTG TTG ACG CAG TCT CCA GGC ACC CTG TCT

TTG TCT CCA GGG GAA AGA GCC ACC CTC TCC TGC !  A27  (SEQ ID NO: 303)
GAA ATT GTG TTG ACG CAG TCT CCA GCC ACC CTG TCT

TTG TCT CCA GGG GAA AGA GCC ACC CTC TCC TGC !  A11  (SEQ ID NO: 304)
GAA ATA GTG ATG ACG CAG TCT CCA GCC ACC CTG TCT

GTG TCT CCA GGG GAA AGA GCC ACC CTC TCC TGC !  L2   (SEQ ID NO: 305)
GAA ATA GTG ATG ACG CAG TCT CCA GCC ACC CTG TCT

GTG TCT CCA GGG GAA AGA CCC ACC CTC TCC TGC !  L16  (SEQ ID NO: 306)
GAA ATT GTG TTG ACA CAG TCT CCA GCC ACC CTG TCT

TTG TCT CCA GGG GAA AGA GCC ACC CTC TCC TGC !  L6   (SEQ ID NO: 307)
GAA ATT GTG TTG ACA CAG TCT CCA GCC ACC CTG TCT

TTG TCT CCA GGG GAA AGA GCC ACC CTC TCC TGC !  L20  (SEQ ID NO: 308)
GAA ATT GTA ATG ACA CAG TCT CCA GCC ACC CTG TCT

TTG TCT CCA GGG GAA AGA GCC ACC CTC TCC TGC !  L25  (SEQ ID NO: 309)
GAC ATC GTG ATG ACC CAG TCT CCA GAC TCC CTG GCT

GTG TCT CTG GGC GAG AGG GCC ACC ATC AAC TGC !  B3   (SEQ ID NO: 310)
GAA ACG ACA CTC ACG CAG TCT CCA GCA TTC ATG TCA

GCG ACT CCA GGA GAC AAA GTC AAC ATC TCC TGC !  B2   (SEQ ID NO: 311)
GAA ATT GTG CTG ACT CAG TCT CCA GAC TTT CAG TCT

GTG ACT CCA AAG GAG AAA GTC ACC ATC ACC TGC !  A26  (SEQ ID NO: 312)
GAA ATT GTG CTG ACT CAG TCT CCA GAC TTT CAG TCT

GTG ACT CCA AAG GAG AAA GTC ACC ATC ACC TGC !  A10  (SEQ ID NO: 313)
GAT GTT GTG ATG ACA CAG TCT CCA GCT TTC CTC TCT

GTG ACT CCA GGG GAG AAA GTC ACC ATC ACC TGC !  A14  (SEQ ID NO: 314)
```

TABLE 9

RERS sites found in Human Kappa FR1 GLGs

| | | FokI | | | | | | | | HpyCH |
| | MslI | --> | <-- | --> | PflFI | BsrI | BsmAI | | MnlI | 4V |
| --- | --- | --- | --- | --- | --- | --- | --- | --- | --- | --- |
| VKI | | | | | | | | | | |
| O12 | 1-69 | 3 | 3 | | 23 | 12 | 49 | 15 | 18 | 47 | 26 | 36 |
| O2  | 101-169 | 103 | 103 | | 123 | 112 | 149 | 115 | 118 | 147 | 126 | 136 |
| O18 | 201-269 | 203 | 203 | | 223 | 212 | 249 | 215 | 218 | 247 | 226 | 236 |
| O8  | 301-369 | 303 | 303 | | 323 | 312 | 349 | 315 | 318 | 347 | 326 | 336 |
| A20 | 401-469 | 403 | 403 | | 423 | 412 | 449 | 415 | 418 | 447 | 426 | 436 |

TABLE 9-continued

| | | | | | | | | | | | | | |
|---|---|---|---|---|---|---|---|---|---|---|---|---|---|
| A30 | 501-569 | 503 | 503 | | 523 | 512 | 549 | | 515 | 518 | 547 | 526 | | 536 |
| L14 | 601-669 | 603 | 603 | | | 612 | 649 | | 615 | 618 | 647 | — | | 636 |
| L1 | 701-769 | 703 | 703 | | 723 | 712 | 749 | | 715 | 718 | 747 | 726 | | 736 |
| L15 | 801-869 | 803 | 803 | | 823 | 812 | 849 | | 815 | 818 | 847 | 826 | | 836 |
| L4 | 901-969 | | 903 | | 923 | 912 | 949 | 906 | 915 | 918 | 947 | 926 | | 936 |
| L18 | 1001-1069 | — | 1003 | | | 1012 | 1049 | 1006 | 1015 | 1018 | 1047 | 1026 | | 1036 |
| L5 | 1101-1169 | 1103 | — | | | 1112 | 1149 | | 1115 | 1118 | 1147 | — | | 1136 |
| L19 | 1201-1269 | 1203 | 1203 | | | 1212 | 1249 | | 1215 | 1218 | 1247 | — | | 1236 |
| L8 | 1301-1369 | | 1303 | | 1323 | 1312 | 1349 | 1306 | 1315 | 1318 | 1347 | — | | 1336 |
| L23 | 1401-1469 | 1403 | 1403 | 1408 | | 1412 | 1449 | | 1415 | 1418 | 1447 | — | | 1436 |
| L9 | 1501-1569 | 1503 | 1503 | 1508 | 1523 | 1512 | 1549 | | 1515 | 1518 | 1547 | 1526 | | 1536 |
| L24 | 1601-1669 | 1603 | | 1608 | 1623 | 1612 | 1649 | | 1615 | 1618 | 1647 | — | | 1636 |
| L11 | 1701-1769 | 1703 | 1703 | | 1723 | 1712 | 1749 | | 1715 | 1718 | 1747 | 1726 | | 1736 |
| L12 | 1801-1869 | 1803 | 1803 | | | 1812 | 1849 | | 1815 | 1818 | 1847 | — | | 1836 |
| VKII | | | | | | | | | | | | | | |
| O11 | 1901-1969 | — | — | | | — | — | | — | — | | 1956 | | — |
| O1 | 2001-2069 | — | — | | | — | — | | — | — | | 2056 | | — |
| A17 | 2101-2169 | — | — | | 2112 | | — | | 2118 | | | 2156 | | — |
| A1 | 2201-2269 | — | — | | 2212 | | — | | 2218 | | | 2256 | | — |
| A18 | 2301-2369 | — | — | | | | — | | — | | | 2356 | | — |
| A2 | 2401-2469 | — | — | | | | — | | — | | | 2456 | | — |
| A19 | 2501-2569 | — | — | | 2512 | | — | | 2518 | | | 2556 | | — |
| A3 | 2601-2669 | — | — | | 2612 | | — | | 2618 | | | 2656 | | — |
| A23 | 2701-2769 | — | — | | | | — | | — | | 2729 | 2756 | | — |
| VKIII | | | | | | | | | | | | | | |
| A27 | 2801-2869 | — | — | | 2812 | | — | | 2818 | 2839 | | | 2860 | — |
| A11 | 2901-2969 | — | — | | 2912 | | — | | 2918 | 2939 | | | 2960 | — |
| L2 | 3001-3069 | — | — | | 3012 | | — | | 3018 | 3039 | | | 3060 | — |
| L16 | 3101-3169 | — | — | | 3112 | | — | | 3118 | 3139 | | | 3160 | — |
| L6 | 3201-3269 | — | — | | 3212 | | — | | 3218 | 3239 | | | 3260 | — |
| L20 | 3301-3369 | — | — | | 3312 | | — | | 3318 | 3339 | | | 3360 | — |
| L25 | 3401-3469 | — | — | | 3412 | | — | | 3418 | 3439 | | | 3460 | — |
| VKIV | | | | | | | | | | | | | | |
| B3 | 3501-3569 | 3503 | — | | 3512 | | | 3515 | 3518 | 3539 | | 3551< | | — |
| VKV | | | | | | | | | | | | | | |
| B2 | 3601-3669 | — | — | | | 3649 | — | | 3618 | | 3647 | | | — |
| VKVI | | | | | | | | | | | | | | |
| A26 | 3701-3769 | — | — | | 3712 | | — | | 3718 | | | | | — |
| A10 | 3801-3869 | — | — | | 3812 | | — | | 3818 | | | | | — |
| A14 | 3901-3969 | — | — | | 3912 | | — | | 3918 | | 3930> | | | — |

| | | SfaNI | SfcI | HinfI | MlyI --> | MaeIII Tsp45I --> | same <-- | sites | HphI xx38 | xx56 | xx62 | HpaII MspI xx06 | xx52 |
|---|---|---|---|---|---|---|---|---|---|---|---|---|---|
| VKI | | | | | | | | | | | | | |
| O12 | 1-69 | 37 | 41 | | 53 | | 53 | | 55 | | 56 | — | | |
| O2 | 101-169 | 137 | 141 | | 153 | | 153 | | 155 | | 156 | — | | |
| O18 | 201-269 | 237 | 241 | | 253 | | 253 | | 255 | | 256 | — | | |
| O8 | 301-369 | 337 | 341 | | 353 | | 353 | | 355 | | 356 | — | | |
| A20 | 401-469 | 437 | 441 | | 453 | | 453 | | 455 | | 456 | — | | |
| A30 | 501-569 | 537 | 541 | | 553 | | 553 | | 555 | | 556 | — | | |
| L14 | 601-669 | 637 | 641 | | 653 | | 653 | | 655 | | 656 | — | | |
| L1 | 701-769 | 737 | 741 | | 753 | | 753 | | 755 | | 756 | — | | |
| L15 | 801-869 | 837 | 841 | | 853 | | 853 | | 855 | | 856 | — | | |
| L4 | 901-969 | 937 | 941 | | 953 | | 953 | | 955 | | 956 | — | | |
| L18 | 1001-1069 | 1037 | 1041 | | 1053 | | 1053 | | 1055 | | 1056 | — | | |
| L5 | 1101-1169 | 1137 | 1141 | | 1153 | | 1153 | | 1155 | | 1156 | — | | |
| L19 | 1201-1269 | 1237 | 1241 | | 1253 | | 1253 | | 1255 | | 1256 | — | | |
| L8 | 1301-1369 | 1337 | 1341 | | 1353 | | 1353 | | 1355 | | 1356 | — | | |
| L23 | 1401-1469 | 1437 | 1441 | | 1453 | | 1453 | | 1455 | | 1456 | 1406 | | |
| L9 | 1501-1569 | 1537 | 1541 | | 1553 | | 1553 | | 1555 | | 1556 | 1506 | | |
| L24 | 1601-1669 | 1637 | 1641 | | 1653 | | 1653 | | 1655 | | 1656 | | | |
| L11 | 1701-1769 | 1737 | 1741 | | 1753 | | 1753 | | 1755 | | 1756 | | | |
| L12 | 1801-1869 | 1837 | 1841 | | 1853 | | 1853 | | 1855 | | 1856 | | | |
| VKII | | | | | | | | | | | | | |
| O11 | 1901-1969 | — | — | 1918 | | 1918 | | 1937 | 1938 | | | | 1952 |
| O1 | 2001-2069 | — | — | 2018 | | 2018 | | 2037 | 2038 | | | | 2052 |
| A17 | 2101-2169 | — | — | 2112 | 2112 | | | 2137 | 2138 | | | | 2152 |
| A1 | 2201-2269 | — | — | 2212 | 2212 | | | 2237 | 2238 | | | | 2252 |
| A18 | 2301-2369 | — | — | 2318 | | 2318 | | 2337 | 2338 | | | | 2352 |
| A2 | 2401-2469 | — | — | 2418 | | 2418 | | 2437 | 2438 | | | | 2452 |

TABLE 9-continued

| | | | | | | | | | | | |
|---|---|---|---|---|---|---|---|---|---|---|---|
| A19 | 2501-2569 | — | — | 2512 | | 2512 | | 2537 | 2538 | | | 2552 |
| A3 | 2601-2669 | — | — | 2612 | | 2612 | | 2637 | 2638 | | | 2652 |
| A23 | 2701-2769 | — | — | 2718 | | 2718 | | 2737 | 2731* | 2738* | — | |
| VKIII | | | | | | | | | | | | |
| A27 | 2801-2869 | — | — | — | | | | | | | — | |
| A11 | 2901-2969 | — | — | — | | | | | | | — | |
| L2 | 3001-3069 | — | — | — | | | | | | | — | |
| L16 | 3101-3169 | — | — | — | | | | | | | — | |
| L6 | 3201-3269 | — | — | — | | | | | | | — | |
| L20 | 3301-3369 | — | — | — | | | | | | | — | |
| L25 | 3401-3469 | — | — | — | | | | | | | — | |
| VKIV | | | | | | | | | | | | |
| B3 | 3501-3569 | — | — | 3525 | | 3525 | | | | | — | |
| VKV | | | | | | | | | | | | |
| B2 | 3601-3669 | — | — | | 3639 | | 3639 | | | | — | |
| VKVI | | | | | | | | | | | | |
| A26 | 3701-3769 | — | — | 3712 | 3739 | 3712 | 3739 | 3737 | 3755 | 3756 | 3762 | — |
| A10 | 3801-3869 | — | — | 3812 | 3839 | 3812 | 3839 | 3837 | 3855 | 3856 | 3862 | — |
| A14 | 3901-3969 | — | — | | 3939 | | 3939 | 3937 | 3955 | 3956 | 3962 | — |

RERS sites found in Human Kappa FR1

| | | BsaJI | | BssKI (NstNI) | | | BpmI | | | BsrFI Cac8I NaeI | | | |
|---|---|---|---|---|---|---|---|---|---|---|---|---|---|
| | | xx29 | xx42 | xx43 | xx22 | xx30 | xx43 | xx20 --> | xx41 --> | xx44 <-- | NgoMIV | HaeIII | Tsp509I |
| VKI | | | | | | | | | | | | | |
| O12 | 1-69 | — | | | — | | | | | | — | — | — |
| O2 | 101-169 | — | | | — | | | | | | — | — | — |
| O18 | 201-269 | — | | | — | | | | | | — | — | — |
| O8 | 301-369 | — | | | — | | | | | | — | — | — |
| A20 | 401-469 | — | | | — | | | | | | — | — | — |
| A30 | 501-569 | — | | | — | | | | | | — | — | — |
| L14 | 601-669 | — | | | — | | | | | | — | — | — |
| L1 | 701-769 | — | | | — | | | | | | — | — | — |
| L15 | 801-869 | — | | | — | | | | | | — | — | — |
| L4 | 901-969 | — | | | — | | | | | | — | — | — |
| L18 | 1001-1069 | — | | | — | | | | | | — | — | — |
| L5 | 1101-1169 | — | | | — | | | | | | — | — | — |
| L19 | 1201-1269 | — | | | — | | | | | | — | — | — |
| L8 | 1301-1369 | — | | | — | | | | | | — | — | — |
| L23 | 1401-1469 | — | | | — | | | | | | — | — | — |
| L9 | 1501-1569 | — | | | — | | | | | | — | — | — |
| L24 | 1601-1669 | — | | | — | | | | | | — | — | — |
| L11 | 1701-1769 | — | | | — | | | | | | — | — | — |
| L12 | 1801-1869 | — | | | — | | | | | | — | — | — |
| VKII | | | | | | | | | | | | | |
| O11 | 1901-1969 | | 1942 | | | 1943 | | | | 1944 | 1951 | 1954 | — |
| O1 | 2001-2069 | | 2042 | | | 2043 | | | | 2044 | 2051 | 2054 | — |
| A17 | 2101-2169 | | 2142 | | — | | | | | | 2151 | 2154 | — |
| A1 | 2201-2269 | | 2242 | | — | | | | | | 2251 | 2254 | — |
| A18 | 2301-2369 | | 2342 | | | 2343 | | — | | | 2351 | 2354 | — |
| A2 | 2401-2469 | | 2442 | | | 2443 | | — | | | 2451 | 2454 | — |
| A19 | 2501-2569 | | 2542 | | | 2543 | | | | 2544 | 2551 | 2554 | — |
| A3 | 2601-2669 | | 2642 | | | 2643 | | | | 2644 | 2651 | 2654 | — |
| A23 | 2701-2769 | | 2742 | | — | | | | | | 2751 | 2754 | — |
| VKIII | | | | | | | | | | | | | |
| A27 | 2801-2869 | | | 2843 | 2822 | | 2843 | 2820 | 2841 | | — | — | 2803 |
| A11 | 2901-2969 | | | 2943 | | | 2943 | 2920 | 2941 | | — | — | 2903 |
| L2 | 3001-3069 | | | 3043 | | | 3043 | | 3041 | | — | — | — |
| L16 | 3101-3169 | | | 3143 | | | 3143 | 3120 | 3141 | | — | — | — |
| L6 | 3201-3269 | | | 3243 | | | 3243 | 3220 | 3241 | | — | — | 3203 |
| L20 | 3301-3369 | | | 3343 | | | 3343 | 3320 | 3341 | | — | — | 3303 |
| L25 | 3401-3469 | | | 3443 | | | 3443 | 3420 | 3441 | | — | — | 3403 |

TABLE 9-continued

VKIV

| B3 | 3501-3569 | 3529 | | 3530 | 3520 | | — | 3554 |
|---|---|---|---|---|---|---|---|---|

VKV

| B2 | 3601-3669 | | | | 3643 | 3620 | 3641 | — | — |
|---|---|---|---|---|---|---|---|---|---|

VKVI

| A26 | 3701-3769 | | — | | 3720 | | — | — | 3703 |
|---|---|---|---|---|---|---|---|---|---|
| A10 | 3801-3869 | | — | | 3820 | | — | — | 3803 |
| A14 | 3901-3969 | 3943 | | 3943 | 3920 | 3941 | — | — | — |

TABLE 10

Lambda FR1 GLG sequences

!VL1  CAG TCT GTG CTG ACT CAG CCA CCC TCG GTG TCT GAA
      GCC CCC AGG CAG AGG GTC ACC ATC TCC TGT !   1a
      (SEQ ID NO: 315)

cag tct gtg ctg acG cag ccG ccc tcA gtg tct gGG
      gcc ccA Ggg cag agg gtc acc atc tcc tgC !   1e
      (SEQ ID NO: 316)

cag tct gtg ctg act cag cca ccc tcA gCg tct gGG
      Acc ccc Ggg cag agg gtc acc atc tcT tgt !   1c
      (SEQ ID NO: 317)

cag tct gtg ctg act cag cca ccc tcA gCg tct gGG
      Acc ccc Ggg cag agg gtc acc atc tcT tgt !   1g
      (SEQ ID NO: 318)

cag tct gtg Ttg acG cag ccG ccc tcA gtg tct gCG
      gcc ccA GgA cag aAg gtc acc atc tcc tgC !   1b
      (SEQ ID NO: 319)

!VL2  CAG TCT GCC CTG ACT CAG CCT CCC TCC GCG TCC GGG
      TCT CCT GGA CAG TCA GTC ACC ATC TCC TGC !   2c
      (SEQ ID NO: 320)

cag tct gcc ctg act cag cct cGc tcA gTg tcc ggg
      tct cct gga cag tca gtc acc atc tcc tgc!   2e
      (SEQ ID NO: 321)

cag tct gcc ctg act cag cct Gcc tcc gTg tcT ggg
      tct cct gga cag tcG Atc acc atc tcc tgc !   2a2
      (SEQ ID NO: 322)

cag tct gcc ctg act cag cct ccc tcc gTg tcc ggg
      tct cct gga cag tca gtc acc atc tcc tgc !   2d
      (SEQ ID NO: 323)

cag tct gcc ctg act cag cct Gcc tcc gTg tcT ggg
      tct cct gga cag tcG Atc acc atc tcc tgc !   2b2
      (SEQ ID NO: 324)

!VL3  TCC TAT GAG CTG ACT CAG CCA CCC TCA GTG TCC GTG
      TCC CCA GGA CAG ACA GCC AGC ATC ACC TGC!    3r
      (SEQ ID NO: 325)

tcc tat gag ctg act cag cca cTc tca gtg tcA gtg
      Gcc cTG gga cag acG gcc agG atT acc tgT !   3j
      (SEQ ID NO: 326)

tcc tat gag ctg acA cag cca ccc tcG gtg tcA gtg
      tcc cca gga caA acG gcc agG atc acc tgc!   3p
      (SEQ ID NO: 327)

tcc tat gag ctg acA cag cca ccc tcG gtg tcA gtg
      tcc cTa gga cag aTG gcc agG atc acc tgc !   3a
      (SEQ ID NO: 328)

tcT tCt gag ctg act cag GAC ccT GcT gtg tcT gtg
      Gcc TTG gga cag aca gTc agG atc acA tgc !   3l
      (SEQ ID NO: 329)

TABLE 10-continued

Lambda FR1 GLG sequences

```
    tcc tat gTg ctg act cag cca ccc tca gtg tcA gtg
    Gcc cca gga Aag acG gcc agG atT acc tgT !  3h
    (SEQ ID NO: 330)

tcc tat gag ctg acA cag cTa ccc tcG gtg tcA gtg
    tcc cca gga cag aca gcc agG atc acc tgc !  3e
    (SEQ ID NO: 331)

tcc tat gag ctg aTG cag cca ccc tcG gtg tcA gtg
    tcc cca gga cag acG acc agG atc acc tgc !  3m
    (SEQ ID NO: 332)

tcc tat gag ctg acA cag cca Tcc tca gtg tcA gtg
    tcT ccG gga cag aca gcc agG atc acc tgc !  V2-19
    (SEQ ID NO: 333)

!VL4  CTG CCT GTG CTG ACT CAG CCC CCG TCT GCA TCT GCC
    TTG CTG GGA GCC TCG ATC AAG CTC ACC TGC !  4c
    (SEQ ID NO: 334)

cAg cct gtg ctg act caA TcA TcC tct gcC tct gcT
    tCC ctg gga Tcc tcg Gtc aag ctc acc tgc !  4a
    (SEQ ID NO: 335)

cAg cTt gtg ctg act caA TcG ccC tct gcC tct gcc
    tCC ctg gga gcc tcg Gtc aag ctc acc tgc !  4b
    (SEQ ID NO: 336)

!VL5  CAG CCT GTG CTG ACT CAG CCA CCT TCC TCC TCC GCA
    TCT CCT GGA GAA TCC GCC AGA CTC ACC TGC !  5e
    (SEQ ID NO: 337)

cag Gct gtg ctg act cag ccG Gct tcc CTc tcT gca
    tct cct gga gCa tcA gcc agT ctc acc tgc !  5c
    (SEQ ID NO: 338)

cag cct gtg ctg act cag cca Tct tcc CAT tcT gca
    tct Tct gga gCa tcA gTc aga ctc acc tgc !  5b
    (SEQ ID NO: 339)

!VL6  AAT TTT ATG CTG ACT CAG CCC CAC TCT GTG TCG GAG
    TCT CCG GGG AAG ACG GTA ACC ATC TCC TGC !  6a
    (SEQ ID NO: 340)

!VL7  CAG ACT GTG GTG ACT CAG GAG CCC TCA CTG ACT GTG
    TCC CCA GGA GGG ACA GTC ACT CTC ACC TGT !  7a
    (SEQ ID NO: 341)

cag Gct gtg gtg act cag gag ccc tca ctg act gtg
    tcc cca gga ggg aca gtc act ctc acc tgt !  7b
    (SEQ ID NO: 342)

!VL8  CAG ACT GTG GTG ACC CAG GAG CCA TCG TTC TCA GTG
    TCC CCT GGA GGG ACA GTC ACA CTC ACT TGT !  8a
    (SEQ ID NO: 343)

!VL9  CAG CCT GTG CTG ACT CAG CCA CCT TCT GCA TCA GCC
    TCC CTG GGA GCC TCG GTC ACA CTC ACC TGC !  9a
    (SEQ ID NO: 344)

!VL10 CAG GCA GGG CTG ACT CAG CCA CCC TCG GTG TCC AAG
    GGC TTG AGA CAG ACC GCC ACA CTC ACC TGC !  10a
    (SEQ ID NO: 345)
```

TABLE 11

RERSs found in human lambda FR1 GLGs

! There are 31 lambda GLGs
MlyI    NnnnnnGACTC (SEQ ID NO: 346)    25
1: 6    3: 6    4: 6    6: 6    7: 6    8: 6
9: 6    10: 6   11: 6   12: 6   15: 6   16: 6
20: 6   21: 6   22: 6   23: 6   23: 50  24: 6

TABLE 11-continued

RERSs found in human lambda FR1 GLGs

25: 6   25: 50  26: 6   27: 6   28: 6   30: 6
31: 6
There are 23 hits at base# 6
-"-    GAGTCNNNNNn (SEQ ID NO: 347)    1
26: 34

TABLE 11-continued

RERSs found in human lambda FR1 GLGs

| MwoI | GCNNNNNnngc (SEQ ID NO: 348) | | | 20 | |
|---|---|---|---|---|---|
| 1:9 | 2:9 | 3:9 | 4:9 | 11:9 | 11:56 |
| 12:9 | 13:9 | 14:9 | 16:9 | 17:9 | 18:9 |
| 19:9 | 20:9 | 23:9 | 24:9 | 25:9 | 26:9 |
| 30:9 | 31:9 | | | | |

There are 19 hits at base# 9

| HinfI | Gantc | | | 27 | |
|---|---|---|---|---|---|
| 1:12 | 3:12 | 4:12 | 6:12 | 7:12 | 8:12 |
| 9:12 | 10:12 | 11:12 | 12:12 | 15:12 | 16:12 |
| 20:12 | 21:12 | 22:12 | 23:12 | 23:46 | 23:56 |
| 24:12 | 25:12 | 25:56 | 26:12 | 26:34 | 27:12 |
| 28:12 | 30:12 | 31:12 | | | |

There are 23 hits at base# 12

| PleI | gactc | | | 25 | |
|---|---|---|---|---|---|
| 1:12 | 3:12 | 4:12 | 6:12 | 7:12 | 8:12 |
| 9:12 | 10:12 | 11:12 | 12:12 | 15:12 | 16:12 |
| 20:12 | 21:12 | 22:12 | 23:12 | 23:56 | 24:12 |
| 25:12 | 25:56 | 26:12 | 27:12 | 28:12 | 30:12 |
| 31:12 | | | | | |

There are 23 hits at base# 12

| -"- | gagtc | | | 1 | |
|---|---|---|---|---|---|
| 26:34 | | | | | |

| DdeI | Ctnag | | | 32 | |
|---|---|---|---|---|---|
| 1:14 | 2:24 | 3:14 | 3:24 | 4:14 | 4:24 |
| 5:24 | 6:14 | 7:14 | 7:24 | 8:14 | 9:14 |
| 10:14 | 11:14 | 11:24 | 12:14 | 12:24 | 15:5 |
| 15:14 | 16:14 | 16:24 | 19:24 | 20:14 | 23:14 |
| 24:14 | 25:14 | 26:14 | 27:14 | 28:14 | 29:30 |
| 30:14 | 31:14 | | | | |

There are 21 hits at base# 14

| BsaJI | Ccnngg | | | 38 | |
|---|---|---|---|---|---|
| 1:23 | 1:40 | 2:39 | 2:40 | 3:39 | 3:40 |
| 4:39 | 4:40 | 5:39 | 11:39 | 12:38 | 12:39 |
| 13:23 | 13:39 | 14:23 | 14:39 | 15:38 | 16:39 |
| 17:23 | 17:39 | 18:23 | 18:39 | 21:38 | 21:39 |
| 21:47 | 22:38 | 22:39 | 22:47 | 26:40 | 27:39 |
| 28:39 | 29:14 | 29:39 | 30:38 | 30:39 | 30:47 |
| 31:23 | 31:32 | | | | |

There are 17 hits at base# 39
There are 5 hits at base# 38
There are 5 hits at base# 40 Makes cleavage ragged.

| MnlI | cctc | | | 35 | |
|---|---|---|---|---|---|
| 1:23 | 2:23 | 3:23 | 4:23 | 5:23 | 6:19 |
| 6:23 | 7:19 | 8:23 | 9:19 | 9:23 | 10:23 |
| 11:23 | 13:23 | 14:23 | 16:23 | 17:23 | 18:23 |
| 19:23 | 20:47 | 21:23 | 21:29 | 21:47 | 22:23 |
| 22:29 | 22:35 | 22:47 | 23:26 | 23:29 | 24:27 |
| 27:23 | 28:23 | 30:35 | 30:47 | 31:23 | |

There are 21 hits at base# 23
There are 3 hits at base# 19
There are 3 hits at base# 29
There are 1 hits at base# 26
There are 1 hits at base# 27 These could make cleavage ragged.

| -"- | gagg | | | 7 | |
|---|---|---|---|---|---|
| 1:48 | 2:48 | 3:48 | 4:48 | 27:44 | 28:44 |
| 29:44 | | | | | |

| BssKI | Nccngg | | | 39 | |
|---|---|---|---|---|---|
| 1:40 | 2:39 | 3:39 | 3:40 | 4:39 | 4:40 |
| 5:39 | 6:31 | 6:39 | 7:31 | 7:39 | 8:39 |
| 9:31 | 9:39 | 10:39 | 11:39 | 12:38 | 12:52 |
| 13:39 | 13:52 | 14:52 | 16:39 | 16:52 | 17:39 |
| 17:52 | 18:39 | 18:52 | 19:39 | 19:52 | 21:38 |
| 22:38 | 23:39 | 24:39 | 26:39 | 27:39 | 28:39 |
| 29:14 | 29:39 | 30:38 | | | |

There are 21 hits at base# 39
There are 4 hits at base# 38
There are 3 hits at base# 31
There are 3 hits at base# 40 Ragged

| BstNI | CCwgg | | | 30 | |
|---|---|---|---|---|---|
| 1:41 | 2:40 | 5:40 | 6:40 | 7:40 | 8:40 |
| 9:40 | 10:40 | 11:40 | 12:39 | 12:53 | 13:40 |
| 13:53 | 14:53 | 16:40 | 16:53 | 17:40 | 17:53 |
| 18:40 | 18:53 | 19:53 | 21:39 | 22:39 | 23:40 |
| 24:40 | 27:40 | 28:40 | 29:15 | 29:40 | 30:39 |

There are 17 hits at base# 40
There are 7 hits at base# 53
There are 4 hits at base# 39
There are 1 hits at base# 41 Ragged

| PspGI | ccwgg | | | 30 | |
|---|---|---|---|---|---|
| 1:41 | 2:40 | 5:40 | 6:40 | 7:40 | 8:40 |
| 9:40 | 10:40 | 11:40 | 12:39 | 12:53 | 13:40 |
| 13:53 | 14:53 | 16:40 | 16:53 | 17:40 | 17:53 |
| 18:40 | 18:53 | 19:53 | 21:39 | 22:39 | 23:40 |
| 24:40 | 27:40 | 28:40 | 29:15 | 29:40 | 30:39 |

There are 17 hits at base# 40
There are 7 hits at base# 53
There are 4 hits at base# 39
There are 1 hits at base# 41

| ScrFI | CCngg | | 39 | | |
|---|---|---|---|---|---|
| 1:41 | 2:40 | 3:40 | 3:41 | 4:40 | 4:41 |
| 5:40 | 6:32 | 6:40 | 7:32 | 7:40 | 8:40 |
| 9:32 | 9:40 | 10:40 | 11:40 | 12:39 | 12:53 |
| 13:40 | 13:53 | 14:53 | 16:40 | 16:53 | 17:40 |
| 17:53 | 18:40 | 18:53 | 19:40 | 19:53 | 21:39 |
| 22:39 | 23:40 | 24:40 | 26:40 | 27:40 | 28:40 |
| 29:15 | 29:40 | 30:39 | | | |

There are 21 hits at base# 40
There are 4 hits at base# 39
There are 3 hits at base# 41

| MaeIII | gtnac | | | 16 | |
|---|---|---|---|---|---|
| 1:52 | 2:52 | 3:52 | 4:52 | 5:52 | 6:52 |
| 7:52 | 9:52 | 26:52 | 27:10 | 27:52 | 28:10 |
| 28:52 | 29:10 | 29:52 | 30:52 | | |

There are 13 hits at base# 52

| Tsp45I | gtsac | | | 15 | |
|---|---|---|---|---|---|
| 1:52 | 2:52 | 3:52 | 4:52 | 5:52 | 6:52 |
| 7:52 | 9:52 | 27:10 | 27:52 | 28:10 | 28:52 |
| 29:10 | 29:52 | 30:52 | | | |

There are 12 hits at base# 52

| HphI | tcacc | | | 26 | |
|---|---|---|---|---|---|
| 1:53 | 2:53 | 3:53 | 4:53 | 5:53 | 6:53 |
| 7:53 | 8:53 | 9:53 | 10:53 | 11:59 | 13:59 |
| 14:59 | 17:59 | 18:59 | 19:59 | 20:59 | 21:59 |
| 22:59 | 23:59 | 24:59 | 25:59 | 27:59 | 28:59 |
| 30:59 | 31:59 | | | | |

There are 16 hits at base# 59
There are 10 hits at base# 53

| BspMI | ACCTGCNNNNn (SEQ ID NO: 349) | | | 14 | |
|---|---|---|---|---|---|
| 11:61 | 13:61 | 14:61 | 17:61 | 18:61 | 19:61 |
| 20:61 | 21:61 | 22:61 | 23:61 | 24:61 | 25:61 |
| 30:61 | 31:61 | | | | |

There are 14 hits at base# 61 Goes into CDR1

TABLE 12

Matches to URE FR3 adapters in 79 human HC.

A. List of Heavy-chains genes sampled

| AF008566 | AF103367 | HSA235674 | HSU94417 | S83240 |
|---|---|---|---|---|
| AF035043 | AF103368 | HSA235673 | HSU94418 | SABVH369 |
| AF103026 | AF103369 | HSA240559 | HSU96389 | SADEIGVH |
| af103033 | AF103370 | HSCB201 | HSU96391 | SAH2IGVH |
| AF103061 | af103371 | HSIGGVHC | HSU96392 | SDA3IGVH |
| Af103072 | AF103372 | HSU44791 | HSU96395 | SIGVHTTD |
| af103078 | AF158381 | HSU44793 | HSZ93849 | SUK4IGVH |

TABLE 12-continued

Matches to URE FR3 adapters in 79 human HC.

| | | | |
|---|---|---|---|
| AF103099 | E05213 | HSU82771 | HSZ93850 |
| AF103102 | E05886 | HSU82949 | HSZ93851 |
| AF103103 | E05887 | HSU82950 | HSZ93853 |
| AF103174 | HSA235661 | HSU82952 | HSZ93855 |
| AF103186 | HSA235664 | HSU82961 | HSZ93857 |
| af103187 | HSA235660 | HSU86522 | HSZ93860 |
| AF103195 | HSA235659 | HSU86523 | HSZ93863 |
| af103277 | HSA235678 | HSU92452 | MCOMFRAA |
| af103286 | HSA235677 | HSU94412 | MCOMFRVA |
| AF103309 | HSA235676 | HSU94415 | S82745 |
| af103343 | HSA235675 | HSU94416 | S82764 |

Table 12B. Testing all distinct GLGs from bases 89.1 to 93.2 of the heavy variable domain

| Id | Nb | 0 | 1 | 2 | 3 | 4 | | | SEQ ID NO: |
|---|---|---|---|---|---|---|---|---|---|
| 1 | 38 | 15 | 11 | 10 | 0 | 2 | Seq1 | gtgtattactgtgc | 25 |
| 2 | 19 | 7 | 6 | 4 | 2 | 0 | Seq2 | gtAtattactgtgc | 26 |
| 3 | 1 | 0 | 0 | 1 | 0 | 0 | Seq3 | gtgtattactgtAA | 27 |
| 4 | 7 | 1 | 5 | 1 | 0 | 0 | Seq4 | gtgtattactgtAc | 28 |
| 5 | 0 | 0 | 0 | 0 | 0 | 0 | Seq5 | Ttgtattactgtgc | 29 |
| 6 | 0 | 0 | 0 | 0 | 0 | 0 | Seq6 | TtgtatCactgtgc | 30 |
| 7 | 3 | 1 | 0 | 1 | 1 | 0 | Seq7 | ACAtattactgtgc | 31 |
| 8 | 2 | 0 | 2 | 0 | 0 | 0 | Seq8 | ACgtattactgtgc | 32 |
| 9 | 9 | 2 | 2 | 4 | 1 | 0 | Seq9 | ATgtattactgtgc | 33 |
| Group | | 26 | 26 | 21 | 4 | 2 | | | |
| Cumulative | | 26 | 52 | 73 | 77 | 79 | | | |

Table 12C Most important URE recognition seqs in FR3 Heavy

| 1 | VHSzy1 | GTGtattactgtgc | (ON_SHC103) | (SEQ ID NO: 25) |
|---|---|---|---|---|
| 2 | VHSzy2 | GTAtattactgtgc | (ON_SHC323) | (SEQ ID NO: 26) |
| 3 | VHSzy4 | GTGtattactgtac | (ON_SHC349) | (SEQ ID NO: 28) |
| 4 | VHSzy9 | ATGtattactgtgc | (ON_SHC5a) | (SEQ ID NO: 33) |

Table 12D, testing 79 human HC V genes with four probes
Number of sequences . . . . . . . . . . . . . 79
Number of bases . . . . . . . . . . . . . . . 29143

| | | Number of mismatches | | | | | | | |
|---|---|---|---|---|---|---|---|---|---|
| Id | Best | 0 | 1 | 2 | 3 | 4 | 5 | | |
| 1 | 39 | 15 | 11 | 10 | 1 | 2 | 0 | Seq1 | gtgtattactgtgc (SEQ ID NO: 25) |
| 2 | 22 | 7 | 6 | 5 | 3 | 0 | 1 | Seq2 | gtAtattactgtgc (SEQ ID NO: 26) |
| 3 | 7 | 1 | 5 | 1 | 0 | 0 | 0 | Seq4 | gtgtattactgtAc (SEQ ID NO: 28) |
| 4 | 11 | 2 | 4 | 4 | 1 | 0 | 0 | Seq9 | ATgtattactgtgc (SEQ ID NO: 33) |
| Group | | 25 | 26 | 20 | 5 | 2 | | | |
| Cumulative | | 25 | 51 | 71 | 76 | 78 | | | |

One sequence has five mismatches with sequences 2, 4, and 9; it is scored as best for 2.
Id is the number of the adapter.
Best is the number of sequence for which the identified adapter was the best available.
The rest of the table shows how well the sequences match the adapters. For example, there are 10 sequences that match VHSzy1(Id = 1) with 2 mismatches and are worse for all other adapters. In this sample, 90% come within 2 bases of one of the four adapters.?

TABLE 13

The following list of enzymes was taken from
http://rebase.neb.com/cgi-bin/asymmlist.
I have removed the enzymes that a) cut within the recognition,
b) cut on both sides of the recognition, or c) have fewer than
2 bases between recognition and closest cut site.
REBASE Enzymes
Apr. 13, 2001
Type II restriction enzymes with asymmetric
recognition sequences:

| Enzymes | Recognition Sequence | Isoschizomers | Suppliers |
|---|---|---|---|
| AarI | CACCTGCNNNN^NNNN_ | − | y |
| AceIII | CAGCTCNNNNNNN^NNNN_ | − | − |

TABLE 13-continued

| | | | |
|---|---|---|---|
| Bbr7I | GAAGACNNNNNNN^NNNN_ | — | — |
| BbvI | GCAGCNNNNNNNN^NNNN_ | | y |
| BbvII | GAAGACNN^NNNN_ | | |
| Bce83I | CTTGAGNNNNNNNNNNNNNNN_NN^ | — | — |
| BceAI | ACGGCNNNNNNNNNNN^NN_ | — | y |
| BcefI | ACGGCNNNNNNNNNNN^N_ | — | — |
| BciVI | GTATCCNNNNN_N^ | BfuI | y |
| BfiI | ACTGGGNNNN_N^ | BmrI | y |
| BinI | GGATCNNNN^N_ | | |
| BscAI | GCATCNNNN^NN_ | — | — |
| BseRI | GAGGAGNNNNNNNN_NN^ | — | y |
| BsmFI | GGGACNNNNNNNNNN^NNNN_ | BspLU11III | y |
| BspMI | ACCTGCNNNN^NNNN_ | Acc36I | y |
| EciI | GGCGGANNNNNNNNN_NN^ | — | y |
| Eco57I | CTGAAGNNNNNNNNNNNNNNN_NN^ | BspKT5I | y |
| FauI | CCCGCNNNN^NN_ | BstFZ438I | y |
| FokI | GGATGNNNNNNNNN^NNNN_ | BstPZ418I | y |
| GauI | CTGGAGNNNNNNNNNNNNNN_NN^ | — | y |
| HgaI | GACGCNNNNN^NNNNN_ | — | y |
| HphI | GGTGANNNNNNNN_N^ | AsuHPI | y |
| MboII | GAAGANNNNNNN_N^ | — | y |
| MlyI | GAGTCNNNNN^ | SchI | y |
| MmeI | TCCRACNNNNNNNNNNNNNNNNNNNN_NN^ | — | — |
| MnlI | CCTCNNNNNN_N^ | — | y |
| PleI | GAGTCNNNN^N_ | PpsI | y |
| RleAI | CCCACANNNNNNNNN_NNN^ | — | — |
| SfaNI | GCATCNNNNN^NNNN_ | BspST5I | y |
| SspD5I | GGTGANNNNNNNN^ | — | — |
| Sth132I | CCCGNNNN^NNNN_ | — | — |
| StsI | GGATGNNNNNNNNNN^NNNN_ | — | — |
| TaqII | GACCGANNNNNNNNN_NN^, CACCCANNNNNNNNN_NN^ | — | — |
| Tth111II | CAARCANNNNNNNNN_NN^ | — | — |
| UbaPI | CGAACG | — | — |
| (SEQ ID NOS 359-390, respectively in order of appearance) | | | |

The notation is ^ means cut the upper strand and _ means cut the lower strand. If the upper and lower strand are cut at the same place, then only ^ appears.

TABLE 14

```
(FOKIact)   5'-cAcATccgTg TTgTT cAcggATgTg-3' (SEQ ID NO: 350)
(VHEx881)   5'-AATAgTAgAc TgcAgTgTcc TcAgcccTTA AgcTgTTcAT cTgcAAgTAg-
               AgAgTATTcT TAgAgTTgTc TcTAgAcTTA gTgAAgcg-3' (SEQ ID NO: 351)
| note that VHEx881 is the reverse complement of the ON below
|        [RC]  5'-cgCttcacTaag-
|               Scab........
|               Synthetic 3-23 as in Table 206
|               |TCT|AGA|gac|aac|tct|aag|aat|act|ctc|tac|ttg|cag|atg|-
|               XbaI...
|               |aac|agC|TTA|AGg|gct|gag|gac|aCT|GCA|Gtc|tac|tat|t-3' (SEQ ID NO: 352)
|                         AflIl...
(VHBA881)       5'-cgCttcacTaag-
                |TCT|AGA|gac|aac|tct|aag|aat|act|ctc|tac|ttg|cag|atg|-
                |aac|agC|TTA|AGg|gct|gag|gac|aCT|GCA|Gtc|tac|tat|tgt gcg ag-3' (SEQ ID NO: 353)
(VHBB881)       5'-cgCttcacTaag-
                |TCT|AGA|gac|aac|tct|aag|aat|act|ctc|tac|ttg|cag|atg|-
                |aac|agC|TTA|AGg|gct|gag|gac|aCT|GCA|Gtc|tac|tat|tgt Acg ag-3' (SEQ ID NO: 354)
(VH881PCR)  5'-cgCttcacTaag|TCT|AGA|gac|aac-3' (SEQ ID NO: 355)
```

TABLE 15

Use of FokI as "Universal Restriction Enzyme"

FokI-for dsDNA, | represents sites of cleavage

```
                              sites of cleavage
    5'-cacGGATGtg--nnnnnnn|nnnnnnn-3' (SEQ ID NO: 15)
    3'-gtgCCTACac--nnnnnnnnnnn|nnn-5' (SEQ ID NO: 16)
        RECOG-
        NITion of FokI
```

Case I

```
        5'-...gtg|tatt-actgtgc..Substrate....-3' (SEQ ID NO: 17)
        3'-cac-ataa|tgacacg┐
                      gtGTAGGcac\
                    5'-caCATCCgtg/ (SEQ ID NO: 18)
```

Case II

```
        5'-...gtgtatt|agac-tgc..Substrate....-3' (SEQ ID NO: 19)
               ┌cacataa-tctg|acg-5'
    /gtgCCTACac
    \cacGGATGtg-3' (SEQ ID NO: 20)
```

Case III (Case I rotated 180 degrees)

```
    /gtgCCTACac-5'
    \cacGGATGtg┐
                gtgtctt|acag-tcc-3' Adapter (SEQ ID NO: 21)
              3'-...cacagaa-tgtc|agg..substrate....-5' (SEQ ID NO: 22)
```

Case IV (Case II rotated 180 degrees)

```
                        3'-gtGTAGGcac\ (SEQ ID NO: 23)
                          ┌caCATCCgtg/
            5'-gag|tctc-actgagc
Substrate 3'-...ctc-agag|tgactcg...-5' (SEQ ID NO: 24)
```

Improved FokI adapters
FokI-for dsDNA, | represents sites of cleavage
Case I
Stem 11, loop 5, stem 11, recognition 17

```
        5'-...catgtg|tatt-actgtgc..Substrate....-3' (SEQ ID NO: 1)
        3'-gtacac-ataa|tgacacg┐          ┌T┐
                        gtGTAGGcacG    T
                      5'-caCATCCgtgc    C    (SEQ ID NO: 2)
                                      └TT┘
```

Case II
Stem 10, loop 5, stem 10, recognition 18 (SEQ ID NO: 3)

```
        5'-...gtgtatt|agac-tgctgcc..Substrate....-3'
    ┌T┐      ┌cacataa-tctg|acgacgg-5'
    T    gtgCCTACac
    C    cacGGATGtg-3' (SEQ ID NO: 4)
    └TT┘
```

TABLE 15-continued

Use of FokI as "Universal Restriction Enzyme"

Case III (Case I rotated 180 degrees)
Stem 11, loop 5, stem 11, recognition 20

```
   ┌T┐
 T    TgtgCCTACac-5'  (SEQ ID NO: 5)
 G    AcacGGATGtg┐
 └TT┘           gtgtctt|acag-tccattctg-3' Adapter 3'-...cacagaa-tgtc|aggtaagac..substrate....-5'
                    (SEQ ID NO: 6)
```

Case IV (Case II rotated 180 degrees)
Stem 11, loop 4, stem 11, recognition 17

```
                                    ┌T┐
                        3'-gtGTAGGcacc   T
      (SEQ ID NO: 7)         ┌caCATCCgtgg   T
              5'-atcgag|tctc-actgagc       └T┘
```

Substrate 3'-...tagctc-agag|tgactcg...-5' (SEQ ID NO: 8)

BseRI

```
           (SEQ ID NO: 9)      |sites of cleavage
    5'-cacGAGGAGnnnnnnnnnn|nnnnn-3'
    3'-gtgctcctcnnnnnnnn|nnnnnnn-5'
         RECOG-
         NITion of BseRI
```

Stem 11, loop 5, stem 11, recognition 19

```
                  3'-.......gaacat|cg-ttaagccagta.....5' (SEQ ID NO: 10)
      ┌T—T┐              cttgta-gc|aattcggtcat-3'
      C     GCTGAGGAGTC┘
      T     cgactcctcag-5' An adapter for BseRI to cleave
      └T───┘                      the substrate above.
              (SEQ ID NO: 11)
```

TABLE 16

Human heavy chains bases 88.1 to 94.2

Number of sequences.......... 840
           Number of Mismatchers.........              Probe

| Id | Ntot | 0 | 1 | 2 | 3 | 4 | 5 | 6 | 7 | Name | Sequence | Dot form |
|---|---|---|---|---|---|---|---|---|---|---|---|---|
| 1 | 364 | 152 | 97 | 76 | 26 | 7 | 4 | 2 | 0 | VHS881-1.1 | gctgtgtattactgtgcgag | gctgtgtattactgtgcgag |
| 2 | 265 | 150 | 60 | 33 | 13 | 5 | 4 | 0 | 0 | VHS881-1.2 | gccgtgtattactgtgcgag | ..c................. |
| 3 | 96 | 14 | 34 | 16 | 10 | 5 | 7 | 9 | 1 | VHS881-2.1 | gccgtatattactgtgcgag | ..c..a.............. |
| 4 | 20 | 0 | 3 | 4 | 9 | 2 | 2 | 0 | 0 | VHS881-4.1 | gccgtgtattactgtacgag | ..c...........a.... |
| 5 | 95 | 25 | 36 | 18 | 11 | 2 | 2 | 0 | 1 | VHS881-9.1 | gccatgtattactgtgcgag | ..ca................ |
| | 840 | 341 | 230 | 147 | 69 | 21 | 19 | 11 | 2 | (SEQ ID NOS 391-395, respectively in order of | | |
| | | 341 | 571 | 718 | 787 | 808 | 827 | 838 | 840 | appearance) | | |

88 89 90 91 92 93 94 95 Codon number as in Table 195
     Recognition.......... Stem...... Loop. Stem......

(VHS881-1.1) 5'-gctgtgtat|tact-gtgcgag cAcATccgTg TTgTT cAcggATgTg-3'

(VHS881-1.2) 5'-gccgtgtat|tact-gtgcgag cAcATccgTg TTgTT cAcggATgTg-3'

(VHS881-2.1) 5'-gccgtatat|tact-gtgcgag cAcATccgTg TTgTT cAcggATgTg-3'

(VHS881-4.1) 5'-gccgtgtat|tact-gtacgag cAcATccgTg TTgTT cAcggATgTg-3'

(VHS881-9.1) 5'-gccatgtat|tact-gtgcgag cAcATccgTg TTgTT cAcggATgTg-3'

| site of substrate cleavage

TABLE 16-continued

Human heavy chains bases 88.1 to 94.2

(Sequences in the left column above are SEQ ID NOS 391-395, repectively in order of
appearance; sequences in the right column are all SEQ ID NO: 369)

```
(FOKIact)  5'-cAcATccgTg TTgTT cAcggATgTg-3' (SEQ ID NO: 396)

(VHEx881)  5'-AATAgTAgAc TgcAgTgTcc TcAgcccTTA AgcTgTTcAT cTgcAAgTAg-
              AgAgTATTcT TAgAgTTgTc TcTAgAcTTA gTgAAgcg-3' (SEQ ID NO: 397)
| note that VHEx881 is the reverse complement of the ON below
|      [RC] 5'-cgCttcacTaag-
|           Scab........
|           Synthetic 3-23 as in Table 206
|           |TCT|AGA|gac|aac|tct|aag|aat|act|ctc|tac|ttg|cag|atg|-
|            XbaI...
|           |aac|agC|TTA|AGg|gct|gag|gac|aCT|GCA|Gtc|tac|tat|t-3'
|             AflI1...
(VHBA881)       5'-cgCttcacTaag-
              |TCT|AGA|gac|aac|tct|aag|aat|act|ctc|tac|ttg|cag|atg|-
              |aac|agC|TTA|AGg|gct|gag|gac|aCT|GCA|GTc|tac|tat|tgt gcg ag-3' (SEQ ID NO: 398)
(VHBB881)       5'-cgCttcacTaag-
              |TCT|AGA|gac|aac|tct|aag|aat|act|ctc|tac|ttg|cag|atg|-
              |aac|agC|TTA|AGg|gct|gag|gac|aCT|GCA|GTc|tac|tat|tgt Acg ag-3' (SEQ ID NO: 618)
(VH881PCR) 5'-cgCttcacTaag|TCT|AGA|gac|aac-3' (SEQ ID NO: 399)
```

TABLE 17

Kappa, bases 12-30

| ID | Ntot | 0 | 1 | 2 | 3 | 4 | 5 | 6 | Name | Sequence | Dot Form |
|----|------|---|---|---|---|---|---|---|------|----------|----------|
| 1 | 84 | 40 | 21 | 20 | 1 | 2 | 0 | 0 | SK12O12 | gacccagtctccatcctcc | gacccagtctccatcctcc (residues 26-44 of SEQ ID NO: 400) |
| 2 | 32 | 19 | 3 | 6 | 2 | 1 | 0 | 1 | SK12A17 | gactcagtctccactctcc | ...t.........ct.... (residues 26-44 of SEQ ID NO: 401) |
| 3 | 26 | 17 | 8 | 1 | 0 | 0 | 0 | 0 | SK12A27 | gacgcagtctccaggcacc | ...g.........gg.a.. (residues 26-44 of SEQ ID NO: 402) |
| 4 | 40 | 21 | 18 | 1 | 0 | 0 | 0 | 0 | SK12A11 | gacgcagtctccagccacc | ...g.........g...a.. (residues 26-44 of SEQ ID NO: 403) |
| | 182 | 97 | 50 | 28 | 3 | 3 | 0 | 1 | | | |
| | | 97 | 147 | 175 | 178 | 181 | 181 | 182 | | | |

TABLE 17-continued

Kappa, bases 12-30

```
URE adapters:

Stem......  Loop. Stem......  Recognition........
(SzKB1230-O12)    5'-cAcATccgTg TTgTT cAcggATgTg ggAggATggAgAcTgggTc-3' (SEQ ID NO: 400)
       [RC]  5'-gacccagtctccatcctcc cAcATccgTg AAcAA cAcggATgTg-3'
              Recognition........   Stem......  loop. Stem......
                      FokI.         FokI.

Stem......  Loop. Stem......  Recognition........
(SzKB1230-A17)    5'-cAcATccgTg TTgTT cAcggATgTg ggAgAgTggAgAcTgAgTc-3' (SEQ ID NO: 401)
       [RC]  5'-gactcagtctccactctcc cAcATccgTg AAcAA cAcggATgTg-3'
              Recognition........   Stem......  loop. Stem......
                      FokI.         FokI.

Stem......  Loop. Stem......  Recognition........
(SzKB1230-A27)    5'-cAcATccgTg TTgTT cAcggATgTg ggTgccTggAgAcTgcgTc-3' (SEQ ID NO: 402)
       [RC]  5'-gacgcagtctccaggcacc cAcATccgTg AAcAA cAcggATgTg-3'
              Recognition........   Stem......  loop. Stem......
                      FokI.         FokI.

Stem......  Loop. Stem......  Recognition........
(SzKB1230-A11)    5'-cAcATccgTg TTgTT cAcggATgTg ggTggcTggAgAcTgcgTc-3' (SEQ ID NO: 403)
       [RC]  5'-gacgcagtctccagccacc cAcATccgTg AAcAA cAcggATgTg-3'
              Recognition........   Stem......  loop. Stem......
                      FokI.         FokI.

What happens in the upper strand:

(SzKB1230-O12*)  5'-gac cca gtc|tcc a-tc ctc c-3' (residues 26-44 of SEQ ID NO: 400)
                |     | Site of cleavage in substrate
|
(SzKB1230-A17*)  5'-gac tca gtc|tcc a-ct ctc c-3' (residues 26-44 of SEQ ID NO: 401)
|
(SzKB1230-A27*)  5'-gac gca gtc|tcc a-gg cac c-3' (residues 26-44 of SEQ ID NO: 402)
|
(SzKB1230-A11*)  5'-gac gca gtc|tcc a-gc cac c-3' (residues 26-44 of SEQ ID NO: 403)

(kapextURE)      5'-ccTctactctTgTcAcAgTgcAcAA gAc ATc cAg-3' |sense strand (SEQ ID NO: 404)
                    Scab............ApaLI.

(kapextUREPCR)   5'-ccTctactctTgTcAcAgTg-3' (SEQ ID NO: 405)
                    Scab.............
(kaBRO1UR)       5'-ggAggATggA cTggATgTcT TgTgcAcTgT gAcAAgAgTA gAgg-3' (SEQ ID NO: 406)
       [RC]  5'-ccTctactctTgTcAcAgTgcAcAA gAc ATc cAg tcc a-tc ctc c-3'
              ON above is R.C. of this one
(kaBRO2UR)       5'-ggAgAgTggA cTggATgTcT TgTgcAcTgT gAcAAgAgTA gAgg-3' (SEQ ID NO: 407)
       [RC]  5'-ccTctactctTgTcAcAgTgcAcAA gAc ATc cAg tcc a-tc ctc c-3'
              ON above is R.C. of this one
(kaBRO3UR)       5'-ggTgccTggA cTggATgTcT TgTgcAcTgT gAcAAgAgTA gAgg-3' (SEQ ID NO: 408)
       [RC]  5'-ccTctactctTgTcAcAgTgcAcAA gAc ATc cAg tcc a-gg cac c-3'
              ON above is R.C. of this one
(kaBRO4UR)       5'-ggTggcTggA cTggATgTcT TgTgcAcTgT gAcAAgAgTA gAgg-3' (SEQ ID NO: 409)
       [RC]  5'-ccTctactctTgTcAcAgTgcAcAA gAc ATc cAg tcc a gc cac c-3'
              ON above is R.C. of this one
                    Scab............ApaLI.
```

TABLE 18

Lambda URE adapters bases 13.3 to 19.3

Number of sequences.............. 128
Number of mismatches........

| ID | Ntot | 0 | 1 | 2 | 3 | 4 | 5 | 6 | 7 | 8 | Name | Sequence........... | Dot form........... |
|----|------|---|---|---|---|---|---|---|---|---|------|---------------------|---------------------|
| 1 | 58 | 45 | 7 | 1 | 0 | 0 | 0 | 2 | 2 | 1 | VL133-2a2 | gtctcctggacagtcgatc | gtctcctggacagtcgatc (residues 632-635 of SEQ ID NO: 410) |
| 2 | 16 | 10 | 1 | 0 | 1 | 0 | 1 | 1 | 0 | 2 | VL133-31 | ggccttgggacagacagtc | .g.cttg......a.ag.. (residues 632-635 of SEQ ID NO: 411) |
| 3 | 17 | 6 | 0 | 0 | 0 | 4 | 1 | 1 | 5 | 0 | VL133-2c | gtctcctggacagtcagtc | ................ag.. (residues 632-635 of SEQ ID NO: 412) |
| 4 | 37 | 3 | 0 | 10 | 4 | 4 | 3 | 7 | 4 | 2 | VL133-1c | ggccccagggcagagggtc | .g.c...a..g...ag.g.. (residues 632-635 of SEQ ID NO: 413) |
|   | 128 | 64 | 8 | 11 | 5 | 8 | 5 | 11 | 11 | 5 | | | |
|   |     | 64 | 72 | 83 | 88 | 96 | 101 | 112 | 123 | 128 | | | |

```
              Stem......  Loop. Stem......  Recognition........
(VL133-2a2)  5'-cAcATccgTg TTgTT cAcggATgTg gATcgAcTgTccAggAgAc-3' (SEQ ID NO: 410)
      [RC]  5'-gtctcctggacagtcgatc cAcATccgTg AAcAA cAcggATgTg-3'
              Recognition........  Stem......  loop. Stem......

Stem......  Loop. Stem......  Recognition........
(VL133-31)   5'-cAcATccgTg TTgTT cAcggATgTg gAcTgTcTgTcccAAggcc-3' (SEQ ID NO: 411)
      [RC]  5'-ggccttgggacagacagtc cAcATccgTg AAcAA cAcggATgTg-3'
              Recognition........  Stem......  loop. Stem......

Stem......  Loop. Stem......  Recognition........
(VL133-2c)   5'-cAcATccgTg TTgTT cAcggATgTg gAcTgAcTgTccAggAgAc-3' (SEQ ID NO: 412)
      [RC]  5'-gtctcctggacagtcagtc cAcATccgTg AAcAA cAcggATgTg-3'
              Recognition........  Stem......  loop. Stem......

Stem......  Loop. Stem......  Recognition........
(VL133-1c)   5'-cAcATccgTg TTgTT cAcggATgTg gAcccTcTgcccTggggcc-3' (SEQ ID NO: 413)
      [RC]  5'-ggccccagggcagagggtc cAcATccgTg AAcAA cAcggATgTg-3'
```

What happens in the top strand:

```
           |site of cleavage in the upper strand
(VL133-2a2*) 5'-g tct cct g|ga cag tcg atc (residues 632-635 of SEQ ID NO: 410)

(VL133-31*)  5'-g gcc ttg g|ga cag aca gtc (residues 632-635 of SEQ ID NO: 411)

(VL133-2c*)  5'-g tct cct g|ga cag tca gtc (residues 632-635 of SEQ ID NO: 412)

(VL133-1c*)  5'-g gcc cca g|gg cag agg gtc (residues 632-635 of SEQ ID NO: 413)
```

The following Extenders and Bridges all encode the AA sequence of 2a2 for codons 1-15

```
                  1
(ON_LamEx133) 5'-ccTcTgAcTgAgT gcA cAg- 2  3   4  5   6   7   8   9  10  11 12
             AGt gcT TtA acC caA ccG gcT AGT gtT AGC ggT- 13 14  15
             tcC ccG g| 2a2 (SEQ ID NO: 414)
```

TABLE 18-continued

Lambda URE adapters bases 13.3 to 19.3

```
|                          1
(ON_LamB1-133) [RC] 5'-ccTcTgAcTgAgT gcA cAg-
|
|        2 3    4 5 6 7 8 9 10  11 12
         AGt gcT TtA acC caA ccG gcT AGT gtT AGC ggT-
|
|        13 14 15
         tcC ccG g ga cag tcg at-3'| 2a2 N.B. the actual seq is the
|        (SEQ ID NO: 415)              reverse complement of the
|                                      one shown.
|
(ON_LamB2-133) [RC] 5'-ccTcTgAcTgAgT gcA cAg-
|
|        2 3    4 5 6 7 8 9 10  11 12
         AGt gcT TtA acC caA ccG gcT AGT gtT AGC ggT-
|
|        13 14 15
         tcC ccG g ga cag aca gt-3'| 3l N.B. the actual seq is the
|        (SEQ ID NO: 416)              reverse complement of the
|                                      one shown.
|
|
(ON_LamB3-133) [RC] 5'-ccTcTgAcTgAgT gcA cAg-
|
|        2 3    4 5 6 7 8 9 10  11 12
         AGt gcT TtA acC caA ccG gcT AGT gtT AGC ggT-
|
|        13 14 15
         tcC ccG g ga cag tca gt-3'| 2c N.B. the actual seq is the
|        (SEQ ID NO: 417)              reverse complement of the
|                                      one shown.
|
(ON_LamB4-133) [RC] 5'-ccTcTgAcTgAgT gcA cAg-
|
|        2  3   4 5 6 7 8 9 10  11 12
         AGt gcT TtA acC caA ccG gcT AGT gtT AGC ggT-s
|
|        13 14 15
         tcC ccG g gg cag agg gt-3'| 1c N.B. the actual seq is the
|        (SEQ ID NO: 418)              reverse complement of the
|                                      one shown.
|
(ON_Lam133PCR) 5'-ccTcTgAcTgAgT gcA cAg AGt gc-3' (SEQ ID NO: 419)
```

TABLE 19

Cleavage of 75 human light chains.

| Enzyme | Recognition* | Nch | Ns | Planned location of site |
|---|---|---|---|---|
| AfeI | AGCgct | 0 | 0 | |
| AflII | Cttaag | 0 | 0 | HC FR3 |
| AgeI | Accggt | 0 | 0 | |
| AscI | GGcgcgcc | 0 | 0 | After LC |
| BglII | Agatct | 0 | 0 | |
| BsiWI | Cgtacg | 0 | 0 | |
| BspDI | ATcgat | 0 | 0 | |
| BssHII | Gcgcgc | 0 | 0 | |
| BstBI | TTcgaa | 0 | 0 | |
| DraIII | CACNNNgtg | 0 | 0 | |
| EagI | Cggccg | 0 | 0 | |
| FseI | GGCCGGcc | 0 | 0 | |
| FspI | TGCgca | 0 | 0 | |
| HpaI | GTTaac | 0 | 0 | |
| MfeI | Caattg | 0 | 0 | HC FR1 |
| MluI | Acgcgt | 0 | 0 | |
| NcoI | Ccatgg | 0 | 0 | Heavy chain signal |
| NheI | Gctagc | 0 | 0 | HC/anchor linker |
| NotI | GCggccgc | 0 | 0 | In linker after HC |
| NruI | TCGcga | 0 | 0 | |
| PacI | TTAAttaa | 0 | 0 | |
| PmeI | GTTTaaac | 0 | 0 | |
| PmlI | CACgtg | 0 | 0 | |
| PvuI | CGATcg | 0 | 0 | |

TABLE 19-continued

Cleavage of 75 human light chains.

| Enzyme | Recognition* | Nch | Ns | Planned location of site |
|---|---|---|---|---|
| SacII | CCGCgg | 0 | 0 | |
| SalI | Gtcgac | 0 | 0 | |
| SfiI | GGCCNNNNnggcc | 0 | 0 | Heavy Chain signal (SEQ ID NO: 436) |
| SgfI | GCGATcgc | 0 | 0 | |
| SnaBI | TACgta | 0 | 0 | |
| StuI | AGGcct | 0 | 0 | |
| XbaI | Tctaga | 0 | 0 | HC FR3 |
| AatII | GACGTc | 1 | 1 | |
| AclI | AAcgtt | 1 | 1 | |
| AseI | ATtaat | 1 | 1 | |
| BsmI | GAATGCN | 1 | 1 | |
| BspEI | Tccgga | 1 | 1 | HC FR1 (SEQ ID NO: 437) |
| BstXI | CCANNNNNntgg | 1 | 1 | HC FR2 (SEQ ID NO: 438) |
| DrdI | GACNNNNNngtc | 1 | 1 | |
| HindIII | Aagctt | 1 | 1 | |
| PciI | Acatgt | 1 | 1 | |
| SapI | gaagagc | 1 | 1 | |
| ScaI | AGTact | 1 | 1 | |
| SexAI | Accwggt | 1 | 1 | |
| SpeI | Actagt | 1 | 1 | |
| TliI | Ctcgag | 1 | 1 | |
| XhoI | Ctcgag | 1 | 1 | |
| BcgI | cgannnnnntgc | 2 | 2 | (SEQ ID NO: 439) |
| BlpI | GCtnagc | 2 | 2 | |
| BssSI | Ctcgtg | 2 | 2 | |
| BstAPI | GCANNNNNtgc | 2 | 2 | (SEQ ID NO: 440) |
| EspI | GCtnagc | 2 | 2 | |
| KasI | Ggcgcc | 2 | 2 | |
| PflMI | CCANNNNNtgg | 2 | 2 | (SEQ ID NO: 441) |
| XmnI | GAANNnnttc | 2 | 2 | (SEQ ID NO: 442) |
| ApaLI | Gtgcac | 3 | 3 | LC signal seq |
| NaeI | GCCggc | 3 | 3 | |
| NgoMI | Gccggc | 3 | 3 | |
| PvuII | CAGctg | 3 | 3 | |
| RsrII | CGgwccg | 3 | 3 | |
| BsrBI | GAGcgg | 4 | 4 | |
| BsrDI | GCAATGNNn | 4 | 4 | |
| BstZ17I | GTAtac | 4 | 4 | |
| EcoRI | Gaattc | 4 | 4 | |
| SphI | GCATGc | 4 | 4 | |
| SspI | AATatt | 4 | 4 | |
| AccI | GTmkac | 5 | 5 | |
| BclI | Tgatca | 5 | 5 | |
| BsmBI | Nnnnnngagacg | 5 | 5 | (SEQ ID NO: 443) |
| BsrGI | Tgtaca | 5 | 5 | |
| DraI | TTTaaa | 6 | 6 | |
| NdeI | CAtatg | 6 | 6 | HC FR4 |
| SwaI | ATTTaaat | 6 | 6 | |
| BamHI | Ggatcc | 7 | 7 | |
| SacI | GAGCTc | 7 | 7 | |
| BciVI | GTATCCNNNNNN | 8 | 8 | (SEQ ID NO: 444) |
| BsaBI | GATNNnnatc | 8 | 8 | (SEQ ID NO: 619) |
| NsiI | ATGCAt | 8 | 8 | |
| Bsp120I | Gggccc | 9 | 9 | CH1 |
| ApaI | GGGCCc | 9 | 9 | CH1 |
| PspOMI | Gggccc | 9 | 9 | |
| BspHI | Tcatga | 9 | 11 | |
| EcoRV | GATatc | 9 | 9 | |
| AhdI | GACNNNnngtc | 11 | 11 | (SEQ ID NO: 445) |
| BbsI | GAAGAC | 11 | 14 | |
| PsiI | TTAtaa | 12 | 12 | |
| BsaI | GGTCTCNnnnn | 13 | 15 | (SEQ ID NO: 446) |
| XmaI | Cccggg | 13 | 14 | |
| AvaI | Cycgrg | 14 | 16 | |
| BglI | GCCNNNNnggc | 14 | 17 | (SEQ ID NO: 447) |
| AlwNI | CAGNNNctg | 16 | 16 | |
| BspMI | ACCTGC | 17 | 19 | |
| XcmI | CCANNNNNnnntgg | 17 | 26 | (SEQ ID NO: 448) |
| BstEII | Ggtnacc | 19 | 22 | HC FR4 |
| Sse8387I | CCTGCAgg | 20 | 20 | |
| AvrII | Cctagg | 22 | 22 | |
| HincII | GTYrac | 22 | 22 | |
| BsgI | GTGCAG | 27 | 29 | |
| MscI | TGGcca | 30 | 34 | |
| BseRI | NNnnnnnnnnctcctc | 32 | 35 | (SEQ ID NO: 449) |
| Bsu36I | CCtnagg | 35 | 37 | |
| PstI | CTGCAg | 35 | 40 | |
| EciI | nnnnnnnnntccgcc | 38 | 40 | (SEQ ID NO: 450) |
| PpuMI | RGgwccy | 41 | 50 | |
| StyI | Ccwwgg | 44 | 73 | |
| EcoO109I | RGgnccy | 46 | 70 | |
| Acc65I | Ggtacc | 50 | 51 | |
| KpnI | GGTACc | 50 | 51 | |
| BpmI | ctccag | 53 | 82 | |
| AvaII | Ggwcc | 71 | 124 | |

*cleavage occurs in the top strand after the last upper-case base. For REs that cut palindromic sequences, the lower strand is cut at the symmetrical site.

TABLE 20

Cleavage of 79 human heavy chains

| Enzyme | Recognition | Nch | Ns | Planned location of site |
|---|---|---|---|---|
| AfeI | AGCgct | 0 | 0 | |
| AflII | Cttaag | 0 | 0 | HC FR3 |
| AscI | GGcgcgcc | 0 | 0 | After LC |
| BsiWI | Cgtacg | 0 | 0 | |
| BspDI | ATcgat | 0 | 0 | |
| BssHII | Gcgcgc | 0 | 0 | |
| FseI | GGCCGGcc | 0 | 0 | |
| HpaI | GTTaac | 0 | 0 | |
| NheI | Gctagc | 0 | 0 | HC Linker |
| NotI | GCggccgc | 0 | 0 | In linker, HC/anchor |
| NruI | TCGcga | 0 | 0 | |
| NsiI | ATGCAt | 0 | 0 | |
| PacI | TTAATtaa | 0 | 0 | |
| PciI | Acatgt | 0 | 0 | |
| PmeI | GTTTaaac | 0 | 0 | |
| PvuI | CGATcg | 0 | 0 | |
| RsrII | CGgwccg | 0 | 0 | |
| SapI | gaagagc | 0 | 0 | |
| sfiI | GGCCNNNNnggcc | 0 | 0 | HC signal seq (SEQ ID NO: 420) |
| SgfI | GCGATcgc | 0 | 0 | |
| SwaI | ATTTaaat | 0 | 0 | |
| AclI | AAcgtt | 1 | 1 | |
| AgeI | Accggt | 1 | 1 | |
| AseI | ATtaat | 1 | 1 | |
| AvrII | Cctagg | 1 | 1 | |
| BsmI | GAATGCN | 1 | 1 | |
| BsrBI | GAGcgg | 1 | 1 | |
| BsrDI | GCAATGNNn | 1 | 1 | |
| DraI | TTTaaa | 1 | 1 | |
| FspI | TGCgca | 1 | 1 | |
| HindIII | Aagctt | 1 | 1 | |
| MfeI | Caattg | 1 | 1 | HC FR1 |
| NaeI | GCCggc | 1 | 1 | |
| NgoMI | Gccggc | 1 | 1 | |
| SpeI | Actagt | 1 | 1 | |
| Acc65I | Ggtacc | 2 | 2 | |
| BstBI | TTcgaa | 2 | 2 | |
| KpnI | GGTACc | 2 | 2 | |
| MluI | Acgcgt | 2 | 2 | |
| NcoI | Ccatgg | 2 | 2 | In HC signal seq |
| NdeI | CAtatg | 2 | 2 | HC FR4 |
| PmlI | CACgtg | 2 | 2 | |
| XcmI | CCANNNNNnnntgg | 2 | 2 | (SEQ ID NO: 421) |
| BcgI | cgannnnnntgc | 3 | 3 | (SEQ ID NO: 422) |
| BclI | Tgatca | 3 | 3 | |
| BglI | GCCNNNNnggc | 3 | 3 | (SEQ ID NO: 423) |

TABLE 20-continued

Cleavage of 79 human heavy chains

| Enzyme | Recognition | Nch | Planned Ns of location site |
|---|---|---|---|
| BsaBI | GATNNnnatc | 3 | 3 (SEQ ID NO: 424) |
| BsrGI | Tgtaca | 3 | 3 |
| SnaBI | TACgta | 3 | 3 |
| Sse8387I | CCTGCAgg | 3 | 3 |
| ApaLI | Gtgcac | 4 | 4 LC Signal/FR1 |
| BspHI | Tcatga | 4 | 4 |
| BssSI | Ctcgtg | 4 | 4 |
| PsiI | TTAtaa | 4 | 5 |
| SphI | GCATGc | 4 | 4 |
| AhdI | GACNNNnngtc | 5 | 5 (SEQ ID NO: 425) |
| BspEI | Tccgga | 5 | 5 HC FR1 |
| MscI | TGGcca | 5 | 5 |
| SacI | GAGCTc | 5 | 5 |
| ScaI | AGTact | 5 | 5 |
| SexAI | Accwggt | 5 | 6 |
| SspI | AATatt | 5 | 5 |
| TliI | Ctcgag | 5 | 5 |
| XhoI | Ctcgag | 5 | 5 |
| BbsI | GAAGAC | 7 | 8 |
| BstAPI | GCANNNNntgc | 7 | 8 (SEQ ID NO: 426) |
| BstZ17I | GTAtac | 7 | 7 |
| EcoRV | GATatc | 7 | 7 |
| EcoRI | Gaattc | 8 | 8 |
| BlpI | GCtnagc | 9 | 9 |
| Bsu36I | CCtnagg | 9 | 9 |
| DraIII | CACNNNgtg | 9 | 9 |
| EspI | GCtnagc | 9 | 9 |
| StuI | AGGcct | 9 | 13 |
| XbaI | Tctaga | 9 | 9 HC FR3 |
| Bsp120I | Gggccc | 10 | 11 CH1 |
| ApaI | GGGCCc | 10 | 11 CH1 |
| PspOMI | Gggccc | 10 | 11 |
| BciVI | GTATCCNNNNNN | 11 | 11 (SEQ ID NO: 427) |
| SalI | Gtcgac | 11 | 12 |
| DrdI | GACNNNNnngtc | 12 | 12 (SEQ ID NO: 428) |
| KasI | Ggcgcc | 12 | 12 |
| XmaI | Cccggg | 12 | 14 |
| BglII | Agatct | 14 | 14 |
| HincII | GTYrac | 16 | 18 |
| BamHI | Ggatcc | 17 | 17 |
| PflMI | CCANNNNntgg | 17 | 18 (SEQ ID NO: 429) |
| BsmBI | Nnnnnngagacg | 18 | 21 (SEQ ID NO: 430) |
| BstXI | CCANNNNNNntgg | 18 | 19 HC FR2 (SEQ ID NO: 431) |
| XmnI | GAANNnnttc | 18 | 18 (SEQ ID NO: 432) |
| SacII | CCGCgg | 19 | 19 |
| PstI | CTGCAg | 20 | 24 |
| PvuII | CAGctg | 20 | 22 |
| AvaI | Cycgrg | 21 | 24 |
| EagI | Cggccg | 21 | 22 |
| AatII | GACGTc | 22 | 22 |
| BspMI | ACCTGC | 27 | 33 |
| AccI | GTmkac | 30 | 43 |
| StyI | Ccwwgg | 36 | 49 |
| AlwNI | CAGNNNctg | 38 | 44 |
| BsaI | GGTCTCNnnnn | 38 | 44 (SEQ ID NO: 433) |
| PpuMI | RGgwccy | 43 | 46 |
| BsgI | GTGCAG | 44 | 54 |
| BseRI | NNnnnnnnnnctcctc | 48 | 60 (SEQ ID NO: 434) |
| EciI | nnnnnnnnntccgcc | 52 | 57 (SEQ ID NO: 435) |
| BstEII | Ggtnacc | 54 | 61 HC Fr4, 47/79 have one |
| EcoO109I | RGgnccy | 54 | 86 |
| BpmI | ctccag | 60 | 121 |
| AvaII | Ggwcc | 71 | 140 |

Table 21

```
            MALIA3, annotated
!    MALIA3 9532 bases
! -----------------------------------------------------------------
    (SEQ ID NO: 451)
      1 aat gct act act att agt aga att gat gcc acc ttt tca gct cgc gcc
!         gene ii continued 49 cca aat gaa aat ata gct aaa cag gtt att gac cat ttg cga aat gta 97 tct aat ggt caa act aaa tct act cgt tcg cag aat tgg gaa tca act 145 gtt aca tgg aat gaa act tcc aga cac cgt act tta gtt gca tat tta 193 aaa cat gtt gag cta cag cac cag att cag caa tta agc tct aag cca 241 tcc gca aaa atg acc tct tat caa aag gag caa tta aag gta ctc tct 289 aat cct gac ctg ttg agt ttt gct tcc ggt ctg gtt cgc ttt gaa gct 337 cga att aaa acg cga tat ttg aag tct ttc ggg ctt cct ctt aat ctt 385 ttt gat gca atc cgc ttt gct tct gac tat aat agt cag ggt aaa gac 433 ctg att ttt gat tta tgg tca ttc tcg ttt tct gaa ctg ttt aaa gca 481 ttt gag ggg gat tca ATG aat att tat gac gat tcc gca gta ttg gac
!                    RBS?......   Start gene x, ii continues 529 gct atc cag tct aaa cat ttt act att acc ccc tct ggc aaa act tct 577 ttt gca aaa gcc tct cgc tat ttt ggt ttt atc gtc gtc tgg taa aac 625 gag ggt tat gat agt gtt gct ctt act atg cct cgt aat tcc ttt tgg 673 cgt tat gta tct gca tta gtt gaa tgt ggt att cct aaa tct caa ctg 721 atg aat ctt tct acc tgt aat aat gtt gtt ccg tta gtt cgt ttt att
```

Table 21-continued

```
    769 aac gta gat ttt tct tcc caa cgt cct gac tgg tat aat gag cca gtt 817 ctt aaa atc gca TAA
!                End X & II 832 ggtaattca ca !
  (SEQ ID NO: 623)
!        M1              E5              Q10             T15
    843 ATG att aaa gtt gaa att aaa cca tct caa gcc caa ttt act act cgt
!       Start gene V !
!        S17        S20                  P25             E30
    891 tct ggt gtt tct cgt cag ggc aag cct tat tca ctg aat gag cag ctt !
!                V35             E40             V45
    939 tgt tac gtt gat ttg ggt aat gaa tat ccg gtt ctt gtc aag att act !
!            D50             A55             L60
    987 ctt gat gaa ggt cag cca gcc tat gcg cct ggt cTG TAC Acc gtt cat
!                                                  BsrGI...

!         L65             V70             S75             R80
    1035 ctg tcc tct ttc aaa gtt ggt cag ttc ggt tcc ctt atg att gac cgt !
!                  P85     K87 end of V
    1083 ctg cgc ctc gtt ccg gct aag TAA C !
    1108 ATG gag cag gtc gcg gat ttc gag aca att tat cag gcg atg
!        Start gene VII !
    1150 ata caa atc tcc gtt gta ctt tgt ttc gcg ctt ggt ata atc
!                      VII and IX overlap.
!                 ..... S2  V3  L4  V5 (SEQ ID NO: 624)        S10
    1192 gct ggg ggt caa agA TGA gt gtt tta gtg tat tct ttc gcc tct ttc gtt
!                       End VII
!                       |start IX !         L13     W15                  G20             T25             E29
    1242 tta ggt tgg tgc ctt cgt agt ggc at-
         t acg tat ttt acc cgt tta atg gaa !
    1293 act tcc tc !
!         .... stop of IX, IX and VIII overlap by four bases
    1301 ATG aaa aag tct tta gtc ctc aaa gcc tct gta gcc gtt gct acc ctc
!        Start signal sequence of viii.

!
    1349 gtt ccg atg ctg tct ttc gct gct gag ggt gac gat ccc gca aaa gcg
!                                      mature VIII --->

1397 gcc ttt aac tcc ctg caa gcc tca gcg acc gaa tat atc ggt tat gcg 1445 tgg gcg atg gtt gtt gtc att 1466 gtc ggc gca act atc ggt atc aag ctg ttt aag 1499 aaa ttc acc tcg aaa gca !1515
!            .......... -35 ..

!
    1517      agc tga taaaccgat acaattaaag gctccttttg
!                      ..... -10  ...

!
    1552 gagcctttt ttttGGAGAt ttt !S.D. underlined
```

Table 21-continued

```
!             <------ III signal sequence ----------------------------->
!             M   K   K   L   L   F   A   I   P   L   V  (SEQ ID NO: 452)
     1575 caac GTG aaa aaa tta tta ttc gca att cct tta gtt !1611

!         V   P   F   Y   S   H   S   A   Q
     1612 gtt cct ttc tat tct cac aGT gcA Cag tCT
!                                         ApaLI...

!
     1642 GTC GTG ACG CAG CCG CCC TCA GTG TCT GGG GCC CCA GGG GAG
          AGG GTC ACC ATC TCC TGC ACT GGG AGC AGC TCC AAC ATC GGG GCA
!            BstEII...

1729 GGT TAT GAT GTA CAC TGG TAC CAG CAG CTT CCA GGA ACA GCC CCC AAA

1777 CTC CTC ATC TAT GGT AAC AGC AAT CGG CCC TCA GGG GTC CCT GAC CGA

1825 TTC TCT GGC TCC AAG TCT GGC ACC TCA GCC TCC CTG GCC ATC ACT

1870 GGG CTC GAG GCT GAG GAT GAG GCT GAT TAT

1900 TAC TGC CAG TCC TAT GAC AGC AGC CTG AGT

1930 GGC CTT TAT GTC TTC GGA ACT GGG ACC AAG GTC ACC GTC
!                                                BstEII...

1969 CTA GGT CAG CCC AAG GCC AAC CCC ACT GTC ACT

2002 CTG TTC CCG CCC TCC TCT GAG GAG CTC CAA GCC AAC AAG GCC ACA CTA

2050 GTG TGT CTG ATC AGT GAC TTC TAC CCG GGA GCT GTG ACA GTG GCC TGG

2098 AAG GCA GAT AGC AGC CCC GTC AAG GCG GGA GTG GAG ACC ACC ACA CCC

2146 TCC AAA CAA AGC AAC AAC AAG TAC GCG GCC AGC AGC TAT CTG AGC CTG

2194 ACG CCT GAG CAG TGG AAG TCC CAC AGA AGC TAC AGC TGC CAG GTC ACG

2242 CAT GAA GGG AGC ACC GTG GAG AAG ACA GTG GCC CCT ACA GAA TGT TCA

2290 TAA TAA ACCG CCTCCACCGG GCGCGCCAAT TCTATTTCAA GGAGACAGTC ATA
!                                AscI.....
!           (SEQ ID NO: 453)

!         PelB signal-------------------------------------------->
!          M   K   Y   L   L   P   T   A   A   A   G   L   L   L   L
     2343 ATG AAA TAC CTA TTG CCT ACG GCA GCC GCT GGA TTG TTA TTA CTC !
!                  16  17  18  19  20 21  22
!                   A   A   Q   P   A  M   A
     2388 gcG GCC cag ccG GCC        atg gcc
!            SfiI............
!                    NgoMI...(1/2)
!                            NcoI.........
!
!                                       FR1(DP47/V3-23)---------------
!                                       23  24  25  26  27  28  29  30
!                                        E   V   Q   L   L   E   S   G
     2409                              gaa|gtt|CAA|TTG|tta|gag|tct|ggt|
!                                             |MfeI   |

!
!          --------------FR1----------------------------------------
!          31  32  33  34  35  36  37  38  39  40  41  42  43  44  45
!           G   G   L   V   Q   P   G   G   S   L   R   L   S   C   A
     2433 |ggc|ggt|ctt|gtt|cag|cct|ggt|ggt|tct|tta|cgt|ctt|tct|tgc|gct|

!
!          ----FR1----------------->|...CDR1.................|---FR2------
!          46  47  48  49  50  51  52  53  54  55  56  57  58  59  60
!           A   S   G   F   T   F   S   S   Y   A   M   S   W   V   R
     2478 |gct|TCC|GGA|ttc|act|ttc|tct|tCG|TAC|Gct|atg|tct|tgg|gtt|cgC|
!              |BspEI  |              |BsiWI|                    |BstXI.

!
!          -------FR2--------------------------->|...CDR2.........
```

Table 21-continued

```
         61  62  63  64  65  66  67  68  69  70  71  72  73  74  75
          Q   A   P   G   K   G   L   E   W   V   S   A   I   S   G
    2523 |CAa|gct|ccT|GGt|aaa|ggt|ttg|gag|tgg|gtt|tct|gct|atc|tct|ggt|
         ...BstXI        |

.....CDR2.........................................|---FR3---
          76  77  78  79  80  81  82  83  84  85  86  87  88  89  90
          S   G   G   S   T   Y   Y   A   D   S   V   K   G   R   F
    2568 |tct|ggt|ggc|agt|act|tac|tat|gct|gac|tcc|gtt|aaa|ggt|cgc|ttc|

--------FR3-------------------------------------------------
          91  92  93  94  95  96  97  98  99 100 101 102 103 104 105
          T   I   S   R   D   N   S   K   N   T   L   Y   L   Q   M
    2613 |act|atc|TCT|AGA|gac|aac|tct|aag|aat|act|ctc|tac|ttg|cag|atg|
                    |XbaI   |

---FR3------------------------------------------------------>|
         106 107 108 109 110 111 112 113 114 115 116 117 118 119 120
          N   S   L   R   A   E   D   T   A   V   Y   Y   C   A   K
    2658 |aac|agC|TTA|AGg|gct|gag|gac|aCT|GCA|Gtc|tac|tat|tgc|gct|aaa|
                    |AflII  |           |PstI   |

........CDR3..................|----FR4-----------------------
         121 122 123 124 125 126 127 128 129 130 131 132 133 134 135
          D   Y   E   G   T   G   Y   A   F   D   I   W   G   Q   G
    2703 |gac|tat|gaa|ggt|act|ggt|tat|gct|ttc|gaC|ATA|TGg|ggt|caa|ggt|
                                                 |NdeI   |(1/4)

---------------FR4---------->|
         136 137 138 139 140 141 142
          T   M   V   T   V   S   S
    2748 |act|atG|GTC|ACC|gtc|tct|agt|
                 |BstEII |
! From BstEII onwards, pV323 is same as pCES1, except as noted.
! BstEII sites may occur in light chains; not likely to be unique in fi-
! nal
! vector.

143 144 145 146 147 148 149 150 151 152
                          A   S   T   K   G   P   S   V   F   P
    2769                 gcc tcc acc aaG GGC CCa tcg GTC TTC ccc
                                         Bsp120I.     BbsI...(2/2)
                                         ApaI....

153 154 155 156 157 158 159 160 161 162 163 164 165 166 157
          L   A   P   S   S   K   S   T   S   G   G   T   A   A   L
    2799 ctg gca ccC TCC TCc aag agc acc tct ggg ggc aca gcg gcc ctg
                    BseRI...(2/2)

168 169 170 171 172 173 174 175 176 177 178 179 180 181 182
          G   C   L   V   K   D   Y   F   P   E   P   V   T   V   S
    2844 ggc tgc ctg GTC AAG GAC TAC TTC CCC gaA CCG GTg acg gtg tcg
                                                     AgeI....

183 184 185 186 187 188 189 190 191 192 193 194 195 196 197
          W   N   S   G   A   L   T   S   G   V   H   T   F   P   A
    2889 tgg aac tca GGC GCC ctg acc agc ggc gtc cac acc ttc ccg gct
                     KasI...(1/4)

198 199 200 201 202 203 204 205 206 207 206 209 210 211 212
          V   L   Q   S   S   G   L   Y   S   L   S   S   V   V   T
    2934 gtc cta cag tCt agc GGa ctc tac tcc ctc agc agc gta gtg acc
                         (Bsu36I...) (knocked out)

213 214 215 216 217 218 219 220 221 222 223 224 225 226 227
          V   P   S   S   S   L   G   T   Q   T   Y   I   C   N   V
    2979 gtg ccC tCt tct agc tTG Ggc acc cag acc tac atc tgc aac gtg
                (BstXI..........)N.B. destruction of BstXI & BpmI sites.
```

Table 21-continued

```
!       228 229 230 231 232 233 234 235 236 237 238 239 240 241 242
!        N   H   K   P   S   N   T   K   V   D   K   K   V   E   P
     3024 aat cac aag ccc agc aac acc aag gtg gac aag aaa gtt gag ccc !       243 244 245
!        K   S   C   A   A   A   H   H   H   H   H   S   A
     3069 aaa tct tgt GCG GCC GCt cat cac cac cat cat cac tct gct
!                     NotI......

!        E   Q   K   L   I   S   E   E   D   L   N   G   A   A
     3111 gaa caa aaa ctc atc tca gaa gag gat ctg aat ggt gcc gca !
!        D   I   N   D   D   R   M   A   S   G   A
     3153 GAT ATC aac gat gat cgt atg gct AGC ggc ggc
!        rEK cleavage site.......... NheI... KasI...
!        EcoRV..

! Domain 1 ------------------------------------------------------------
!        A   E   T   V   E   S   C   L   A
     3183 gct gaa act gtt gaa agt tgt tta gca !
!        K   p   H   T   E   N   S   F
     3210 aaa ccc cat aca gaa aat tca ttt !        T   N   V   W   K   D   D   K   T
     3234 aCT AAC GTC TGG AAA GAC GAC AAA ACt !        L   D   R   Y   A   N   Y   E   G   C   L   W   N   A   T   G   V
     3261 tta gat cgt tac gct aac tat gag ggt-
              tgt ctg tgG AAT GCt aca ggc gtt
!                                                       BsmI !        V   V   C   T   G   D   E   T   Q   C   Y   G   T   W   V   P   I
     3312 gta gtt tgt act ggt GAC GAA ACT CAG T-
              GT TAC GGT ACA TGG GTT cct att !        G   L   A   I   P   E   N
     3363 ggg ctt gct atc cct gaa aat ! L1 linker -----------------------------------
!        E   G   G   G   S   E   G   G   G   S
     3384 gag ggt ggt ggc tct gag ggt ggc ggt tct !        E   G   G   G   S   E   G   G   G   T
     3414 gag ggt ggc ggt tct gag ggt ggc ggt act ! Domain 2 ------------------------------------

3444 aaa cct cct gag tac ggt gat aca c-
              ct att ccg ggc tat act tat atc aac 3495 cct ctc gac ggc act tat ccg cct gg-
              t act gag caa aac ccc gct aat cct 3546 aat cct tct ctt GAG GAG tct cag c-
              ct ctt aat act ttc atg ttt cag aat
!                         BseRI_

3597 aat agg ttc cga aat agg cag ggg gca tta act gtt tat acg ggc act 3645 gtt act caa ggc act gac ccc gtt aaa act tat tac cag tac act cct 3693 gta tca tca aaa gcc atg tat gac gct tac tgg aac ggt aaa ttC AGA
!                                                                    AlwNI
```

Table 21-continued

```
   3741 GAC TGc gct ttc cat tct ggc ttt aat gaa gat cca ttc gtt tgt gaa
!       AlwNI 3789 tat caa ggc caa tcg tct gac ctg cct caa cct cct gtc aat gct !
   3834 ggc ggc ggc tct
! start L2 ----------------------------------------------------------

3846 ggt ggt ggt tct 3858 ggt ggc ggc tct 3870 gag ggt ggt ggc tct gag ggt ggc ggt tct 3900 gag ggt ggc ggc tct gag gga ggc ggt tcc 3930 ggt ggt ggc tct ggt    |end L2

!
! Domain 3 --------------------------------------------------------
(SEQ ID NO: 454)
!       S   G   D   F   D   Y   E   K   M   A   N   A   N   K   G   A
   3945 tcc ggt gat ttt gat tat gaa aag atg gca aac gct aat aag ggg gct !
!       M   T   E   N   A   D   E   N   A   L   Q   S   D   A   K   G
   3993 atg acc gaa aat gcc gat gaa aac gcg cta cag tct gac gct aaa ggc !
!       K   L   D   S   V   A   T   D   Y   G   A   A   I   D   G   F
   4041 aaa ctt gat tct gtc gct act gat tac ggt gct gct atc gat ggt ttc !
!       I   G   D   V   S   G   L   A   N   G   N   G   A   T   G   D
   4089 att ggt gac gtt tcc ggc ctt gct aat ggt aat ggt gct act ggt gat !
!       F   A   G   S   N   S   Q   M   A   Q   V   G   D   G   D   N
   4137 ttt gct ggc tct aat tcc caa atg gct caa gtc ggt gac ggt gat aat !
!       S   P   L   M   N   N   F   R   Q   Y   L   P   S   L   P   Q
   4185 tca cct tta atg aat aat ttc cgt caa tat tta cct tcc ctc cct caa !
!       S   V   E   C   R   P   F   V   F   S   A   G   K   P   Y   E
   4233 tcg gtt gaa tgt cgc cct ttt gtc ttt agc gct ggt aaa cca tat gaa !
!       F   S   I   D   C   D   K   I   N   L   F   R
   4281 ttt tct att gat tgt gac aaa ata aac tta ttc cgt
!                                                     End Domain 3

!       G   V   F   A   F   L   L   Y   V   A   T   F   M   Y   V   F140
   4317 ggt gtc ttt gcg ttt ctt tta tat gtt gcc acc ttt atg tat gta ttt
!       start transmembrane segment !
!       S   T   F   A   N   I   L
   4365 tct acg ttt gct aac ata ctg !
!       R   N   K   E   S
   4386 cgt aat aag gag tct TAA !stop of iii
!       Intracellular anchor.

!
            (SEQ ID NO: 455)
!           M1  P2  V   L   L5  G   I   P   L10 L   R   F   G15
    4404 tc ATG cca gtt ctt ttg ggt att ccg tta tta ttg cgt ttc ctc ggt
!          Start VI !
    4451 ttc ctt ctg gta act ttg ttc ggc tat ctg ctt act ttt ctt aaa aag 4499 ggc ttc ggt aag ata gct att gct att tca ttg ttt ctt gct ctt att 4547 att ggg ctt aac tca att ctt gtg ggt tat ctc tct gat att agc gct
```

Table 21-continued

```
4595 caa tta ccc tct gac ttt gtt cag ggt gtt cag tta att ctc ccg tct 4643 aat gcg ctt ccc tgt ttt tat gtt att ctc tct gta aag gct gct att 4691 ttc att ttt gac gtt aaa caa aaa atc gtt tct tat ttg gat tgg gat (SEQ ID NO: 456)
              M1  A2  V3      F5                      L10         G13
4739 aaa TAA t ATG gct gtt tat ttt gta act ggc aaa tta ggc tct gga
     end VI   Start gene I 14  15  16  17  18  19  20  21  22  23  24  25  26  27  28
       K   T   L   V   S   V   G   K   I   Q   D   K   I   V   A
4785 aag acg ctc gtt agc gtt ggt aag att cag gat aaa att gta gct 29  30  31  32  33  34  35  36  37  38  39  40  41  42  43
       G   C   K   I   A   T   N   L   D   R   L   Q   N   L
4830 ggg tgc aaa ata gca act aat ctt gat tta agg ctt caa aac ctc 44  45  46  47  48  49  50  51  52  53  54  55  56  57  58
       P   Q   V   G   R   F   A   K   T   P   R   V   L   R   I
4875 ccg caa gtc ggg agg ttc gct aaa acg cct cgc gtt ctt aga ata 59  60  61  62  63  64  65  66  67  68  69  70  71  72  73
       P   D   K   P   S   I   S   D   L   L   A   I   G   R   G
4920 ccg gat aag cct tct ata tct gat ttg ctt gct att ggg cgc ggt 74  75  76  77  78  79  80  81  82  83  84  85  86  87  88
       N   D   S   Y   D   E   N   K   N   G   L   L   V   L   D
4965 aat gat tcc tac gat gaa aat aaa aac ggc ttg ctt gtt ctc gat 89  90  91  92  93  94  95  96  97  98  99 100 101 102 103
       E   C   G   T   W   F   N   T   R   S   W   N   D   K   E
5010 gag tgc ggt act tgg ttt aat acc cgt tct tgg aat gat aag gaa 104 105 106 107 108 109 110 111 112 113 114 115 116 117 118
       R   Q   P   I   I   D   W   F   L   H   A   R   K   L   G
5055 aga cag ccg att att gat tgg ttt cta cat gct cgt aaa tta gga 119 120 121 122 123 124 125 126 127 128 129 130 131 132 133
       W   D   I   I   F   L   V   Q   D   L   S   I   V   D   K
5100 tgg gat att att ttt ctt gtt cag gac tta tct att gtt gat aaa 134 135 136 137 138 139 140 141 142 143 144 145 146 147 148
       Q   A   R   S   A   L   A   E   H   V   V   Y   C   R   R
5145 cag gcg cgt tct gca tta gct gaa cat gtt gtt tat tgt cgt cgt 149 150 151 152 153 154 155 156 157 158 159 160 161 162 163
       L   D   R   I   T   L   P   F   V   G   T   L   Y   S   L
5190 ctg gac aga att act tta cct ttt gtc ggt act tta tat tct ctt 164 165 166 167 168 169 170 171 172 173 174 175 176 177 178
       I   T   G   S   K   M   P   L   P   K   L   H   V   G   V
5235 att act ggc tcg aaa atg cct ctg cct aaa tta cat gtt ggc gtt 179 180 181 182 183 184 185 186 187 188 189 190 191 192 193
       V   K   Y   G   D   S   Q   L   S   P   T   V   E   R   W
5280 gtt aaa tat ggc gat tct caa tta agc cct act gtt gag cgt tgg 194 195 196 197 198 199 200 201 202 203 204 205 206 207 208
       L   Y   T   G   K   N   L   Y   N   A   Y   D   T   K   Q
5325 ctt tat act ggt aag aat ttg tat aac gca tat gat act aaa cag 209 210 211 212 213 214 215 216 217 218 219 220 221 222 223
```

Table 21-continued

```
!         A   F   S   S   N   Y   D   S   G   V   Y   S   Y   L   T
    5370 gct ttt tct agt aat tat gat tcc ggt gtt tat tct tat tta acg !
!         224 225 226 227 228 229 230 231 232 233 234 235 236 237 238
!          P   Y   L   S   H   G   R   Y   F   K   P   L   N   L   G
    5415 cct tat tta tca cac ggt cgg tat ttc aaa cca tta aat tta ggt !
!         239 240 241 242 243 244 245 246 247 248 249 250 251 252 253
!          Q   K   M   K   L   T   K   I   Y   L   K   K   F   S   R
    5460 cag aag atg aaa tta act aaa ata tat ttg aaa aag ttt tct cgc !
!         254 255 256 257 258 259 260 261 262 263 264 265 266 267 268
!          V   L   C   L   A   I   G   F   A   S   A   F   T   Y   S
    5505 gtt ctt tgt ctt gcg att gga ttt gca tca gca ttt aca tat agt !
!         269 270 271 272 273 274 275 276 277 278 279 280 281 282 283
!          Y   I   T   Q   P   K   P   E   V   K   K   V   V   S   Q
    5550 tat ata acc caa cct aag ccg gag gtt aaa aag gta gtc tct cag !
!         284 285 286 287 288 289 290 291 292 293 294 295 296 297 298
!          T   Y   D   F   D   K   F   T   I   D   S   S   Q   R   L
    5595 acc tat gat ttt gat aaa ttc act att gac tct tct cag cgt ctt !
!         299 300 301 302 303 304 305 306 307 308 309 310 311 312 313
!          N   L   S   Y   R   Y   V   F   K   D   S   K   G   K   L
    5640 aat cta agc tat cgc tat gtt ttc aag gat tct aag gga aaa TTA
!                                                                  PacI !
!         314 315 316 317 318 319 320 321 322 323 324 325 326 327 328
!          I   N   S   D   D   L   Q   K   Q   G   Y   S   L   T   Y
    5685 ATT AAt agc gac gat tta cag aag caa ggt tat tca ctc aca tat
!         PacI !
!         329 330 331 332 333 334 335 336 337 338 339 340 341 342 343
!          i   I   D   L   C   T   V   S   I   K   K   G   N   S   E
                                                          (SEQ ID NO: 620)
!   iv                                                            M1  K
    5730 att gat tta tgt act gtt tcc att aaa aaa ggt aat tca aAT Gaa
!                                                              Start IV !
!         344 345 345 347 348 349
!          i   I   V   K   C   N   .End of I
!   iv    L3  L   N5  V   I7  N   F   V10
    5775 att gtt aaa tgt aat TAA T TTT GTT
! IV continued.....

5800 ttc ttg atg ttt gtt tca tca tct tct ttt gct cag gta att gaa atg 5848 aat aat tcg cct ctg cgc gat ttt gta act tgg tat tca aag caa tca 5896 ggc gaa tcc gtt att gtt tct ccc gat gta aaa ggt act gtt act gta 5944 tat tca tct gac gtt aaa cct gaa aat cta cgc aat ttc ttt att tct 5992 gtt tta cgt gct aat aat ttt gat atg gtt ggt tca att cct tcc ata 6040 att cag aag tat aat cca aac cat cag gat tat att gat gaa ttg cca 6088 tca tct gat aat cag gaa tat gat gat aat tcc gct cct tct ggt ggt 6136 ttc ttt gtt ccg caa aat gat aat gtt act caa act ttt aaa att aat 6184 aac gtt cgg gca aag gat tta ata cga gtt gtc gaa ttg ttt gta aag 6232 tct aat act tct aaa tcc tca aat gta tta tct att gac ggc tct aat 6280 cta tta gtt gtt TCT gca cct aaa gat att tta gat aac ctt cct caa
!                       ApeLI removed 6328 ttc ctt tct act gtt gat ttg cca act gac cag ata ttg att gag ggt
```

Table 21-continued

```
6376 ttg ata ttt gag gtt cag caa ggt gat gct tta gat ttt tca ttt gct 6424 gct ggc tct cag cgt ggc act gtt gca ggc ggt gtt aat act gac cgc 6472 ctc acc tct gtt tta tct tct gct ggt ggt tcg ttc ggt att ttt aat 6520 ggc gat gtt tta ggg cta tca gtt cgc gca tta aag act aat agc cat 6568 tca aaa ata ttg tct gtg cca cgt att ctt acg ctt tca ggt cag aag 6616 ggt tct atc tct gtT GGC CAg aat gtc cct ttt att act ggt cgt gtg
!                      MscI____

6664 act ggt gaa tct gcc aat gta aat aat cca ttt cag acg att gag cgt 6712 caa aat gta ggt att tcc atg agc gtt ttt cct gtt gca atg gct ggc 6760 ggt aat att gtt ctg gat att acc agc aag gcc gat agt ttg agt tct 6808 tct act cag gca agt gat gtt att act aat caa aga agt att gct aca 6856 acg gtt aat ttg cgt gat gga cag act ctt tta ctc ggt ggc ctc act 6904 gat tat aaa aac act tct caa gat tct ggc gta ccg ttc ctg tct aaa 6952 atc cct tta atc ggc ctc ctg ttt agc tcc cgc tct gat tcc aac gag 7000 gaa agc acg tta tac gtg ctc gtc aaa gca acc ata gta cgc gcc ctg 7048 TAG cggcgcatt
!    End IV 7060 aagcgcggcg ggtgtggtgg ttacgcgcag cctgaccgct acacttgcca gcgccctagc 7120
gcccgctcct ttcgctttct tcccttcctt tctcgccacg ttcGCCGGCt ttccccgtca
!                                                 NgoMI_

7180 agctctaaat cgggggctcc ctttagggtt ccgatttagt gctttacggc acctcgaccc 7240 caaaaaactt gatttgggtg atggttCACG TAGTGggcca tcgccctgat agacggtttt
!                                 DraIII_____

7300 tcgccctttG ACGTTGGAGT Ccacgttctt taatagtgga ctcttgttcc aaactggaac
!              DrdI_____

7360 aacactcaac cctatctcgg gctattcttt tgatttataa gggattttgc cgatttcgga 7420 accaccatca aacaggattt tcgcctgctg gggcaaacca gcgtggaccg cttgctgcaa 7480 ctctctccgg gccaggcggt gaagggcaat CAGCTGttgc cCGTCTCact ggtgaaaaga
!                                  PvuII.      BamBI.

7540 aaaaccaccc tGGATCC    AAGCTT
!                BamHI    HindIII (1/2)
!                Insert carrying bla gene 7563    gcaggtg gcactttcg gggaaatgtg cgcggaaccc
7600 ctatttgttt attttctaa atacattcaa atatGTATCC gctcatgaga caataaccct
                                         BciVI 7660 gataaatgct tcaataatat tgaaaaAGGA AGAgt
!                                   RBS.?...

!    Start bla gene

7695 ATG agt att caa cat ttc cgt gtc gc-
     c ctt att ccc ttt ttt gcg gca ttt 7746 tgc ctt cct gtt ttt gct cac cca-
     gaa acg ctg gtg aaa gta aaa gat gct 7797 gaa gat cag ttg ggC gCA CGA Gtg ggt-
     tac atc gaa ctg gat ctc aac agc
!                  BsssI...
!              ApaLI removed 7848 ggt aag atc ctt gag agt ttt cgc-
     ccc gaa gaa cgt ttt cca atg atg agc
```

Table 21-continued

```
7699 act ttt aaa gtt ctg cta tgt cat aca c-
     ta tta tcc cgt att gac gcc ggg 7950 caa gaG CAA CTC GGT CGc cgg gcg cgg-
     tat tct cag aat gac ttg gtt gAG                                              ScaI
             BcgI_____

8001 TAC Tca cca gtc aca gaa aag cat ct-
     t acg gat ggc atg aca gta aga gaa
     ScaI_

8052 tta tgc agt gct gcc ata acc atg agt-
     gat aac act gcg gcc aac tta ctt 8103 ctg aca aCG ATC Gga gga ccg aag-
     gag cta acc gct ttt ttg cac aac atg
             PvuI____

8154 ggg gat cat gta act cgc ctt gat cgt-
     tgg gaa ccg gag ctg aat gaa gcc 8205 ata cca aac gac gag cgt gac acc ac-
     g atg cct gta gca atg cca aca acg 8256 tTG CGC Aaa cta tta act ggc gaa c-
     ta ctt act cta gct tcc cgg caa caa
     FspI....

8307 tta ata gac tgg atg gag gcg-
     gat aaa gtt gca gga cca ctt ctg cgc tcg

8358 GCC ctt ccG GCt ggc tgg ttt att gct-
     gat aaa tct gga gcc ggt gag cgt
     BglI_____

8409 gGG TCT Cgc ggt atc att gca g-
     ca ctg ggg cca gat ggt aag ccc tcc cgt
     BsaI____

8460 atc gta gtt atc tac acG ACg ggg aGT-
     Cag gca act atg gat gaa cga aat
                       AhdI_____

8511 aga cag atc gct gag ata ggt gcc tca ctg att aag cat tgg TAA ctgt
                                                             stop 8560 cagaccaagt ttactcatat atactttaga ttgatttaaa acttcatttt taatttaaaa 8620
ggatctaggt gaagatcctt tttgataatc tcatgaccaa aatcccttaa cgtgagtttt 8680
cgttccactg tacgtaagac cccc 8704 AAGCTT    GTCGAC tgaa tggcgaatgg cgctttgcct
     HindIII  SalI..
     (2/2)    HincII 8740 ggtttccggc accagaagcg gtgccggaaa gctggctgga gtgcgatctt 8790 CCTGAGG
     Bsu36I_

8797      ccgat actgtcgtcg tcccctcaaa ctggcagatg 8832 cacggttacg atgcgcccat ctacaccaac gtaacctatc ccattacggt caatccgccg 8892 tttgttccca cggagaatcc gacgggttgt tactcgctca catttaatgt tgatgaaagc 8952 tggctacagg aaggccgac gcgaattatt tttgatgcg ttcctattgg ttaaaaaatg 9012 agctgattta acaaaaattt aacgcgaatt ttaacaaaat attaacgttt acaATTTAAA SwaI...
9072 Tatttgctta tacaatcttc ctgtttttgg ggcttttctg attatcaacc GGGGTAcat
                                                           RBS?

9131 ATG att gac atg cta gtt tta cga tta c-
     cg ttc atc gat tct ctt gtt tgc
     Start gene II
```

Table 21-continued

```
9182 tcc aga ctc tca ggc aat gac ctg at-
     a gcc ttt gtA GAT CTc tca aaa ata                    BglII...
!

9233 gct acc ctc tcc ggc atg aat tta t-
     ca gct aga acg gtt gaa tat cat att 9284 gat ggt gat ttg act gtc tcc ggc-
     ctt tct cac cct ttt gaa tct tta cct 9335 aca cat tac tca ggc att gca tt-
     t aaa ata tat gag ggt tct aaa aat ttt 9386 tat cct tgc gtt gaa ata aag gct tct c-
     cc gca aaa gta tta cag ggt cat 9437 aat gtt ttt ggt aca acc gat tta gct t-
     ta tgc tct gag gct tta ttg ctt 9488 aat ttt gct aat tct ttg cct tgc ctg tat gat tta ttg gat gtt !9532
! gene II continues
```

Table 21B: Sequence of MALIA3, condensed

```
LOCUS
ORIGIN  MALIA3     9532          CIRCULAR
```

(SEQ ID NO: 451)

```
   1  AATGCTACTA CTATTAGTAG AATTGATGCC ACCTTTTCAG CTCGCGCCCC AAATGAAAAT
  61  ATAGCTAAAC AGGTTATTGA CCATTTGCGA AATGTATCTA ATGGTCAAAC TAAATCTACT
 121  CGTTCGCAGA ATTGGGAATC AACTGTTACA TGGAATGAAA CTTCCAGACA CCGTACTTTA
 181  GTTGCATATT TAAAACATGT TGAGCTACAG CACCCGATTC AGCAATTAAG CTCTAAGCCA
 241  TCCGCAAAAA TGACCTCTTA TCAAAGGAG CAATTAAAGG TACTCTCTAA TCCTGACCTG
 301  TTGGAGTTTG CTTCCGGTCT GGTTCGCTTT GAAGCTCGAA TTAAAACGCG ATATTTGAAG
 361  TCTTTCGGGC TTCCTCTTAA TCTTTTTGAT GCAATCCGCT TTGCTTCTGA CTATAATAGT
 421  CAGGGTAAAG ACCTGATTTT TGATTTATGG TCATTCTCGT TTTCTGAACT GTTTAAAGCA
 481  TTTGAGGGGG ATTCAATGAA TATTTATGAC GATTCCGCAG TATTGGACGC TATCCAGTCT
 541  AAACATTTTA CTATTACCCC CTCTGGCAAA ACTTCTTTTG CAAAAGCCTC TCGCTATTTT
 601  GGTTTTTATC GTCGTCTGGT AAACGAGGGT TATGATAGTG TTGCTCTTAC TATGCCTCGT
 661  AATTCCTTTT GGCGTTATGT ATCTGCATTA GTTGAATGTG GTATTCCTAA ATCTCAACTG
 721  ATGAATCTTT CTACCTGTAA TAATGTTGTT CCGTTAGTTC GTTTTATTAA CGTAGATTTT
 781  TCTTCCCAAC GTCCTGACTG GTATAATGAG CCAGTTCTTA AAATCGCATA AGGTAATTCA
 841  CAATGATTAA AGTTGAAATT AAACCATCTC AAGCCCAATT TACTACTCGT TCTGGTGTTT
 901  CTCGTCAGGG CAAGCCTTAT TCACTGAATG AGCAGCTTTG TTACGTTGAT TTGGGTAATG
 961  AATATCCGGT TCTTGTCAAG ATTACTCTTG ATGAAGGTCA GCCAGCCTAT GCGCCTGGTC
1021  TGTACACCGT TCATCTGTCC TCTTTCAAAG TTGGTCAGTT CGGTTCCCTT ATGATTGACC
1081  GTCTGCGCCT CGTTCCGGCT AAGTAACATG GAGCAGGTCG CGGATTTCGA CACAATTTAT
1141  CAGGCGATGA TACAAATCTC CGTTGTACTT TGTTTCGCGC TTGGTATAAT CGCTGGGGGT
1201  CAAAGATGAG TGTTTTAGTG TATTCTTTCG CCTCTTTCGT TTAGGTTGG TGCCTTCGTA
1261  GTGGCATTAC GTATTTTACC CGTTTAATGG AAACTTCCTC ATGAAAAAGT CTTTAGTCCT
1321  CAAAGCCTCT GTAGCCGTTG CTACCCTCGT TCCGATGCTG TCTTTCGCTG CTGAGGGTGA
1381  CGATCCCGCA AAAGCGGCCT TTAACTCCCT GCAAGCCTCA GCGACCGAAT ATATCGGTTA
1441  TGCGTGGGCG ATGGTTGTTG TCATTGTCGG CGCAACTATC GGTATCAAGC TGTTTAAGAA
1501  ATTCACCTCG AAAGCAAGCT GATAAACCGA TACAATTAAA GGCTCCTTTT GGAGCCTTTT
```

Table 21-continued

```
1561  TTTTTGGAGA TTTTCAACGT GAAAAAATTA TTATTCGCAA TTCCTTTAGT TGTTCCTTTC
1621  TATTCTCACA GTGCACAGTC TGTCGTGACG CAGCCGCCCT CAGTGTCTGG GGCCCCAGGG
1681  CAGAGGGTCA CCATCTCCTG CACTGGGAGC AGCTCCAACA TCGGGGCAGG TTATGATGTA
1741  CACTGGTACC AGCAGCTTCC AGGAACAGCC CCCAAACTCC TCATCTATGG TAACAGCAAT
1801  CGGCCCTCAG GGGTCCCTGA CCGATTCTCT GGCTCCAAGT CTGGCACCTC AGCCTCCCTG
1861  GCCATCACTG GCTCCAGGC TGAGGATGAG GCTGATTATT ACTGCCAGTC CTATGACAGC
1921  AGCCTGAGTG GCCTTTATGT CTTCGGAACT GGGACCAAGG TCACCGTCCT AGGTCAGCCC
1981  AAGGCCAACC CCACTGTCAC TCTGTTCCCG CCCTCCTCTG AGGAGCTCCA AGCCAACAAG
2041  GCCACACTAG TGTGTCTGAT CAGTGACTTC TACCCGGGAG CTGTGACAGT GGCCTGGAAG
2101  GCAGATAGCA GCCCCGTCAA GGCGGGAGTG GAGACCACCA CACCCTCCAA ACAAAGCAAC
2161  AACAAGTACG CGGCCAGCAG CTATCTGAGC CTGACGCCTG AGCAGTGGAA GTCCCACAGA
2221  AGCTACAGCT GCCAGGTCAC GCATGAAGGG AGCACCGTGG AGAAGACAGT GGCCCCTACA
2281  GAATGTTCAT AATAAACCGC CTCCACCGGG CGCGCCAATT CTATTTCAAG GAGACAGTCA
2341  TAATGAAATA CCTATTGCCT ACGGCAGCCG CTGGATTGTT ATTACTCGCG CCCAGCCGG
2401  CCATGGCCGA AGTTCAATTG TTAGAGTCTG GTGGCGGTCT TGTTCAGCCT GGTGGTTCTT
2461  TACGTCTTTC TTGCGCTGCT TCCGGATTCA CTTTCTCTTC GTACGCTATG TCTTGGGTTC
2521  GCCAAGCTCC TGGTAAAGGT TTGGAGTGGG TTTCTGCTAT CTCTGGTTCT GGTGGCAGTA
2581  CTTACTATGC TGACTCCGTT AAAGGTCGCT TCACTATCTC TAGAGACAAC TCTAAGAATA
2641  CTCTCTACTT GCAGATGAAC AGCTTAAGGG CTGAGGACAC TGCAGTCTAC TATTGCGCTA
2701  AAGACTATGA AGGTACTGGT TATGCTTTCG ACATATGGGG TCAAGGTACT ATGGTCACCG
2761  TCTCTAGTGC CTCCACCAAG GGCCCATCGG TCTTCCCCCT GGCACCCTCC TCCAAGAGCA
2821  CCTCTGGGGG CACAGCGGCC CTGGGCTGCC TGGTCAAGGA CTACTTCCCC GAACCGGTGA
2881  CGGTGTCGTG GAACTCAGGC GCCCTGACCA GCGGCGTCCA CACCTTCCCG GCTGTCCTAC
2941  AGTCTAGCGG ACTCTACTCC CTCAGCAGCG TAGTGACCGT GCCCTCTTCC AGCTTGGGCA
3001  CCCAGACCTA CATCTGCAAC GTGAATCACA AGCCCAGCAA CACCAAGGTG GACAAGAAAG
3061  TTGAGCCCAA ATCTTGTGCG GCCGCTCATC ACCACCATCA TCACTCTGCT GAACAAAAAC
3121  TCATCTCAGA AGAGGATCTG AATGGTGCCG CAGATATCAA CGATGATCGT ATGGCTGGCG
3181  CCGCTGAAAC TGTTGAAAGT TGTTTAGCAA AACCCATAC AGAAAATTCA TTTACTAACG
3241  TCTGGAAAGA CGACAAAACT TTAGATCGTT ACGCTAACTA TGAGGGTTGT CTGTGGAATG
3301  CTACAGGCGT TGTAGTTTGT ACTGGTGACG AAACTCAGTG TTACGGTACA TGGGTTCCTA
3361  TTGGGCTTGC TATCCCTGAA AATGAGGGTG GTGGCTCTGA GGGTGGCGGT TCTGAGGGTG
3421  GCGGTTCTGA GGGTGGCGGT ACTAAACCTC CTGAGTACGG TGATACACCT ATTCCGGGCT
3481  ATACTTATAT CAACCCTCTC GACGGCACTT ATCCGCCTGG TACTGAGCAA AACCCCGCTA
3541  ATCCTAATCC TTCTCTTGAG GAGTCTCAGC CTCTTAATAC TTTCATGTTT CAGAATAATA
3601  GGTTCCGAAA TAGGCAGGGG GCATTAACTG TTTATACGGG CACTGTTACT CAAGGCACTG
3661  ACCCCGTTAA AACTTATTAC CAGTACACTC CTGTATCATC AAAAGCCATG TATGACGCTT
3721  ACTGGAACGG TAAATTCAGA GACTGCGCTT CCATTCTGG CTTTAATGAA GATCCATTCG
3781  TTTGTGAATA TCAAGGCCAA TCGTCTGACC TGCCTCAACC TCCTGTCAAT GCTGGCGGCG
3841  GCTCTGGTGG TGGTTCTGGT GGCGGCTCTG AGGGTGGTGG CTCTGAGGGT GGCGGTTCTG
3901  AGGGTGGCGG CTCTGAGGGA GGCGGTTCCG GTGGTGGCTC TGGTTCCGGT GATTTTGATT
```

Table 21-continued

```
3961  ATGAAAAGAT GGCAAACGCT AATAAGGGGG CTATGACCGA AAATGCCGAT GAAAACGCGC
4021  TACAGTCTGA CGCTAAAGGC AAACTTGATT CTGTCGCTAC TGATTACGGT GCTGCTATCG
4081  ATGGTTTCAT TGGTGACGTT TCCGGCCTTG CTAATGGTAA TGGTGCTACT GGTGATTTTG
4141  CTGGCTCTAA TTCCCAAATG GCTCAAGTCG GTGACGGTGA TAATTCACCT TTAATGAATA
4201  ATTTCCGTCA ATATTTACCT TCCCTCCCTC AATCGGTTGA ATGTCGCCCT TTTGTCTTTA
4261  GCGCTGGTAA ACCATATGAA TTTTCTATTG ATTGTGACAA AATAAACTTA TTCCGTGGTG
4321  TCTTTGCGTT TCTTTTATAT GTTGCCACCT TTATGTATGT ATTTTCTACG TTTGCTAACA
4381  TACTGCGTAA TAAGGAGTCT TAATCATGCC AGTTCTTTTG GGTATTCCGT TATTATTGCG
4441  TTTCCTCGGT TTCCTTCTGG TAACTTTGTT CGGCTATCTG CTTACTTTTC TTAAAAAGGG
4501  CTTCGGTAAG ATAGCTATTG CTATTTCATT GTTTCTTGCT CTTATTATTG GGCTTAACTC
4561  AATTCTTGTG GGTTATCTCT CTGATATTAG CGCTCAATTA CCCTCTGACT TTGTTCAGGG
4621  TGTTCAGTTA ATTCTCCCGT CTAATGCGCT TCCCTGTTTT TATGTTATTC TCTCTGTAAA
4681  GGCTGCTATT TTCATTTTTG ACGTTAAACA AAAATCGTT TCTTATTTGG ATTGGGATAA
4741  ATAATATGGC TGTTTATTTT GTAACTGGCA AATTAGGCTC TGGAAAGACG CTCGTTAGCG
4801  TTGGTAAGAT TCAGGATAAA ATTGTAGCTG GGTGCAAAAT AGCAACTAAT CTTGATTTAA
4861  GGCTTCAAAA CCTCCCGCAA GTCGGGAGGT TCGCTAAAAC GCCTCGCGTT CTTAGAATAC
4921  CGGATAAGCC TTCTATATCT GATTTGCTTG CTATTGGGCG CGGTAATGAT TCCTACGATG
4981  AAAATAAAAA CGGCTTGCTT GTTCTCGATG AGTGCGGTAC TTGGTTTAAT ACCCGTTCTT
5041  GGAATGATAA GGAAAGACAG CCGATTATTG ATTGGTTTCT ACATGCTCGT AAATTAGGAT
5101  GGGATATTAT TTTTCTTGTT CAGGACTTAT CTATTGTTGA TAAACAGGCG CGTTCTGCAT
5161  TAGCTGAACA TGTTGTTTAT TGTCGTCGTC TGGACAGAAT TACTTTACCT TTTGTCGGTA
5221  CTTTATATTC TCTTATTACT GGCTCGAAAA TGCCTCTGCC TAAATTACAT GTTGGCGTTG
5281  TTAAATATGG CGATTCTCAA TTAAGCCCTA CTGTTGAGCG TTGGCTTTAT ACTGGTAAGA
5341  ATTTGTATAA CGCATATGAT ACTAAACAGG CTTTTTCTAG TAATTATGAT TCCGGTGTTT
5401  ATTCTTATTT AACGCCTTAT TTATCACACG GTCGGTATTT CAAACCATTA AATTTAGGTC
5461  AGAAGATGAA ATTAACTAAA ATATATTTGA AAAGTTTTC TCGCGTTCTT TGTCTTGCGA
5521  TTGGATTTGC ATCAGCATTT ACATATAGTT ATATAACCCA ACCTAAGCCG GAGGTTAAAA
5581  AGGTAGTCTC TCAGACCTAT GATTTTGATA AATTCACTAT TGACTCTTCT CAGCGTCTTA
5641  ATCTAAGCTA TCGCTATGTT TTCAAGGATT CTAAGGGAAA ATTAATTAAT AGCGACGATT
5701  TACAGAAGCA AGGTTATTCA CTCACATATA TTGATTTATG TACTGTTTCC ATTAAAAAAG
5761  GTAATTCAAA TGAAATTGTT AAATGTAATT AATTTTGTTT TCTTGATGTT TGTTTCATCA
5821  TCTTCTTTTG CTCAGGTAAT TGAAATGAAT AATTCGCCTC TGCGCGATTT TGTAACTTGG
5881  TATTCAAAGC AATCAGGCGA ATCCGTTATT GTTTCTCCCG ATGTAAAAGG TACTGTTACT
5941  GTATATTCAT CTGACGTTAA ACCTGAAAAT CTACGCAATT TCTTTATTTC TGTTTTACGT
6001  GCTAATAATT TTGATATGGT TGGTTCAATT CCTTCCATAA TTCAGAAGTA TAATCCAAAC
6061  AATCAGGATT ATATTGATGA ATTGCCATCA TCTGATAATC AGGAATATGA TGATAATTCC
6121  GCTCCTTCTG GTGGTTTCTT TGTTCCGCAA AATGATAATG TTACTCAAAC TTTTAAAATT
6181  AATAACGTTC GGGCAAAGGA TTTAATACGA GTTGTCGAAT TGTTTGTAAA GTCTAATACT
6241  TCTAAATCCT CAAATGTATT ATCTATTGAC GGCTCTAATC TATTAGTTGT TTCTGCACCT
6301  AAAGATATTT TAGATAACCT TCCTCAATTC CTTTCTACTG TTGATTTGCC AACTGACCAG
```

Table 21-continued

```
6361  ATATTGATTG AGGGTTTGAT ATTTGAGGTT CAGCAAGGTG ATGCTTTAGA TTTTTCATTT
6421  GCTGCTGGCT CTCAGCGTGG CACTGTTGCA GGCGGTGTTA ATACTGACCG CCTCACCTCT
6481  GTTTTATCTT CTGCTGGTGG TTCGTTCGGT ATTTTTAATG GCGATGTTTT AGGGCTATCA
6541  GTTCGCGCAT TAAAGACTAA TAGCCATTCA AAAATATTGT CTGTGCCACG TATTCTTACG
6601  CTTTCAGGTC AGAAGGGTTC TATCTCTGTT GGCCAGAATG TCCCTTTTAT TACTGGTCGT
6661  GTGACTGGTG AATCTGCCAA TGTAAATAAT CCATTTCAGA CGATTGAGCG TCAAAATGTA
6721  GGTATTTCCA TGAGCGTTTT TCCTGTTGCA ATGGCTGGCG GTAATATTGT TCTGGATATT
6781  ACCAGCAAGG CCGATAGTTT GAGTTCTTCT ACTCAGGCAA GTGATGTTAT TACTAATCAA
6841  AGAAGTATTG CTACAACGGT TAATTTGCGT GATGGACAGA CTCTTTTACT CGGTGGCCTC
6901  ACTGATTATA AAAACACTTC TCAAGATTCT GGCGTACCGT TCCTGTCTAA ATCCCTTTA
6961  ATCGGCCTCC TGTTTAGCTC CCGCTCTGAT TCCAACGAGG AAAGCACGTT ATACGTGCTC
7021  GTCAAAGCAA CCATAGTACG CGCCCTGTAG CGGCGCATTA AGCGCGGCGG GTGTGGTGGT
7081  TACGCGCAGC GTGACCGCTA CACTTGCCAG CGCCCTAGCG CCCGCTCCTT TCGCTTTCTT
7141  CCCTTCCTTT CTCGCCACGT TCGCCGGCTT TCCCCGTCAA GCTCTAAATC GGGGGCTCCC
7201  TTTAGGGTTC CGATTTAGTG CTTTACGGCA CCTCGACCCC AAAAAACTTG ATTTGGGTGA
7261  TGGTTCACGT AGTGGGCCAT CGCCCTGATA GACGGTTTTT CGCCCTTTGA CGTTGGAGTC
7321  CACGTTCTTT AATAGTGGAC TCTTGTTCCA AACTGGAACA ACACTCAACC CTATCTCGGG
7381  CTATTCTTTT GATTTATAAG GGATTTTGCC GATTTCGGAA CCACCATCAA ACAGGATTTT
7441  CGCCTGCTGG GGCAAACCAG CGTGGACCGC TTGCTGCAAC TCTCTCAGGG CCAGGCGGTG
7501  AAGGGCAATC AGCTGTTGCC CGTCTCACTG GTGAAAAGAA AAACCACCCT GGATCCAAGC
7561  TTGCAGGTGG CACTTTTCGG GGAAATGTGC GCGGAACCCC TATTTGTTTA TTTTTCTAAA
7621  TACATTCAAA TATGTATCCG CTCATGAGAC AATAACCCTG ATAAATGCTT CAATAATATT
7681  GAAAAAGGAA GAGTATGAGT ATTCAACATT TCCGTGTCGC CCTTATTCCC TTTTTTGCGG
7741  CATTTTGCCT TCCTGTTTTT GCTCACCCAG AAACGCTGGT GAAAGTAAAA GATGCTGAAG
7801  ATCAGTTGGG CGCACGAGTG GGTTACATCG AACTGGATCT CAACAGCGGT AAGATCCTTG
7861  AGAGTTTTCG CCCCGAAGAA CGTTTTCCAA TGATGAGCAC TTTTAAAGTT CTGCTATGTC
7921  ATACACTATT ATCCCGTATT GACGCCGGGC AAGAGCAACT CGGTCGCCGG GCGCGGTATT
7981  CTCAGAATGA CTTGGTTGAG TACTCACCAG TCACAGAAAA GCATCTTACG GATGGCATGA
8041  CAGTAAGAGA ATTATGCAGT GCTGCCATAA CCATGAGTGA TAACACTGCG GCCAACTTAC
8101  TTCTGACAAC GATCGGAGGA CCGAAGGAGC TAACCGCTTT TTTGCACAAC ATGGGGGATC
8161  ATGTAACTCG CCTTGATCGT TGGGAACCGG AGCTGAATGA AGCCATACCA AACGACGAGC
8221  GTGACACCAC GATGCCTGTA GCAATGCCAA CAACGTTGCG CAAACTATTA ACTGGCGAAC
8281  TACTTACTCT AGCTTCCCGG CAACAATTAA TAGACTGGAT GGAGGCGGAT AAAGTTGCAG
8341  GACCACTTCT GCGCTCGGCC CTTCCGGCTG GCTGGTTTAT TGCTGATAAA TCTGGAGCCG
8401  GTGAGCGTGG GTCTCGCGGT ATCATTGCAG CACTGGGGCC AGATGGTAAG CCCTCCCGTA
8461  TCGTAGTTAT CTACACGACG GGGAGTCAGG CAACTATGGA TGAACGAAAT AGACAGATCG
8521  CTGAGATAGG TGCCTCACTG ATTAAGCATT GGTAACTGTC AGACCAAGTT TACTCATATA
8581  TACTTTAGAT TGATTTAAAA CTTCATTTTT AATTTAAAAG GATCTAGGTG AAGATCCTTT
8641  TTGATAATCT CATGACCAAA ATCCCTTAAC GTGAGTTTTC GTTCCACTGT ACGTAAGACC
8701  CCCAAGCTTG TCGACTGAAT GGCGAATGGC GCTTTGCCTG GTTTCCGGCA CCAGAAGCGG
```

Table 21-continued

```
8761  TGCCGGAAAG CTGGCTGGAG TGCGATCTTC CTGAGGCCGA TACTGTCGTC GTCCCCTCAA

8821  ACTGGCAGAT GCACGGTTAC GATGCGCCCA TCTACACCAA CGTAACCTAT CCCATTACGG

8881  TCAATCCGCC GTTTGTTCCC ACGGAGAATC CGACGGGTTG TTACTCGCTC ACATTTAATG

8941  TTGATGAAAG CTGGCTACAG GAAGGCCAGA CGCGAATTAT TTTTGATGGC GTTCCTATTG

9001  GTTAAAAAAT GAGCTGATTT AACAAAAATT TAACGCGAAT TTAACAAAA TATTAACGTT

9061  TACAATTTAA ATATTTGCTT ATACAATCTT CCTGTTTTTG GGGCTTTTCT GATTATCAAC

9121  CGGGGTACAT ATGATTGACA TGCTAGTTTT ACGATTACCG TTCATCGATT CTCTTGTTTG

9181  CTCCAGACTC TCAGGCAATG ACCTGATAGC CTTTGTAGAT CTCTCAAAAA TAGCTACCCT

9241  CTCCGGCATG AATTTATCAG CTAGAACGGT TGAATATCAT ATTGATGGTG ATTTGACTGT

9301  CTCCGGCCTT TCTCACCCTT TTGAATCTTT ACCTACACAT TACTCAGGCA TTGCATTTAA

9361  AATATATGAG GGTTCTAAAA ATTTTTATCC TTGCGTTGAA ATAAAGGCTT CTCCCGCAAA

9421  AGTATTACAG GGTCATAATG TTTTTGGTAC AACCGATTTA GCTTTATGCT CTGAGGCTTT

9481  ATTGCTTAAT TTTGCTAATT CTTTGCCTTG CCTGTATGAT TTATTGGATG TT
```

TABLE 22

| Primers used in RACE amplification: | |
|---|---|
| Heavy chain | |
| HuCμ-FOR (1st PCR) | 5'-TGG AAG AGG CAC GTT CTT TTC TTT-3' (SEQ ID NO: 457) |
| HuCμ-Nested (2nd PCR) | 5' CTT TTC TTT GTT GCC GTT GGG GTG-3' (SEQ ID NO: 458) |
| Kappa light chain | |
| HuCkFor (1st PCR) | 5'-ACA CTC TCC CCT GTT GAA GCT CTT-3' (SEQ ID NO: 459) |
| HuCkForAscI (2nd PCR) | 5'-ACC GCC TCC ACC GGG CGC GCC TTA TTA ACA CTC TCC CCT GTT GAA GCT CTT-3' (SEQ ID NO: 460) |
| Lambda light chain | |
| HuClambdaFor (1st PCR) | |
| HuCL2-FOR | 5'-TGA ACA TTC TGT AGG GGC CAC TG-3' (SEQ ID NO: 461) |
| HuCL7-FOR | 5'-AGA GCA TTC TGC AGG GGC CAC TG-3' (SEQ ID NO: 462) |
| HuClambdaForAscI (2nd PCR) | |
| HuCL2-FOR-ASC | 5'-ACC GCC TCC ACC GGG CGC GCC TTA TTA TGA ACA TTC TGT AGG GGC CAC TG-3' (SEQ ID NO: 463) |
| HuCL7-FOR-ASC | 5'-ACC GCC TCC ACC GGG CGC GCC TTA TTA AGA GCA TTC TGC AGG GGC CAC TG-3' (SEQ ID NO: 465) |
| GeneRAcer 5' Primers provided with the kit (Invitrogen) | |
| 5'A 1st PCR | (SEQ ID NO: 465) 5'CGACTGGAGCACGAGGACACTGA 3' |
| 5'NA 2nd pCR | 5'GGACACTGACATGGACTGAAGGAGTA-3' (SEQ ID NO: 466) |

TABLE 23

ONs used in Capture of kappa light chains using CJ method and BsmAI

All ONs are written 5' to 3'.

REdapters (6)

| | |
|---|---|
| ON_2OSK15O12 | gggAggATggAgAcTgggTc (SEQ ID NO: 467) |
| ON_2OSK15L12 | gggAAgATggAgAcTgggTc (SEQ ID NO: 468) |
| ON_2OSK15A17 | gggAgAgTggAgAcTgAgTc (SEQ ID NO: 469) |
| ON_2OSK15A27 | gggTgccTggAgAcTgcgTc (SEQ ID NO: 470) |
| ON_2OSK15A11 | gggTggcTggAgAcTgcgTc (SEQ ID NO: 471) |
| ON_2OSK15B3 | gggAgTcTggAgAcTgggTc (residue 1-20 of SEQ ID NO: 477) |

Bridges (6)

| | |
|---|---|
| kapbri1O12 | gggAggATggAgAcTgggTcATcTggATgTcTTgTgcAcTgTgAcAgAgg (SEQ ID NO: 472) |
| kapbri1L12 | gggAAgATggAgAcTgggTcATcTggATgTcTTgTgcAcTgTgAcAgAgg (SEQ ID NO: 473) |
| kapbri1A17 | gggAgAgTggAgAcTgggTcATcTggATgTcTTgTgcAcTgTgAcAgAgg (SEQ ID NO: 474) |
| kapbri1A27 | gggTgccTggAgAcTgggTcATcTggATgTcTTgTgcAcTgTgAcAgAgg (SEQ ID NO: 475) |
| kapbri1A11 | gggTggcTggAgAcTgggTcATcTggATgTcTTgTgcAcTgTgAcAgAgg (SEQ ID NO: 476) |
| kapbri1B3 | gggAgTcTggAgAcTgggTcATcTggATgTcTTgTgcAcTgTgAcAgAgg (SEQ ID NO: 477) |

Extender (5' biotinylated)

| | |
|---|---|
| kapextIbio | ccTcTgTcAcAgTgcAcAAgAcATccAgATgAcccAgTcTcc (SEQ ID NO: 478) |

Primers

| | |
|---|---|
| kaPCRII | ccTcTgTcAcAgTgcAcAAgAc (SEQ ID NO: 479) |
| kapfor | 5'-aca ctc tcc cct gtt gaa gct ctt-3' (SEQ ID NO: 480) |

TABLE 24

PCR program for amplification of kappa DNA

| | |
|---|---|
| 95° C. | 5 minutes |
| 95° C. | 15 seconds |
| 65° C. | 30 seconds |
| 72° C. | 1 minute |
| 72° C. | 7 minutes |
| 4° C. | hold |

TABLE 24-continued

PCR program for amplification of kappa DNA

Reagents (100 ul reaction):

| | |
|---|---|
| Template | 50 ng |
| 10x turbo PCR buffer | 1x |
| turbo Pfu | 4 U |
| dNTPs | 200 µM each |
| kaPCRt1 | 300 nM |
| kapfor | 300 nM |

TABLE 25 h3401-h2 captured Via CJ with BsmAI
(Nucleotide sequence is SEQ ID NO: 481, Amino acid sequence is SEQ ID NO: 482)

```
! 1   2   3   4   5   6   7   8   9   10  11  12  13  14  15
! S   A   Q   D   I   Q   M   T   Q   S   P   A   T   L   S
 aGT GCA Caa gac atc cag atg acc cag tct cca gcc acc ctg tct
! ApaLI...                        a   gcc acc ! L25, L6, L20, L2, L16, A11
! Extender............................Bridge...

! 16  17  18  19  20  21  22  23  24  25  26  27  28  29  30
! V   S   P   G   E   R   A   T   L   S   C   R   A   S   Q
 gtg tct cca ggg gaa agg gcc acc ctc tcc tgc agg gcc agt cag ! 31  32  33  34  35  36  37  38  39  40  41  42  43  44  45
! S   V   S   N   N   L   A   W   Y   Q   Q   K   P   G   Q
 agt gtt agt aac aac tta gcc tgg tac cag cag aaa cct ggc cag ! 46  47  48  49  50  51  52  53  54  55  56  57  58  59  60
! V   P   R   L   L   I   Y   G   A   S   T   R   A   T   D
 gtt ccc agg ctc ctc atc tat ggt gca tcc acc agg gcc act gat
```

TABLE 25-continued h3401-h2 captured Via CJ with BsmAI
(Nucleotide sequence is SEQ ID NO: 481, Amino acid sequence is SEQ ID NO: 482)

```
! 61  62  63  64  65  66  67  68  69  70  71  72  73  74  75
!  I   P   A   R   F   S   G   S   G   S   T   D   F   T
  atc cca gcc agg ttc agt ggc agt ggg tct ggg aca gac ttc act ! 76  77  78  79  80  81  82  83  84  85  86  87  88  89  90
!  L   T   I   S   R   L   E   P   E   D   F   A   V   Y   Y
  ctc acc atc agc aga ctg gag cct gaa gat ttt gca gtg tat tac ! 91  92  93  94  95  96  97  98  99  100 101 102 103 104 105
!  C   Q   R   Y   G   S   S   P   G   W   T   F   G   Q   G
  tgt cag cgg tat ggt agc tca ccg ggg tgg acg ttc ggc caa ggg ! 106 107 108 109 110 111 112 113 114 115 116 117 118 119 120
!  T   K   V   E   I   K   R   T   V   A   A   P   S   V   F
  acc aag gtg gaa atc aaa cga act gtg gct gca cca tct gtc ttc ! 121 122 123 124 125 126 127 128 129 130 131 132 133 134 135
!  I   F   P   P   S   D   E   Q   L   K   S   G   T   A   S
  atc ttc ccg cca tct gat gag cag ttg aaa tct gga act gcc tct ! 136 137 138 139 140 141 142 143 144 145 146 147 148 149 150
!  V   V   C   L   L   N   N   F   Y   P   R   E   A   K   V
  gtt gtg tgc ctg ctg aat aac ttc tat ccc aga gag gcc aaa gta ! 151 152 153 154 155 156 157 158 159 160 161 162 163 164 165
!  Q   W   K   V   D   N   A   L   Q   S   G   N   S   Q   E
  cag tgg aag gtg gat aac gcc ctc caa tcg ggt aac tcc cag gag ! 166 167 168 169 170 171 172 173 174 175 176 177 178 179 180
!  S   V   T   E   Q   D   S   K   D   S   T   Y   S   L   S
  agt gtc aca gag cag gac agc aag gac agc acc tac agc ctc agc ! 181 182 183 184 185 186 187 188 189 190 191 192 193 194 195
!  S   T   L   T   L   S   K   A   D   Y   E   K   H   K   V
  agc acc ctg acg ctg agc aaa gca gac tac gag aaa cac aaa gtc ! 196 197 198 199 200 201 202 203 204 205 206 207 208 209 210
!  Y   A   C   E   V   T   H   Q   G   L   S   S   P   V   T
  tac gcc tgc gaa gtc acc cat cag ggc ctg agc tcg cct gtc aca ! 211 212 213 214 215 216 217 218 219 220 221 222 223
!  K   S   F   N   K   G   E   C   K   G   E   F   A
  aag agc ttc aac aaa gga gag tgt aag ggc gaa ttc gc.....
```

TABLE 26 h3401-d8 KAPPA captured with CJ and BsmAI
(Nucleotide sequence is SEQ ID NO: 484; Amino acid sequence is SEQ ID NO: 485)

```
!  1   2   3   4   5   6   7   8   9  10  11  12  13  14  15
!  S   A   Q   D   I   Q   M   T   Q   S   P   A   T   L   S
  aGT GCA Caa gac atc cag atg acc cag tct cct gcc acc ctg tct
! ApaLI...Extender.....................a gcc acc ! L25, L6, L20, L2, L16, A11
!                                    A GCC ACC CTG TCT ! L2 (SEQ ID NO: 483)

! 16  17  18  19  20  21  22  23  24  25  26  27  28  29  30
!  V   S   P   G   E   R   A   T   L   S   C   R   A   S   Q
  gtg tct cca ggt gaa aga gcc acc ctc tcc tgc agg gcc agt cag
! GTC TCT CCA GGG GAA AGA GCC ACC CTC TCC TGC ! L2

! 31  32  33  34  35  36  37  38  39  40  41  42  43  44  45
!  N   L   L   S   N   L   A   W   Y   Q   Q   K   P   G   Q
  aat ctt ctc agc aac tta gcc tgg tac cag cag aaa cct ggc cag ! 46  47  48  49  50  51  52  53  54  55  56  57  58  59  60
!  A   P   R   L   L   I   Y   G   A   S   T   G   A   I   G
  gct ccc agg ctc ctc atc tat ggt gct tcc acc ggg gcc att ggt ! 61  62  63  64  65  66  67  68  69  70  71  72  73  74  75
!  I   P   A   R   F   S   G   S   G   S   T   E   F   T
  atc cca gcc agg ttc agt ggc agt ggg tct ggg aca gag ttc act
```

TABLE 26-continued h3401-d8 KAPPA captured with CJ and BsmAI
(Nucleotide sequence is SEQ ID NO: 484; Amino acid sequence is SEQ ID NO: 485)

```
! 76  77  78  79  80  81  82  83  84  85  86  87  88  89  90
!  L   T   I   S   S   L   Q   S   E   D   F   A   V   Y   F
  ctc acc atc agc agc ctg cag tct gaa gat ttt gca gtg tat ttc ! 91  92  93  94  95  96  97  98  99 100 101 102 103 104 105
!  C   Q   Q   Y   G   T   S   P   P   T   F   G   G   G   T
  tgt cag cag tat ggt acc tca ccg ccc act ttc ggc gga ggg acc !106 107 108 109 110 111 112 113 114 115 116 117 118 119 120
!  K   V   E   I   K   R   T   V   A   A   P   S   V   F   I
  aag gtg gag atc aaa cga act gtg gct gca cca tct gtc ttc atc !121 122 123 124 125 126 127 128 129 130 131 132 133 134 135
!  F   P   P   S   D   E   Q   L   K   S   G   T   A   S   V
  ttc ccg cca tct gat gag cag ttg aaa tct gga act gcc tct gtt !136 137 138 139 140 141 142 143 144 145 146 147 148 149 150
!  V   C   P   L   N   N   F   Y   P   R   E   A   K   V   Q
  gtg tgc ccg ctg aat aac ttc tat ccc aga gag gcc aaa gta cag !151 152 153 154 155 156 157 158 159 160 161 162 163 164 165
!  W   K   V   D   N   A   L   Q   S   G   N   S   Q   E   S
  tgg aag gtg gat aac gcc ctc caa tcg ggt aac tcc cag gag agt !166 167 168 169 170 171 172 173 174 175 176 177 178 179 180
!  V   T   E   Q   D   N   K   D   S   T   Y   S   L   S   S
  gtc aca gag cag gac aac aag gac agc acc tac agc ctc agc agc !181 182 183 184 185 186 187 188 189 190 191 192 193 194 195
!  T   L   T   L   S   K   V   D   Y   E   K   H   E   V   Y
  acc ctg acg ctg agc aaa gta gac tac gag aaa cac gaa gtc tac !196 197 198 199 200 201 202 203 204 205 206 207 208 209 210
!  A   C   E   V   T   H   Q   G   L   S   S   P   V   T   K
  gcc tgc gaa gtc acc cat cag ggc ctt agc tcg ccc gtc acg aag !211 212 213 214 215 216 217 218 219 220 221 222 223
!  S   F   N   R   G   E   C   K   K   E   F   V
  agc ttc aac agg gga gag tgt aag aaa gaa ttc gtt t
```

TABLE 27

V3-23 VH framework with variegated codons shown

```
!(Nucleotide sequence is SEQ ID NO: 486; Amino acid sequence is
SEQ ID NO: 487)
!          17  18  19  20  21  22
!           A   Q   P   A   M   A
 5'-ctg tct gaa cG GCC cag ccG GCC atg gcc                          29
 3'-gac aga ctt gc cgg gtc ggc cgg tac cgg
!    Scab.........SfiI................
!                 NgoMI...
!                    NcoI....
!
!              FR1(DP47/V3-23)--------------
!              23  24  25  26  27  28  29  30
!               E   V   Q   L   L   E   S   G
              gaa|gtt|CAA|TTG|tta|gag|tct|ggt|                       53
              ctt|caa|gtt|aac|aat|ctc|aga|cca|
                     |MfeI |
!
!
!        -------------FR1------------------------
!         31  32  33  34  35  36  37  38  39  40  41  42  43  44  45
!          G   G   L   V   Q   P   G   G   S   L   R   L   S   C   A
         |ggc|ggt|ctt|gtt|cag|cct|ggt|ggt|tct|tta|cgt|ctt|tct|tgc|gct|  98
         |ccg|cca|gaa|caa|gtc|gga|cca|cca|aga|aat|gca|gaa|aga|acg|cga|
```

TABLE 27-continued

V3-23 VH framework with variegated codons shown

```
!       Sites to be varied-->    ***      ***      ***
!        ---FR1---------->|...CDR1.................|--FR2----
!        46  47  48  49  50  51  52  53  54  55  56  57  58  59  60
!        A   S   G   F   T   F   S   S   Y   A   M   S   W   V   R
!       |gct|TCC|GGA|ttc|act|ttc|tct|tCG|TAC|Gct|atg|tct|tgg|gtt|cgC|    143
!       |cga|agg|cct|aag|tga|aag|aga|agc|atg|cga|tac|aga|acc|caa|gcg|
!        |BspEI|         |BsiWI|                           |BstXI.
!
!              Sites to be varies--> ***      *** ***
!        ----FR2------------------->|...CDR2.......
!        61  62  63  64  65  66  67  68  69  70  71  72  73  74  75
!        Q   A   P   G   K   G   L   E   W   V   S   A   I   S   G
!       |CAa|gct|ccT|GGt|aaa|ggt|ttg|gag|tgg|gtt|tct|gct|atc|tct|ggt|    188
!       |gtt|cga|gga|cca|ttt|cca|aac|ctc|acc|caa|aga|cga|tag|aga|cca|
! ...BstXI    |
!
!              ***      ***
!       .....CDR2............................................|---FR3---
!        76  77  78  79  80  81  82  83  84  85  86  87  88  89  90
!        S   G   G   S   T   Y   Y   A   D   S   V   K   G   R   F
!       |tct|ggt|ggc|agt|act|tac|tat|gct|gac|tcc|gtt|aaa|ggt|cgc|ttc|    233
!       |aga|cca|ccg|tca|tga|atg|ata|cga|ctg|agg|caa|ttt|cca|gcg|aag|
!
!        --------FR3----------------------------------------
!        91  92  93  94  95  96  97  98  99 100 101 102 103 104 105
!        T   I   S   R   D   N   S   K   N   T   L   Y   L   Q   M
!       |act|atc|TCT|AGA|gac|aac|tct|aag|aat|act|ctc|tac|ttg|cag|atg|    278
!       |tga|tag|aga|tct|ctg|ttg|aga|ttc|tta|tga|gag|atg|aac|gtc|tac|
!             |XbaI |
!
!        --FR3---------------------------------------------->|
!        106 107 108 109 110 111 112 113 114 115 116 117 118 119 120
!        N   S   L   R   A   E   D   T   A   V   Y   Y   C   A   K
!       |aac|agC|TTA|AGg|gct|gag|gac|aCT|GCA|Gtc|tac|tat|tgc|gct|aaa|    323
!       |ttg|tcg|aat|tcc|cga|ctc|ctg|tga|cgt|cag|atg|ata|acg|cga|ttt|
!             |AflII|         |PstI|
!
!       .......CDR3................|---FR4--------------------
!        121 122 123 124 125 126 127 128 129 130 131 132 133 134 135
!        D   Y   E   G   T   G   Y   A   F   D   I   W   G   Q   G
!       |gac|tat|gaa|ggt|act|ggt|tat|gct|ttc|gaC|ATA|TGg|ggt|caa|ggt|    368
!       |ctg|ata|ctt|cca|tga|cca|ata|cga|aag|ctg|tat|acc|cca|gtt|cca|
!                                            | NdeI|
!
!        -----------FR4------->|
!        136 137 138 139 140 141 142
!        T   M   V   T   V   S   S
!       |act|atG|GTC|ACC|gtc|tct|agt-                                    389
!       |tga|tac|cag|tgg|cag|aga|tca-
!            | BstEII|
!
!                143 144 145 146 147 148 149 150 151 152
!                 A   S   T   K   G   P   S   V   F   P
!                gcc tcc acc aaG GGC CCa tcg GTC TTC ccc-3'               419
!                cgg agg tgg ttc ccg ggt agc cag aag ggg-5'
!                        Bsp120I.  BbsI...(2/2)
!                        ApaI....

(SFPRMET) 5'-ctg tct gaa cG GCC cag ccG-3' (SEQ ID NO: 488)
(TOPFR1A) 5'-ctg tct gaa cG GCC cag ccG GCC atg gcc-
       gaa|gtt|CAA|TTG|tta|gag|tct|ggt|-
      |ggc|ggt|ctt|gtt|cag|cct|ggt|ggt|tct|tta-3' (SEQ ID NO: 489)
(BOTFR1B)       3'-caa|gtc|gga|cca|cca|aga|aat|gca|gaa|aga|acg|cga|-
      |cga|agg|cct|aag|tga|aag-5' ! bottom strand (SEQ ID NO: 490)
(BOTFR2) 3'-acc|caa|gcg|-
      |gtt|cga|gga|cca|ttt|cca|aac|ctc|acc|caa|aga|-5' ! bottom strand
         (SEQ ID NO: 491)
(BOTFR3) 3'-a|cga|ctg|agg|caa|ttt|cca|gcg|aag|-
       |tga|tag|aga|tct|ctg|ttg|aga|ttc|tta|tga|gag|atg|aac|gtc|tac|-
      |ttg|tcg|aat|tcc|cga|ctc|ctg|tga-5' (SEQ ID NO: 492)
```

TABLE 27-continued

V3-23 VH framework with variegated codons shown

```
(F06)    5'-gC|TTA|AGg|gct|gag|gac|aCT|GCA|Gtc|tac|tat|tgc|gct|aaa|-
     |gac|tat|gaa|ggt|act|ggt|tat|gct|ttc|gaC|ATA|TGg|ggt|c-3'
     (SEQ ID NO: 493)
(BOTFR4) 3'-cga|aag|ctg|tat|acc|cca|gtt|cca|-
         |tga|tac|cag|tgg|cag|aga|tca-
          cgg agg tgg ttc ccg ggt agc cag aag ggg-5' ! bottom strand
     (SEQ ID NO: 494)
(BOTPRCPRIM)            3'-gg ttc ccg ggt agc cag aag ggg-5'
                        (SEQ ID NO: 495)
!
! CDR1 diversity
!
! (ON-vgC1) 5'-|gct|TCC|GGA|ttc|act|ttc|tct|<1>|TAC|<1>|atg|<1>|-
!                         CDR1.................6859
|tgg|gtt|cgC|CAa|gct|ccT|GG-3' (SEQ ID NO: 496)
!

!<1> stands for an equimolar mix of {ADEFGHIKLMNPQRSTVWY}; no C
!              (this is not a sequence)
!
! CDR2 diversity
(ON-vgC2) 5'-ggt|ttg|gag|tgg|gtt|tct|<2>|atc|<2>|<3>|-
!                  CDR2............
     |tct|ggt|ggc|<1>|act|<1>|tat|gct|gac|tcc|gtt|aaa|gg-3'
     (SEQ ID NO: 497)
!    CDR2..............................................

! <1> is an equimolar mixture of {ADEFGHIKLMNPQRSTVWY}; no C
! <2> is an equimolar mixture of {YRWVGS}; no ACDEFHIKLMNPQT
! <3> is an equimolar mixture of {PS}; no ACDEFGHIKLMNQRTVWY
```

TABLE 28

Stuffer used in VH (SEQ ID NO: 498)

```
  1 TCCGGAGCTT CAGATCTGTT TGCCTTTTTG TGGGGTGGTG
    CAGATCGCGT TACGGAGATC

61 GACCGACTGC TTGAGCAAAA GCCACGCTTA ACTGCTGATC
    AGGCATGGGA TGTTATTCGC

121 CAAACCAGTC GTCAGGATCT TAACCTGAGG CTTTTTTTAC
    CTACTCTGCA AGCAGCGACA

181 TCTGGTTTGA CACAGAGCGA TCCGCGTCGT CAGTTGGTAG
    AAACATTAAC ACGTTGGGAT

241 GGCATCAATT TGCTTAATGA TGATGGTAAA ACCTGGCAGC
    AGCCAGGCTC TGCCATCCTG

301 AACGTTTGGC TGACCAGTAT GTTGAAGCGT ACCGTAGTGG
    CTGCCGTACC TATGCCATTT

361 GATAAGTGGT ACAGCGCCAG TGGCTACGAA CAACCCAGG
    ACGGCCCAAC TGGTTCGCTG

421 AATATAAGTG TTGGAGCAAA AATTTTGTAT GAGGCGGTGC
    AGGGAGACAA ATCACCAATC

481 CCACAGGCGG TTGATCTGTT TGCTGGGAAA CCACAGCAGG
    AGGTTGTGTT GGCTGCGCTG

541 GAAGATACCT GGGAGACTCT TTCCAAACGC TATGGCAATA
    ATGTGAGTAA CTGGAAAACA

601 CCTGCAATGG CCTTAACGTT CCGGGCAAAT AATTTCTTTG
    GTGTACCGCA GGCCGCAGCG

661 GAAGAAACGC GTCATCAGGC GGAGTATCAA AACCGTGGAA
    CAGAAAACGA TATGATTGTT

721 TTCTCACCAA CGACAAGCGA TCGTCCTGTG CTTGCCTGGG
    ATGTGGTCGC ACCCGGTCAG

781 AGTGGGTTTA TTGCTCCCGA TGGAACAGTT GATAAGCACT
    ATGAAGATCA GCTGAAAATG

841 TACGAAAATT TTGGCCGTAA GTCGCTCTGG TTAACGAAGC
    AGGATGTGGA GGCGCATAAG

901 GAGTCGTCTA GA
```

TABLE 29

DNA sequence of pCES5

```
!pCES5 6680 bases = pCes4 with stuffers in CDR1-2 and CDR3 2000.12.13
!Ngene = 6680
!Useful REs (cut MAnoLI fewer than 3 times) 2000.06.05
!Non-cutters
!Acc65I Ggtacc     AfcI AGCgct          AvrII Cctagg
!BsaBI GAT-        BsiWI Cgtacg         BsmFI Nnnnnnnnnnnnnnngtccc
NNnnatc
```

TABLE 29-continued

DNA sequence of pCES5

```
(SEQ ID NO: 499)                           (SEQ ID NO: 500)
!BsrGI  Tgtaca      BstAPI  GCANNNNntgc    BstBI   TTcgaa
                            (SEQ ID NO: 501)
!BstZ17I GTAtac     BtrI    CACgtg         Ecl136I GAGctc
!EcoRV  GATatc      FseI    GGCCGGcc       KpnI    GGTACc
!MscI   TGGcca      NruI    TCGcga         NsiI    ATGCAt
!PacI   TTAATtaa    PmeI    GTTTaaac       PmlI    CACgtg
!PpuMI  RGgwccy     PshAI   GACNNnngtc     SacI    GAGCTc
                            (SEQ ID NO: 502)
!SacII  CCGCgg      SbfI    CCTGCAgg       SexAI   Accwggt
!SgfI   GCGATcgc    SnaBI   TACgta         SpeI    Actagt
!SphI   GCATGc      Sse8387I CCTGCAgg      StuI    AGGcct
!SwaI   ATTTaaat    XmaI    Cccggg
!
!cutters
!Enzymes that cut more than 3 times
!AlwNI  CAGNNNctg        5
!BsgI   ctgcac           4
!BsrFI  Rccggy           5
!EarI   CTCTTCNnnn       4
(SEQ ID NO: 625)
!FauI   nNNNNNNGCGGG    10
(SEQ ID NO: 503)
!Enzymes that cut from 1 to 3 times
!
!EcoO109I RGgnccy        3       7    2636    4208
!BssSI  Ctcgtg           1      12
!-"-    Cacgag           1    1703
!BspHI  Tcatga           3      43     148    1156
!AatII  GACGTc           1      65
!BciYI  GTATCCNNNNNN     2     140    1667
(SEQ ID NO: 504)
!Eco57I CTGAAG           1     301
!-"-    cttcag           2    1349
!AvaI   Cycgrg           3     319    2347    6137
!BsiHKAIGWGCWc           3     401    2321    4245
!HgiAI  GWGCWc           3     401    2321    4245
!BcgI   gcannnnntcg      1     461
(SEQ ID NO: 505)
!ScaI   AGTact           1     505
!PvuI   CGATcg           3     616    3598    5926
!FspI   TGCgca           2     763    5946
!BglI   GCCNNNNaggc      3     864    2771    5952
(SEQ ID NO: 506)
!BpmI   CTGGAG           1     898
!-"-    ctccag           1    4413
!BsaI   GGTCTCNnnnn      1     916
(SEQ ID NO: 507)
!AhdI   GACNNNnngtc      1     983
(SEQ ID NO: 509)
!DrdI   GACNNNNnngtc     3    1768    6197    6579
(SEQ ID NO: 510)
!SapI   gaagagc          1    1998
!PvuII  CAGctg           3    2054    3689    5896
!PflMI  CCANNNNatgg      3    2233    3943    3991
(SEQ ID NO: 511)
!HindIII Aagctt          1    2235
!ApaLI  Gtgcac           1    2321
!BspMI  Nnnnnnnnngcaggt  1    2328
(SEQ ID NO: 512)
!-"-    ACCTGCNNNNn      2    3460
(SEQ ID NO: 513)
!PsiI   CTGCAg           1    2335
!AccI   GTmkac           2    2341    2611
!HincII GTYrac           2    2341    3730
!SalI   Gtcgac           1    2341
!XhoI   Ctcgag           1    2347
!XhoI   Ctcgag           1    2347
!BbsI   gtcttc           2    2383    4219
!BlpI   GCtnagc          1    2580
!EspI   GCtnagc          1    2580
!SgrAI  CRccggyg         1    2648
!AgeI   Accggt           2    2649    4302
!AscI   GGcgcgcc         1    2689
!BssHII Gcgcgc           1    2690
!SfiI   GGCCNNNNnggcc    1    2770
```

TABLE 29-continued

DNA sequence of pCES5

```
(SEQ ID NO: 514)
!NacI    GCCggc              2   2776   6349
!NgcMIV  Gccggc              2   2776   6349
!BtgI    Ccrygg              3   2781   3553   5712
!DsaI    Ccrygg              3   2781   3553   5712
!NcoI    Ccatgg              1   2781
!StyI    Ccwwgg              3   2781   4205   4472
!MfeI    Caattg              1   2795
!BspEI   Tccgga              1   2861
!BgtII   Agatct              1   2872
!BclI    Tgatca              1   2956
!Bsu36I  CCtaagg             3   3004   4143   4373
!XcmI    CCANNNNNnnnntgg     1   3215
(SEQ ID NO: 515)
!MluI    Acgcgt              1   3527
!HpaI    GTTunc              1   3730
!XbaI    Tctaga              1   3767
!
!AflII   Cttaag              1   3811
!BsmI    NGcattc             1   3821
!-"-     GAATGCN             1   4695
!RsrII   CGgwccg             1   3827
!NheI    Gctagc              1   4166
!BstEII  Ggtaacc             1   4182
!BsmBI   CGTCTCNnnnn         1   4188   6625
(SEQ ID NO: 516)
!-"-     Nnnnnngagacg        1   6673
(SEQ ID NO: 517)
!ApaI    GGGCCc              1   4209
!BanII   GRGCYc              3   4209   4492   6319
!Bspi20I Gggccc              1   4209
!PspOMI  Gggccc              1   4209
!BseRI   NNnnnnnnnnctcctc    1   4226
(SEQ ID NO: 518)
!-"-     GAGGAGNNNNNNNNNN    1   4957
(SEQ ID NO: 519)
!EcoNI   CCTNNnnnagg         1   4278
(SEQ ID NO: 520)
!PflFI   GACNnngtc           1   4308
!Tth111I GACNnngtc           1   4308
!KasI    Ggcgcc              2   4327   5967
!BstXI   CCANNNNNntgg        1   4415
(SEQ ID NO: 521)
!NotI    GCggccgc            1   4507
!EagI    Cggccg              1   4508
!BamHI   Ggatcc              1   5169
!BspDI   ATcgat              1   5476
!NdeI    CAtatg              1   5672
!EcoRI   Gaattc              1   5806
!PsiI    TTAtaa              1   6118
!DraIII  CACNNNgtg           1   6243
!BsaAI   YACgtr              1   6246
!-----------------------------------------
```

(Nucleotide sequence is SEQ ID NO: 522 and Amino acid sequence is SEQ ID NO: 523, respectively)

```
   1 gacgaaaggg cCTCGTGata cgcctatttt tataggttaa tgtcatgata ataatggttt
!           BsssI(1/2)

61 cttaGACGTC aggtggcact tttcggggaa atgtgcgcgg aacccctatt tgtttatttt
!       AatII 121 tctaaataca ttcatatatG TATCCgctca tgagacaata accctgataa atgcttcaat
!                 BciVI (1 of 2)
 181 aatattgaaa aaggaagagt ! Base # 201 to 1061 = ApR gene from pUC119 with some RE sites removed
!
!    1   2   3   4   5   6   7   8   9  10  11  12  13  14  15
!    fM  S   I   Q   H   F   R   V   A   L   I   P   F   F   A
 201 atg agt att caa cat ttc cgt gtc gcc ctt att ccc ttt ttt gcg
!

!   16  17  18  19  20  21  22  23  24  25  26  27  28  29  30
!    A   F   C   L   P   V   F   A   H   P   E   T   L   V   K
```

TABLE 29-continued

DNA sequence of pCES5

```
246 gca ttt tgc ctt cct gtt ttt gct cac cca gaa ccg ctg gtg aaa
!
!    31  32  33  34  35  36  37  38  39  40  41  42  43  44  45
!    V   K   D   A   E   D   Q   L   G   A   R   V   G   Y   I
291 gta aaa gat gct gaa gat cag ttg ggt gcc cga gtg ggt tac atc
!
!    46  47  48  49  50  51  52  53  54  55  56  57  58  59  60
!    E   L   D   L   N   S   G   K   I   L   E   S   F   R   P
336 gaa ctg gat ctc aac agc ggt aag atc ctt gag agt ttt cgc ccc
!
!    61  62  63  64  65  66  67  68  69  70  71  72  73  74  75
!    E   E   R   F   P   M   M   S   T   F   K   V   L   L   C
381 gaa gaa cgt ttt cca ctg atg agc act ttt caa gtt ctg cta tgt
!
!    76  77  78  79  80  81  82  83  84  85  86  87  88  89  90
!    G   A   V   L   S   R   I   D   A   G   Q   E   Q   L   G
426 ggc gcg gta tta tcc cgt att gac gcc ggg caa gaG CAa ctc ggT
!
!                                             BcgI..........
!    91  92  93  94  95  96  97  98  99 100 101 102 103 104 105
!    R   R   I   H   Y   S   Q   N   D   L   V   E   Y   S   P
471 CGc cgc ata cac tat tct cag aat gac ttg gtt gAG TAC Tca cca
!
!..BcgI......              ScaI....
!   106 107 108 109 110 111 112 113 114 115 116 117 118 119 120
!    V   T   E   K   H   L   T   D   G   M   T   V   R   E   L
516 gtc aca gaa aag cat ctt acg gat ggc atg aca gta aga gaa tta
!
!   121 122 123 124 125 126 127 128 129 130 131 132 133 134 135
!    C   S   A   A   I   T   M   S   D   N   T   A   A   N   L
561 tgc agt gct gcc ata acc atg agt gat aac act gcg gcc aac tta
!
!   136 137 138 139 140 141 142 143 144 145 146 147 148 149 150
!    L   L   T   T   I   G   G   P   K   E   L   T   A   F   L
606 ctt ctg aca aCG ATC Gga gga ccg aag gag cta acc gct ttt ttg
!
!            PvuI....(1/2)
!   151 152 153 154 155 156 157 158 159 160 161 162 163 164 165
!    H   N   M   G   D   H   V   T   R   L   D   R   W   E   P
651 cac aac atg ggg gat gat cat gta act cgc ctt gat cgt tgg gaa ccg
!
!   166 167 168 169 170 171 172 173 174 175 176 177 178 179 180
!    E   L   N   E   A   I   P   N   D   E   R   D   T   T   M
696 gag ctg aat gaa gcc ata cct aac gac gag cgt gac acc acg atg
!
!   181 182 183 184 185 186 187 188 189 190 191 192 193 194 195
!    P   V   A   M   A   T   T   L   R   K   L   L   T   G   E
741 cct gta GCA ATG gca aca acg tTG CGC Aaa cta tta act ggc gaa
!
!          BsrDI..(1/2)     FspI...(1/2)
!   196 197 198 199 200 201 202 203 204 205 206 207 208 209 210
!    L   L   T   L   A   S   R   Q   Q   L   I   D   W   M   E
786 cta ctt act cta gct tcc cgg caa caa tta ata gac tgg atg gag
!
!   211 212 213 214 215 216 217 218 219 220 221 222 223 224 225
!    A   D   K   V   A   G   P   L   L   R   S   A   L   P   A
831 gcg gat aaa gtt gca gga cca ctt ctg cgc tcg gcc ctt ccg gct
!
!   226 227 228 229 230 231 232 233 234 235 236 237 238 239 240
!    G   W   F   I   A   D   K   S   G   A   G   E   R   G   S
```

TABLE 29-continued

DNA sequence of pCES5

```
 876 ggc tgg ttt att gct gat aaa tCT GGA Gcc ggt gag cgt gGG TCT
!
!                            BpmI....(1/2)    BsaI....
!     241 242 243 244 245 246 247 248 249 250 251 252 253 254 255
!      R   G   I   I   A   A   L   G   P   D   G   K   P   S   R
 921 Cgc ggt atC ATT GCa gca ctg ggg cca gat ggt aag ccc tcc cgt
!
!        BsaI......  BstDI...(2/2)
!     256 257 258 259 260 261 262 263 264 265 266 267 268 269 270
!      I   V   V   I   Y   T   T   G   S   Q   A   T   M   D   E
 966 atc gta gtt atc tac acG ACg ggg aGT Cag gca act atg gat gaa
!
!                  AhdI..........
!     271 272 273 274 275 276 277 278 279 280 281 282 283 284 285
!      R   N   R   Q   I   A   E   I   G   A   S   L   I   K   H
1011 cga aat aga cag atc gct gag ata ggt gcc tca ctg att aag cat
!
!     286 287
!      W
1056 tgg taa 1062                                     ctgtcagac caagtttact 1081 catatatact ttagattgat ttaaaacttc attttaatt taaaaggatc taggtgaaga 1141 tccttttga taatctcatg accaaaatcc cttaacgtga gttttcgttc cactgagcgt 1201 cagaccccgt agaaaagatc aaaggatctt cttgagatcc ttttttctg cgcgtaatct 1261 gctgcttgca acaaaaaaa ccaccgctac cagcggtggt ttgtttgccg gatcaagagc 1321 taccaactct ttttccgaag gtaactggct tcagcagagc gcagatacca aatactgtcc 1381 ttctagtgta gccgtagtta ggccaccact tcaagaactc tgtagcaccg cctacatacc 1441 tcgctctgct aatcctgtta ccagtggctg ctgccagtgg cgataagtcg tgtcttaccg 1501 ggttggactc aagacgatag ttaccggata aggcgcagcg gtcgggctga acggggggtt 1561 cgtgcataca gcccagcttg gagcgaacga cctacaccga actgagatac ctacagcgtg 1621 agcattgaga aagcgccacg cttcccgaag ggagaaaggc ggacagGTAT CCggtaagcg
!                                                        BciVI.. (2 of 2)

1681 gcagggtcgg aacaggagag cgCACGAGgg agcttccagg gggaaacgcc tggtatcttt
!                          BssSI.(2/2)

1741 atagtcctgt cgggtttcgc cacctctgac ttgagcgtcg attttgtga tgctcgtcag 1801 gggggcggag cctatggaaa aacgccagca acgcggcctt tttacggttc ctggccttt 1861 gctggccttt tgctcACATG Ttcttttcctg cgttatcccc tgattctgtg gataaccgta
!              PciI...

1921 ttaccgcctt tgagtgagct gataccgctc gccgcagccg aacgaccgag cgcagcgagt 1981 cagtgagcga ggaagcgGAA GAGCgcccaa tacgcaaacc gcctctcccc gcgcgttggc
!              SapI...

2041 cgattcatta atgCAGCTGg cacgacaggt ttcccgactg gaaagcgggc agtgagcgca
!           PvuII.(1/3)

2101 acgcaatTAA TGTgagttag ctcactcatt aggcaccca ggcTTTACAc tttatgcttc
!          ..-35..     Plac              ..-10.

2161 cggctcgtat gttgtgtgga attgtgagcg gataacaatt tcacaCAGGA AACAGCTATG
!                                         M13Rev_seq_primer 2221 ACcatgatta cgCCAAGCTT TGGagccttt tttttggaga ttttcaac
!          PflMI......
!           Hind3.
!      signal::linker::CLight
```

TABLE 29-continued

DNA sequence of pCES5

```
!
!      1   2   3   4   5   6   7   8   9  10  11  12  13  14  15
!     fM   K   K   L   L   F   A   I   P   L   V   V   P   F   Y
      (Amino acid sequence is SEQ ID NO: 524)
2269  gtg aaa aaa tta tta ttc gca att cct tta gtt gtt cct ttc tat
!

!              Linker........................End of FR4
!     16  17  18  19  20  21  22  23  24  25  26  27  28  29  30
!      S   H   S   A   Q   V   Q   L   Q   V   D   L   E   I   K
2314  tct cac aGT GCA Cag gtc caa CTG CAG GTC GAC CTC GAG atc aaa
!         ApaLI......    PstI...     XhcI...
!                        BspMI...
!                        SalI...
!                        AccI...(1/2)
!                        HincII.(1/2)
!

! Vlight domains could be cloned in as ApaLI-XhoI fragments.
! VL-CL(kappa) segments can be cloned in as ApaLI-AscI fragments. <----------
!

!     Ckappa----------------------------------------
!     31  32  33  34  35  36  37  38  39  40  41  42  43  44  45
!      R   G   T   V   A   A   P   S   V   F   I   F   P   P   S
2359  cgt gga act gtg gct gca cca tct GTC TTC atc ttc ccg cca tct
!                                 BbsI...(1/2)
!

!     46  47  48  49  50  51  52  53  54  55  56  57  58  59  60
!      D   E   Q   L   K   S   G   T   A   S   V   V   C   L   L
2404  gat gag cag ttg aaa tct gga act gcc tct gtt gtg tgc ctg ctg
!

!     61  62  63  64  65  66  67  68  69  70  71  72  73  74  75
!      N   N   F   Y   P   R   E   A   K   V   Q   W   K   V   D
2449  aat aac ttc tat ccc aga gag gcc aaa gta cag tgg aag gtg gat
!

!     76  77  78  79  80  81  82  83  84  85  86  87  88  89  90
!      N   A   L   Q   S   G   N   S   Q   E   S   V   T   E   Q
2494  aac gcc ctc caa tcg ggt aac tcc cag gag agt gtc aca gag cag
!

!     91  92  93  94  95  96  97  98  99 100 101 102 103 104 105
!      D   S   K   D   S   T   Y   S   L   S   S   T   L   T   L
2539  gac agc aag gac agc acc tac agc ctc agc agc acc ctg acG CTG
!                                           EspI...
!

!    106 107 108 109 110 111 112 113 114 115 116 117 118 119 120
!      S   K   A   D   Y   E   K   H   K   V   Y   A   C   E   V
2584  AGC aaa gca gac tac gag aaa cac aaa GTC TAC gcc tgc gaa gtc
!     ...EspI...          AccI...(2/2)
!

!    121 122 123 124 125 126 127 128 129 130 131 132 133 134 135
!      T   H   Q   G   L   S   S   P   V   T   K   S   F   N   R
2629  acc cat cag ggc ctg agt tcA CCG GTg aca aag agc ttc aac agg
!                            AgcI....(1/2)
!

!    136 137 138 139 140
!      G   E   C   .   .
2674  gga gag tgt taa taa GG CGCGCCaatt
!                            AscI....
!                            BssHII.
```

TABLE 29-continued

DNA sequence of pCES5

!
2701 ctatttcaag gagacagtca ta
!
! PelB::3-23(stuffed)::CH1::III fusion gene
!    1   2   3   4   5   6   7   8   9  10  11  12  13  14  15
!    M   K   Y   L   L   P   T   A   A   A   G   L   L   L   L
!    (Amino acid sequence is SEQ ID NO: 525)
2723 atg aaa tac cta ttg cct acg gca gcc gct gga ttg tta tta ctc
!
!-----------------------------------------
!
!   16  17  18  19  20  21  22
!    A   A   Q   P   A   M   A
2768 gcG GCC cag ccG GCC atg gcc
!    StiI.............
!       NgoMIV..(1/2)
!          NcoI...
!
!   FR1(DP47/V3-23)--------------
!   23  24  25  26  27  28  29  30
!    E   V   Q   L   L   E   S   G
2789 gaa|gtt|CAA|TTG|tta|gag|tct|ggt|
!                       |MfeI|
!
!   ------------------FR1------------------------------------
!   31  32  33  34  35  36  37  38  39  40  41  42  43  44  45
!    G   G   L   V   Q   P   G   S   L   R   L   S   C   A
2813 |ggc|ggt|ctt|gtt|cag|cct|ggt|ggt|tct|tta|cgt|ctt|tct|tgc|gct|
!
!   -----FR1-------
!   46  47  48
!    A   S   G
2858 |gct|TCC|GGA|
!    |BspEI|
!
!   Stuffer for CDR1, FR2, and CDR2------------------------->
!   There are no stop codons in this stuffer.
2867                                   gcttcAGATC Tgtttgcctt
!                                           BgIII..
2887 tttgtggggt ggtgcagatc gcgttacgga gatcgaccga ctgcttgagc aaaagccacg
2947 cttaactgcT GATCAggcat gggatgttat tcgccaaacc agtcgtcagg atcttaacct
!          BclI...
3007 gaggcttttt ttacctactc tgcaagcagc gacatctggt ttgacacaga gcgatccgcg
3067 tcgtcagttg gtagaaacat taacacgttg ggatggcatc aatttgctta atgatgatgg
3127 taaaacctgg cagcagccag gctctgccat cctgaacgtt tggctgacca gtatgttgaa
3187 gcgtaccgta gtgctgccg tacctatgCC Atttgataag TGGtacagcg ccagtggcta
!              XcmI............
3247 cgaaacaacc caggacggcc caactggttc gctgaatata agtgttggag caaaattttt
3307 gtatgaggcg gtgcagggag acaaatcacc aatcccacag gcggttgatc tgtttgctgg
3367 gaaaccacag caggaggttg tgttggctgc gctggaagat acctgggaga ctctttccaa
3427 acgctatggc aataatgtga gtaactggaa aacacctgca atggccttaa cgttccgggc
3487 aaataatttc tttggtgtac cgcaggccgc agcggaagaa ACGCGTcatc aggcggagta
!                                              MluI..
3547 tcaaaaccgt ggaacagaaa acgatatgat tgttttctca ccaacgacaa gcgatcgtcc
3607 tgtgcttgcc tgggatgtgg tcgcacccgg tcagagtggg tttattgctc ccgatggaac
3667 agttgataag cactatgaag atcagctgaa aatgtacgaa aattttggcc gtaagtcgct
!              PvuII.

TABLE 29-continued

DNA sequence of pCES5

```
3727 ctgGTTAACg aagcaggatg tggaggcgca taaggagtcg
!    Hpa1.
!    HincII(2/2)
!
!
!    ----------FR3------------------------------------
!    4   5   6   7   8   9   10  11  12  13  14  15  16
!    93  94  95  96  97  98  99  100 101 102 103 104 105
!    S   R   D   N   S   K   N   T   L   Y   L   Q   M
     (Amino acid sequence is SEQ ID NO: 526)
3767 |TCT|AGA|gac|aac|tct|aag|aat|act|ctc|tac|ttg|cag|atg|
!    |XbaI|
!
!
!    ---FR3-----------------------------------
!    17  18  19  20
!    106 107 108 109
!    N   S   L   s   l   s   i   r   s   g
3806 |aac|agC|TTA|AG t ctg agc att CGG TCC G
!         |AflII|        RsrII..
!
!
!    q   h   s   p   n   .
3834 gg  caa cat tct cca aac tga ccagacga cacaaacggc 3872 ttacgctaaa tcacgcgcat gggatggtaa agaggtggcg tctttgctgg cctggactca 3932 tcagatgaag gccaaaaatt ggcaggagtg gacacagcag gcagcgaaac aagcactgac 3992 catcaactgg tactatgctg atgtaaacgg caatattggt tatgttcata ctggtgctta 4052 tccagatcgt caatcaggcc atgatccgcg attacccgtt cctggtacgg gaaaatggga 4112 ctggaaaggg ctattgcctt ttgaaatgaa ccctaaggtg tataaccccc ag 4164     aa GCTAGC ctgcggcttc
!           NheI..
!
!
4182 G|GTC|ACC|                    gtc tca agc
!    |BstEII|
!
!
     (Amino acid sequence is SEQ ID NO: 527)
!    136 137 138 139 140 141 142 143 144 145 146 147 148 149 150
!    A   S   T   K   G   P   S   V   F   P   L   A   P   S   S
4198 gcc tcc acc aag ggc cca tcg gtc ttc ccc ctg gca ccc tcc tcc
!
!
!    151 152 153 154 155 156 157 158 159 160 161 162 163 164 165
!    K   S   T   S   G   G   T   A   A   L   G   C   L   V   K
4243 aag agc acc tct ggg ggc aca gcg gcc ctg gcc tgc ctg gtc aag
!
!
!    166 167 168 169 170 171 172 173 174 175 176 177 178 179 180
!    D   Y   F   P   E   P   V   T   V   S   W   N   S   G   A
4288 gac tac ttc ccc gca ccg gtg acg gtg tcg tgg aac tca ggc gcc
!
!
!    181 182 183 184 185 186 187 188 189 190 191 192 193 194 195
!    L   T   S   G   V   H   T   F   P   A   V   L   Q   S   S
4333 ctg acc agc ggc gtc cac acc ttc ccg gct gtc cta cag tcc tca
!
!
!    196 197 198 199 200 201 202 203 204 205 206 207 208 209 210
!    G   L   Y   S   L   S   S   V   V   T   V   P   S   S   S
4378 gga ctc tac tcc ctc agc agc gta gtg acc gtg ccc tcc agc agc
!
!
!    211 212 213 214 215 216 217 218 219 220 221 222 223 224 225
!    L   G   T   Q   T   Y   I   C   N   V   N   H   K   P   S
4423 ttg ggc acc cag acc tac atc tgc aac gtg aat cac aag ccc agc
!
!
!    226 227 228 229 230 231 232 233 234 235 236 237 238
!    N   T   K   V   D   K   K   V   E   P   K   S   C
```

TABLE 29-continued

DNA sequence of pCES5

```
4468 aac acc aag gtg gac aaG AAA GTT GAG CCC AAA TCT TGT
!                    ON-TQHCforw.......................
!

!         Poly His linker
!     139 140 141 142 143 144 145 146 147 148 149 150
!      A   A   A   H   H   H   H   H   H   G   A   A
4507 GCG GCC GCa cat cat cat cac cat cac gg gcc gca
!    NotI......
!     EagI.....
!

!     151 152 153 154 155 156 157 158 159 160 161 162 163 164 165
!      E   Q   K   L   I   S   E   E   D   L   N   G   A   A   .
4543 gaa caa aaa ctc atc tca gaa gag gat ctg aat ggg gcc gca tag
!

!    Mature III----------------------------------------->...
!     166 167 168 169 170 171 172 173 174 175 176 177 178 179 180
!      T   V   E   S   C   L   A   K   P   H   T   E   N   S   F
4588 act gtt gaa agt tgt tta gca aaa cct cat aca gaa aat tca ttt
!

!     181 182 183 184 185 186 187 188 189 190 191 192 193 194 195
!      T   N   V   W   K   D   D   K   T   L   D   R   Y   A   N
4633 act aac gtc tgg aaa gac gac aaa act tta gat cgt tac gct aac
!

!     196 197 198 199 200 201 202 203 204 205 206 207 208 209 210
!      Y   E   G   C   L   W   N   A   T   G   V   V   C   T
4678 tat gag ggc tgt ctg tgG AAT GCt aca ggc gtt gtg gtt tgt act
!                   BsmI....
!

!     211 212 213 214 215 216 217 218 219 220 221 222 223 224 225
!      G   D   E   T   Q   C   Y   G   T   W   V   P   I   G   L
4723 ggt gac gaa act cag tgt tac ggt aca tgg gtt cct att ggg ctt
!

!     226 227 228 229 230 231 232 233 234 235 236 237 238 239 240
!      A   I   P   E   N   E   G   G   G   S   E   G   G   G   S
4768 gct atc cct gaa aat gag ggt ggt ggc tct gag ggt ggc ggt tct
!

!     241 242 243 244 245 246 247 248 249 250 251 252 253 254 255
!      E   G   G   G   S   E   G   G   G   T   K   P   P   E   Y
4813 gag ggt ggc ggt tct gag ggt ggc ggt act aaa cct cct gag tac
!

!     256 257 258 259 260 261 262 263 264 265 266 267 268 269 270
!      G   D   T   P   I   P   G   Y   T   Y   I   N   P   L   D
4858 ggt gat aca cct att ccg ggc tat act tat atc aac cct ctc gac
!

!     271 272 273 274 275 276 277 278 279 280 281 282 283 284 285
!      G   T   Y   P   P   G   T   E   Q   N   P   A   N   P   N
4903 ggc act tat ccg cct ggt act gag caa aac ccc gct aat cct aat
!

!     286 287 288 289 290 291 292 293 294 295 296 297 298 299 300
!      P   S   L   E   E   S   Q   P   L   N   T   F   M   F   Q
4948 cct tct ctt GAG GAG tct cag cct ctt aat act ttc atg ttt cag
!            BseRI..(2/2)
!

!     301 302 303 304 305 306 307 308 309 310 311 312 313 314 315
!      N   N   R   F   R   N   R   Q   G   A   L   T   V   Y   T
4993 aat aat agg ttc cga aat agg cag ggt gca tta act gtt tat acg
!

!     316 317 318 319 320 321 322 323 324 325 326 327 328 329 330
!      G   T   V   T   Q   G   T   D   P   V   K   T   Y   Y   Q
5038 ggc act gtt act caa ggc act gac ccc gtt aaa act tat tac cag
!

!     331 332 333 334 335 336 337 338 339 340 341 342 343 344 345
!      Y   T   P   V   S   S   K   A   M   Y   D   A   Y   W   N
```

TABLE 29-continued

DNA sequence of pCES5

```
5083 tac act cct gta tca tca caa gcc atg tat gac gct tac tgg aac 346 347 348 349 350 351 352 353 354 355 356 357 358 359 360
      G   K   F   R   D   C   A   F   H   S   G   F   N   E   D
5128 ggt aaa ttc aga gac tgc gct ttc cat tct ggc ttt aat gaG GAT
                                                  BamHI..

361 362 363 364 365 366 367 368 369 370 371 372 373 374 375
      P   F   V   C   E   Y   Q   G   Q   S   S   D   L   P   Q
5173 CCa ttc gtt tgt gaa tat caa ggc caa tcg tct gAC CTG Cct caa
     BamHI...                              =BspMI..(2/2)

376 377 378 379 380 381 382 383 384 385 386 387 388 389 390
      P   P   V   N   A   G   G   G   S   G   G   G   S   G   G
5218 cct cct gtc aat gct ggc ggc ggc tct ggt ggt ggt tct ggt ggc 391 392 393 394 395 396 397 398 399 400 401 402 403 404 405
      G   S   E   G   G   G   S   E   G   G   G   S   E   G   G
5263 ggc tct gag ggt ggc ggc tct gag ggt ggc ggt tct gag ggt ggc 406 407 408 409 410 411 412 413 414 415 416 417 418 419 420
      G   S   E   G   G   G   S   G   G   G   S   G   S   G   D
5308 ggc tct gag ggt ggc ggt tcc ggt ggc ggc tcc ggt tcc ggt gat 421 422 423 424 425 426 427 428 429 430 431 432 433 434 435
      F   D   Y   E   K   M   A   N   A   N   K   G   A   M   T
5353 ttt gat tat gaa aaa atg gca aac gct aat aag ggg gct atg acc 436 437 438 439 440 441 442 444 443 445 446 447 448 449 450
      E   N   A   D   E   N   A   L   Q   S   D   A   K   G   K
5398 gaa aat gcc gat gaa aac gcg cta cag tct gac gct aaa ggc aaa 451 452 453 454 455 456 457 458 459 460 461 462 463 464 465
      L   D   S   V   A   T   D   Y   G   A   A   I   D   G   F
5443 ctt gat tct gtc gct act gat tac ggt gct gct ACT GAT ggt ttc
                                              BspDI..

466 467 468 469 470 471 472 473 474 475 476 477 478 479 480
      I   G   D   V   S   G   L   A   N   G   N   G   A   T   G
5488 att ggt gac gtt tcc ggc ctt gct aat ggt aat ggt gct act ggt 481 482 483 484 485 486 487 488 489 490 491 492 493 494 495
      D   F   A   G   S   N   S   Q   M   A   Q   V   G   D   G
5533 gat ttt gct ggc tct aat tcc caa atg gct caa gtc ggt gac ggt 496 497 498 499 500 501 502 503 504 505 506 507 508 509 510
      D   N   S   P   L   M   N   N   F   R   Q   Y   L   P   S
5578 gat aat tca cct tta atg aat aat ttc cgt caa tat tta cct tct 511 512 513 514 515 516 517 518 519 520 521 522 523 524 5255
      L   P   Q   S   V   E   C   R   P   Y   V   F   G   A   G
5623 ttg cct cag tcg gtt gaa tgt cgc cct tat gtc ttt ggc gct ggt 526 527 528 529 530 531 532 533 534 535 536 537 538 539 540
      K   P   Y   E   F   S   I   D   C   D   K   I   N   L   F
5668 aaa cCa TAT Gaa ttt tct att gat tgt gac aaa ata aac tta ttc
         NdeI....

541 542 543 544 545 546 547 548 549 550 551 552 553 554 555
      R   G   V   F   A   F   L   L   Y   V   A   T   F   M   Y
```

TABLE 29-continued

DNA sequence of pCES5

```
5713 cgt ggt gtc ttt gcg ttt ctt tta tat gtt gcc acc ttt atg tat
!
!    556 557 558 559 560 561 562 563 564 565 566 567 568 569 570
!     V   F   S   T   F   A   N   I   L   R   N   K   E   S   .
5758 gta ttt tcg acg ttt gct aac ata ctg cgt aat aag gag tct taa
!
!    571
!
5803 taa GAATTC
!     EcoRI.

5812 actggccgt cgttttacaa cgtcgtgact gggaaaaccc tggcgttacc caacttaatc 5871 gccttgcagc acatcccct ttcgccagct ggcgtaatag cgaagaggcc cgcacCGATC
!                                                              PvuI..

5931 GcccttCCCA acagtTGCGC AgcctgaatG gcgaatGGCG CCtgatgcgg tattttctcc
!   ...PvuI... (3/3)     FspI.. (2/2) KasI...(2/2)

5991 ttacgcatct gtgcggtatt tcacaccgca tataaattgt aaacgttaat attttgttaa 6051 aattcgcgtt aaattttgt taaatcagct cattttttaa ccaatcggcc gaaatcggca 6111 aaatcccTTA TAAatcaaaa gaatagcccg atagggggtt gagtgttgtt ccagtttgga
!         PsiI...

6171 acaagagtcc actattaaag aacgtggact ccaacgtcaa agggcgaaaa accgtctatc 6231 agggcgatgg ccCACtacGT Gaaccatcac ccaaatcaag ttttttgggg tcgaggtgcc
!          DraIII....

6291 gtaaagcact aaatcggaac cctaaaggga gcccccgatt tagagcttga cggggaaaGC
!                                                         NgoMIV..

6351 CGGCgaacgt ggcgagaaag gaagggaaga aagcgaaagg agcgggcgct agggcgctgg
!   ..NgoMIV.(2/2)

6411 caagtgtagc ggtcacgctg cgcgtaacca ccacacccgc cgcgcttaat gcgccgctac 6471 agggcgcgta ctatggttgc tttgacgggg cagtctcag tacaatctgc tctgatgccg 6531 catagttaag ccagccccga cacccgccaa cacccgctga cgcgccctga cgggcttgtc 6591 tgctcccggc atccgcttac agacaagctg tgaccgtctc cgggagctgc atgtgtcaga 6651 ggttttcacc gtcatcaccg aaacgcgcga
```

TABLE 30

Oligonucleotides used to clone CDR1/2 diversity

All sequences are 5' to 3'.

1) ON_CD1Bsp, 30 bases (SEQ ID NO: 528)
```
A c c T c A c T g g c T T c c g g A
1 2 3 4 5 6 7 8 9 10 11 12 13 14 15 16 17 18

T T c A c T T T c T c T
19 20 21 22 23 24 25 26 27 28 29 30
```

2) ON_BrI2; 42 bases (SEQ ID NO: 529)
```
A g A A A c c c A c T c c A A A c c
1 2 3 4 5 6 7 8 9 10 11 12 13 14 15 16 17 18

T T T A c c A g g A g c T T g g c
19 20 21 22 23 24 25 26 27 28 29 30 31 32 33 34 35 g A A c c A
36 37 38 39 40 41 42
```

3) ON_CD2Xba, 51 bases (SEQ ID NO: 530)
```
g g A A g g c A g T g A T c T A g A
1 2 3 4 5 6 7 8 9 10 11 12 13 14 15 16 17 18 g A T A g T g A A g c g A c c T T
19 20 21 22 23 24 25 26 27 28 29 30 31 32 33 34 35

T A A c g g A g T c A g c A T A
36 37 38 39 40 41 42 43 44 45 46 47 48 49 50 51
```

4) ON_BotXba, 23 bases (SEQ ID NO: 531)
```
g g A A g g c A g T g A T c T A g A
1 2 3 4 5 6 7 8 9 10 11 12 13 14 15 16 17 18 g A T A g
19 20 21 22 23
```

TABLE 31

Bridge/Extender Oligonucleotides
(SEQ ID NOS 532-546, respectively in order of appearance)

| | | |
|---|---|---|
| ON_Lam1aB7(rc) | ..........................GTGCTGACTCAGCCACCCTC. | 20 |
| ON_Lam2aB7(rc) | ..........................GCCCTGACTCAGCCTGCCTC. | 20 |
| ON_Lam3$$B7(rc) | ..........................GAGCTGACTCAGG.ACCCTGC | 20 |
| ON_Lam3fB7(rc) | ..........................GAGCTGACTCAGCCACCCTC. | 20 |
| ON_LamHf1cBrg(rc) | CCTCGACAGCGAAGTGCACAGAGCGTCTTGACTCAGCC....... | 38 |
| ON_LamHf1cExt | CCTCGACAGCGAAGTGCACAGAGCGTCTTG............... | 30 |
| ON_LamHf2b2Brg(rc) | CCTCGACAGCGAAGTGCACAGAGCGCTTTGACTCAGCC....... | 38 |
| ON_LamHf2b2Ext | CCTCGACAGCGAAGTGCACAGAGCGCTTTG............... | 30 |
| ON_LamHf2dBrg(rc) | CCTCGACAGCTAAGTGCACAGAGCGCTTTGACTCAGCC....... | 38 |
| ON_LamHf2dExt | CCTCGACAGCGAAGTGCACAGAGCGCTTTG............... | 30 |
| ON_LamHf3$$Brg(rc) | CCTCGACAGCGAAGTGCACAGAGCGAATTGACTCAGCC....... | 38 |
| ON_LamHf3$$Ext | CCTCGACAGCGAAGTGCACAGAGCGAATTG............... | 30 |
| ON_LamHf3rBrg(rc) | CCTCGACAGCGAAGTGCACAGTACGAATTGACTCAGCC....... | 38 |
| ON_LamHf3rExt | CCTCGACAGCGAAGTGCACAGTACGAATTG............... | 30 |
| ON_LamP1cPCR | CCTCGACAGCGAAGTGCACAG........................ | 21 |
| Consenses | | |

TABLE 32

Oligonucleotides used to make SSDNA locally double-stranded
(SEQ ID NOS 548-552, respectively in order of appearance)

Adapters (8)
H43HF3.1-02#1     5'-cc gtg tat tac tgt gcg aga g-3'

H43.77.97.1-03#2  5'-ct gtg tat tac tgt gcg aga g-3'

H43.77.97.323#22  5'-cc gta tat tac tgt gcg aaa g-3'

H43.77.97.330#23  5'-ct gtg tat tac tgt gcg aaa g-3'

H43.77.97.439#44  5'-ct gtg tat tac tgt gcg aga c-3'

H43.77.97.551#48  5'-cc atg tat tac tgt gcg aga c-3'

TABLE 33

Bridge/extender pairs

Bridges (2)
H43.XABr1
5'ggtgtagtgaTCTAGtgacaactctaagaatactctctacttgcagat
gaacagCTTtAGggctgaggacaCTGCAGtctactattgtgcgaga-3'
(SEQ ID NO: 553)

H43.XABr2
5'ggtgtagtgaTCTAGtgacaactctaagaatactctctacttgcagat
gaacagCTTtAGggctgaggacaCTGCAGtctactattgtgcgaaa-3'
(SEQ ID NO: 554)

TABLE 33-continued

Bridge/extender pairs

Extender
H43.XAExt
5'ATAgTAgAcTgcAgTgTccTcAgcccTTAAgcTgTTcATcTgcAAgTA
gAgAgTATTcTTAgAgTTgTcTcTAgATcAcTAcAcc-3'
(SEQ ID NO: 555)

TABLE 34

| | PCR primers |
|---|---|
| Primers | |
| H43.XAPCR2 | gactgggTgTAgTgATcTAg<br>(SEQ ID NO: 556) |
| Hucmnest | cttttctttgttgccgttggggtg<br>(SEQ ID NO: 557) |

TABLE 35

PCR program for amplification of heavy chain CDR3 DNA

| | | |
|---|---|---|
| 95 degrees C. | 5 minutes | |
| 95 degreee C. | 20 seconds | |
| 60 degrees C. | 30 seconds | repeat 20x |
| 72 degrees C. | 1 minute | |
| 72 degrees C. | 7 minutes | |
| 4 degrees C. | hold | |

Reagents (100 ul reaction):

| | |
|---|---|
| Template | 5 ul ligation mix |
| 10x PCR buffer | 1x |

TABLE 35-continued

PCR program for amplification of heavy chain CDR3 DNA

| | |
|---|---|
| Taq | 5 U |
| dNTPs | 200 uM each |
| MgCl$_2$ | 2 mM |

TABLE 35-continued

PCR program for amplification of heavy chain CDR3 DNA

| | |
|---|---|
| H43.XA9CR2-biotin | 400 nM |
| Hucmnest | 200 nM |

TABLE 36

Annotated sequence of CJR DY3F7(CJR-A05) 10251 bases

```
!
!Non-cutters
!
!BclI Tgatca     BsiWI Cgtacg    BssSI Cacgag
!BstZ17I GTAtacBtrI CACgtg       EcoRV GATatc
!FseI GGCCGGcc   HpaI GTTaac     MluI Acgcgt
!PmeI GTTTaaac   PmlI CACgtg     PpuMI RGgwccy
!RsrII CGgwccg   SapI GCTCTTC    SexAI Accwggt
!SgfI GCGATcgc   SgrAI CRccggyg  SphI GCATGc
!StuI AGGcct     XmaI Cccggg
!
!cutters
!
!Enzymes that cut from 1 to 4 times and other features
!
!End of genes II and X            829
!Start gene V                     843
!BsrGI Tgtaca                  1 1021
!BspMI Nnnnnnnnngcaggt         3 1104 5997 9183
(SEQ ID NO: 558)
!-"- ACCTGCNNNNn               1 2281
(SEQ ID NO: 559)
!End of gene V                    1106
!Start gene VII                   1108
!BsaBI GATNNnnatc              2 1149 3967
(SEQ ID NO: 560)
!Start gene IX                    1208
!End gene VII                     1211
!SnaBI TACgta                  2 1268 7133
!BspHI Tcatga                  3 1299 6085 7093
!Start gene VIII                  1301
!End gene IX                      1304
!End gene VIII                    1522
!Start gene III                   1578
!EagI Cggccg                   2 1630 8905
!XbaI Tctaga                   2 1643 8436
!KasI Ggcgcc                   4 1650 8724 9039 9120
!BsmI GAATGCN                  2 1769 9065
!BseRI GAGGAGNNNNNNNNNN        2 2031 8516
(SEQ ID NO: 561)
!-"- NNnnnnnnnnctcctc          2 7603 8623
(SEQ ID NO: 562)
!AlwNI CAGNNNctg               3 2210 8072 8182
!BspDI ATcgat                  2 2520 9883
!NdeI CAtatg                   3 2716 3796 9847
!End gene III                     2846
!Start gene VI                    2848
!AfeI AGCgct                   1 3032
!End gene VI                      3187
!Start gene I                     3189
!EarI CTCTTCNnnn               2 4067 9274
(SEQ ID NO: 563)
!-"- Nnnnngaagag               2 6126 8953
(SEQ ID NO: 564)
!PacI TTAATtaa                 1 4125
!Start gene IV                    4213
!End gene I                       4235
!BsmFI Nnnnnnnnnnnnnnnngtccc   2 5068 9515
(SEQ ID NO: 565)
!MscI TGGcca                   3 5073 7597 9160
!PsiI TTAtaa                   2 5349 5837
!End gene IV                      5493
!Start ori                        5494
!NgoMIV Gccggc                 3 5606 8213 9315
!BanII GRGCYc                  4 5636 8080 8606 8889
```

TABLE 36-continued

Annotated sequence of CJR DY3F7(CJR-A05) 10251 bases

| | | | | |
|---|---|---|---|---|
| !DraIII CACNNNgtg | 1 | 5709 | | |
| !DrdI GACNNNNnngtc (SEQ ID NO: 566) | 1 | 5752 | | |
| !AvaI Cycgrg | 2 | 5818 | 7240 | |
| !PvuII CAGctg | 1 | 5953 | | |
| !BsmBI CGTCTCNnnnn (SEQ ID NO: 567) | 3 | 5964 | 8585 | 9271 |
| !End ori region | | 5993 | | |
| !BamHI Ggatcc | 1 | 5994 | | |
| !HindIII Aagctt | 3 | 6000 | 7147 | 7384 |
| !BciVI GTATCCNNNNNN (SEQ ID NO: 568) | 1 | 6077 | | |
| !Start bla | | 6138 | | |
| !Eco57I CTGAAG | 2 | 6238 | 7716 | |
| !SpeI Actagt | 1 | 6257 | | |
| !BcgI gcannnnnntcg (SEQ ID NO: 569) | 1 | 6398 | | |
| !ScaI AGTact | 1 | 6442 | | |
| !PvuI CGATcg | 1 | 6553 | | |
| !FspI TGCgca | 1 | 6700 | | |
| !BglI GCCNNNNnggc (SEQ ID NO: 570) | 3 | 6801 | 8208 | 8976 |
| !BsaI GGTCTCNnnnn (SEQ ID NO: 571) | 1 | 6853 | | |
| !AhdI GACNNNnngtc (SEQ ID NO: 572) | 1 | 6920 | | |
| !Eam1105I GACNNNnngtc (SEQ ID NO: 573) | 1 | 6920 | | |
| !End bla | | 6998 | | |
| !AccI GTmkac | 2 | 7153 | 8048 | |
| !HincII GTYrac | 1 | 7153 | | |
| !SalI Gtcgac | 1 | 7153 | | |
| !XhoI Ctcgag | 1 | 7240 | | |
| !Start PlacZ region | | 7246 | | |
| !End PlacZ region | | 7381 | | |
| !PflMI CCANNNNntgg (SEQ ID NO: 574) | 1 | 7382 | | |
| !RBS1 | | 7405 | | |
| !start M13-iii signal seq- for LC | | 7418 | | |
| !ApaLI Gtgcac | 1 | 7470 | | |
| !end M13-iii signal seq | | 7471 | | |
| !Start light chain kappa L20: JK1 | | 7472 | | |
| !PflFI GACnnngtc | 3 | 7489 | 8705 | 9099 |
| !SbfI CCTGCAgg | 1 | 7542 | | |
| !PstI CTGCAg | 1 | 7543 | | |
| !KpnI GGTACc | 1 | 7581 | | |
| !XcmI CCANNNNNnnnntgg (SEQ ID NO: 575) | 2 | 7585 | 9215 | |
| !NsiI ATGCAt | 2 | 7626 | 9503 | |
| !BsgI ctgcac | 1 | 7809 | | |
| !BbsI gtcttc | 2 | 7820 | 8616 | |
| !BlpI GCtnagc | 1 | 8017 | | |
| !EspI GCtnagc | 1 | 8017 | | |
| !EcoO109I RGgnccy | 2 | 8073 | 8605 | |
| !Ecl136I GAGctc | 1 | 8080 | | |
| !SacI GAGCTc | 1 | 8080 | | |
| !End light chain | | 8122 | | |
| !AscI GGcgcgcc | 1 | 8126 | | |
| !BssHII Gcgcgc | 1 | 8127 | | |
| !RBS2 | | 8147 | | |
| !SfiI GGCCNNNNnggcc (SEQ ID NO: 576) | 1 | 8207 | | |
| !NcoI Ccatgg | 1 | 8218 | | |
| !Start 3-23, FR1 | | 8226 | | |
| !MfeI Caattg | 1 | 8232 | | |
| !BspEI Tccgga | 1 | 8298 | | |
| !Start CDR1 | | 8316 | | |
| !Start FR2 | | 8331 | | |
| !BstXI CCANNNNNntgg (SEQ ID NO: 577) | 2 | 8339 | 8812 | |
| !EcoNI CCTNNnnnagg (SEQ ID NO: 578) | 2 | 8346 | 8675 | |
| !Start FR3 | | 8373 | | |
| !XbaI Tctaga | 2 | 8436 | 1643 | |
| !AflII Cttaag | 1 | 8480 | | |
| !Start CDR3 | | 8520 | | |

TABLE 36-continued

Annotated sequence of CJR DY3F7(CJR-A05) 10251 bases

```
!AatII GACGTc                  1 8556
!Start FR4                       8562
!PshAI GACNNnngtc              2 8573 9231
 (SEQ ID NO: 579)
!BstEII Ggtnacc                1 8579
!Start CH1                       8595
!ApaI GGGCCc                   1 8606
!Bspl20I Gggccc                1 8606
!PspOMI Gggccc                 1 8606
!AgeI Accggt                   1 8699
!Bsu36I CCtnagg                2 8770 9509
!End of CH1                      8903
!NotI GCggccgc                 1 8904
!Start His6 tag                  8913
 (SEQ ID NO: 12)
!Start cMyc tag                  8931
!Amber codon                     8982
!NheI Gctagc                   1 8985
!Start M13 III Domain 3          8997
!NruI TCGcga                   1 9106
!BstBI TTcgaa                  1 9197
!EcoRI Gaattc                  1 9200
!XcmI CCANNNNNnnnntgg          1 9215
 (SEQ ID NO: 580)
!BstAPI GCANNNNntga            1 9337
 (SEQ ID NO: 581)
!SacII CCGCgg                  1 9365
!End IIIstump anchor             9455
!AvrII Cctagg                  1 9462
!trp terminator                  9470
!SwaI ATTTaaat                 1 9784
!Start gene II                   9850
!BglII Agatct                  1 9936
!-----------------------------------------------------------------
(SEQ ID NO: 582)
    1 aat gct act act att agt aga att gat gcc acc ttt tca gct cgc
      gcc
!  gene ii continued
   49 cca aat gaa aat ata gct aaa cag gtt att gac cat ttg cga aat
      gta 97 tct aat ggt caa act aaa tct act cgt tcg cag aat tgg gaa tca
      act 145 gtt aTa tgg aat gaa act tcc aga cac cgt act tta gtt gca tat
      tta 193 aaa cat gtt gag cta cag caT TaT att cag caa tta agc tct aag
      cca 241 tcc gca aaa atg acc tct tat caa aag gag caa tta aag gta ctc
      tct 289 aat cct gac ctg ttg gag ttt gct tcc ggt ctg gtt cgc ttt gaa
      gct 337 cga att aaa acg cga tat ttg aag tcc ttc ggg ctt cct ctt aat
      ctt 385 ttt gat gca atc cgc ttt gct tct gac tat aat agt cag ggt aaa
      gac 433 ctg att ttt gat tta tgg tca ttc tcg ttt tct gaa ctg ttt aaa
      gca 481 ttt gag ggg gat tca ATG aat att tat gac gat tcc gca gta ttg
      gac
!                 Start gene x, ii continues
  529 gct atc cag tct aaa cat ttt act att acc ccc tct ggc aaa act
      tct 577 ttt gca aaa gcc tct cgc tat att ggt ttt atc gt cgt ctg gta
      aac 625 gag ggt tat gat agt gtt gct ctt act atg cct cgt aat tcc ttt
      tgg
```

TABLE 36-continued

Annotated sequence of CJR DY3F7(CJR-A05) 10251 bases

```
 673 cgt tat gta tct gca tta gtt gaa tgt ggt att cct aaa tct caa
     ctg 721 atg aat ctt tct acc tgt aat aat gtt gtt ccg tta gtt cgt ttt
     att 769 aac gta gat ttt tct tcc caa cgt cct cct tgg tat aat gag cca
     gtt 817 ctt aaa atc gca TAA
!                End X & II 832 ggtaattca ca
!(SEQ ID NO: 626)

!    M1               E5            Q10                     T15
 843 ATG att aaa gtt gaa att aaa cca tct caa gcc caa ttt act act
     cgt
!    Start gene V
!
!    S17        S20            P25              E30
 891 tct ggt gtt tct cgt cag ggc aag cct tat tca ctg aat gag cag
     ctt
!

!              V35            E40                V45
 939 tgt tac gtt gat ttg ggt aat gaa tat ccg gtt ctt gtc aag att
     act
!

!         D50              A55              L60
 987 ctt gat gaa ggt cag cca gcc tat gcg cct ggt cTG TAC Acc gtt
     cat
!
!                                            BsrGI...
!    L65          V70              S75
!    R80
1035 ctg tcc tct ttc aaa gtt ggt cag ttc ggt tcc ctt atg att gac
     cgt
!

!                  P85     K87 end of V
1083 ctg cgc ctc gtt ccg gct aag TAA C
!

1108 ATG gag cag gtc gcg gat ttc gac aca att tat cag gcg atg
!    Start gene VII
!
1150 ata caa atc tcc gtt gta ctt tgt ttc gcg ctt ggt ata atc
!

!              VII and IX overlap.
!             ..... S2  V3  L4  V5 (SEQ ID NO: 621) S10
1192 gct ggg ggt caa agA TGA gt gtt tta gtg tat tct ttT gcc tct ttc
 gtt !              End VII
!             |start IX
!    L13       W15              G20                 T25
 E29
1242 tta ggt tgg tgc ctt cgt agt ggc att acg tat ttt acc cgt tta atg
 gaa
!

1293 act tcc tc
!

!    .... stop of IX, IX and VIII overlap by four bases
1301 ATG aaa aag tct tta gtc ctc aaa gcc tct gta gcc gtt gct acc
     ctc
!    Start signal sequence of viii.
!
1349 gtt ccg atg ctg tct ttc gct gct gag ggt gac gat ccc gca aaa
     gcg !                      mature VIII --->
```

TABLE 36-continued

Annotated sequence of CJR DY3F7(CJR-A05) 10251 bases

```
1397 gcc ttt aac tcc ctg caa gcc tca gcg acc gaa tat atc ggt tat
     gcg 1445 tgg gcg atg gtt gtt gtc att 1466 gtc ggc gca act atc ggt atc aag ctg ttt aag
!
! bases 1499-1539 are probable promoter for iii
1499 aaa ttc acc tcg aaa gca | 1515
!           ..........  -35  ..
!
1517 agc tga taaaccgat acaattaaag gctccttttg
!                  ..... -10  ...
!

1552 gagccttttt ttt GGAGAt ttt | S.D. uppercase, thare may be 9 Ts
!

!        <------ III signal sequence ----------------------------->
(SEQ ID NO: 583)
!          M   K   K   L   L   F   A   I   P   L   V   V   P   F
1574 caac GTG aaa aaa tta tta ttc gca att cct tta gtt gtt cct ttc |
1620
!

!    Y   S   G   A   A   E   S   H   L   D   G   A
1620 tat tct ggc gCG GCC Gaa tca caT CTA GAc ggc gcc
!                    EagI....        XbaI....
!

! Domain 1 ----------------------------------------------------------
!    A   E   T   V   E   S   C   L   A
1656 gct gaa act gtt gaa agt tgt tta gca
!

!    K   S   H   T   E   I   S   F   T   N   V   W   K   D   D   K   T
1683 aaA Tcc cat aca gaa aat tca ttt aCT AAC GTC TGG AAA GAC GAC
     AAA ACt
!

!    L   D   R   Y   A   N   Y   E   G   S   L   W   N   A   T   G   V
1734 tta gat cgt tac gct aac tat gag ggC tgt ctg tgG AAT GGt aca
     ggc gtt
!                                               BsmI....
!

!    V   V   C   T   G   D   E   T   Q   C   Y   G   T   W   V   P   I
1785 gta gtt tgt act ggt GAC GAA ACT CAG TGT TAC GGT ACA TGG GTT
     cct att
!

!    G   L   A   I   P   E   N
1836 ggg ctt gct atc cct gaa aat
!

! L1 linker -------------------------------
!    E   G   G   S   E   G   G   G   S
1857 gag ggt ggt ggc tct gag ggt ggc ggt tct
!

!    E   G   G   G   S   E   G   G   G   T
1887 gag ggt ggc ggc tct gag ggt ggc ggt act
!

! Domain 2 -----------------------------------
1917 aaa cct cct gag tac ggt gat aca cct att ccg ggc tat act tat
     atc aac 1968 cct ctc gac ggc act tat ccg cct ggt act gag caa aac ccc gct
     aat cct 2018 aat cct tct ctt GAG GAG tct cag cct ctt aat act ttc atg ttt
     cag aat
!                 BseRI..
```

TABLE 36-continued

Annotated sequence of CJR DY3F7(CJR-A05) 10251 bases

```
2070 aat agg ttc cga aat agg cag ggg gca tta act gtt tat acg ggc
     act 2118 gtt act caa ggc act gac ccc gtt aaa act tat tac cag tac act
     cct 2166 gta tca tca aaa gcc atg tat gac gct tac tgg aac ggt aaa ttC
     AGA
!                                                         AlwNI
2214 GAC TGc gct ttc cat tct ggc ttt aat gaG gat TTa ttT gtt tgt
     gaa !    AlwNI
2262 tat caa ggc caa tcg tct gac ctg cct caa cct cct gtc aat gct
!

2307 ggc ggc ggc tct
! start L2 -------------------------------------------------------
2319 ggt ggt ggt tct 2331 ggt ggc ggc tct 2343 gag ggt ggt ggc tct gag gga ggc ggt tcc 2373 ggt ggt ggc tct ggt    ! end L2
!
! Many published sequences of M13-derived phage have a longer linker
! than shown here by repeats of the EGGGS (SEQ ID NO: 589) motif two
more times.
!
! Domain 3
(SEQ ID NO: 584)
----------------------------------------------------------
!    S   G   D   F   D   Y   E   K   M   A   N   A   N   K   G   A
2388 tcc ggt gat ttt gat tat gaa aag atg gca aac gct aat aag ggg gct
   !

!    M   T   E   N   A   D   E   N   A   L   Q   S   D   A   K   G
2436 atg acc gaa aat gcc gat gaa aac gcg cta cag tct gac gct aaa ggc
!

!    K   L   D   S   V   A   T   D   Y   G   A   A   M   D   G   F
2484 aaa ctt gat tct gtc gct act gat tac ggt gct gct atc gat ggt ttc
!

!    I   G   D   V   S   G   L   A   N   G   N   G   A   T   G   D
2532 att ggt gac gtt tcc ggc ctt gct aat ggt aat ggt gct act ggt gat
!

!    F   A   G   S   N   S   Q   M   A   Q   V   G   D   G   D   N
2580 ttt gct ggc tct aat tcc caa atg gct caa gtc ggt gac ggt gat aat
!

!    S   P   L   M   N   N   F   R   Q   Y   L   P   S   L   P   Q
2628 tca cct tta atg aat aat ttc cgt caa tat tta cct tcc ctc cct caa
!

!    S   V   E   C   R   P   F   V   F   G   A   G   K   P   Y   E
2676 tcg gtt gaa tgt cgc cct ttt gtc ttt Ggc gct ggt aaa cca tat gaa
!

!    F   S   I   D   C   D   K   I   N   L   F   R
2724 ttt tct att gat tgt gac aaa ata aac tta ttc cgt
!                                                    End Domain 3

!    G   V   F   A   F   L   L   Y   V   A   T   F   M   Y   V   F140
2760 ggt gtc ttt gcg ttt ctt tta tat gtt gcc acc ttt atg tat gta ttt
!    start transmembrane segment
!

!    S   T   F   A   N   I   L
2808 tct acg ttt gct aac ata ctg
!

!    R   N   K   E   S
```

TABLE 36-continued

Annotated sequence of CJR DY3F7(CJR-A05) 10251 bases

```
2829 cgt aat aag gag tct TAA ! stop of iii
!         Intracellular anchor.
!         (SEQ ID NO: 585)

!         M1  P2  V   L   L5  G   I   P   L   L10 L   R   F   L   G15
2847 tc  ATG cca gtt ctt ttg ggt att ccg tta tta ttg cgt ttc ctc ggt
!         Start VI
!

2894 ttc ctt ctg gta act ttg ttc ggc tat ctg ctt act ttt ctt aaa aag 2942 ggc ttc ggt aag ata gct att gct att tca ttg ttt ctt gct ctt att 2990 att ggg ctt aac tca att ctt gtg ggt tat ctc tct gat att agc gct 3038 caa tta ccc tct gac ttt gtt cag ggt gtt cag tta att ctc ccg tct 3086 aat gcg ctt ccc tgt ttt tat gtt att ctc tct gta aag gct gct att 3134 ttc att ttt gac gtt aaa caa aaa atc gtt tct tat ttg gat tgg gat
!

!             M1  A2  V3          F5                  L10         G13
3182 aaa TAA t ATG gct gtt tat ttt gta act ggc aaa tta ggc tct gga
!         end VI   Start gene I
!

(SEQ ID NO: 586)

!     K   T   L   V   S   V   G   K   I   Q   D   K   I   V   A
3228 aag acg ctc gtt agc gtt ggt aag att cag gat aaa att gta gct
!

!     G   C   K   I   A   T   N   L   D   L   R   L   Q   N   L
3273 ggg tgc aaa ata gca act aat ctt gat tta agg ctt caa aac ctc
!

!     P   Q   V   G   R   F   A   K   T   P   R   V   L   R   I
3318 ccg caa gtc ggg agg ttc gct aaa acg cct cgc gtt ctt aga ata
!

!     P   D   K   P   S   I   S   D   L   L   A   I   G   R   G
3363 ccg gat aag cct tct ata tct gat ttg ctt gct att ggg cgc ggt
!

!     N   D   S   Y   D   E   N   K   N   G   L   L   V   L   D
3408 aat gat tcc tac gat gaa aat aaa aac ggc ttg ctt gtt ctc gat
!

!     E   C   G   T   W   F   N   T   R   S   W   N   D   K   E
3453 gag tgc ggt act tgg ttt aat acc cgt tct tgg aat gat aag gaa
!

!     R   Q   P   I   I   D   W   F   L   H   A   R   K   L   G
3498 aga cag ccg att att gat tgg ttt cta cat gct cgt aaa tta gga
!

!     W   D   I   I   F   L   V   Q   D   L   S   I   V   D   K
3543 tgg gat att att ttt ctt gtt cag gac tta tct att gtt gat aaa
!

!     Q   A   R   S   A   L   A   E   H   V   V   Y   C   R   R
3588 cag gcg cgt tct gca tta gct gaa cat gtt gtt tat tgt cgt cgt
!

!     L   D   R   I   T   L   P   F   V   G   T   L   Y   S   L
3633 ctg gac aga att act tta cct ttt gtc ggt act tta tat tct ctt
!

!     I   T   G   S   K   M   P   L   P   K   L   H   V   G   V
```

TABLE 36-continued

Annotated sequence of CJR DY3F7(CJR-A05) 10251 bases

```
3678 att act ggc tcg aaa atg cct ctg cct aaa tta cat gtt ggc gtt

V   K   Y   G   D   S   Q   L   S   P   T   V   E   R   W
3723 gtt aaa tat ggc gat tct caa tta agc cct act gtt gag cgt tgg L   Y   T   G   K   N   L   Y   N   A   Y   D   T   K   Q
3768 ctt tat act ggt aag aat ttg tat aac gca tat gat act aaa cag A   F   S   S   N   Y   D   S   G   V   Y   S   Y   L   T
3813 gct ttt tct agt aat tat gat tcc ggt gtt tat tct tat tta acg P   Y   L   S   H   G   R   Y   F   K   P   L   N   L   G
3858 cct tat tta tca cac ggt cgg tat ttc aaa cca tta aat tta ggt Q   K   M   K   L   T   K   I   Y   L   K   K   F   S   R
3903 cag aag atg aaa tta act aaa ata tat ttg aaa aag ttt tct cgc V   L   C   L   A   I   G   F   A   S   A   F   T   Y   S
3948 gtt ctt tgt ctt gcg att gga ttt gca tca gca ttt aca tat agt Y   I   T   Q   P   K   P   E   V   K   K   V   S   Q
3993 tat ata acc caa cct aag ccg gag gtt aaa aag gta gtc tct cag T   Y   D   F   D   K   F   T   I   D   S   S   Q   R   L
4038 acc tat gat ttt gat aaa ttc act att gac tct tct cag cgt ctt N   L   S   Y   R   Y   V   F   K   D   S   K   G   K   L
4083 aat cta agc tat cgc tat gtt ttc aag gat tct aag gga aaa TTA
                                                            PacI I   N   S   D   D   L   Q   K   Q   G   Y   S   L   T   Y
4128 ATT AAt agc gac gat tta cag aag caa ggt tat tca ctc aca tat
     PacI i   I   D   L   C   T   V   S   I   K   K   G   N   S   N   E
!       iv                                                      M1  K
4173 att gat tta tgt act gtt tcc att aaa aaa ggt aat tca aAT Gaa
                                                        Start IV
```

! (SEQ ID NO: 527)

```
!       i   I   V   K   C   N   .End of I
!       iv  L3  L   N5  V   I7  N       F   V10
4218 att gtt aaa tgt aat TAA T TTT GTT
! IV continued.....
4243 ttc ttg atg ttt gtt tca tca tct tct ttt gct cag gta att gaa
     atg 4291 aat aat tcg cct ctg cgc gat ttt gta act tgg tat tca aag caa
     tca 4339 ggc gaa tcc gtt att gtt tct ccc gat gta aaa ggt act gtt act
     gta 4387 tat tca tct gac gtt aaa cct gaa aat cta cgc aat ttc ttt att
     tct 4435 gtt tta cgt gcA aat aat ttt gat atg gtA ggt tcT aAC cct tcc
     atT 4483 att cag aag tat aat cca aac aat cag gat tat att gat gaa ttg
     cca 4531 tca tct gat aat cag gaa tat gat gat aat tcc gct cct tct ggt
     ggt 4579 ttc ttt gtt ccg caa aat gat aat gtt act caa act ttt aaa att
     aat
```

TABLE 36-continued

Annotated sequence of CJR DY3F7(CJR-A05) 10251 bases

```
4627  aac gtt cgg gca aag gat tta ata cga gtt gtc gaa ttg ttt gta
      aag 4675  tct aat act tct aaa tcc tca aat gta tta tct att gac ggc tct
      aat 4723  cta tta gtt gtt agt gcT cct aaa gat att tta gat aac ctt cct
      caa 4771  ttc ctt tcA act gtt gat ttg cca act gac cag ata ttg att gag
      ggt 4819  ttg ata ttt gag gtt cag caa ggt gat gct tta gat ttt tca ttt
      gct 4867  gct ggc tct cag cgt ggc act gtt gca ggc ggt gtt aat act gac
      cgc 4915  ctc acc tct gtt tta tct tct gct ggt ggt tcg ttc ggt att ttt
      aat 4963  ggc gat gtt tta ggg cta tca gtt cgc gca tta aag act aat agc
      cat 5011  tca aaa ata ttg tct gtg cca cgt att ctt acg ctt tca ggt cag
      aag 5059  ggt tct atc tct gtT GGC CAg aat gtc cct ttt att act ggt cgt
      gtg
!                          MscI....

5107  act ggt gaa tct gcc aat gta aat aat cca ttt cag acg att gag
      cgt 5155  caa aat gta ggt att tcc atg agc gtt ttt cct gtt gca atg gct
      ggc 5203  ggt aat att gtt ctg gat att acc agc aag gcc gat agt ttg agt
      tct 5251  tct act cag gca agt gat gtt att act aat caa aga agt att gct
      aca 5299  acg gtt aat ttg cgt gat gga cag act ctt tta ctc ggt ggc ctc
      act 5347  gat tat aaa aac act tct caG gat tct ggc gta ccg ttc ctg tct
      aaa 5395  atc cct tta atc ggc ctc ctg ttt agc tcc cgc tct gat tcT aac
      gag 5443  gaa agc acg tta tac gtg ctc gtc aaa gca acc ata gta cgc gcc
      ctg 5491  TAG cggcgcatt
!     End IV 5503  aagcgcggcg ggtgtggtgg ttacgcgcag cgtgaccgct acacttgcca
      gcgccctagc 5563  gcccgctcct ttcgctttct tcccttcctt tctcgccacg ttcGCCGGCt
      ttccccgtca
!                                               NgoMI.

5623  agctctaaat cggggggctcc ctttagggtt ccgatttagt gctttacggc
      acctcgaccc 5683  caaaaaactt gatttgggtg atggttCACG TAGTGggcca tcgccctgat
      agacggtttt
!                          DraIII....

5743  tcgccccttG ACGTTGGAGT Ccacgttctt taatagtgga ctcttgttcc
      aaactggaac
!            DrdI.........
```

TABLE 36-continued

Annotated sequence of CJR DY3F7(CJR-A05) 10251 bases

```
5803 aacactcaac cctatctcgg gctattcttt tgatttataa gggattttgc
     cgatttcgga 5863 accaccatca aacaggattt tcgcctgctg gggcaaacca gcgtggaccg
     cttgctgcaa 5923 ctctctcagg gccaggcggt gaagggcaat CAGCTGttgc cCGTCTCact
     ggtgaaaaga
!                                    PvuII.    BsmBI.

5983 aaaaccaccc tGGATCC AAGCTT
!               BamHI   HindIII (1/2)
!               Insert carrying bla gene 6006    gcaggtg gcacttttcg gggaaatgtg cgcgcaaccc 6043 ctatttgttt attttctaa atacattcaa atatGTATCC gctcatgaga
     caataaccct
!                                       BciVI 6103 gataaatgct tcaataatat tgaaaaAGGA AGAgt
!                                   R8S.?...
!    Start bla gene
6138 ATG agt att caa cat ttc cgt gtc gcc ctt att ccc ttt ttt gcg
     gca ttt 6189 tgc ctt cct gtt ttt gct cac cca gaa acg ctg gtg aaa gta aaa
     gat gct 6240 gaa gat cag ttg ggC gcA CTA GTg ggt tac atc gaa ctg gat ctc
     aac agc
!                  SpeI....
!          ApaLI & BssSI Removed 6291 ggt aag atc ctt gag agt ttt cgc ccc gaa gaa cgt ttt cca atg
     atg agc 6342 act ttt aaa gtt ctg cta tgt GGC GcG Gta tta tcc cgt att gac
     gcc ggg 6393 caa gaG CAA CTC GGT CGc cgC ATA cAC tat tct cag aat gac ttg
     gtt gAG
!           BcgI............
     ScaI 6444 TAC Tca cca gtc aca gaa aag cat ctt acg gat ggc atg aca gta
     aga gaa
!    ScaI.

6495 tta tgc agt gct gcc ata acc atg agt gat aac act gcg gcc aac
     tta ctt 6546 ctg aca aCG ATC Gga gga ccg aag gag cta acc gct ttt ttg cac
     aac atg
!              PvuI....

6597 ggg gat cat gta act cgc ctt gat cgt tgg gaa ccg gag ctg aat
     gaa gcc 6648 ata cca aac gac gag cgt gac acc acg atg cct gta gca atg Gca
     aca acg 6699 tTG CGC Aaa cta tta act ggc gaa cta ctt act cta gct tcc cgg
     caa caa
!    FspI....
!

6750 tta ata gac tgg atg gag gcg gat aaa gtt gca gga cca ctt ctg
     cgc tcg

6801 GCC ctt ccG GCt ggc tgg ttt att gct gat aaa tct gga gcc ggt
     gag cgt
!    BglI..........

6852 gGG TCT Cgc ggt atc att gca gca ctg ggg cca gat ggt aag ccc
     tcc cgt
!    BsaI....
```

TABLE 36-continued

Annotated sequence of CJR DY3F7(CJR-A05) 10251 bases

```
6903  atc gta gtt atc tac acG ACg ggg aGT Cag gca act atg gat gaa
      cga aat
!                             AhdI..........

6954  aga cag atc gct gag ata ggt gcc tca ctg att aag cat tgg TAA
      ctgt
!                                                             stop 7003  cagaccaagt ttactcatat atactttaga ttgatttaaa acttcatttt
      taatttaaaa 7063  ggatctaggt gaagatcctt tttgataatc tcatgaccaa aatcccttaa
      cgtgagtttt 7123  cgttccactg tacgtaagac cccc 7147  AAGCTT    GTCGAC tgaa tggcgaatgg cgctttgcct
!     HindIII   SalI..
!     (2/2)    HincII 7183  ggtttccggc accagaagcg gtgccggaaa gctggctgga gtgcgatctt
!
! Start of Fab-display cassette, the Fab DSR-A05, selected for
! binding to a protein antigen.
7233  CCTGAcG CTCGAG
!     xBsu36I XhoI..
!

! PlacZ promoter is in the following block
!
7246                          cgcaacgc aattaatgtg agttagctca 7274  ctcattaggc accccaggct ttacacttta tgcttccggc tcgtatgttg 7324  tgtggaattg tgagcggata acaatttcac acaggaaaca gctatgacca 7374  tgattacgCC AagcttTGGa gccttttttt tggagatttt caac
!           PflMI.......
!              Hind3. (there are 3)

! Gene iii signal sequence: (Amino acid sequence is SEQ ID NO: 587)
!     1  2  3  4  5  6  7  8  9  10 11 12 13 14 15
!     M  K  K  L  L  F  A  I  P  L  V  V  P  F  Y
7418  gtg aaa aaa tta tta ttc gca att cct tta gtt gtt cct ttc tat
!

!     16 17 18        Start light chain (L20:JK1)
!     S  H  S    A  Q  D  I  Q  M  T  Q  S  P  A
7463  tct cac aGT GCA Caa gac atc cag atg acc cag tct cca gcc
!            ApaLI...
!            Sequence supplied by extender............
!

!     T  L  S  L
7505  acc ctg tct ttg
!

!     S  P  G  E  R  A  T  L  S  C  R  A  S  Q  G
7517  tct cca ggg gaa aga gcc acc ctc tcc tgc agg gcc agt cag Ggt
!

!     V  S  S  Y  L  A  W  Y  Q  Q  K  P  G  Q  A
7562  gtt agc agc tac tta gcc tgg tac cag cag aaa cct ggc cag gct
!

!     P  R  L  L  I  Y  D  A  S  S  R  A  T  G  I
7607  ccc agg ctc ctc atc tat gAt gca tcc aAc agg gcc act ggc atc
!

!     P  A  R  F  S  G  S  P  G  T  D  F  T  L
7652  cca gCc agg ttc agt ggc agt ggg Cct ggg aca gac ttc act ctc
!

!     T  I  S  S  L  E  P  E  D  F  A  V  Y  Y  C
```

TABLE 36-continued

Annotated sequence of CJR DY3F7(CJR-A05) 10251 bases

```
7697 acc atc agc agC ctA gag cct gaa gat ttt gca gtT tat tac tgt

Q   Q   R   S   W   H   P   W   T   F   G   Q   G   T   R
7742 cag cag CGt aAc tgg cat ccg tgg ACG TTC GGC CAA GGG ACC AAG V   E   I   K   R   T   V   A   A   P   S   V   F   I   F
7787 gtg gaa atc aaa cga act gtg gCT GCA Cca tct gtc ttc atc ttc BsgI....
          P   P   S   D   E   Q   L   K   S   G   T   A   S   V   V
7832 ccg cca tct gat gag cag ttg aaa tct gga act gcc tct gtt gtg C   L   L   N   N   F   Y   P   R   E   A   K   V   Q   W
7877 tgc ctg ctg aat aac ttc tat ccc aga gag gcc aaa gta cag tgg K   V   D   N   A   L   Q   S   G   N   S   Q   E   S   V
7922 aag gtg gat aac gcc ctc caa tcg ggt aac tcc cag gag agt gtc T   E   R   D   S   K   D   S   T   Y   S   L   S   S   T
7967 aca gag cgg gac agc aag gac agc acc tac agc ctc agc agc acc L   T   L   S   K   A   D   Y   E   K   H   K   V   Y   A
8012 ctg acG CTG AGC aaa gca gac tac gag aaa cac aaa gtc tac gcc
             EspI.....

C   E   V   T   H   Q   G   L   S   S   P   V   T   K   S
8057 tgc gaa gtc acc cat cag ggc ctG AGC TCg ccc gtc aca aag agc
                                          SacI....
          F   N   R   G   E   C   .   .
8102 ttc aac agg gga gag tgt taa taa 8126      GGCGCG CCaattctat ttcaaGGAGA cagtcata
             AscI.....            RBS2.
       (Amino acid sequence is SEQ ID NO: 588)

PelB signal sequence------(22 codons)----->
          1   2   3   4   5   6   7   8   9  10  11  12  13  14  15
          M   K   Y   L   L   P   T   A   A   A   G   L   L   L   L
8160 atg aaa tac cta ttg cct acg gca gcc gct gga ttg tta tta ctc ...PelB signal------------> Start VH, FR1----------------->
         16  17  18  19  20  21  22  23  24  25  26  27  28  29  30
          A   A   Q   P   A   M   A   E   V   Q   L   L   E   S   G
8205 gcG GCC cag ccG GCC atg gcc gaa gtt CAA TTG tta gag tct ggt
          SfiI.............                   MfeI...
                     NcoI....

31  32  33  34  35  36  37  38  39  40  41  42  43  44  45
          G   G   L   V   Q   P   G   G   S   L   R   L   S   C   A
8250 ggc ggt ctt gtt cag cct ggt ggt tct tta cgt ctt tct tgc gct ...FR1---------------------> CDR1---------------> FR2-------->
         46  47  48  49  50  51  52  53  54  55  56  57  58  59  60
          A   S   G   F   T   F   S   T   Y   E   M   R   W   V   R
8295 gct TCC GGA ttc act ttc tct act tac gag atg cgt tgg gtt cgC
             BspEI..
          BstXI...

FR2--------------------------------------> CDR2 ----------
         61  62  63  64  65  66  67  68  69  70  71  72  73  74  75
          Q   A   P   G   K   G   L   E   W   V   S   Y   I   A   P
```

TABLE 36-continued

Annotated sequence of CJR DY3F7(CJR-A05) 10251 bases

```
8340 CAa gct ccT GGt aaa ggt ttg gag tgg gtt tct tat atc gct cct
!    BstX1................
!

!    ...CDR2---------------------------------------> FR3---->
!     76  77  78  79  80  81  82  83  84  85  86  87  88  89  90
!      S   G   G   D   T   A   Y   A   D   S   V   K   G   R   F
8385 tct ggt ggc gat act gct tat gct gac tcc gtt aaa ggt cgc ttc
!

!     91  92  93  94  95  96  97  98  99 100 101 102 103 104 105
!      T   I   S   R   D   N   S   K   N   T   L   Y   L   Q   M
8430 act atc TCT AGA gac aac tct aag aat act ctc tac ttg cag atg
!            XbaI...
!            Supplied by extender-------------------------------
!

!    -----------------------------------------FR3--------------->
!    106 107 108 109 110 111 112 113 114 115 116 117 118 119 120
!      N   S   L   R   A   E   D   T   A   V   Y   Y   C   A   R
8475 aac agC TTA AGg gct gag gac act gca gtc tac tat tgt gcg agg
!         AflII...
!         from extender-------------------------->
!

!    CDR3------------------------------------------------>
FR4-->
!    121 122 123 124 125 126 127 128 129 130 131 132 133 134 135
!      R   L   D   G   Y   I   S   Y   Y   Y   G   M   D   V   W
8520 agg ctc gat ggc tat att tcc tac tac tac ggt atg GAC GTC tgg
!                                                    AatII..
!

!    136 137 138 139 140 141 142 143 144 145
!      G   Q   G   T   T   V   T   V   S   S
8565 ggc caa ggg acc acG GTC ACC gtc tca agc
!

!                BstEII...
!    CH1 of IgG1---------->
!      A   S   T   K   G   P   S   V   F   P   L   A   P   S   S
8595 gcc ccc acc aag ggc cca tcg gtc ttc ccc ctg gca ccc tcc tcc
!

!      K   S   T   S   G   G   T   A   A   L   G   C   L   V   K
8640 aag agc acc tct ggg ggc aca gcg gcc ctg ggc tgc ctg gtc aag
!

!      D   Y   F   P   E   P   V   T   V   S   W   N   S   G   A
8685 gac tac ttc ccc gaa ccg gtg acg gtg tcg tgg aac tca ggc gcc
!

!      L   T   S   G   V   H   T   F   P   A   V   L   Q   S   S
8730 ctg acc agc ggc gtc cac acc ttc ccg gct gtc cta cag tCC TCA
!
Bsu36I....
!

!      G   L   Y   S   L   S   S   V   V   T   V   P   S   S   S
8775 GGa ctc tac tcc ctc agc agc gta gtg acc gtg ccc tcc agc agc
!    Bsu36I....
!

!      L   G   T   Q   T   Y   I   C   N   V   N   H   K   P   S
```

TABLE 36-continued

Annotated sequence of CJR DY3F7(CJR-A05) 10251 bases

```
8820 ttg ggc acc cag acc tac atc tgc aac gtg aat cac aag ccc agc
!
!       N   T   K   V   D   K   K   V   E   P   K   S   C   A   A
8865 aac acc aag gtg gac aag aaa gtt gag ccc aaa tct tgt GCG GCC
!
NotI......
!
!       A   H   H   H   H   H   H   G   A   A   E   Q   K   L   I
8910 GCa cat cat cat cac cat cac ggg gcc gca gaa caa aaa ctc atc
!      ..NotI.... H6 tag................ Myc-Tag................
!
!       S   E   E   D   L   N   G   A   A   q   A   S   S   A
8955 tca gaa gag gat ctg aat ggg gcc gca tag GCT AGC tct gct
!      Myc-Tag....................          ... NheI...
!                                           Amber
!
!      III'stump
!      Domain 3 of III
--------------------------------------------------------
!
!       S   G   D   F   D   Y   E   K   M   A   N   A   N   K   G   A
8997 agt ggc gac ttc gac tac gag aaa atg gct aat gcc aac aaa GGC GCC
!     tcc   t   t   t   t     a   g       a   c   t       g   g   t
!W.T.
!
KasI...(2/4)
!
!       M   T   E   N   A   D   E   N   A   L   Q   S   D   A   K   G
9045 atG ACT GAG AAC GCT GAC GAG aat gct ttg caa agc gat gcc aag ggt
!         c   a   t   c   t   a       c     gca   g tct   c   t   a   c
!W.T.
!
!       K   L   D   S   V   A   T   D   Y   G   A   A   I   D   G   F
9093 aag tra gac agc gTC GCG Acc gac tat GGC GCC gcc ATC GAc ggc ttt
!       a   c   t   t tct       t       t   c   t   t       t   t   c
!W.T.
!                   NruI....          KasI...(3/4)
!
!       I   G   D   V   S   G   L   A   N   G   N   G   A   T   G   D
9141 atc ggc gat gtc agt ggt tTG GCC Aac ggc aac ggc gcc acc gga gac
!       t   t   c   t tcc   c c t     t   t   t   t   t   t   t   t
!W.T.
!             MscI....(3/3)
!
!       F   A   G   S   N   S   Q   M   A   Q   V   G   D   G   D   N
9189 ttc GCA GGT tcG AAT TCt cag atg gcC CAG GTT GGA GAT GGg gac aac
!       t   t   c   t       c   a       t   a   c   t   c   t   t   t
!W.T.
!      BspMI..(2/2)              XcmI................
!             EcoRI...
!
!       S   P   L   M   N   N   F   R   Q   Y   L   P   S   L   P   Q
9237 agt ccg ctt atg aac aac ttt aga cag tac ctt ccg tct ctt ccg cag
!       tca   t t a       t   t   cct   a tta   t   c   c   t     a
!W.T.
!
!       S   V   E   C   R   P   F   V   F   S   A   G   K   P   Y   E
9285 agt gtc gag tgc cgt cca ttc gtt ttc tct gcc ggc aag cct tac gag
!       tcg   t   a   t   c   t   t   c   t agc   t   a   a   t   a
!W.T.
!
!       F   S   I   D   C   D   K   I   N   L   F   R
```

TABLE 36-continued

Annotated sequence of CJR DY3F7(CJR-A05) 10251 bases

```
 9333 ttc aGC Atc gac TGC gat aag atc aat ctt ttC CGC
!        t tct    t   t   t   c   a   a   c t a    c  t   !W.T.
!          BstAPI........                       SacII...
!                                                  End Domain 3

!       G   V   F   A   F   L   L   Y   V   A   T   F   M   Y   V   F
 9369 GGc gtt ttc gct ttc ttg cta tac gtc gct act ttc atg tac gtt ttc
        t   c   t   g   tctta   t   t   c   c   t       t   a       t
!W.T.
!      start transmembrane segment
!
!       S   T   F   A   N   I   L   R   N   K   E   S
 9417 aGC ACT TTC GCC AAT ATT TTA Cgc aac aaa gaa agc
!     tct   g   t   t   c   acg   t   t   g   g tct !W.T.
!                                Intracellular anchor.
!
!              .   .

9453 tag tga cct CCT AGG
!                    AvrII..
!

9468 aag ccc gcc taa tga gcg ggc ttt ttt ttt ct ggt
!         | Trp terminator               |
!
! End Fab cassette
!

9503 ATGCAT CCTGAGG ccgat actgtcgtcg tccctcaaa ctggcagatg
!     NsiI.. Bsu36I.(3/3)

9551 cacggttacg atgcgcccat ctacaccaac gtgacctatc ccattacggt
      caatccgccg 9611 tttgttccca cggagaatcc gacgggttgt tactcgctca catttaatgt
      tgatgaaagc 9671 tggctacagg aaggccagac gcgaattatt tttgatggcg ttcctattgg
      ttaaaaaatg 9731 agctgattta acaaaaattt aaTgcgaatt ttaacaaaat attaacgttt
      acaATTTAAA
!
SwaI...

9791 Tatttgctta tacaatcttc ctgttttttgg ggcttttctg attatcaacc
      GGGGTAcat

9850 ATG att gac atg cta gtt tta cga tta ccg ttc atc gat tct ctt gtt tgc
!     Start gene II
 9901 tcc aga ctc tca ggc aat gac ctg ata gcc ttt gtA GAT CTc tca aaa ata
!                                                    BglII...

9952 gct acc ctc tcc ggc atT aat tta tca gct aga acg gtt gaa tat cat atc 1003 gat ggt gat ttg act gtc tcc ggc ctt tct cac cct ttt gaa tct tta cct 10054 aca cat tac tca ggc att gca ttt aaa ata tat gag ggt tct aaa aat ttt 10105 tat cct tgc gtt gaa ata aag gct tct ccc gca aaa gta tta cag ggt cat 10156 aat gtt ttt ggt aca acc gat tta gct tta tgc tct gag gct tta ttg ctt 10207 aat ttt gct aat tct ttg cct tgc ctg tat gat tta ttg gat gtt !
! gene II continues
!----------------------- End of Table ------------------------
```

TABLE 37

DNA seq of w.t. M13 gene iii
(Nucleotide sequence is SEQ ID NO: 590; Amino acid sequence is SEQ ID NO: 591)

```
        1   2   3   4   5   6   7   8   9  10  11  12  13  14  15
        fM  K   K   L   L   F   A   I   P   L   V   V   P   F   Y
   1579 gtg aaa aaa tta tta ttc gca att cct tta gtt gtt cct ttc tat
        Signal sequence.................................

16  17  18  19  20  21  22  23  24  25  26  27  28  29  30
        S   H   S   A   E   T   V   E   S   C   L   A   K   P   H
   1624 tct cac tcc gct gaa act gtt gaa agt tgt tta gca aaa ccc cat
        Signal sequence> Domain 1--------------------------------

31  32  33  34  35  36  37  38  39  40  41  42  43  44  45
        T   E   N   S   F   T   N   V   W   K   D   D   K   T   L
   1669 aca gaa aat tca ttt act aac gtc tgg aaa gac gac aaa act tta
        Domain 1-------------------------------------------------

46  47  48  49  50  51  52  53  54  55  56  57  58  59  60
        D   R   Y   A   N   Y   E   G   C   L   W   N   A   T   G
   1714 gat cgt tac gct aac tat gag ggt tgt ctg tgG AAT GCt aca ggc
                                                    BsmI....
        Domain 1-------------------------------------------------

61  62  63  64  65  66  67  68  69  70  71  72  73  74  75
        V   V   V   C   T   G   D   E   T   Q   C   Y   G   T   W
   1759 gtt gta gtt tgt act ggt gac gaa act cag tgt tac ggt aca tgg
        Domain 1-------------------------------------------------

76  77  78  79  80  81  82  83  84  85  86  87  88  89  90
        V   P   I   G   L   A   I   P   E   N   E   G   G   G   S
   1804 gtt cct att ggg ctt gct atc cct gaa aat gag ggt ggt ggc tct
        Domain 1---------------------------> Linker 1-----------

91  92  93  94  95  96  97  98  99 100 101 102 103 104 105
        E   G   G   G   S   E   G   G   G   S   E   G   G   G   T
   1849 gag ggt ggc ggt tct gag ggt ggc ggt tct gag ggt ggc ggt act
        Linker 1------------------------------------------------>

106 107 108 109 110 111 112 113 114 115 116 117 118 119 120
        K   P   P   E   Y   G   D   T   P   I   P   G   Y   T   Y
   1894 aaa cct cct gag tac ggt gat aca cct att ccg ggc tat act tat
        Domain 2-----------------------------------------------

121 122 123 124 125 126 127 128 129 130 131 132 133 134 135
        I   N   P   L   D   G   T   Y   P   P   G   T   E   Q   N
   1939 atc aac cct ctc gac ggc act taT CCG CCt ggt act gag caa aac
                                        EciT....
        Domain 2-----------------------------------------------

136 137 138 139 140 141 142 143 144 145 146 147 148 149 150
        P   A   N   P   N   P   S   L   E   E   S   Q   P   L   N
   1984 ccc gct aat cct aat cct tct ctt GAG GAG tct cag cct ctt aat
                                        BseRI..
        Domain 2-----------------------------------------------

151 152 153 154 155 156 157 158 159 160 161 162 163 164 165
        T   F   M   F   Q   N   N   R   F   R   N   R   Q   G   A
   2029 act ttc atg ttt cag aat aat agg ttc cga aat agg cag ggg gca
        Domain 2-----------------------------------------------

166 167 168 169 170 171 172 173 174 175 176 177 178 179 180
        L   T   V   Y   T   G   T   V   T   Q   G   T   D   P   V
```

TABLE 37-continued

DNA seq of w.t. M13 gene iii
(Nucleotide sequence is SEQ ID NO: 590; Amino acid sequence is SEQ ID NO: 591)

```
     2074   tta act gtt tat acg ggc act gtt act caa ggc act gac ccc gtt
!           Domain 2-----------------------------------------------------
!
!
!           181 182 183 184 185 186 187 188 189 190 191 192 193 194 195
!            K   T   Y   Y   Q   Y   T   P   V   S   S   K   A   M   Y
     2119   aaa act tat tac cag tac act cct gta tca tca aaa gcc atg tat
!           Domain 2-----------------------------------------------------
!
!
!           196 197 198 199 200 201 202 203 204 205 206 207 208 209 210
!            D   A   Y   W   N   G   K   F   R   D   C   A   F   H   S
     2164   gac gct tac tgg aac ggt aaa ttC AGa gaC TGc gct ttc cat tct
!                                           AlwNI.......
!           Domain 2-----------------------------------------------------
!
!
!           211 212 213 214 215 216 217 218 219 220 221 222 223 224 225
!            G   F   N   E   D   P   F   V   C   E   Y   Q   G   Q   S
     2209   ggc ttt aat gaG GAT CCa ttc gtt tgt gaa tat caa ggc caa tcg
!                               BamHI...
!           Domain 2-----------------------------------------------------
!
!
!           226 227 228 229 230 231 232 233 234 235 236 237 238 239 240
!            S   D   L   P   Q   P   P   V   N   A   G   G   G   S   G
     2254   tct gac ctg cct caa cct cct gtc aat gct ggc ggc ggc tct ggt
!           Domain 2---------------------------> Linker 2-----------
!
!
!           241 242 243 244 245 246 247 248 249 250 251 252 253 254 255
!            G   G   S   G   G   G   S   E   G   G   G   S   E   G   G
     2299   ggt ggt tct ggt ggc ggc tct gag ggt ggt ggc tct gag ggt ggc
!           Linker 2-----------------------------------------------
!
!
!           256 257 258 259 260 261 262 263 264 265 266 267 268 269 270
!            G   S   E   G   G   G   S   E   G   G   G   S   G   G   G
     2344   ggt tct gag ggt ggc ggc tct gag gga ggc ggt tcc ggt ggt ggc
!           Linker 2-----------------------------------------------
!
!
!           271 272 273 274 275 276 277 278 279 280 281 282 283 284 285
!            S   G   S   G   D   F   D   Y   E   K   M   A   N   A   N
     2389   tct ggt tcc ggt gat ttt gat tat gaa aag atg gca aac gct aat
!Linker 2>       Domain 3-----------------------------------------------
!
!
!           286 287 288 289 290 291 292 293 294 295 296 297 298 299 300
!            K   G   A   M   T   E   N   A   D   E   N   A   L   Q   S
     2434   aag ggg gct atg acc gaa aat gcc gat gaa aac gcg cta cag tct
!           Domain 3-----------------------------------------------------
!
!
!           301 302 303 304 305 306 307 308 309 310 311 312 313 314 315
!            D   A   K   G   K   L   D   S   V   A   T   D   Y   G   A
     2479   gac gct aaa ggc aaa ctt gat tct gtc gct act gat tac ggt gct
!           Domain 3-----------------------------------------------------
!
!
!           316 317 318 319 320 321 322 323 324 325 326 327 328 329 330
!            A   I   D   G   F   I   G   D   V   S   G   L   A   N   G
     2524   gct atc gat ggt ttc att ggt gac gtt tcc ggc ctt gct aat ggt
!           Domain 3-----------------------------------------------------
!
!
!           331 332 333 334 335 336 337 338 339 340 341 342 343 344 345
!            N   G   A   T   G   D   F   A   G   S   N   S   Q   M   A
     2569   aat ggt gct act ggt gat ttt gct ggc tct aat tcc caa atg gct
!           Domain 3-----------------------------------------------------
!
!
!           346 347 348 349 350 351 352 353 354 355 356 357 358 359 360
!            Q   V   G   D   G   D   N   S   P   L   M   N   N   F   R
```

TABLE 37-continued

DNA seq of w.t. M13 gene iii
(Nucleotide sequence is SEQ ID NO: 590; Amino acid sequence is SEQ ID NO: 591)

```
  2614  caa gtc ggt gac ggt gat aat tca cct tta atg aat aat ttc cgt
!       Domain 3-----------------------------------------------

!       361 362 363 364 365 366 367 368 369 370 371 372 373 374 375
!        Q   Y   L   P   S   L   P   Q   S   V   E   C   R   P   F
  2659  caa tat tta cct tcc ctc cct caa tcg gtt gaa tgc cgc cct ttt
!       Domain 3-----------------------------------------------

!       376 377 378 379 380 381 382 383 384 385 386 387 388 389 390
!        V   F   S   A   G   K   P   Y   E   F   S   I   D   C   D
  2704  gtc ttt agc gct ggt aaa cca tat gaa ttt tct att gat tgt gac
!       Domain 3-----------------------------------------------

!       391 392 393 394 395 396 397 398 399 400 401 402 403 404 405
!        K   I   N   L   F   R   G   V   F   A   F   L   L   Y   V
  2749  aaa ata aac tta ttc cgt ggt gtc ttt gcg ttt ctt tta tat gtt
!       Domain 3--------------> Transmembrane segment--------------

!       406 407 408 409 410 411 412 413 414 415 416 417 418 419 420
!        A   T   F   M   Y   V   F   S   T   F   A   N   I   L   R
  2794  gcc acc ttt atg tat gta ttt tct acg ttt gct aac ata ctg cgt
!       Transmembrane segment--------------------------> ICA--

!       421 422 423 424 425
!        N   K   E   S
  2839  aat aag gag tct taa ! 2853
!       ICA----------->          ICA = intracellular anchor !---------------- End of Table ---------------------
```

TABLE 38

Whole mature III anchor M13-III derived anchor with recoded DNA

```
!     1   2   3
!     A   A   A    (SEQ ID NO: 594)
  1   GCG gcc gca  (SEQ ID NO: 593)
!     Not I......

!     4   5   6   7   8   9   10  11  12  13  14  15  16  17
!     H   H   H   H   H   H   G   A   A   E   Q   K   L   I
  10  cat cat cat cac cat cac ggg gcc gca gaa caa aaa ctc atc !     18  19  20  21  22  23  24  25  26  27  28  29
!     S   E   E   D   L   N   G   A   A   .   A   S
  52  tca gaa gag gat ctg aat ggg gcc gca Tag GCT AGC
!                                             NheI...

!     30  31  32  33  34  35  36    37  38  39
!     D   I   N   D   D   R   M     A   S   T
  88  GAT ATC aac gat gat cgt atg   gct tct act
!    (ON_G37bot) [RC] 5'-c aac gat gat cgt atg gcG CAt Gct gcc gag aca g-3'
!     EcoRV..           (SEQ ID NO: 592)
!     Enterokinase cleavage site.

! Start mature III (recoded) Domain 1 ---->
!     40  41  42  43
!     A   E   T   V
```

TABLE 38-continued

Whole mature III anchor M13-III
derived anchor with recoded DNA

```
118 |gcC|gaG|acA|gtC|
    !   t   a   t   t ! W.T.
    !

!    44  45  46  47  48  49  50  51  52  53  54  55  56  57  58
    !    E   S   C   L   A   K   P   H   T   E   N   S   F   T   N
130 |gaa|TCC|tgC|CTG|GCC|AaG|ccT|caC|acT|gaG|aat|AGT|ttC|aCA|Aat|
    !       agt  t   t  a   a   c   t   a   a       tca  t   t   c ! W.T.
    !            MscI....
    !

!    59  60  61  62  63  64  65  66  67  68  69  70  71  72  73
    !    V   W   K   D   D   K   T   L   D   R   Y   A   N   Y   E
175 |gtg|TGG|aaG|gaT|gaT|aaG|acC|CtT|gAT|CGA|TaT|gcC|aaT|taC|gaA|
    !   c       a   c   c   a   t   ta       t       c   t   g ! W.T.
    !                            BspDI...
    !

!    74  75  76  77  78  79  80  81  82  83  84  85  86  87  88
    !    G   C   L   W   N   A   T   G   V   V   C   T   G   D
220 |ggC|tgC|TtA|tgg|aat|gcC|ACC|GGC|GtC|gtT|gtC|TGC|ACG|ggC|gaT|
    !    t   t cg           t   a   t   a   t   t   t   c ! W.T.
    !                    SgrAI......        BsgI....
    !

!    89  90  91  92  93  94  95  96  97  98  99 100 101 102 103
    !    E   T   Q   C   Y   G   T   W   V   P   I   G   L   A   I
265 |gaG|acA|caA|tgC|taT|ggC|ACG|TGg|gtG|ccG|atA|gGC|TTA|GCC|atA|
    !    a   t   g   c   t   a       t   t   gct  t   c ! W.T.
    !                        PmlI....          BlpI.....
    !

! Domain 1-----> Linker 1----------------->
    !   104 105 106 107 108 109 110 111 112 113 114 115 116 117 118
    !    P   E   N   E   G   G   G   S   E   G   G   G   S   E   G
310 |ccG|gaG|aaC|gaA|ggC|ggC|ggT|AGC|gaA|ggC|ggT|ggC|AGC|gaA|ggC|
    !    t   a   g   t   t   c tct  g   t   c   t tct  g   t ! W.T.
    !

! Linker 1----------------------> Domain 2---------------->
    !   119 120 121 122 123 124 125 126 127 128 129 130 131 132 133
    !    G   G   S   E   G   G   G   T   K   P   P   E   Y   G   D
355 |ggT|GGA|TCC|gaA|ggA|ggT|ggA|acC|aaG|ccG|ccG|gaA|taT|ggC|gaC|
    !    c   t   t   g   t   c   t   t   a   t   t   g   c   t   t ! W.T.
    !        BamHI..(2/2)
    !

!   134 135 136 137 138 139 140 141 142 143 144 145 146 147 148
    !    T   P   I   P   G   Y   T   Y   I   N   P   L   D   G   T
400 |acT|ccG|atA|CCT|GGT|taC|acC|taC|atT|aaT|ccG|TtA|gaT|ggA|acC|
    !    a   t   g   c   t   t   t   c   c   t cc  c   c   t ! W.T.
    !            SexAI....
    !

!   149 150 151 152 153 154 155 156 157 158 159 160 161 162 163
    !    Y   P   P   G   T   E   Q   N   P   A   N   P   N   P   S
445 |taC|ccT|ccG|ggC|acC|gaA|caG|aaT|ccT|gcC|aaC|ccG|aaC|ccA|AGC|
    !    T   G   t   t   g   a   c   c   t   t       t  tct ! W.T.
    !                                                    HindIII...
    !

!   164 165 166 167 168 169 170 171 172 173 174 175 176 177 178
    !    L   E   E   S   Q   P   L   N   T   F   M   F   Q   N   N
490 |TTA|gaA|gaA|AGC|caA|ccG|TtA|aaC|acC|ttT|atg|ttC|caA|aaC|aaC|
    !    c   t   G tct   g   t tct  t   c       t   g   t   t ! W.T.
    !    HindIII.
    !

!   179 180 181 182 183 184 185 186 187 188 189 190 191 192 193
    !    R   F   R   N   R   Q   G   A   L   T   V   Y   T   G   T
535 |CgT|ttT|AgG|aaC|CgT|caA|gGT|GCT|CtT|acC|gTG|TAC|AcT|ggA|acC|
    !    ag   c   c a   t  ag  g   a   ata  t   t   g   c   t ! W.T.
    !                                HgiAI...   BsrGI...
    !

!   194 195 196 197 198 199 200 201 202 203 204 205 206 207 208
    !    V   T   Q   G   T   D   P   V   K   T   Y   Y   Q   Y   T
```

TABLE 38-continued

Whole mature III anchor M13-III
derived anchor with recoded DNA

```
580 |gtC|acC|caG|GGT|ACC|gaT|ccT|gtC|aaG|acC|taC|taT|caA|taT|acC|
!      t    a    c    t         c    c    t    a    t    t    c    g    c    t ! W.T.
!                    KpnI...
!

!         209 210 211 212 213 214 215 216 217 218 219 220 221 222 223
!          P   V   S   S   K   A   M   Y   D   A   Y   W   N   G   K
625      |ccG|gtC|TCG|AGt|aaG|gcT|atg|taC|gaT|gcC|taT|tgg|aaT|ggC|aaG|
!          t    a    atca a    c         t    c    t    c              c    t    a ! W.T.
!          BsaI....
!              XhoI....
!

!         224 225 226 227 228 229 230 231 232 233 234 235 236 237 238
!          F   R   D   C   A   F   H   S   G   F   N   E   D   P   F
670      |ttT|CgT|gaT|tgT|gcC|ttT|caC|AGC|ggT|ttC|aaC|gaa|gac|CCt|ttT|
!          CAa  C    c    t    c    ttct c         t    t    G    T    a    c ! W.T.
!

!         239 240 241 242 243 244 245 246 247 248 249 250 251 252 253
!          V   C   E   Y   Q   G   Q   S   S   D   L   P   Q   P   P
715      |gtC|tgC|gaG|taC|caG|ggT|caG|AGT|AGC|gaT|TtA|ccG|caG|ccA|CCG|
!          t    t    a    t         a    c         atcg tct c    c    g    t    a    t    t ! W.T.
!          DrdI.....                                                              AgeI.....
!

! Domain 2--------> Linker 2--------------------->
!         254 255 256 257 258 259 260 261 262 263 264 265 266 267 268
!          V   N   A   G   G   G   S   G   G   G   S   G   G   G   S
760      |GTT|AAC|gcG|ggT|ggT|ggT|AGC|ggC|ggA|ggC|AGC|ggC|ggT|ggT|AGC|
!                       c    t    c         c    c    tct t    t    t tct t    c    c    tct ! W.T.
!
! AgeI.....
!     HpaI...
!     HincII.
!

!         Linker 2------------------------------------> Domain 3-->
!         269 270 271 272 273 274 275 276 277 278 279 280 281 282 283
!          E   G   G   G   S   E   G   G   G   S   G   G   G   S   G
805      |gaA|ggC|ggA|ggT|AGC|gaA|ggA|ggT|ggC|AGC|ggA|ggC|ggT|AGC|ggC|
!               g    t    c    tct g    t    c    ttct g    t    c    tct t    ! W.T.
!

!         ------------Domain 3-------------------->
!         284 285 286 287 288 289 290 291 292 293 294 295 296 297 298
!          S   G   D   F   D   Y   E   K   M   A   N   A   N   K   G
850      |AGT|ggC|gac|ttc|gac|tac|gag|aaa|atg|gct|aat|gcc|aac|aaa|GGC|
!          tcc  t    t    t    t    a    g              a    c    t    g    g    g ! W.T.
!                                                                              KasI....
!

!         299 300 301 302 303 304 305 306 307 308 309 310 311 312 313
!          A   M   T   E   N   A   D   E   N   A   L   Q   S   D   A
895      |GCC|atg|act|gag|aac|gct|gac|gaG|AAT|GCA|ctg|caa|agt|gat|gCC|
!            t    c    a    t    c         a    c         g    a    gtct c    t ! W.T.
!          KasI....                         BsmI....                        StyI...
!

!         314 315 316 317 318 319 320 321 322 323 324 325 326 327 328
!          K   G   K   L   D   S   V   A   T   D   Y   G   A   A   I
940      |AAG|GGt|aag|tta|gac|agc|gTC|GCc|Aca|gac|tat|ggt|GCt|gcc|atc|
!            a    c    a    c    t    t tct       t    t    c              t         ! W.T.
!          StyI......             PflFI......
!

!         329 330 331 332 333 334 335 336 337 338 339 340 341 342 343
!          D   G   F   I   G   D   V   S   G   L   A   N   G   N   G
985      |gac|ggc|ttt|atc|ggc|gat|gtc|agt|ggt|ctg|gct|aac|ggc|aac|gga|
!            t    t    c         t    c    t tcc  c    c    t              t    t    t ! W.T.
!

!         344 345 346 347 348 349 350 351 352 353
!          A   T   G   D   F   A   G   S   N
```

TABLE 38-continued

Whole mature III anchor M13-III
derived anchor with recoded DNA

```
1030 |gcc|acc|gga|gac|ttc|GCA|GGT|tcG|AAT|TCt|
!      t   t   t   t   t   t  c  ! W.T.
!                           BstBI...
!                               EcoRI...
!                       BspMI..
!

!     354 355 356 357 358 359 360 361 362 363
!      Q   M   A   Q   V   G   D   G   D   N
1060 cag atg gcC CAG GTT GGA GAT GGg gac aac
!      a       t   a   t   c   t   t   t ! W.T.
!             XcmI................
!

!     364 365 366 367 368 369 370 371 372 373 374 375 376 377 378 379
!      S   P   L   M   N   N   F   R   Q   Y   L   P   S   L   P   Q
1090 agt ccg ctt atg aac aac ttt aga cag tac ctt ccg tct ctt ccg cag
      tca     tta     t   t   cct a   tta t   cct     a ! W.T.
!

!     380 381 382 383 384 385 386 387 388 389 390 391 392 393 394 395
!      S   V   E   C   R   P   F   V   F   S   A   G   K   P   Y   E
1138 agt gtc gag tgc cgt cca ttc gtt ttc tct gcc ggc aag cct tac gag
      tcg t   a   c   t   t   c       tagc t       a   t       a ! W.T.
!

!     Domain 3------------------------------------>
!     396 397 398 399 400 401 402 403 404 405 406 407
!      F   S   I   D   C   D   K   I   N   L   F   R
1186 ttc aGC Atc gac TGC gat aag atc aat ctt ttC CGC
!      t   tct t   c   a   a   c   ta      t
!         BstAPI........                   SacII...
!

!     transmembrane segment-------------->
!     408 409 410 411 412 413 414 415 416 417 418 419 420 421 422 423
!      G   V   F   A   F   L   L   Y   V   A   T   F   M   Y   V   F
1222 GGc gtt ttc gct ttc ttg cta tac gtc gct act ttc atg tac gtt ttc
         t   c   t   g   tctta t   c   c   t       t   a   t ! W.T.
!

!     424 425 426 427 428 429 430 431 432 433 434 435
!      S   T   F   A   N   I   L   R   N   K   E   S
1270 aGC ACT TTC GCC AAT ATT TTA Cgc aac aaa gaa agc
      tct g   t   c   acg t   t   g   g tct ! W.T.
!                          Intracellular anchor.
!

!          . .
1306       tag tga tct CCT AGG
!                          AvrII..
!

1321 aag ccc gcc taa tga gcg ggc ttt ttt ttt ct ggt
!        | Trp terminator              |
!
! End Fab cassette
!-------------------------- End of Table ------------------------
```

TABLE 39

ONs to make deletions in III

```
! ONs for use with NheI
!
!                                                                    N
(SEQ ID NO: 595)
(ON_G29bot)              5'-c gTT gAT ATc gcT Agc cTA Tgc-3'     !  22
this is the reverse complement of 5'-gca tag gct agc gat atc aac g-3'
!
!                          NheI... scab........
(ON_G104top) 5'-g|ata|ggc|tta|gcT|aGC|ccg|gag|aac|gaa|gg-3'      !  30
```

TABLE 39-continued

ONs to make deletions in III (SEQ ID NO: 596)

```
!              Scab..........NheI...  104 105 106 107 108
(ON_G236top) 5'-c|ttt|cac|agc|ggt|ttc|GCT|AGC|gac|cct|ttt|gtc|tgc-3'       !  37

NheI...  236 237 238 239 240
(ON_G236tCS) 5'-a|ttt|cac|agc|ggt|ttc|GCT|AGC|gac|cct|ttt|gtc|Agc-
(SEQ ID NO: 597)
                           NheI...  236 237 238 239 240
            gag|tac|cag|ggt|c-3'   (SEQ ID NO: 598)                        !  50

! ONs for use with SphI G CAT Gc
(ON_X37bot) 5'-gAc TgT cTc ggc Agc ATg cgc cAT Acg ATc ATc gTT g-3'         !  37
(SEQ ID NO: 599)

!             N   D   D   R   M   A   H   A (SEQ ID NO: 601)
(ON_X37bot) = (RC) 5'-c aac gat gat cgt atg gcG CAt Gct gcc gag aca gtc-3'
              (SEQ ID NO: 600)

!                                   SphI....Scab...........
(ON_X104top) 5'-g|gtG ccg|ata|ggc|ttG|CAT|GCa|ccg|gag|aac|gaa|gg-3'          !  36
(SEQ ID NO: 617)

!          Scab..............SphI....  104 105 106 107 108
(ON_X236top) 5'-c|ttt|cac|agc|ggt|ttG|CaT|gCa|gac|cct|ttt|gtc|tgc-3'         !  37
(SEQ ID NO: 602)

!                  SphI....  236 237 238 239 240
(ON_X236tCS) 5'-c|ttt|cac|agc|ggt|ttG|CaT|gCa|gac|cct|ttt|gtc|Agc-
!                           NheI...  236 237 238 239 240
            gag|tac|cag|ggt|c-3'   (SEQ ID NO: 603)                         !  50
```

TABLE 40

Phage titers and enrichments of selections with a DY3F31-based human Fab library

|  | Input (total cfu) | Output (total cfu) | Output/input ratio |
|---|---|---|---|
| R1-ox selected on phOx-BSA | $4.5 \times 10^{12}$ | $3.4 \times 10^{5}$ | $7.5 \times 10^{-8}$ |
| R2-Strep selected on Strep-beads | $9.2 \times 10^{12}$ | $3 \times 10^{8}$ | $3.3 \times 10^{-5}$ |

TABLE 41

Frequency of ELISA positives in DY3F31-based Fab libraries

|  | Anti-M13 HRP | 9E10/RAM-HRP | Anti-CK/CL Gar-HRP |
|---|---|---|---|
| R2-ox (with IPTG induction) | 18/44 | 10/44 | 10/44 |
| R2-ox (without IPTG) | 13/44 | ND | ND |
| R3-strep (with IPTG) | 39/44 | 38/44 | 36/44 |
| R3-strep (without IPTG) | 33/44 | ND | ND |

We claim:

1. A vector comprising:
   (i) a DNA sequence encoding an antibody variable region linked to a fragment of a wild-type PIII anchor which does not mediate infection of phage particles; and
   (ii) wild-type gene III;
   wherein the nucleic acid sequence encoding the fragment of the wild-type pIII anchor differs from the wild-type gene III to an extent sufficient to reduce homologous recombination between the nucleic acid encoding the fragment of the wild-type PIII anchor and the wild-type gene III,
   wherein all the codons in the nucleic acid encoding the fragment of the wild-type pIII anchor have at least one base change introduced per codon compared to the wild-type gene III.

2. The vector of claim 1, wherein the DNA encodes a Fab.

3. The vector of claim 1, wherein the DNA encodes heavy chain VHCH1.

4. The vector of claim 3, wherein the heavy chain VHCH1 is linked to trpIII.

5. The vector of claim 1, wherein the DNA encodes light chain VLCL.

6. The vector of claim 5, wherein the light chain VLCL is linked to trpIII.

7. The vector of claim 1, wherein the DNA encodes scFv.

8. The vector of claim 7, wherein the scFv is VL-VH.

9. The vector of claim 7, wherein the scFv is VH-VL.

10. The vector of claim 1, wherein the DNA sequence encoding the antibody variable region further comprises an inducible promoter.

11. The vector of claim 10, wherein the inducible promoter regulates expression of the DNA sequence encoding the antibody variable region.

12. The vector of claim 1, wherein the DNA sequence encoding the antibody variable region further comprises an amber stop codon.

13. The vector of claim 12, wherein the amber stop codon is located between the antibody variable region and the fragment of the wild-type PIII anchor.

14. The vector of claim 1, wherein the vector is phage or phagemid.

* * * * *